United States Patent [19]
TenBrink et al.

[11] Patent Number: 5,541,324
[45] Date of Patent: Jul. 30, 1996

[54] IMIDAZO[1,5-A]QUINOXALINES

[75] Inventors: Ruth E. TenBrink, Richland; E. Jon Jacobsen, Plainwell; Ronald B. Gammill, Kalamazoo, all of Mich.

[73] Assignee: The Upjohn Company, Kalamazoo, Mich.

[21] Appl. No.: 166,037

[22] Filed: Dec. 13, 1993

Related U.S. Application Data

[63] Continuation-in-part of Ser. No. 843,650, Feb. 28, 1992, abandoned, which is a continuation-in-part of Ser. No. 715,930, Jun. 14, 1991, abandoned.

[51] Int. Cl.$^6$ .................. C07D 487/16; C07D 413/06
[52] U.S. Cl. .................. 544/346; 544/115; 544/230
[58] Field of Search .................. 544/346, 115, 544/346, 230

[56] References Cited

U.S. PATENT DOCUMENTS

| | | | |
|---|---|---|---|
| 4,128,716 | 12/1978 | Treuner | 544/346 |
| 4,254,123 | 3/1981 | Ramm | 424/250 |
| 4,291,033 | 9/1981 | Barnes | 424/250 |
| 4,774,245 | 9/1988 | Wätjen | 514/250 |
| 4,795,749 | 1/1989 | Wätjen | 514/250 |
| 4,999,353 | 3/1991 | Watjen et al. | 514/250 |
| 5,075,304 | 12/1991 | Hansen et al. | 514/233.2 |

FOREIGN PATENT DOCUMENTS

| | | | |
|---|---|---|---|
| 0220845 | 5/1987 | European Pat. Off. | C07D 487/04 |
| 225013 | 6/1987 | European Pat. Off. | C07D 487/04 |
| 0320136 | 6/1988 | European Pat. Off. | C07D 487/04 |
| 0283162 | 9/1988 | European Pat. Off. | C07D 487/04 |
| 0347094 | 12/1989 | European Pat. Off. | C07D 487/04 |
| 0344943 | 12/1989 | European Pat. Off. | C07D 487/04 |
| 0368652 | 5/1990 | European Pat. Off. | C07D 487/04 |
| 92/22552 | 12/1992 | WIPO | C07D 487/04 |

*Primary Examiner*—Johann Richter
*Assistant Examiner*—Laura L. Stockton
*Attorney, Agent, or Firm*—Bruce Stein

[57] ABSTRACT

An invention relating to Imidazo[1,5-a]quinoxalines (I)

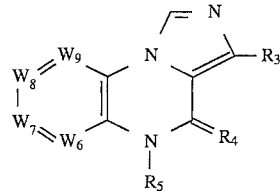

which do not contain an endocyclic carbonyl group and which are useful as anxiolytic and sedative/hypnotic agents.

20 Claims, No Drawings

IMIDAZO[1,5-A]QUINOXALINES

CROSS-REFERENCE TO RELATED APPLICATIONS

The present patent application is a continuation-in-part (national phase) patent application of PCT application PCT/US92/04434, filed Jun. 1, 1992 which was a continuation-in-part patent application of U.S. patent application Ser. No. 07/843,650, filed Feb. 28, 1992 (now abandoned) which was a continuation-in-part patent application of U.S. patent application Ser. No. 07/715,930, filed Jun. 14, 1991 (now abandoned).

BACKGROUND OF THE INVENTION

1. Field of the Invention

The compounds of the present invention are imidazo[1.5-a]quinoxalines (I) which are useful pharmaceutical agents.

2. Description of the Related Art

Many commercially available anxiolytic agents are from the chemical group known as benzodiazepines. The benzodiazepines are characterized by a seven member ring attached to an aromatic ring.

U.S. Pat. No. 4,774,245 discloses a group of non-benzodiazepine anxiolytic agents which possess a six member ring rather than a seven member ring attached to the aromatic ring (imidazo[1.5-a]quinoxalines). These compounds have an endocyclic carbonyl group.

EP 344,943A discloses a group of imidazo[1,5-a]quinoxaline compounds, useful as anxiolytic and anticonvulsant agents, having an exocyclic carbonyl at the $N_5$ position attached to a methyl group and not attached directly to the $N_5$ nitrogen, and an endocyclic carbonyl at $C_4$.

EP 347,094A discloses imidazo[1,5-a]quinoxaline4,5-enes useful for treating CNS disorders with no substitution at $N_5$.

EP 320,136 discloses $N_5$-isopropyl-imidazo[1,5-a]quinoxalines having an endocyclic carbonyl at $C_4$, useful as anxiolytic and anticonvulsant agents.

EP 368,652A discloses $N_5$-(t-butyl)-imidazo[1,5-a]quinoxalines having an endocyclic carbonyl at $C_4$, useful as anxiolytic and anticonvulsant agents.

EP 283,162A discloses imidazole fused ring compounds of varying types including quinoxalines. The quinoxalines have an endocyclic carbonyl group and alkyl substitution at $N_5$ or 4,5-ene and were useful as anxiolytic and anticonvulsant agents.

BE 878,028 and 881,631 disclose imidazo[1,2-a]quinoxaline-2-carboxylic acids, and derivatives, useful for treating allergic asthma and asthmatic bronchitis.

U.S Pat. No. 4,128,716 discloses 4-halo-4,5 -ene-pyrazolo[1,5-a]quinoxaline-3-carboxylates useful as antiinflammatory agents.

U.S. Pat. Nos. 4,774,245 and 4,795,749 (EP 220 845 A) and EP 0 225 013 A discloses $N_5$ -alkyl and cycloalkyl substituted imidazo[1,5-a]quinoxalines without an endocyclic carbonyl. The imidazo[1,5-a]quinoxalines (I) of the present invention have a —CO— or —CS— in the side chain attached to $N_5$.

U.S. Pat. No. 5,075,304 discloses imidazo[1,5-a]quinoxalin-4-ones with a carbonyl function at $C_4$ and a (substituted) methyl at $N_5$ (—$CH_2$—CO—O—alkyl) useful as anticonvulsants, anxiolytics and hypnotics.

International Publication WO 92/22552 is the parent PCT application of the national phase application.

The imidazo[1,5-a]quinoxalines (LX) of the present invention do not have a —CO— or —CS— in the side chain attached to $N_5$.

SUMMARY OF INVENTION

Disclosed are imidazo[1,5-a]quinoxalines of formula (I)

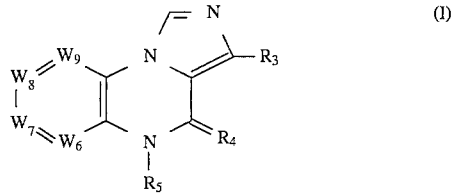

where $R_3$ is ($C_3$-1) —$COOR_{3-1}$ where $R_{3-1}$ is
(1) —H,
(2) $C_1$–$C_9$ alkyl,
(3) $C_3$–$C_7$ cycloalkyl,
(4) —$(CH_2)_{n6}$—O—$R_{3-3}$ where $n_6$ is 2 thru 4 and $R_{3-3}$ is —H, $C_1$–$C_4$ alkyl or $C_3$–$C_7$ cycloalkyl,
(5) —$(CH_2)_{n6}$—$NR_{3-4}R_{3-5}$ where $R_{3-4}$ is —H, $C_1$–$C_4$ alkyl, $C_3$–$C_7$ cycloalkyl or —φ, $R_{3-5}$ is —H, $C_1$–$C_6$ alkyl or $C_3$–$C_7$ cycloalkyl and where $R_{3-4}$ and $R_{3-5}$ are taken together with the attached nitrogen atom to form a heterocyclic ring —N*—$(CHR_{3-8})_{nA}$—$(CH_2)_{n1}$—$R_{3-6}$—$(CH_2)_{n2}$—$(C*HR_{3-9})$($C_3$-1a)

—N*—$(CH_2)_{n1}$—$(CHR_{3-8})_{nA}$—$R_{3-6}$—$(CHR_{3-9})_{nB}$—$(C*H_2)$($C_3$-1b)

where $R_{3-8}$ is —H or $C_1$–$C_3$ alkyl, $n_A$ is 1 or 2, $n_1$ is 0 thru 2, $n_2$ is 0 thru 2, $R_{3-9}$ is —H or $C_1$–$C_3$ alkyl, $n_B$ is 1 or 2, where the atoms marked with an asterisk (*) are bonded to each other resulting in the formation of a ring, with the proviso that the ring not contain more than 8 atoms, and where $R_{3-6}$ is
—O—,
—S—,
—CO—
—$CR_{3-61}R_{3-62}$ where $R_{3-61}$ and $R_{3-62}$ are the same or different and are —H or $C_1$–$C_3$ alkyl,
—$NR_{3-7}$ where $R_{3-7}$ is
—H,
$C_1$–$C_4$ alkyl,
$C_3$–$C_7$ cycloalkyl,
—$(CH_2)_{n7}$—φ where $n_7$ is 0 thru 4 and φ is optionally substituted with 1, 2 or 3 $R_{3-2}$ where $R_{3-2}$ is selected from the group consisting of
—F,
—Cl,
—Br,
—CN,
—$NO_2$,
—O—CO—$R_{3-2a}$ where $R_{3-2a}$ is —H, $C_1$–$C_4$ alkyl or $C_3$–$C_7$ cycloalkyl,
—$(CH_2)_{n30}$—$CF_3$ where $n_{30}$ is 0 thru 3,
—O—$CF_3$,
$C_1$–$C_6$ alkyl,
$C_3$–$C_7$ cycloalkyl,
—$CH_2$—($C_3$–$C_7$ cycloalkyl),
—$CH_2CH(CF_3)CH_3$,
—$C(OH)(CH_2OH)(CH_2CH_3)$,
—$C(OH)(CH_2OH)CH_3$,
—$C(CH_3)(OH)(CH_2OH)$,
—$CH(OH)(CH_2OH)$,
—$CH(OH)(CH_3)$,
—$CH_2CH_2OH$, —C(CH$_3$)$_2$(CH$_2$OH),
—CH(CH$_2$OH)$_2$,
—C(CH$_2$—OH)$_3$,
—C(CH$_3$)$_2$—OH,
—C(CH$_3$)$_2$—F,
—NR$_{3-2b}$—CO—R$_{3-2c}$ where R$_{3-2b}$ is —H or C$_1$-C$_4$ alkyl, and where R$_{3-2c}$ is
—H,
C$_1$-C$_6$ alkyl,
—φ,
—CH$_2$—φ,
—(CH$_2$)$_{n8}$—OR$_{3-2d}$ where n$_8$ is 0 thru 3 and R$_{3-2d}$ is —H or C$_1$-C$_4$ alkyl,
—(CH$_2$)$_{n21}$—OH where n$_{21}$ is 3 thru 4,
—(CH$_2$)$_{n22}$—φ where n$_{22}$ is 0 thru 3 and where φ is optionally substituted with —F, —Cl, —Br, —I or C$_1$-C$_4$ alkyl,
—(CH$_2$)$_{n8}$—N(R$_{3-2}$d)$_2$ where n$_8$ and R$_{3-2d}$ are as defined above and where the two R$_{3-2d}$'s can be taken together with the attached nitrogen atom to form a ring selected from the group consisting of 1-pyrrolidinyl, 1-piperidinyl, 1-piperazinyl, 4-morpholinyl, 1-(4-methyl)piperazinyl,
—S—R$_{3-2d}$ where R$_{3-2d}$ is as defined above,
—SO$_2$—N(R$_{3-2e}$)$_2$ where R$_{3-2e}$ is —H or C$_1$-C$_4$ alkyl,
—CO—N(R$_{3-2e}$)$_2$ where R$_{3-2e}$ is as defined above and where the two R$_{3-2e}$'s can be taken together with the attached nitrogen atom to from a ring selected frown the group consisting of 1-pyrrolidinyl, 1-piperidinyl, 1-piperazinyl, 4-morpholinyl, 1-(4-methyl)piperazinyl,
—NR$_{3-2f}$R$_{3-2g}$ where R$_{3-2f}$ and R$_{3-2g}$ are the same or different and are —H or C$_1$-C$_4$ alkyl and where R$_{3-2f}$ and R$_{3-2g}$ can be taken together with the attached nitrogen atom to form a ring, which may contain an additional heteroatom, selected from the group consisting of piperazine, morpholine, pyrrolidine or piperidine,
with the proviso that when R$_{3-6}$ is —O—, —S— or —NR$_{3-7}$—, n$_1$ and n$_2$ are 1 or 2,
(6) aryl, where aryl is
(F-Aryl-I)
—φ optionally substituted with one or two R$_{3-2}$ where R$_{3-2}$ is as defined above,
(F-Aryl-II)
1-naphthyl optionally substituted with one or two R$_{3-2}$ where R$_{3-2}$ is as defined above,
(F-Aryl-III)
2-naphthyl optionally substituted with one or two R$_{3-2}$ where R$_{3-2}$ is as defined above,
(F-Aryl-IV)
2-pyridyl optionally substituted with one or two R$_{3-2}$ where R$_{3-2}$ is as defined above,
(F-Aryl-V)
3-pyridyl optionally substituted with one or two R$_{3-2}$ where R$_{3-2}$ is as defined above,
(F-Aryl-VI)
4-pyridyl optionally substituted with one or two R$_{3-2}$ where R$_{3-2}$ is as defined above,
(F-Aryl-VII)
2-pyrimidinyl optionally substituted with one or two R$_{3-2}$ where R$_{3-2}$ is as defined above,
(F-Aryl-VIII)
4-pyrimidinyl optionally substituted with one or two R$_{3-2}$ where R$_{3-2}$ is as defined above,
(F-Aryl-IX)
5-pyrimidinyl optionally substituted with one or two R$_{3-2}$ where R$_{3-2}$ is as defined above,
(F-Aryl-X)
3-pyridazinyl optionally substituted with one or two R$_{3-2}$ where R$_{3-2}$ is as defined above,
(F-Aryl-XI)
4-pyridazinyl optionally substituted with one or two R$_{3-2}$ where R$_{3-2}$ is as defined above,
(F-Aryl-XII)
3-pyrazinyl optionally substituted with one or two R$_{3-2}$ where R$_{3-2}$ is as defined above,
(F-Aryl-XIII)
2-quinolyl optionally substituted with one or two R$_{3-2}$ where R$_{3-2}$ is as defined above,
(F-Aryl-XIV)
3-quinolyl optionally substituted with one or two R$_{3-2}$ where R$_{3-2}$ is as defined above,
(F-Aryl-XV)
4-quinolyl optionally substituted with one or two R$_{3-2}$ where R$_{3-2}$ is as defined above,
(F-Aryl-XVI)
1-isoquinolyl optionally substituted with one or two R$_{3-2}$ where R$_{3-2}$ is as defined above,
(F-Aryl-XVII)
3-isoquinolyl optionally substituted with one or two R$_{3-2}$ where R$_{3-2}$ is as defined above,
(F-Aryl-XVIII)
4-isoquinolyl optionally substituted with one or two R$_{3-2}$ where R$_{3-2}$ is as defined above,
(F-Aryl-XIX)
2-quinazolinyl optionally substituted with one or two R$_{3-2}$ where R$_{3-2}$ is as defined above,
(F-Aryl-XX)
4-quinazolinyl optionally substituted with one or two R$_{3-2}$ where R$_{3-2}$ is as defined above,
(F-Aryl-XXI)
2-quinoxalinyl optionally substituted with one or two R$_{3-2}$ where R$_{3-2}$ is as defined above,
(F-Aryl-XXII)
1-phthalazinyl optionally substituted with one or two R$_{3-2}$ where R$_{3-2}$ is as defined above,
(F-Aryl-XXIII)
2-imidazolyl optionally substituted with one or two R$_{3-2}$ and R$_{3-12}$ where R$_{3-2}$ and R$_{3-12}$ are as deemed above,
(F-Aryl-XXIV)
4-imidazolyl optionally substituted with one or two R$_{3-2}$ where R$_{3-2}$ is as defined above and where R$_{3-12}$ is —H, C$_1$-C$_4$ alkyl or —CHO,
(F-Aryl-XXV)
3-isoxazolyl optionally substituted with one or two R$_{3-2}$ where R$_{3-2}$ is as defined above,
(F-Aryl-XXVI)
4-isoxazolyl optionally substituted with one or two R$_{3-2}$ where R$_{3-2}$ is as defined above,
(F-Aryl-XXVII)
5-isoxazolyl optionally substituted with one or two R$_{3-2}$ where R$_{3-2}$ is as defined above,
(F-Aryl-XXVIII)
3-pyrazolyl optionally substituted with one or two R$_{3-2}$ where R$_{3-12}$ and R$_{3-2}$ are as defined above,
(F-Aryl-XXIX)
4-pyrazolyl optionally substituted with one or two R$_{3-2}$ where R$_{3-12}$ and R$_{3-2}$ are as defined above,
(F-Aryl-XXX)
5-pyrazolyl optionally substituted with one or two R$_{3-2}$ where R$_{3-12}$ and R$_{3-2}$ are as defined above,
(F-Aryl-XXXI)
2-oxazolyl optionally substituted with one or two R$_{3-2}$ where R$_{3-2}$ is as defined above,
(F-Aryl-XXXII)
4-oxazolyl optionally substituted with one or two R$_{3-2}$ where R$_{3-2}$ is as defined above,
(F-Aryl-XXXIII)
2-thiazolyl optionally substituted with one or two R$_{3-2}$ where R$_{3-2}$ is as defined above,
(F-Aryl-XXXIV)
4-thiazolyl optionally substituted with one or two R$_{3-2}$ where R$_{3-2}$ is as defined above,
(F-Aryl-XXXV)

2-indolyl optionally substituted with one or two $R_{3-2}$ where $R_{3-12}$ and $R_{3-2}$ are as defined above,
(F-Aryl-XXXVI)
3-indolyl optionally substituted with one or two $R_{3-2}$ where $R_{3-12}$ and $R_{3-2}$ are as defined above,
(F-Aryl-XXXVII)
3-indazolyl optionally substituted with one or twp $R_{3-2}$ where $R_{3-12}$ and $R_{3-2}$ are as defined above,
(F-Aryl-XXXVIII)
2-benzoxazolyl optionally substituted with one or two $R_{3-2}$ where $R_{3-2}$ is as defined above,
(F-Aryl-XXXIX)
2-benzothiazolyl optionally substituted with one or two $R_{3-2}$ where $R_{3-2}$ is as defined above,
(F-Aryl-XL)
2-benzimidazolyl optionally substituted with one or two $R_{3-2}$ where $R_{3-12}$ and $R_{3-2}$ are as defined above,
(F-Aryl-XLI)
2-benzofuranyl optionally substituted with one or two $R_{3-2}$ where $R_{3-2}$ is as defined above,
(F-Aryl-XLII)
3-benzofuranyl optionally substituted with one or two $R_{3-2}$ where $R_{3-2}$ is as defined above,
(F-Aryl-XLIII)
2-furanyl optionally substituted with one or two $R_{3-2}$ where $R_{3-2}$ is as defined above,
(F-Aryl-XLIV)
3-furanyl optionally substituted with one or two $R_{3-2}$ where $R_{3-2}$ is as defined above,
(F-Aryl-XLV)
2-thienyl optionally substituted with one or two $R_{3-2}$ where $R_{3-2}$ is as defined above,
(F-Aryl-XLVI)
3-thienyl optionally substituted with one or two $R_{3-2}$ where $R_{3-2}$ is as defined above,
(F-Aryl-XLVII)
2-pyrrolyl optionally substituted with one or two $R_{3-2}$ where $R_{3-12}$ and $R_{3-2}$ are as defined above,
(F-Aryl-XLVIII)
3-pyrrolyl optionally substituted with one or two $R_{3-2}$ where $R_{3-12}$ and $R_{3-2}$ are as defined above,
(F-Aryl-XLIX)
1,2,4-oxadiazol-3-yl optionally substituted with one $R_{3-2}$ where $R_{3-2}$ is as defined above,
(F-Aryl-L)
1,2,4-oxadiazol-5-yl optionally substituted with one $R_{3-2}$ where $R_{3-2}$ is as defined above,
(F-Aryl-LI)
1,2,4-thiadiazol-3-yl optionally substituted with one $R_{3-2}$ where $R_{3-2}$ is as defined above,
(F-Aryl-LII)
1,2,4-thiadiazol-5-yl optionally substituted with one $R_{3-2}$ where $R_{3-2}$ is as defined above,
(F-Aryl-LIII)
1,2,4-triazol-3-yl optionally substituted with one or two $R_{3-2}$ where $R_{3-12}$ and $R_{3-2}$ are as defined above,
(F-Aryl-LIV)
1,2,4-triazol-5-yl optionally substituted with one or two $R_{3-2}$ where $R_{3-12}$ and $R_{3-2}$ are as defined above,
(F-Aryl-LV)
1,2,3,4-tetrazol-5-yl substituted with $R_{3-12}$ where $R_{3-12}$ is as defined above,
(F-Aryl-LVI)
5-oxazolyl optionally substituted with one or two $R_{3-2}$ where $R_{3-2}$ is as defined above,
(F-Aryl-LVII)
5-thiazolyl optionally substituted with with one or two $R_{3-2}$ where $R_{3-2}$ is as defined above,
(F-Aryl-LXXI)
oxazolo[4,5-b]pyridin-2-yl optionally substituted with one or two $R_{3-2}$ where $R_{3-2}$ is as defined above;

(F-Aryl-LXXII)
imidazo[1,2-a]pyridin-2-yl optionally substituted with one or two $R_{3-2}$ where $R_{3-2}$ is as defined above;
($C_3$-2) —CO—$NR_{3-10}R_{3-11}$ where $R_{3-10}$ and $R_{3-11}$ are the same or different and are $C_1$–$C_4$ alkyl, $C_3$–$C_7$ cycloalkyl or —ϕ,
($C_3$-3) —CN,
($C_3$-4) aryl, where aryl is as defined above,
($C_3$-5) —C≡C—$R_{3-1}$ where $R_{3-1}$ is as defined above,
($C_3$-6) —CO—$R_{3-1}$ where $R_{3-1}$ is as defined above,
($C_3$-7) —CS—$R_{3-1}$ where $R_{3-1}$ is as defined above,
($C_3$-8) —CO—$R_{3-13}$ where $R_{3-13}$ is selected from the group consisting of
(F-Aryl-LVIII)
1-imidazolyl optionally substituted with one or two $R_{3-2}$ where $R_{3-2}$ is as defined above,
(F-Aryl-LIX)
1-pyrrolyl optionally substituted with one or two $R_{3-2}$ where $R_{3-2}$ is as defined above,
(F-Aryl-LX)
1-pyrazolyl optionally substituted with one or two $R_{3-2}$ where $R_{3-2}$ is as defined above,
(F-Aryl-LXI)
1,2,3-triazol-1-yl optionally substituted with one or two $R_{3-2}$ where $R_{3-2}$ is as defined above,
(F-Aryl-LXII)
1,2,4-triazol-1-yl optionally substituted with one or two $R_{3-2}$ where $R_{3-2}$ is as defined above,
(F-Aryl-LXIII)
1-tetrazolyl optionally substituted with one or two $R_{3-2}$ where $R_{3-2}$ is as defined above,
(F-Aryl-LXIV)
1-indolyl optionally substituted with one or two $R_{3-2}$ where $R_{3-2}$ is as defined above,
(F-Aryl-LXV)
1-indazolyl optionally substituted with one or two $R_{3-2}$ where $R_{3-2}$ is as defined above,
(F-Aryl-LXVI)
2-isoindolyl optionally substituted with one or two $R_{3-2}$ where $R_{3-2}$ is as defined above,
(F-Aryl-LXVII)
1-purinyl optionally substituted with one or two $R_{3-2}$ where $R_{3-2}$ is as defined above,
(F-Aryl-XLIII)
2-furanyl optionally substituted with one or two $R_{3-2}$ where $R_{3-2}$ is as defined above,
(F-Aryl-XLIV)
3-furanyl optionally substituted with one or two $R_{3-2}$ where $R_{3-2}$ is as defined above,
(F-Aryl-XLV)
2-thienyl optionally substituted with one or two or two $R_{3-2}$ where $R_{3-2}$ is as defined above,
(F-Aryl-XLVI)
3-thienyl optionally substituted with one or two $R_{3-2}$ where $R_{3-2}$ is as defined above,
(F-Aryl-XXXI)
2-oxazolyl optionally substituted with one or two $R_{3-2}$ where $R_{3-2}$ is as defined above,
(F-Aryl-XXXII)
4-oxazolyl optionally substituted with one or two $R_{3-2}$ where $R_{3-2}$ is as defined above,
(F-Aryl-LVI)
5-oxazolyl optionally substituted with one or two $R_{3-2}$ where $R_{3-2}$ is as defined above,
(F-Aryl-XXV)
3-isoxazolyl optionally substituted with one or two $R_{3-2}$ where $R_{3-2}$ is as defined above,
(F-Aryl-XXVI)
4-isoxazolyl optionally substituted with one or two $R_{3-2}$ where $R_{3-2}$ is as defined above,
(F-Aryl-XXVII)

5-isoxazolyl optionally substituted with one or two $R_{3-2}$ where $R_{3-2}$ is as defined above,
(F-Aryl-XXXIII)
2-thiazolyl optionally substituted with one or two $R_{3-2}$ where $R_{3-2}$ is as defined above,
(F-Aryl-XXXIV)
4-thiazolyl optionally substituted with one or two R3-2 where R3-2 is as defined above,
(F-Aryl-LVII)
5-thiazolyl optionally substituted with one or two $R_{3-2}$ where $R_{3-2}$ is as defined above,
(F-Aryl-LVIII)
3-isothiazolyl optionally substituted with one or two $R_{3-2}$ where $R_{3-2}$ is as defined above,
(F-Aryl-LXIX)
4-isothiazolyl optionally substituted with one or two $R_{3-2}$ where $R_{3-2}$ is as defined above,
(F-Aryl-LXX)
5-isothiazolyl optionally substituted with one or two $R_{3-2}$ where $R_{3-2}$ is as defined above;
(F-Aryl-LXXII)
imidazo[1,2-a]pyridin-2-yl optionally substituted with one or two $R_{3-2}$ where $R_{3-2}$ is as defined above;
($C_3$-9) $-C^*=N-C(R_{3-14})_2-[C(R_{3-15})_2]_{n23}-R^*_{3-16}$
where the atoms marked with an asterisk (*) are bonded to each other resulting in the formation of a ring,
where the $R_{3-14}$'s are the same or different and are —H or $C_1$–$C_3$ alkyl,
where $n_{23}$ is 1 thru 3,
where the $R_{3-15}$'s are the same or different and are —H or $C_1$–$C_3$ alkyl,
where $R_{3-16}$ is —O—, —S—, $-C(R_{3-14})_2-$, $-NR_{3-12}$ where $R_{3-12}$ and $R_{3-14}$ are as defined above,
($C_3$-10) $-CH(OH)R_{3-1}$ where $R_{3-1}$ is as defined above,
($C_3$-11) $-CH_2-O-R_{3-1}$ where $R_{3-1}$ is as defined above,
($C_3$-12) $-CH_2-NR_{3-4}R_{3-5}$ where $R_{3-4}$ and $R_{3-5}$ are as defined above;
($R_4$/$R_5$/$R_6$-1) where $R_4$ is α-$R_{4-1}$:β-$R_{4-2}$ where one of $R_{4-1}$ and $R_{4-2}$ is —H and the other of $R_{4-1}$ and $R_{4-2}$ is taken together with $R_5$ to form a ring of the formula ($R_5$ end)—CO—$R_{45-1}$—$(CH_2)_{n3}$— ($R_4$ end)  ($R_4$/$R_5$/$R_6$-1)

where $n_3$ is 0 thru 3 and $R_{45-1}$ is
—O—,
—CO—,
—S—,
—CH=CH—,
$-C(R_{3-17})_2-$ where the $R_{3-17}$'s are the same or different and are —H or $C_1$–$C_4$ alkyl,
$-NR_{45-2}$ where $R_{45-2}$ is
—H,
$C_1$–$C_6$ alkyl,
$-(CH_2)_{n9}$—φ where $n_9$ is 0 thru 4 and —φ is optionally substituted with —F, —Cl, —Br, —I or $C_1$–$C_4$ alkyl,
$-(CH_2)_{n10}-NR_{45-3}R_{45-4}$ where $n_{10}$ is 2 thru 6, where R45-3 is
—H,
$C_1$–$C_4$ alkyl,
—φ and where $R_{45-4}$ is —H or $C_1$–$C_3$ alkyl, and where $R_6$ is —H,
—F,
—Cl,
—Br,
—I,
—CN,
—$NO_2$,
—O—CO—$R_{6-1}$ where $R_{6-1}$ is —H, $C_1$–$C_4$ alkyl or $C_3$–$C_7$ cycloalkyl,
—$CF_3$,
—O—$CF_3$,
$C_1$–$C_6$ alkyl,
$C_3$–$C_7$ cycloalkyl,
—$CH_2CH_2OH$,
—$NR_{6-2}$—CO—$R_{6-3}$ where $R_{6-2}$ is —H or $C_1$–$C_4$ alkyl, and where $R_{6-3}$ is
—H,
$C_1$–$C_6$ alkyl,
—φ optionally substituted with —F, —Cl, —Br, —I or $C_1$–$C_4$ alkyl,
—$CH_2$—φ,
$-(CH_2)_{n24}-OR_{6-4}$ where $n_{24}$ is 0 thru 3 and $R_{6-4}$ is $C_1$–$C_4$ alkyl,
$-(CH_2)_{n25}$—OH where $n_{25}$ is 2 thru 4,
$-(CH_2)_{n26}$—φ where $n_{26}$ is 0 thru 3,
$-(CH_2)_{n24}-N(R_{6-4})_2$ where $n_{24}$ and $R_{6-4}$ are as defined above,
—S—R6-4 where $R_{6-4}$ is as defined above,
—$SO_2$—$N(R_{6-5})_2$ where $R_{6-5}$ is —H or $C_1$–$C_4$ alkyl,
—CO—$N(R_{6-5})_2$ where $R_{6-5}$ is as defined above,
—$CO_2$—$R_{6-4}$ where $R_{6-4}$ is as defined above,
—$NR_{6-6}R_{6-7}$ where $R_{6-6}$ and $R_{6-7}$ are the same or different and are —H or $C_1$–$C_4$ alkyl and where $R_{6-6}$ and $R_{6-7}$ can be taken together with the attached nitrogen atom to form a ring, which may contain an additional heteroatom, selected from the group consisting of piperazine, morpholine, pyrrolidine or piperidine;
($R_4$/$R_5$/$R_6$-2) where $R_5$ and $R_6$ are taken together to form a heterocyclic ring selected from the group consisting of ($R_6$ end) $-(CH_2)_{n13}-R_{56-1}-(CH_2)_{n14}-CO-(CH_2)_{n15}$ ($R_4$/$R_5$/$R_6$-2a)

where $n_{13}$ is 0 thru 3, $n_{14}$ is 0 thru 3, $n_{15}$ is 0 thru 2, $R_{56-1}$ is —O—, —S—, —$CH_2$—, —CH=CH—, $-C(R_{56-3})_2$ where the $R_{56-3}$'3s are the same or different and are $C_1$–$C_3$ alkyl, or —$NR_{56-2}$ where $R_{56-2}$ is —H, $C_1$–$C_6$ alkyl, $C_3$–$C_7$ cycloalkyl, $-(CH_2)_{n17}$—OH where $n_{17}$ is 2 thru 4, $-(CH_2)_{n16}$—φ where $n_{16}$ is 0 thru 4 and —φ is optionally substituted with —F, —Cl, —Br, —I, $C_1$–$C_4$ alkyl, ($R_6$ end) —$R_{56-1}$—CO—CO— ($R_5$ end)  ($R_4$/$R_5$/$R_6$-2b)

where $R_{56-1}$ is as defined above,
where $R_4$ is α-$R_{4-3}$:β-$R_{4-4}$ where $R_{4-3}$ and $R_{4-4}$ are the same or different and are —H, —OH or $C_1$–$C_4$ alkyl, with the proviso that only one of $R_{4-3}$ and $R_{4-4}$ can be —OH at any one time;
($R_4$/$R_5$/$R_6$-3) where $R_4$ is $C_3$–$C_5$ spirocycloalkyl or α-$R_{4-5}$:β-$R_{4-6}$ where $R_{4-5}$ and $R_{4-6}$ are the same or different and are —H or $C_1$ alkyl,
where $R_5$ is $-(CH_2)_{n29}$—CO—H where $n_{29}$ is 0 thru 4,
$-(CH_2)_{n29}$—CO—($C_1$–$C_6$ alkyl) where $n_{29}$ is as defined above,
$-(CH_2)_{n29}$—CO—($C_3$–$C_7$ cycloalkyl) where $n_{29}$ is as defined above,
$-(CH_2)_{n29}$—CS-($C_1$–$C_6$ alkyl) where $n_{29}$ is as defined above,
$-(CH_2)_{n29}$—CO—$(CH_2)_{n28}$—$NR_{5-4}((CH_2)_{n29}-OR_{5-1})$ where $n_{28}$ is 0 thru 3, where R5-1 is as defined for $R_{3-1}$ with the proviso that $R_{3-1}$ and $R_{5-1}$ may be the same or different, where $R_{5-4}$ is —H, $C_1$–$C_6$ alkyl, —$CH_2$—$CH_2$—OH, —$CH_2$—$CH_2$—$OCH_3$ or —φ optionally substituted with 1 or 2 $R_{3-2}$'s where $R_{3-2}$ is as defined above, and where the $n_{29}$'s may be the same or different and are as defined above,
$(CH_2)_{n29}$—CO—$(CH_2)_{n28}$ —$NR_{5-4}((CH_2)_{n29}-NR_{5-5})$ where $R_{5-5}$ is —H, $C_1$–$C_6$ alkyl, —$CH_2$—$CH_2$—OH, —$CH_2$—$CH_2$—$OCH_3$, where $n_{28}$, $R_{5-1}$, and $R_{5-4}$ are as defined above, where the $n_{29}$'s may be the same or different and are as defined above, and where $R_{5-4}$ and $R_{5-5}$ are taken together with the attached nitrogen atom to form a ring selected from the group consisting of 1-pyrrolidinyl, 1-piperidinyl, 1-piperazinyl, 4-morpholinyl, 1-(4 -methyl)piperazinyl, —$(CH_2)_{n29}$—CS—$(C_3-C_7$ cycloalkyl) where $n_{29}$ is as defined above, —$(CH_2)_{n29}$—CO—aryl where aryl and $n_{29}$ are as defined above, —$(CH_2)_{n29}$—CS—aryl where aryl and $n_{29}$ are as defined above, —$(CH_2)_{n29}$—CO—O—$R_{5-1}$ where $R_{5-1}$ and $n_{29}$ is as defined above, —$(CH_2)_{n29}$—CO—S—$R_{5-1}$ where $R_{5-1}$ and $n_{29}$ are as defined above, —$(CH_2)_{n29}$—CO—$(CH_2)_{n28}$—$NR_{5-4}R_{5-5}$ where $n_{28}$, $n_{29}$, $R_{5-4}$ and $R_{5-5}$ are as defined above and where $R_{5-4}$ and $R_{5-5}$ are taken together with the attached nitrogen atom to from a heterocyclic ring selected from the group consisting of —$N^*$—$(CHR_{5-8})_{nA}$—$(CH_2)_{n1}$—$R_{5-6}$—$(CH_2)_{n2}$—$(C^*HR_{5-9})(C_5$-1a)

—$N^*$—$(CH_2)_{n1}$—$(CHR_{5-8})_{nA}$—$R_{5-6}$—$(CHR_{5-9})_{nB}$—$(C^*H_2)(C_5$-1b)

where $R_{5-8}$ is —H or $C_1-C_3$ alkyl, $n_A$ is 1 or 2, $n_1$ is 0 thru 2, $n_2$ is 0 thru 2, $R_{5-9}$ is —H or $C_1-C_3$ $_{alkyl}$, $n_B$ is 1 or 2, where the atoms marked with an asterisk (*) are bonded to each other resulting in the formation of a ring, with the proviso that the ring not contain more than 8 atoms, and where $R_{5-6}$ is —O—,
—S—,
—CO—,
—$CR_{5-8}R_{5-9}$ where $R_{5-8}$ and $R_{5-9}$ are the same or different and are —H or $C_1-C_4$ alkyl,
—$NR_{5-7}$ where $R_{5-7}$ is —H,
$C_1-C_6$ alkyl,
—$(CH_2)_{n18}$—ϕ where $n_{18}$ is 0 thru 4 and where —ϕ is optionally substituted with —F, —Cl, —Br, —I or $C_1-C_3$ alkyl,
—$(CH_2)_{n19}$—OH where $n_{19}$ is 2 thru 4, with the proviso that when $R_{5-6}$ is —O—, —S— or —$NR_{5-7}$—, $n_1$ and $n_2$ are 1 or 2,
—$(CH_2)_{n29}$—CO—CO—$NR_{5-4}R_{5-5}$ where $R_{5-4}$, $R_{5-5}$ and $n_{29}$ are as defined above,
—$(CH_2)_{n29}$—CO—$COOR_{5-8}$ where $n_{29}$ is as defined above and where $R_{5-8}$ is
—H,
$C_1-C_4$ alkyl,
—$(CH_2)_{n20}$—ϕ where $n_{20}$ is 1 thru 4,
—ϕ optionally substituted with 1 or 2 —F, —Cl, —Br, —I or $C_1-C_3$ alkyl,
—$(CH_2)_{n29}$—CO—$R_{5-13}$ where $n_{29}$ is as defined above and where $R_{5-13}$ is defined as being selected from the same group as $R_{3-13}$
—$(CH_2)_{n29}$—$C^*$=N-$C(R_{5-10})_2$—$[C(R_{5-11})_2]_{n27}$—$R^*_{5-12}$ where the atoms marked with an asterisk (*) are bonded to each other resulting in the formation of a ring,
where the $R_{5-10}$'s are the same or different and are —H or $C_1-C_3$ alkyl,
where $n_{27}$ is 1 thru 3,
where the $R_{5-11}$'s are the same or different and are —H or $C_1-C_3$ alkyl,
where $R_{5-12}$ is —O—, —S—, —$C(R_{5-13})_2$—, —$NR_{5-14}$
where $R_{5-13}$ and $R_{5-14}$ are —H or $C_1-C_3$ alkyl, and
where $R_6$ is as defined for ($R_4/R_5/R_6$-1) above;
where $W_6$ is —N= or —$CR_6$= where $R_6$ is as defined above;
where $W_7$ is —N= or —$CR_7$= where $R_7$ is as defined for $R_6$, the $R_6$, $R_7$, $R_8$ and $R_9$ may be the same or different.

where $W_8$ is —N= or —$CR_8$= where $R_8$ is as defined for $R_6$, the $R_6$, $R_7$, $R_8$ and $R_9$ may be the same or different.
where $W_9$ is —N= or —$CR_9$= where $R_9$ is as defined for $R_6$, the $R_6$, $R_7$, $R_8$ and $R_9$ may be the same or different.
with the proviso that not more than two of $W_6$, $W_7$, $W_8$ and $W_9$ can be —N= at any one time; and pharmaceutically acceptable salts thereof where such exist.

Further disclosed are imidazo[1,5-a]quinoxalines (LX) selected from the group consisting of tert-butyl 7-fluoro-4,5-dihydro-4(R)-methyl-5-(2-pyridylmethyl)imidazo[1,5 -a]quinoxaline-3-carboxylate, 7-fluoro-4,5-dihydro-4(R)-methyl-3-[5-(1 -methylcyclopropyl)-1,2,4-oxadiazol-3-yl]-5-(2-pyridylmethyl)imidazo [1,5-a]quinoxaline, cyclopropylmethylamino 7-fluoro4,5-dihydro4(R)-methyl-5-(2-pyridylmethyl)imidazo-[1,5-a]quinoxaline-3-carboxamide, 7-fluoro-4,5-dihydro-4(R)-methyl-3-[5-(2-methylcyclopropyl)-1,2,4-oxadiazol-3-yl]-5-(2-pyridylmethyl)imidazo [1,5-a]quinoxaline.

DETAILED DESCRIPTION OF THE INVENTION

The imidazo[1,5-a]quinoxalines (I), CHART A, of the present invention are named and numbered following the Chemical Abstracts ring system nomenclature system, see Ring Systems Handbook, Chemical Abstracts Service, Ring Systems File I, see RF 23543, 1988 Edition or according to Chemical Abstracts Science, Columbus, Ohio.

The imidazo[1,5-a]quinoxalines (I) are produced by a number of processes depending on the variable substituents involved, particularly those at positions 3, 4, 5, 6, 7, 8 and 9. In all cases the process to produce the imidazo[1,5-a] quinoxalines (I) can be viewed as a two "sequence" process, as will be explained in more detail below. The first part is the transformation of an appropriately substituted aromatic/heteroaromatic compound to the bicyclic amide "quinoxaline" (IV). The second part is the addition of the appropriately substituted imidazo group and the desired exocyclic carbonyl functionality. Because the imidazo[1,5 -a]quinoxalines (I) are novel, the overall chemical process is novel. However, it is realized that each step is known to those skilled in the art. The combination of known process chemistry in a novel way produces the novel imidazo[1,5-a] quinoxalines.

CHART B discloses one of the general processes for the transformation of diamino compounds (II) to the corresponding bicyclic amides (IV) by two different routes. The diamino compound (II) starting materials are known to those skilled in the art or can be readily prepared by methods known to those skilled in the art. In one route, the diamino compounds (II) are reacted with a haloester (III) in a solvent such as DMF, THF, acetonitrile, ethanol or toluene with a weak base such as carbonate, bicarbonate, Hunig's base or triethylamine to produce the corresponding bicyclic amides (IV). The second route disclosed in CHART B reacts the diamino compounds (II) with glyoxalic acid (CHO—COOH) (V) to produce the corresponding unsaturated bicyclic amides (VI). The unsaturated bicyclic amides (VI) are then reduced by known methods such as sodium borohydride in ethanol or sodium cyanoborohydride in methanol to the corresponding bicyclic amide (IV). See also J. Med. Chem, 24, 93 (1981). The processes of CHART B are operable regardless of whether the $W_6$, $W_7$, $W_8$ and/or $W_9$'s are —$CR_\#$= or —N= and therefore is a very general process for preparation of the important intermediate bicyclic amide (IV).

CHART C discloses another general process for the preparation of the bicyclic amide (IV). The process of CHART C is useful in two ways. First, when the desired substituent is already present in the aromatic/heteromatic ring and second when it is desired to have a substituent which it is best not to carry thru the entire synthesis process but rather add later by displacing a halogen atom (XIa→XIII). In this process the precursor to the desired bicyclic amide (IV) is cyclized to form the bond at the top of the quinoxaline ring. This process is particularly useful when it is desired that the substituent at $W_6$, $W_7$, $W_8$ and/or $W_9$ is other than —CH=; $R_6$, $R_7$, $R_8$ and $R_9$ are ≠—H. When it is desired to functionalize the substituent at $R_6$, $R_7$, $R_8$ or $R_9$ the process of CHART C is a preferred process. The halo-nitro (VII) starting materials are known to those skilled in the art or can be readily prepared by methods known to those skilled in the art from known compounds by methods known to those skilled in the art. When two halo substituents are present they may be the same or different. The particular halo group (XIa) will vary depending on whether it is desired to retain it in the final product (IV) or displace it as will be discussed below. The halo-nitro compounds (VII) are reacted with an amino-alcohol (VIII) to produce the corresponding nitro-alcohol (IX), which is oxidized to the corresponding acid (X) by known methods such as Jones oxidation. The acid (X) is then converted to the corresponding nitro-ester (XI) by known methods such as an alkylhalide, a base such as DBU in DMF. CHART C also discloses that the nitro-esters (XI) can alternatively be prepared by reacting the halo-nitro compounds (VII) with an amino-ester (XII) to form the nitro-esters (XI) directly.

The nitro-acid (X) can also be prepared directly by reaction of the halo-nitro compound (VII) with the amino-acid (XIIa) to form the nitro-acid (X). Should it be desired to retain the halogen in the bicyclic amide (IV) and eventually in the imidazo[1,5-a]quinoxalines (I), then the halo-nitro-ester (XIa) is cyclized by reduction with hydrogen over palladium on carbon in ethanol, platinum on carbon in ethanol, $TiCl_3$ in methanol or with Raney nickel. Alternatively, if it is desired that $R_7$ or $R_9$ be other than halogen, nucleophilic (R⁻) displacement of the halo-nitro-ester (XIa) will give the corresponding aromatic nitro-ester (XIII) where the halogen has been replaced by the nucleophile ($R_7$ and $R_9$≠—H or halogen). Thus the nitro-ester (XIII) or (XI) elm then be reduced and cyclized as described above to provide the bicyclic amide (IV).

CHART D discloses a process to produce the bicyclic amides (IV) starting with the corresponding nitro-amines (XIV). The nitroamines (XIV) are reacted with the haloester (III) to form the corresponding nitroester (XI). The nitro group is reduced (palladium on carbon or $TiCl_3$ or Raney nickel) and the ester and newly formed amino group are cyclized directly to produce the bicyclic amides (IV).

CHART E discloses a route to produce the key intermediate bicyclic amides (IV) when it is convenient to start with a nitromethyl compound (XVI). The methyl group is oxidized to an acid to produce the nitroacid (XVII) with an oxidizing agent such as potassium permanganate or sodium hypochlorite catalyzed by ruthenium tetroxide. The nitroacid (XVII) is then transformed to the corresponding amide (XVIII) with a reagent such as thionyl chloride followed by ammonium hydroxide (30% aqueous solution). The nitroamide (XVIII) is then subjected to a Hoffmann-type rearrangement (lead tetra-acetate in absolute tert-butanol) to produce the rearrangement product (XIX), followed by alkylation with the haloester (III) to provide the alkylated rearrangement product (XX). The alkylated rearrangement product is then hydrogenated with palladium on carbon in methanol to give the amino alkylated rearrangement product (XXI) which is then cyclized to form the N-substituted bicyclic amide (XXII) by stirring in an alcohol, such as methanol with or without catalytic p-toluene-sulfonic acid. EXAMPLES 19–23 disclose this transformation with $W_6$=—CF=. This process is also applicable where $R_6$, $R_7$, $R_8$ or $R_9$ is —Cl, —Br, —I, —$CF_3$, —$OCF_3$, $C_1$-$C_3$ alkoxy, $C_1$-$C_3$ thioalkyl, —CN, —$NO_2$, —O—$CH_2$—COOH. The N-substituted bicyclic amide can then be transformed to the bicyclic amide (IV) using hydrochloric acid in methanol or trifluoroacetic acid in methylene chloride, or can reacted directly to form the side chain at $R_3$. Alternatively, the Hoffman rearrangement product (XIX) can be reacted with trifluoroacetic acid in methylene chloride to give a nitroamine (XIV). The nitroamine can be reduced with hydrogen and palladium on carbon to the diamino compound (II) and used following the process of CHART B, or used as such following the procedure of CHART D.

CHART E also discloses an alternative process from the Hoffman rearrangement product (XIX) to the bicyclic amide (IV). In this alternative process the nitro group of the Hoffman rearrangement product (XIX) is reduced with hydrogen and palladium on carbon, with $TiCl_3$ or with Raney nickel to give the amine amide (XLV). The amine amide (XLV) is then acylated with the dihalo compound (XLVI) to give the diamide (XLVII). The protecting group of the diamide (XLVII) is removed with hydrogen chloride in methanol or with trifluoroacetic acid in methylene chloride to give the bromoamine (XLVIII), which is then heated in toluene in the presence of a base such as Hunig's base to give the bicyclic amide (IV).

CHART F discloses an alternative way of producing the bicyclic amide (IV). Previous processes producing the bicyclic amide (IV) first formed an amine at the "bottom N" at $N_5$ and then cyclized it with the "top" nitrogen to form the cyclic amide. In CHART F the process is reversed, the amide is first formed at the "top" nitrogen and then cyclized with the $N_5$ nitrogen to the desired bicyclic amide (IV). In this process one starts with the nitro-halo compound (XXIII) and replaces the halogen with ammonia in ethanol to form the amino-nitro compounds (XXIV). Alternatively, one can start with the amino-nitro compounds (XXIV) which are reacted with a dihalocarbonyl compound (XXV) to form the acyclic amide (XXVI). The nitro group is reduced by known means and the "top" chain acyclic amide (XXVI) is then cyclized with the newly formed amino group to form the corresponding bicyclic amide (IV).

CHART G discloses a preferred process when $R_4$ is —H:—H and when $R_3$ is phenyl (—φ) or substituted phenyl. The starting material is the nitro-halo compounds (XXVII) which are reacted with a substituted amine such as t-butylamine or veratrylamine to form the nitro protected-amine (XXVIII). The nitro group is then reduced by known methods, such as $TiCl_3$ in aqueous methanol with a base such as sodium acetate or with Raney Nickel in ethanol to give the amino protected-amine (XXIX). This protected amine is then reacted with ethyl oxalyl chloride (XXX) in a solvent such as toluene and diisopropylethylamine followed by heating to give the protected bicyclic amide (XXXI). The protected bicyclic amide (XXXI) has the imidazole ring added to form the protected tricyclic amide (XXXIV) as described below. The protecting group is removed with trifluoroacetic acid in methylene chloride to give the tricyclic amide (XXXV). The tricyclic amide (XXXV) is reduced using a reducing agent such as lithium aluminum hydride or aluminum hydride to give tricyclic amine (XXXVI) which is acylated (as described below) at $N_5$ to give the imidazo[1,5-a]quinoxaline (I). The deprotection and reduction steps may also be carried out in reverse order. Alternatively, the amino protected-amine (XXIX) is reacted with dihalocarbonyl compound (XXV) and base such as Hunigs base to form the protected amide (XXXIA). The protecting group of the protected amide (XXXIA) is then removed by reacting with an agent such as trifluoroacetic acid in methylene chloride to form the bicyclic amide (IV).

CHART H discloses two methods of transforming the bicyclic amide (IV) to the corresponding imidazo[1,5-a]quinoxaline (I). One method involves first adding the appropriate side chain at $N_5$ to form the $N_5$-substituted bicyclic amide (XXXII) followed by the formation of the imidazole ring (appropriately substituted) to give the desired imidazo [1,5-a]quinoxaline (I). The other method revolves reversing the steps, first forming the imidazole ring to give the $N_5$-unsubstituted imidazole (XXXIII) followed by addition of the $N_5$ side chain. With either method there are two ways of adding the $N_5$ sidechain. One way is to react the bicyclic amide (IV) or $N_5$-unsubstituted bicyclic amide (XXXIII) with $R_5$-X (where X is a good leaving group) in a solvent system such as THF and Huing's base. Alternatively, the bicyclic amide (IV) or the $N_5$-unsubstituted imidazole (XXXIII) is contacted with phosgene (Cl—CO—Cl) in a THF/amine solvent system followed by reaction with the desired nucleophile to displace the chlorine. When $R_4$ is —$CH_3$:—$CH_3$ it is preferred to use the phosgene process. When $R_4$ is —H:—H, then either method is useful. The imidazole ring is formed by known methods using known compounds, see J. Med. Chem., 32, 2282 (1989), U.S. Pat. No. 4,774,245, EP 344,943A, EP 347,094A, EP320,136, EP 368,652A and EP 283,102A. A preferred process when R3 is $COOR_{3-1}$, R4 is —H:H, and $R_5$=—$(CH_2)_{n29}CO$—$(CH_2)_{n28}NR_{3-4}R_{3-5}$. The starting material is the $N_5$ unsubstituted imidazole (XXXIII) which is reacted with an alpha halo-amide to afford compound (I). Also, the N5 unsubstituted imidazole (XXXIII) can be reacted with chloroacetyl chloride to yield the N5 alpha chloro amide, which can be reacted with primary or secondary amines to give (I).

Chart I discloses a preferred process when R3 is —$CH_2$—O—$R_{3-1}$ or —$CH_2NR_{3-4}R_{3-5}$, R4 is —H:—H and R5 is —$(CH_2)_{n29}CO$—$(CH_2)_{n28}NR_{3-4}R_{3-5}$. The staffing material is the $N_5$ unsubstituted imidazole (XXXIII) where $R_3$ is an ester or an amide or acid chloride which is reduced with lithium borohydride to give (XXXVI). The $R_3$ alcohol is protected to give the protected hydroxy methyl (XXXVIIa). The $N_5$ sidechain is then added to the protected alcohol (XXXVIIa) to give the protected-$R_5$ (XXXVIII) which is then converted to the unprotected-$R_5$ (XXXVIIIb). After removal of the protecting group, that compound was treated with thionyl chloride followed by the addition of the sodium salt of an alcohol to give the imidazo[1,5-a]quinoxaline (I). Alternately, treatment of the intermediate chloro compound with an amine also leads to compound (I).

The imidazo[1,5-a]quinoxalines (I) where $R_4$ and $R_5$ are cyclized to form a heterocyclic ring (I-$R_4/R_5/R_6$-1) are prepared according to the procedure of CHART J. The dihalonitro compound (VII), CHART C, is transformed to either the halo-nitro-acid (X) or the halo-nitro-ester (XI) as previously described. Then these compounds are transformed to the bicyclic amide (IV) as described above. The bicyclic amide (IV) then is transformed to the corresponding 4,5-cyclic amide (XXXIX) by different processes depending on whether $R_4$ terminates in an ester or carboxylic acid, or an alcohol or amine. When $R_4$ is an ester or carboxylic acid the bicyclic amide (IV) is stirred in solvents such as toluene or methanol to effect ring closure. Heating and the addition of a catalyst such as p-toluenesulfonic acid or camphorsulfonic acid will speed completion of the cyclization. When $R_4$ terminates in an alcohol or a substituted amine, the bicyclic amide (IV) is stirred with or without heating with a carbonyl source such as carbonyldiimidazole or phosgene (the choice of heating or not heating will depend on the reactivity of the carbonyl source) in aprotic solvents such as THF, toluene and methylene chloride to obtain the 4,5-cyclic amide (XXXIX). The 4,5-cyclic amide (XXXIX) is then transformed to the corresponding imidazo [1,5-a]quinoxaline (I) by the standard procedures described above.

CHART K discloses a process whereby imidazo[1,5-a] quinoxalines (I) can be transformed into other imidazo[1,5-a]quinoxalines (I) as is apparent to one skilled in the art. For example, one imidazo[1,5-a]quinoxaline (I) end product is where $R_3$ is an ester (I-ester), —$COOR_{3-1}$ ($C_3$-1), such as —COO—(t-butyl). That compound can readily be transformed into one where $R_3$ is an amide —CO—$NR_{3-4}R_{3-5}$ ($C_3$-2) by means known to those skilled in the art. Also, imidazo[1,5-a]quinoxaline (I) where $R_3$ is an ester can be transformed into the corresponding acid (I-acid) and subsequently to the acid chloride. Reaction of that acid chloride with aromatic systems, i.e. benzene, in the presence of a Lewis Acid such as aluminum chloride, gives R-3 aryl ketones. Furthermore, treatment of those ketones with hydride reagents afford the corresponding alcohols. The 1,2,3-triazol-1-yls (I-F-Aryl-LXI) are prepared as set forth in CHART L. The starting material is the imidazol[1,5-a] quinoxalines (I) where $R_3$ is —$COOR_{3-1}$ ($C_3$-1) where $R_{3-1}$ is alkyl. This compound is treated with trifluoroacetic acid in a solvent such as methylene chloride to remove the alkyl group. The resulting carboxylic acid is treated with thionyl chloride followed by sodium azide to give an acyl azide. The azide is heated in a hydrocarbon solvent to effect a molecular rearrangement followed by trapping of the unstable intermediate with methanol to form a carbamate. The carbamate is then decomposed with a strong base such as hydroxide to give the amine (XLI). This amine (XLI) is treated with (sodium) nitrate in an acidic medium followed by treatment of sodium azide and finally treatment with water to give the azide (XLII). The azide (XLII) is contacted with acetylenes in organic solvents such as toluene to give the 1,2,3-triazol-1-yls (I-F-aryl-LXI).

The isomeric 1,2,3-triazol-4-yls (I-F-Aryl-LXXI/LXXII) are prepared as set forth in CHART M and begin with the same starting material as for the 1,2,3-1-yls (I-F-Aryl-LXI). The alkyl ester is converted to the olefin (XLIII) using standard reduction and Wittig olefination procedures. Treatment of the olefin (XLIII) with bromine followed by treatment of the dibromointermediate with strong base such as sodium amide gives the acetylene (XLIV). The acetylene (XLIV) is contacted with substituted azides under standard conditions to give a mixture of the isomeric 1,2,3-triazol-4-yls (I-F-Aryl-LXXI/LXXII).

CHART N discloses the process to prepare the 5,6-cyclic compounds ($R_4/R_5/R_6$-2). The imidazo[1,5-a]quinoxalines (I) where $R_5$ and $R_6$ are taken together to form a heterocyclic ring are prepared by several methods. For example when $n_{14}$ and $n_{15}$ are 0 and $n_{13}$ is not 0, it is preferred to prepare the desired 5,6-cyclized compounds by the procedure of CHART N. The nitro compound (LI) which is readily available or may be prepared by conventional methods known to those skilled in the art, is the starting material. Reaction of the nitro compound (LI) with phosgene, triphosgene or 1,1'-carbonylctiimidazole in a solvent such as THF between 0 and 100°, preferably in the presence of a base such as triethylamine provides the cyclic amide (LII). Reduction of the nitro group of the cyclic amide (LII) by hydrogenation in ethanol or ethyl acetate in the presence of palladium on carbon gives the amino cyclic amide (LIII). Reaction of the amino cyclic amide (LIII) with chloroacetyl chloride in the presence of a base such as diisopropylethylamine and subsequent treatment of the acylated material with a base such as potassium t-butoxide in THF gives the bis-amide (LIV). The imidazo[1,5-a]quinoxalines (I) are then prepared by cyclization of the bis-amide (LIV) with an isocyanide reagent as described above, see CHARTS G and H. In the situations where $R_5$ contains a alkyl or alkenyl chain, the cyclic amide (LII) is prepared from the nitro amino ester (LV, which is known to those skilled in the art) by heating in an inert solvent such as THF or toluene.

When $n_{13}$ and $n_{15}$ are 0 and $n_{14}$ is 1 thru 3, the 5,6-cyclic-imidazo[1,5-a]quinoxalines (I) are preferably prepared by the process set forth in CHART O. Reaction of the aromatic nitro amino compound (LVI) with ethyl bromoacetate (or a chain extended variant) and diisopropylethylamine at reflux provides a mixture. Exposure of the mixture to ethoxide in ethanol at reflux provides the desired cyclized amide (LVII). Following the procedures described above for CHART N, but using the cyclized amide (LVII) provides the corresponding intermediates and desired 5,6-cyclic-imidazo[1,5-a]quinoxalines (I). When $n_{13}$ and $n_{14}$ are 0 and $n_{15}$ is not 0, similar processes are utilized.

When the bicyclic amide (IV) or 4,5-cyclic amide (XXXIX) has $R_4$=—H:—$CH_3$, there will be an asymmetric center and therefore two enantiomers, one "S" and the other "R", either of which can be (+/d) and the other (−/l).

Both enantiomers (+) and (−) are useful in the same way as the optically impure (racemic, +) mixture. Hence, they may be utilized in the racemic form without separating them. However, if it is desired to utilize one of the enantiomers, two methods are available to produce optically pure forms. The racemic bicyclic amide (IV) or other racemic compounds produced from it can be resolved using methods known to those skilled in the art, see for example, Optical Resolution Procedures for Chemical Compounds, Vol 1,: Amines and Related Compounds, Paul Newman, Optical Resolution Information Center, Manhattan College, Riverdale, N.Y., 10471, 1978. For example, treatment of the above mentioned racemic mixture (IV) with an optically active acid such as (+)-tartaric acid or alternatively with (−)-tartaric acid would yield a mixture of diastereomeric salts, which can be separated most conveniently by fractional crystallization to give a salt containing only one enantiomer of the racemic mixture. Other suitable optically active acids include, (-) dibenzoyltartaric acid, (+)-camphoric acid, (+)- and (−)-malic acid and (+)-camphor-10-sulfonic acid. By reacting the diastereomeric salt with a base one obtains the desired enantiomer as the free amino compound. In addition, treatment of racemic (X) with an optically active amine such as methyl benzylamine and using fractional crystallization gives a salt containing only one enantiomer of the racemic mixture. By reacting the diastereomeric salt with an acid, one obtains the desired enantiomer as the free carboxylic acid. Alternatively (see chart C), either (+) or (−) amino-acid (XIIa) can be added to halo-nitro (VII) to give the acid (X). Catalytic hydrogenation of acid (X) leads directly to bicyclic amides (IV) which are, optically pure. Thus, depending on the chirality of the starting amino acids [(+) or (−)] the corresponding enantiomerically pure compound of formula IV can be prepared. These optically pure compounds are then used in the same way as the racemic mixture. When used in this patent application the term imidazo[1,5-a]quinoxalines (I) includes both enantiomers as well as optically impure forms thereof, the most common of which is a racemic mixture all).

The imidazo[1,5-a]quinoxalines (I) are amines. Many do not form salts, some do. If salts can be made it is preferable to make them because of their increased water solubility. When salts of the imidazo[1,5-a]quinoxalines (I) are made they are produced by reaction with acids of sufficient strength. Pharmaceutically acceptable salts include salts of both inorganic and organic acids. The pharmaceutically acceptable salts are preferred over the corresponding free amines since they produce compounds which are more water soluble. The preferred pharmaceutically acceptable salts include salts of the following acids methanesulfonic, hydrochloric, hydrobromic, sulfuric, phosphoric, nitric, benzoic, citric, tartaric, fumaric, maleic, $CH_3$—$(CH_2)_n$—COOH where n is 0 thru 4, HOOC—$(CH_2)$n—COOH where n is as defined above.

It is preferred that $R_3$ is —$COOR_{3-1}$ or aryl. When $R_3$ is aryl it is preferred that it be 1,2,4-oxadiazol-3-yl, 1,2,4-oxadiazol-5-yl or substituted phenyl. It is preferred that $R_{3-2}$ is $C_2$-$C_4$ alkyl and $C_3$-$C_5$ cycloalkyl. It is more preferred that $R_{3-2}$ is —F, t-butyl and cyclopropyl. $R_5$ can be either free or cyclized with either $R_4$ or $R_6$. It is preferred that $R_5$ is not cyclized. It is preferred that $n_{28}$ and $n_{29}$ be 0. It is preferred that $R_4$ is α-$R_{4-5}$:β-$R_{4-6}$ where $R_{4-5}$ and $R_{4-6}$ are —H:—H or $C_1$ alkyl:$C_1$ alkyl. It is preferred that $R_5$ is selected from the group consisting of —$(CH_2)_{n29}$—CO—($C_1$-$C_6$ alkyl), —$(CH_2)_{n29}$—CO—$(CH_2)_{n28}$—$NR_{5-4}R_{5-5}$, —$(CH_2)_{n29}$—CO—aryl, —$(CH_2)_{n29}$—CO—O—($C_1$-$C_6$ alkyl), —$(CH_2)_{n29}$—CO—($C_3$-$C_7$ cycloalkyl) and —$(CH_2)_{n29}$—CO—$R_{3-13}$. It is more preferred that $R_5$ is —$(CH_2)_{n29}$—CO—$(CH_2)_{n28}$—$NR_{5-4}R_{5-5}$, —$(CH_2)_{n29}$—CO—aryl and —$(CH_2)_{n29}$—CO—O—($C_1$-$C_6$ alkyl). It is preferred that $W_6$, $W_7$, $W_8$ and $W_9$ all be —$CR_x$= where the R's are —H. It is also preferred that $W_6$ or $W_7$ be —CF=, —CCl= or —$CCH_3$=. It is preferred that the imidazo[1,5-a]quinoxaline (I) be selected from the group consisting of the compounds of EXAMPLES 30, 31, 33, 34, 36, 38, 40, 42, 44, 45B, 47–87, 89–93, 100, 102, 104–169, 174–244, 248–262, 264–273, 275, 305–318, 320–362 and 368–559 as well as the 4,5-cyclized compounds of EXAMPLES 281–285, 289, 290. and the 5,6-cyclized compounds of EXAMPLES 363–366. Also preferred is the compound of EXAMPLE 560. It is more preferred that the imidazo[1,5-a]quinoxaline (I) be selected from the group consisting of the compounds of EXAMPLES 30, 31, 33, 34, 36, 38, 40, 42, 44, 45B, 47–87, 89–93, 100, 102, 104–169, 174–244, 248–262, 264–273, 275, 305–318, 320–362, 368–431 and 540–559 as well as the 4,5-cyclized compounds of EXAMPLES 281–285, 289, 290. and the 5,6-cyclized compounds of EXAMPLES 363–366. It is even more preferred that the imidazo[1,5-a]quinoxaline (I) be selected from the group consisting of the compounds of EXAMPLES 51, 113, 128, 136, 332–334, 338, 361, 402, 407, 409, 411–413, 424, 426, 541 and 546. The imidazo[1,5-a]quinoxalines (I) of the present invention have relatively more anxiolytic and less sedative activity than other known anxiolytic compounds such as diazepam and therefore are useful as anxiolytic agents at lower doses and as sedatives at higher doses.

The imidazo[1,5-a]quinoxalines (I) are active orally or parenterally. Orally the imidazo[1,5-a]quinoxalines (I) can be given in solid dosage forms as tablets or capsules, or can be given in liquid dosage forms such as elixirs, syrups or suspensions as is known to those skilled in the art. It is preferred that the imidazo[1,5-a]quinoxalines (I) be given in solid dosage form and that it be a tablet.

For anxiolytic effect the imidazo[1,5-a]quinoxalines (I) should be give in amount of about 0.125 mg to about 100 mg/person, one to three times a day. Preferably, about 0.25 to about 50 mg/day in divided doses.

For sedative/hypnotic effect the imidazo[1,5-a]quinoxalines (I) should be given in the amount of about 0.125 mg to about 500 mg/person, preferably at bedtime or when sedation is needed. It is preferred the sedative/hypnotic dose be from about 0.25 mg to about 50 mg/person.

The exact dosage and frequency of administration depends on the particular imidazo[1,5-a]quinoxalines (I) used, the particular condition being treated, the severity of the condition being treated, the age, weight, general physical condition of the particular patient, other medication the individual may be taking as is well known to those skilled in the art and can be more accurately determined by measuring the blood level or concentration of the imidazo[1,5-a]quinoxalines (I) in the patient's blood and/or the patient's response to the particular condition being treated.

The imidazo[1,5-a]quinoxalines (LX) of the present invention are useful in treating the same conditions in exactly the same way as are the imidazo[1,5-a]quinoxalines (I).

DEFINITIONS AND CONVENTIONS

The definitions and explanations below are for the terms as used throughout this entire document including both the specification and the claims.

I. CONVENTIONS FOR FORMULAS AND DEFINITIONS OF VARIABLES

The chemical formulas representing various compounds or molecular fragments in the specification and claims may contain variable substituents in addition to expressly defined structural features. These variable substituents are identified by a letter or a letter followed by a numerical subscript, for example, "$Z_1$" or "$R_i$" where "i" is an integer. These variable substituents are either monovalent or bivalent, that is, they represent a group attached to the formula by one or two chemical bonds. For example, a group $Z_1$ would represent a bivalent variable if attached to the formula $CH_3$—$C(=Z_1)H$. Groups $R_i$ and $R_j$ would represent monovalent variable substituents if attached to the formula $CH_3$—$CH_2$—$C(R_i)(R_j)$—H. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—$CH(R_i)$—$CH_3$ represents a 2-substituted-1-methoxypropane compound. In a similar fashion, the symbol "=" represents a double bond, e.g., $CH_2$=$C(R_i)$—O—$CH_3$, and the symbol "≡" represents a triple bond, e.g., HC≡C—$CH(R_i)$;$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by N*=$C(CH_3)$—CH=CCl—CH=C*H with the convention that the atoms marked with an asterisk (*) are bonded to each other resulting in the formation of a ring. Likewise, the cyclic molecular fragment, 4-(ethyl)-1-piperazinyl can be represented by —N*—$(CH_2)_2$—$N(C_2H_5)$—$CH_2$—C*$H_2$.

A rigid cyclic (ring) structure for any compounds herein defines an orientation with respect to the plane of the ting for substituents attached to each carbon atom of the rigid cyclic compound. For saturated compounds which have two substituents attached to a carbon atom which is pan of a cyclic system, —$C(X_1)(X_2)$— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol "— — —" or "...". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as —$C(=R_i)$— might be bivalent and be defined as oxo or keto (thus forming a carbonyl group (—CO—) or as two separately attached monovalent variable substituents $\alpha$-$R_{i-j}$ and $\beta$-$R_{i-k}$. When a bivalent variable, $R_i$, is defined to consist of two monovalent variable substituents, the convention used to define the bivalent variable is of the form "$\alpha$-$R_{i-j}$:$\beta$-$R_{i-k}$" or some variant thereof. In such a case both $\alpha$-$R_{i-j}$ and $\beta$-$R_{i-k}$ are attached to the carbon atom to give —$C(\alpha$-$R_{i-j})(\beta$-$R_{i-k})$—. For example, when the bivalent variable $R_6$, —$C(=R_6)$— is defined to consist of two monovalent variable substituents, the two monovalent variable substituents are $\alpha$-$R_{6-1}$:$\beta$-$R_{6-2}$, .... $\alpha$-$R_{6-9}$:$\beta$-$R_{6-10}$, etc, giving —$C(\alpha$-$R_{6-1})(\beta$-$R_{6-2})$—, ..... —$C(\alpha$-$R_{6-9})(\beta$-$R_{6-10})$—, etc. Likewise, for the bivalent variable $R_{11}$, —$C(=R_{11})$—, two monovalent variable substituents are $\alpha$-$R_{11-1}$:$\beta$-$R_{11-2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —$C_1(R_i)H$—$C_2(R_j)H$— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation "... $R_i$ and $R_j$ are taken together to form —$CH_2$—$CH_2$—O—CO— ..." means a lactone in which the carbonyl is bonded to $C_2$. However, when designated "... $R_j$ and $R_i$ are taken together to form —CO—O—$CH_2$—$CH_2$—the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$–$C_j$" designation in parentheses and placing it immediately (no intervening space) before the portion of the definition being defined. By this optional convention ($C_1$–$C_3$)alkoxycarbonyl has the same meaning as $C_2$–$C_4$ alkoxycarbonyl because the "$C_1$–$C_3$" refers only to the carbon atom content of the alkoxy group. Similarly while both $C_2$–$C_6$ alkoxyalkyl and ($C_1$–$C_3$)alkoxy($C_1$–$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

When the claims contain a fairly complex (cyclic) substituent, at the end of the phrase naming/designating that particular substituent will be a notation in (parentheses) which will correspond to the same name/designation in one of the CHARTS which will also set forth the chemical structural formula of that particular substituent.

II. DEFINITIONS

All temperatures are in degrees Centigrade.

TLC refers to thin-layer chromatography.

THF refers to tetrahydrofuran.

DMF refers to dimethylformamide.

DBU refers to 1,8-diazabicyclo[5.4.0]undec-7-ene.

Saline refers to an aqueous saturated sodium chloride solution.

IR refers to infrared spectroscopy.

NMR refers to nuclear (proton) magnetic resonance spectroscopy, chemical shifts are reported in ppm ($\delta$) downfield from tetramethylsilane.

—$\phi$ refers to phenyl ($C_6H_5$).

MS refers to mass spectrometry expressed as to/e or mass/charge unit. $[M+H]^+$ refers to the positive ion of a parent plus a hydrogen atom. EI refers to electron impact. CI refers to chemical ionization. FAB refers to fast atom bombardment.

Hunig's base refers to diisopropylethylamine.

$[\alpha]_D^{25}$ refers to the angle of rotation of plant polarized light (specific optical rotation) at 25° with the sodium D line (5893A).

Ether refers to diethyl ether.

Alcohol refers to ethyl alcohol.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pharmaceutically acceptable anion salts include mesylate, chloride, sulfate, phosphate, nitrate, citrate, $CH_3$—$(CH_2)_{n_1}$—$COO^{-1}$ where $n_1$ is 0 thru 4, $^1OOC$—$(CH_2)n_1$—$COO^{-1}$ where n is as defined above, $^1OOC$—$CH\!=\!CH$—$COO^{-1}$, $\phi$—$COO^{-1}$.

When solvent pairs are used, the ratios of solvents used are volume/volume (v/v).

When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1
5-(2,2-Dimethylpropyl)-3-N-formylaminomethyl-1,2,4-oxadiazole

A mixture of 2-formylaminoethanamidoxime (5.49 g, prepared from N-formylamino-acetonitrile and hydroxylamine), triethylamine (7.19 ml) and dichloromethane (50 ml) is stirred at 0°. To this mixture is added dropwise over 5–10 minutes, tert-butylacetyl chloride (7.16 ml). The reaction is stirred for 3 hr at 0° and then additional triethylamine and tert-butylacetyl chloride are added. The reaction is stirred for 3 hr and then the solvent is removed under reduced pressure. Water (25 ml) is added to the residue and the mixture is heated at 100° for about 24 hr. After cooling, sodium chloride is added and the mixture is partitioned between dichloromethane, water, and saline. The organic phase is separated and dried over sodium sulfate and concentrated. The solid is then chromatographed on silica gel (300 ml) eluting with methanol/dichloromethane (4/96). The appropriate fractions are pooled and concentrated to give the title compound, NMR (CDCl3) 1.06, 2.79, 4.65, 6.40 and 8.32 $\delta$.

PREPARATION 2
5-(2,2-Dimethylpropyl)-3-isocyanomethyl-1,2,4-oxadiazole

To 5-(2,2-dimethylpropyl)-3-N-formylaminomethyl-1,2,4-oxadiazole (PREPARATION 1, 4.94 g), triethylamine (10.5 ml) and dichloromethane (50 ml) at 0° is added, dropwise, phosphorus oxychloride (3.84 g). After stirring for 1 hr at 0°, sodium carbonate (2.65 g) in water (35 ml) is added. The reaction is stirred for 50 min and then partitioned between dichloromethane and saline. The phases are separated, the organic phase is dried over sodium sulfate, concentrated, and the residue chromatographed on silica gel (300 ml) eluting with ethyl acetate/hexane (1/3). The appropriate fractions are pooled and concentrated to give the title compound, NMR (CDCl$_3$) $\delta$ 1.06, 2.83 and 4.75.

PREPARATION 3
2-Chloro-N-(2-hydroxyphenyl)acetamide

To a mixture of 8.90 g (81.5 mmol) of 2-aminophenol and 11.4 ml (81.5 mmol) of triethylamine in 250 ml of ethyl acetate cooled at 0° C. were added over several minutes 6.5 ml (81.5 mmol) of chloroacetyl chloride. The reaction mixture was stirred at 0° C. for 100 min and then washed with saline, aqueous sodium bicarbonate, and saline. The organic layers were dried over magnesium sulfate and concentrated. Dichloromethane was added to the residue and the resulted solid collected and dried to give the title compound, mp 133°–134°; NMR (CDCl$_3$) 4.27, 6.93, 7.02, 7.17, 7.25, 7.80 and 8.53 $\delta$.

PREPARATION 4
2-Chloro-N-(2-hydroxyphenyl)acetamide

A mixture of 14.55 g (78.4 mmol) of 2-chloro-N-(2-hydroxyphenyl)acetamide (PREPARATION 3) and approximately 35 ml of a solution prepared by stirring overnight methanesulfonic acid and phosphorous pentoxide in a 10:1 (wt/wt) ratio was heated with stirring at 100° for 2 hr and then poured onto ice. The aqueous mixture was extracted with dichloromethane. The dichloromethane layers were washed with aq. sodium bicarbonate and the organic layers dried over sodium sulfate. After concentration, the crude product was chromatographed on silica gel (600 ml) eluting with dichloromethane, the appropriate fractions are pooled and concentrated to give the title compound as a liquid, NMR (CDCl$_3$) 4.77, 7.40, 7.57, 7.75 δ.

PREPARATION 5

2-(Azidomethyl)benzoxazole

To a mixture of 8.34 g (49.8 mmol) of 2-chloro-N-(2-hydroxyphenyl)acetamide (PREPARATION 4) and 0.75 g (5 mmol) of sodium iodide in 25 ml of DMSO were added 3.56 g (5.47 mmol) of sodium azide. A moderate exotherm ensued. After stirring for 30 min the reaction was partitioned between ethyl ether and saline. The organic layers were dried over magnesium sulfate and concentrated. The crude product was chromatographed on silica gel (700 ml) eluting with ethyl acetate/hexane (5/95), the appropriate fractions are pooled and concentrated to give the title compound, NMR (CDCl$_3$) 4.60, 7.39, 7.56, 7.76 δ.

PREPARATION 6

2-(Aminomethyl)benzoxazole

A mixture of 8.28 g (47.5 mmol) of 2-(azidomethyl)benzoxazole (PREPARATION 5) and 0.526 g of 10% Palladium on charcoal in absolute ethanol (150 ml) is shaken under hydrogen at 36 psi for 40 min. The catalyst is then filtered off and the filtrate is concentrated. The crude product is chromatographed on silica gel (700 ml) eluting with methanol/dichloromethane (2/98), the appropriate fractions are pooled and concentrated to give the product. Crystallization from ethyl ether/hexane gives the title compound, mp 46.5°–47.5°; MS m/z) at 148; NMR (CDCl$_3$) 1.70, 4.14, 7.33, 7.51, 7.70 δ.

PREPARATION 7

2-(N-Formylaminomethyl)benzoxazole

A mixture of 4.29 g (28.9 mmol) of 2-(aminomethyl)benzoxazole (PREPARATION 6) and 20 ml of ethyl formate is heated at 80° for 2 hr, after which the excess ethyl formate is removed under reduced pressure. The residue is chromatographed on silica gel (350 ml) eluting with methanol/dichloromethane (2/98), the appropriate fractions are pooled and concentrated to give the product, which is crystallized from dichloromethane/hexane to give the title compound, mp 98°–99°; MS (m/z) at 176; IR 1655, 1621, 1519, 1241, 750 cm$^{-1}$; NMR (CDCl$_3$) 4.81, 6.45, 7.36. 7.53, 7.70, 8.39 δ.

PREPARATION 8

2-(Isocyanomethyl)benzoxazole

To 2.83 g (16.1 mmol) of 2-(N-formylaminomethyl)benzoxazole, 7.39 ml (53.0 mmol) of triethylamine, and 30 ml of dichloromethane stirred at 0° are added dropwise 2.71 g (17.7 mmol) of phosphorous oxychloride in 5 ml of dichloromethane. The reaction mixture is stirred at 0° for 45 min and then 2.81 g of sodium carbonate dissolved in 20 ml of water is added. The mixture is stirred for 30 min and then partitioned between dichloromethane and aq. sodium bicarbonate. The organic layers are dried over sodium sulfate and concentrated and the crude product is chromatographed on silica gel (325 ml) eluting with ethyl acetate/hexane (10/90), the appropriate fractions are pooled and concentrated to give the title compound, mp 57.0°–57.5°; MS (m/z) 158; IR 766, 2166, 987, 1167 and 1230 cm$^{-1}$; NMR (CDCl$_3$) 4.94, 7.42, 7.58 and 7.76 δ.

EXAMPLE 1

1,2,3,4-Tetrahydroquinoxalin-2-one (IV)

A solution of ethyl bromoacetate (III, 13.3 ml) in THF (50 ml) is added over 2 hr to a stirred solution of 12-phenylenediamine (II, 10.0 g) and triethylamine (16.8 ml) in THF (22 ml) and methylene chloride (22 ml). The mixture is heated at 60° for 3 hr, and is concentrated. The resulting solids are suspended and shaken vigorously in hexane (250 ml) and water (150 ml). The hexane layer is decanted, and the process is repeated with two additional 250 ml portions of hexane. The solids are filtered, dried and recrystallized from methylene chloride/hexane to give the desired product as a solid. The concentrated filtrate is purified by flash chromatography eluting with ethyl acetate/methylene chloride (25/75) to give additional title compound, mp 135°–136°: NMR (CDCl$_3$) 8.30, 6.85–6.95, 6.65–6.80, 4.00 and 3.86 δ.

EXAMPLE 2

1,2,3,4-Tetrahydro-3,3-dimethylquinoxalin-2-one (IV)

A mixture of 1,2-phenylenediamine (II, 7.55 g), ethyl 2-bromoisobutyrate (III, 12.8 ml), diisopropylamine (15.5 ml) and DMF (30 ml) is heated at 110° for 5 hr, after which an additional ethyl bromoisobutyrate (III, 0.5 ml) and diiopropylethylamine (0.8 ml) is added. After heating for 2 more hours, the reaction is cooled and the DMF is removed in under reduced pressure. The residue is stored overnight in the freezer and then partitioned between ethyl acetate, water, and saline. The phases are separated and the organic phase is dried over magnesium sulfate, the organic phase is removed under reduced pressure. The residue is chromatographed eluting with ethyl acetate/dichloromethane (20/80). The product crystallizes out in the column. The product is recrystallized from dichloromethane/hexane to give the title compound, mp 173°–174°; NMR (CDCl$_3$) 1.41, 3.72, 6.67, 6.76, 6.87 and 8.50 δ.

EXAMPLE 3

6-Chloro-1,2-dihydroquinoxalin-2-one (VI)

Following the procedure of J. Med. Chem., 24, 93 (1981), glyoxylic acid (29.4 ml) is added to a solution of 4-chloro-1,2-phenylenediamine (38.0 g) and methanol (1.87 L) at 15°. The solution is stirred for 24 hr at 20°–25° and is concentrated. The residue is washed with water (4×608 ml), isopropanol (145 ml), and dried under reduced pressure to give a solid. Two successive recrystallizations from hot (ca 90°) 2-methoxyethanol (1.49 l and 0.927 l) gives the title compound, NMR (DMSO-d$_6$) 12.55, 8.22, 7.86, 7.62 and 7.32 δ.

EXAMPLE 4

6-Chloro-1,2,3,4-tetrahydroquinoxalin-2-one (IV)

Sodium borohydride (5.10 g) is added to a mixture of 6-chloro-1,2-dihydroquinoxalin-2 -one (5.60 g), and ethanol (200 ml). The resultant solution is stirred for 2.5 hr at 20°–25°. The material is partitioned between water and ethyl acetate, the phases are separated, the organic phase is dried over magnesium sulfate and concentrated under reduced pressure to give a solid which is recrystallized from ethyl acetate/hexane to give the title compound, mp 171–174°; IR (mineral oil) 2953, 2925, 1687, 1517, 1408, 1307 and 1299 cm$^{-1}$; NMR (CDCl$_3$-MeOD) 6.6–6.8 and 3.95 δ; MS (m/z) 182, 153.

EXAMPLE 5

N-(5-Fluoro-2-nitrophenyl)glycine ethyl ester (XI)

To a mixture of 2,4-difluoronitrobenzene (VII, 19.20 g), glycine ethyl ester hydrochloride (XII, 16.52 g), and acetonitrile (50 ml) is added diisopropylethylamine (42 ml). A mild exotherm ensues. The reaction is stirred (without cooling) for two hours. The acetonitrile is removed under reduced pressure and the residue is partitioned between dichloromethane and water. The organic layers are dried over sodium sulfate and concentrated to give the produce as a solid (single spot by TLC), mp 194°–195°; NMR (CDCl$_3$) 1.33, 4.05, 4.30, 6.35, 6.45, 8.26 and 8.56 δ.

EXAMPLE 6

6-Fluoro-1,2,3,4-tetrahydroquinoxalin-2-one (IV)

A mixture of N-(5-fluoro-2-nitrophenyl)glycine ethyl ester (XI, EXAMPLE 5, 28.60 g), palladium on carbon (10%, 1.01 g) and methanol (500 ml) is shaken under 45 psi of hydrogen on a Parr shaker. After 2 hr an additional 0.54 g of 10% palladium on carbon catalyst is added. The mixture is shaken for an hour at 42 psi and then the catalyst is removed by filtration. p-Toluenesulfonic acid (0.314 g) is added to the filtrate. The solution is concentrated under reduced pressure to a volume of about 250 ml and then stirred at 20°–25°. The reaction is then further concentrated and dichloromethane is added. The solid that formed is collected and chromatographed on 800 ml of silica gel (column) eluting with dichloromethane/methanol (98/2). The appropriate fractions are pooled and concentrated and triturated with a small amount of dichloromethane. The solid is collected, dried, and triturated a second time with dichloromethane and redried to give the title compound, mp 176.0°–177.5°; NMR (CDCl$_3$) 3.95, 3.99, 6.42, 6.63 and 8.33 δ.

EXAMPLE 7

N-(5-Fluoro-2-nitrophenyl)-2-methylalanine methyl ester (XI)

A mixture of 2,4-difluoronitrobenzene (VII, 9.69 g), 2-aminoisobutyric acid (XII, 9.42 g; note—1.1 equivalents would be sufficient), potassium carbonate (21.04 g), acetonitrile (15 ml), and water (25 ml) is heated at 80° for 28 hr. The warm reaction mixture is poured into a separatory funnel and the layers are allowed to separate. The lower layer is discarded and the upper layer is stripped of solvents under high vacuum and then used as is in the next step.

The crude product from above is stirred with potassium carbonate (12.4 g) and DMF (50 ml) at 0°. Methyl iodide (15 ml) is added and the reaction mixture is allowed to stir over the weekend with slow warming to 20°–25°. The DMF is then removed under reduced pressure and the residue is partitioned between ether, water, and aqueous sodium bicarbonate. The organic phase is dried over magnesium sulfate, concentrated, and the crude product is chromatographed on silica gel (600 ml) eluting with ethyl acetate/hexane (10/90) to give the title compound, NMR (CDCl$_3$) 1.68, 3.76, 6.22, 6.41, 8.26 and 8.58 δ.

EXAMPLE 8

6-Fluoro-1,2,3,4-tetrahydro-3,3-dimethylquinoxalin-2-one (IV)

A mixture of N-(5-fluoro-2-nitrophenyl)-2-methylalanine methyl ester (XI, EXAMPLE 7, 11.2 g), palladium on carbon (10%, 0.63 g), and methanol (350 ml) is shaken under 44 psi of hydrogen pressure for 1.5 hr. Additional palladium on carbon (10%, 0.23 g) is added and the mixture is shaken at 36 psi for another 45 min. p-Toluenesulfonic acid (0.46 g) is added and the catalyst is filtered off. The filtrate is concentrated to about 150 ml and warmed at 80° for 75 min. The solvent is then removed under reduced pressure and the residue is chromatographed on silica gel (700 ml) eluting with dichloromethane/methanol (98/2). aaa a solid. The product is crystallized from methanol/dichloromethane/hexane to give the title compound, mp 148.5°–149.0°; NMR (CDCl$_3$) 1.42, 3.80, 6.40, 6.46, 6.66 and 8.35 δ.

EXAMPLE 9

2-[N-(5-Chloro-2-nitrophenyl)]amino-2-methyl-1-propanol (IX)

A solution of 2,4-dichloronitrobenzene (VII, 20.0 g) and 2-amino-2-methyl-1-propanol (VIII, 80 ml) is stirred at 110° for 68 hr. After cooling to 20°–25°, adding water, extracting with methylene chloride, separating the phases and drying the organic phase over magnesium sulfate) gives the desired product sufficiently pure (>90%) to be carried on without further purification. An analytical sample is prepared by recrystallization from ethyl acetate/hexane to give the title compound, mp 102°–104°; IR (mineral oil) 3335, 2954, 2925, 1610, 1577, 1492, 1467, 1331, 1251, 1154 and 748 cm$^{-1}$; NMR (CDCl$_3$) 8.55, 8.13, 7.09, 6.59, 3.71, 2.11 and 1.48 δ; MS (m/z) 244, 213 and 166.

EXAMPLE 10

N-(5-Chloro-2-nitrophenyl)-2-methylalanine (X)

Jones reagent (2.67 M) is added in aliquots (40 ml, 20 ml, 20 ml, 20 ml and 10 ml) every 15 min to a solution of 2-[N-(5-Chloro-2-nitrophenyl)]amino-2-methyl-1-propanol (IX, EXAMPLE 9, 26.9 g) and acetone (2.05 l) at 0° until the reaction is done as measured by TLC. Isopropanol (150 ml) is added and the mixture is allowed to warm to 20°–25°. The mixture is filtered and the solids are washed with acetone several times. The combined filtrates are concentrated and partitioned between ether (800 ml) and potassium hydroxide (10%, 3×100 ml). The basic layers are acidified (3 N hydrochloric acid) and extracted with methylene chloride (3×180 ml). The methylene chloride layers are dried over magnesium sulfate, filtered, and concentrated to provide the title compound, mp 146°–147°; IR (mineral oil) 3363, 2953, 2924, 2855, 1707, 1613, 1573, 1495, 1336, 1272, 1241 and 753 cm$^{-1}$; NMR (CDCl$_3$) 8.48, 8.16, 6.68, 6.64 and 1.74 δ; MS (EI, m/z) 258 and 213.

EXAMPLE 11

N-(5-Chloro-2-nitrophenyl)-2-methylalanine methyl ester (XI)

A mixture of N-(5-chloro-2-nitrophenyl)-2-methylalanine (X, EXAMPLE 10, 22.3 g, DMF (260 ml), potassium carbonate (35.6 g), and iodomethane (26.9 ml) is stirred at 20°–25° for 16 hr. Aqueous workup (ether, water and saline washes, drying over magnesium sulfate) gives the title compound, mp 87°–89°; IR (Nujol) 3349, 2954, 2925, 1737, 1606, 1489, 1330, 1263, 1230, 1149 and 752 cm$^{-1}$; NMR (CDCl$_3$) 8.48, 8.15, 6.65, 6.54, 3.77 and 1.69 δ; MS (EI) 272 and 213 m/z.

EXAMPLE 12

6-Chloro-3,3-dimethyl-1,2,3,4-tetrahydroquinoxalin-2-one (IV)

Aqueous titanium trichloride (20%, 260 ml) is added dropwise over 10 min to a mixture of N-(5-chloro-2-nitrophenyl)-2-methylalanine methyl ester, (XI, EXAMPLE 11, 14.1 g), sodium acetate (240 g), methanol (504 ml) and water (156 ml). The mixture is stirred for 2.5 hr at 20°–25°. The material is partitioned between aqueous sodium bicarbonate and ethyl acetate, the phases are separated, the organic phase is dried over magnesium sulfate and concentrated under reduced pressure with heat to give the title compound, mp 166°–170°; IR (mineral oil) 3311, 2964, 2954, 2925, 1658, 1614, 1505, 1404 and 1355 cm$^{-1}$; NMR (CDCl$_3$) 8.67, 6.73, 6.6–6.7, 3.78 and 1.42 δ; MS (FAB) m/z 210, 195 and 167.

EXAMPLE 13

2-[N-(6-Chloro-2-nitrophenyl)]amino-2-methyl-1-propanol (IX)

A solution of 2,3-dichloronitrobenzene (VII, 20.0 g) and 2-amino-2-methyl-1-propanol (VIII, 80 ml) is stirred at 110° for 50 hr. After cooling to 20°–25°, it is diluted with water, partitioned with methylene chloride, the phases are separated, the organic phase is dried over magnesium sulfate and concentration to give the title compound. An analytical sample is prepared by flash chromatography eluting with ethyl acetate/hexane (1/3). The appropriate fractions are pooled and concentrated to give the title compound, IR (neat) 3370, 2971, 1593, 1532, 1484, 1473, 1449, 1349, 1255, 1053, 754 and 725 cm$^{-1}$; NMR (CDCl$_3$) 7.75, 7.63, 7.12, 3.47 and 1.11 δ; MS (m/z) 244 and 213.

EXAMPLE 14

N-(6-Chloro-2-nitrophenyl)-2-methylalanine (X)

Jones reagent (2.67 M) is added in aliquots (30 ml, 15 ml, 10 ml, 5 ml) every 15 min to a solution of 2-[N-(6-Chloro-2-nitrophenyl)]amino-2-methyl-1-propanol (IX, EXAMPLE 13, 21.6 g) and acetone (1.65 l) at 0° until the reaction is done as measured by TLC analysis. After 1 hr total time, isopropanol (90 ml) is added and the mixture is allowed to warm to 20°–25°. The mixture is filtered and the solids washed with acetone several times. The combined filtrates are concentrated and partitioned between ether (1.0 l) and potassium hydroxide (10%, 3×100 ml). The basic layer is acidified (3N hydrochloric acid) and extracted with methylene chloride (3×200 ml). The methylene chloride phase is dried over magnesium sulfate, filtered, and concentrated to give the title compound sufficient pure to be used in the next step without additional purification, mp 107°–109°; IR (mineral oil) 3358, 2953, 2924, 1715, 1597, 1496, 1330, 1280, 1231, 1174, 1105 and 747 cm$^{-1}$; NMR (CDCl$_3$) 8.00, 7.61, 7.06, 6.5–7.1 and 1.54 δ; MS (m/z) 258 and 213.

EXAMPLE 15

N-(6-Chloro-2-nitrophenyl)-2-methylalanine methyl ester (XI)

A mixture of N-(6-chloro-2-nitrophenyl)-2-methylalanine (X, EXAMPLE 14, 11.4 g), DMF (130 ml), potassium carbonate (18.2 g) and iodomethane (13.8 ml) is stirred at 20°–25° for 16 hr, diluted with water, extracted several times with ether. The ether phases are combined and are washed with water and saline, dried over magnesium sulfate and concentrated to give the title compound, IR (mineral oil) 3369, 2990, 2951, 1738, 1598, 1534, 1492, 1451, 1386, 1337, 1277, 1188, 1145. 1103 and 749 cm$^{-1}$; NMR (CDCl$_3$) 7.97, 7.55, 6.94, 6.89, 3.78 and 1.53 δ; MS (m/z) 272 and 213.

EXAMPLE 16

5-Chloro-3,3-dimethyl-1,2,3,4-tetrahydroquinoxalin-2-one (IV)

Aqueous titanium trichloride (20%, 375 ml) is added dropwise over 15 min to a mixture of N-(6-chloro-2-nitrophenyl)-2-methylalanine methyl ester (XI, EXAMPLE 15, 15.7 g), sodium acetate (268 g), methanol (339 ml) and water (174 ml) at 20°–25°. After stirring for 3 hr at 20°–25°, addition of 950 ml of aqueous sodium bicarbonate, extraction with ethyl acetate several times, stirring with magnesium sulfate and concentration gives the title compound; mp 153°–156°; IR (mineral oil) 3369, 2954, 2924, 2856, 1680, 1594, 1489, 1470, 1450, 1381, 1368, 1357, 1300 and 764 cm$^{-1}$; NMR (CDCl$_3$) 8.25, 6.98, 6.70, 6.6–6.7, 4.25 and 1.45 δ; MS (FAB) m/z 210 and 195.

EXAMPLE 17

N-(6-Methyl-2-nitrophenyl)glycine ethyl ester (XV)

A mixture of 2-methyl-6-nitroaniline (XIV, 2.00 g), ethyl bromoacetate (III, 3.5 ml) and diisopropylethylamine (3.5 ml) is heated at reflux (140°) for 8 hr. The resultant solution is allowed to cool to 20°–25°. After dilution with aqueous sodium bicarbonate, extraction several times with ethyl acetate, drying with magnesium sulfate and concentration the residue is resubmitted to the above reaction conditions for an additional 16 hr. After workup, purification by flash chromatography eluting with a gradient of hexane/ethyl acetate (10/1→5/1), pooling and concentrating the appropriate fractions, the title compound is obtained, mp 49°–52°; IR (mineral oil) 3365, 2953, 2925, 1731, 1536, 1475, 1461, 1374, 1344, 1236, 1207, 1104 and 1022 cm$^{-1}$; NMR (CDCl$_3$) 7.88, 7.33, 6.8–7.0, 6.86, 4.17, 3.94, 2.39 and 1.23 δ.

EXAMPLE 18

1,2,3,4-Tetrahydro-5-methylquinoxalin-2-one (IV)

A mixture of N-(6-methyl-2-nitrophenyl)glycine ethyl ester (XV, EXAMPLE 17, 675 rag), ethanol (60.0 ml) and palladium on carbon (10%, 150 mg) is hydrogenated (48 psi) at 20°–25° for 3.5 hr. The mixture is filtered, the residue washed with ethanol, and the combined filtrates are concentrated to give the title compound, mp 168°–171°; IR (mineral oil) 3382, 2955, 2925, 1671, 1490, 1444, 1393, 1295 and 770 cm$^{-1}$; NMR (CDCl$_3$) 8.68, 6.79, 6.6–6.75, 4.04, 3.76 and 2.17 δ; MS (m/z) 162 and 133.

EXAMPLE 19

2-Fluoro-6-nitrobenzoic acid (XVII)

Prepared from (XVI) by the methods of J. Org. Chem. (1986) 51, 2880 and references cited therein.

EXAMPLE 20

2-Fluoro-6-nitrobenzamide (XVIII)

A mixture of 2-fluoro-6-nitrobenzoic acid (XVII, 5.01 g) and thionyl chloride (20 ml) is stirred at reflux for 2 hr. After cooling, the excess thionyl chloride is removed under reduced pressure. The residue is stirred in methylene chloride (5 ml) and cooled in an ice bath. Ammonium hydroxide (30%) is added cautiously (exotherm!) until no acid chloride remained. The solid is collected, washed with water and a small amount of methylene chloride and dried to give the title compound, mp 161°–162°; NMR (CDCl$_3$) 6.0, 7.50, 7.59 and 7.98 δ.

EXAMPLE 21

N-(tert-butyloxycarbonyl)-2-fluoro-6-nitroaniline (XIX)

Lead tetraacetate (11.08 g, which had been under high vacuum for several hours to remove acetic acid) is added to a slurry of 2-fluoro-6-nitrobenzamide (XVIII, EXAMPLE 20, 4.29 g) in dry tert-butanol (50 ml, dried over activated 4Å molecular sieves for 24 hr). After stirring at reflux for 1.5 hr the reaction is cooled and excess tert-butanol is removed under reduced pressure. Acetone is added to dissolve the product and the slurry is filtered through Celite. The filtrate is concentrated and the crude product is chromatographed on silica gel (350 ml) eluting with ethyl acetate/hexane (5/95). The appropriate fractions are pooled and concentrated to give the title compound which is recrystallized from ethyl ether and hexane, mp 100°–101°; MS (m/z) at 256; NMR (CDCl$_3$) 1.51, 7.28, 7.42 and 7.83 δ.

EXAMPLE 22

N-(tert-Butyloxycarbonyl)-N-(2-fluoro-6-nitrophenyl)-glycine ethyl ester (XX)

Potassium tert-butoxide (1 M in THF, 8,67 ml) is added (dropwise over 5 min) to a solution of N-(tert-butyloxycarbonyl)-2-fluoro-6-nitroaniline (XIX, EXAMPLE 21, 1.85 g) in THF (15 ml) cooled at 0°. After 20 min, ethyl bromoacetate (0.96 ml) is added dropwise over several minutes. The ice bath is removed and the reaction is stirred for 2 h, after which it is partitioned between ethyl acetate, aqueous sodium bicarbonate and saline. The phases are separated, the organic phase is dried over magnesium sulfate and concentrated to give the title compound, NMR (CDCl$_3$) 1.26, 1.35, 1.50, 3.98, 4.10, 4.20, 4.42, 4.45, 7.42 and 7.39 δ.

EXAMPLE 23

4-(tert-Butyloxycarbonyl)-5-fluoro-1,2,3,4-tetrahydroquinoxalin-2-one (XXII)

A mixture of 2.06 g of N-(tert-butyloxycarbonyl)-N-(2-fluoro-6-nitrophenyl)glycine ethyl ester (XX, EXAMPLE 22, 2.06 g) and palladium on carbon (10%, 0.19 g) in methanol (150 ml) is shaken under hydrogen on a Parr apparatus at 37 psi for 1 hr. The catalyst is then filtered off and p-toluenesulfonic acid 0.016 g) is added. The solution is stirred at 80° for 1 hr and then at 20°–25° overnight. The solvent is then removed under reduced pressure and the residue is chromatographed on silica gel (200 ml) elating with ethyl acetate/dichloromethane (5/95). The appropriate fractions are pooled and concentrated to give the title compound, mp 155°–156°; MS (m/z) at 266; NMR (CDCl$_3$) 1.48, 6.70, 6.84, 7.12 and 8.61 δ.

EXAMPLE 24

5-Fluoro-1,2,3,4-tetrahydroquinoxalin-2-one(IV)

A solution of 4-(tert-butyloxy)carbonyl-5-fluoro-1,2,3,4-tetrahydroquinoxalin-2-one (XXII, EXAMPLE 23, 6.13 g) in 75 ml of methanol saturated with HCl(g) is stirred at 20°–25° for 7.5 hr. The solvent is then removed under reduced pressure and aqueous sodium bicarbonate is added to the residue. The solid is collected and washed with a small amount of water and then dichloromethane and dried to give the title compound, mp 246°–248°, NMR (CDCl$_3$) 4.04, 4.10, 6.54, 6.63–6.74 and 8.54 δ.

EXAMPLE 25

N-tert-Butyl-6-chloro-2-nitroaniline (XXVIII)

A mixture of 2,3-dichloronitrobenzene (92.5 g), tert-butylamine (138 ml) and ethanol (50 ml) is heated in a bomb at 150° for 3 days. Dilution with water, extraction with ethylacetate several times, drying with sodium sulfate, and concentration gives the title compound, IR (neat) 2970, 1532, 1484, 1447, 1366, 1348, 1192 and 755 cm$^{-1}$; NMR (CDCl$_3$) 7.73, 7.61, 7.07, 4.77 and 1.22 δ; MS (m/z) 172, 154, 142, 126, 114, 99 and 90.

EXAMPLE 26

2-tert-Butylamine-3-chloroaniline (XXIX)

A solution of hydrazine monohydrate (115 ml) in ethanol (270 ml) is added dropwise with stirring over 30 min to a 0° mixture of N-tert-butyl-6-chloro-2-nitroaniline (XXVIII, EXAMPLE 25, 108 g), Raney nickel (27 g, finely divided, Aldrich 22,167–8, slurry in water at pH 10) and of ethanol (540 ML). The mixture is stirred for 90 min at 0°. Dilution with water, extraction with ethyl acetate several times, drying the organic layer with sodium sulfate and concentration gives the title compound, NMR (CDCl$_3$) 6.82, 6.75, 6.60, 4.11, 3.02 and 1.26 δ.

EXAMPLE 27

4-tert-Butyl-5-chloro-1,2,3,4-tetrahydroquinoxalin-2-one (XXXI)

Chloroacetyl chloride (XXX, 55.2 ml) is added dropwise with stirring over 1 hr to a −78° solution of 2-tert-butylamine-3-chloroaniline (91.7 g) and diisopropylethylamine (241 ml) in THF (900 ml). The mixture is allowed to warm slowly, and is stirred at 20°–25° for 18 hr. Concentration dilution with sodium bicarbonate, extraction several times with methylene chloride, drying over sodium sulfate and concentration gives the uncyclized intermediate, NMR (CDCl$_3$) 9.74, 8.33, 7.05–7.2, 4.20, 3.07 and 1.24 δ.

A solution of the intermediate and diisopropylethylamine (120 ml) in acetonitrile (1.5 l) is heated at reflux in the presence of sodium iodide (9.00 g) for 18 hr. Concentration, dilution with water, extraction several times with methylene chloride, drying with sodium sulfate and concentration gives the product as an oily solid. Flash chromatography eluting with acetone/methylene chloride (10/90), pooling the appropriate fractions, concentration, and trituration with methylene chloride give the title compound, mp 197.5°–198.5°.

The filtrate is concentrated, rechromatographed, and triturated with methanol/ether/hexane (5/30/65) to give additional title compound, IR (mineral oil) 2924, 1677, 1461, 1376 and 1367 cm$^{-1}$; NMR (CDCl$_3$) 8.05, 7.0–7.15, 6.73, 3.72 and 1.27 δ; MS (m/z) 238, 223, 182, 153, 90 and 57.

EXAMPLE 28

5-Chloro-1,2,3,4-tetrahydroquinoxalin-2-one (IV)

A suspension of 4-tert-butyl-5-chloro-1,2,3,4-tetrahydroquinoxalin-2-one (XXXI, EXAMPLE 27, 32.1 g) in sulfuric acid (2 N, 500 ml) is stirred at 20°–25° for 18 hr. The solids are filtered, washed with aqueous sodium bicarbonate, water and dried at 20°–25° to give a 23:1 mixture of the amine and corresponding imine as determined by NMR.

Sodium borohydride (1.84 g) is added in one portion to a 0° slurry of the amine/imine mixture (20.5 g) in ethanol (680 ml). The mixture is allowed to warm to 20°–25° and is stirred for 2 hr at 20°–25°. The ethanol is evaporated and the solids are triturated with water, filtered, washed with water and dried to give the title compound, mp 191°–193°; IR (mineral oil) 3407, 2924, 1690. 1503, 1426, 1387 and 771 cm$^{-1}$; NMR (d$_6$-DMSO) 10.47, 6.89, 6.70, 6.59, 5.84 and 3.80 δ; MS (m/z) 182 and 153.

EXAMPLE 29

5-Fluoro-1,2,3,4-tetrahydro4-[(pyrrolidino)carbonyl]-quinoxalin-2-one (XXXII)

Diisopropylethylamine (1.26 ml) followed by phosgene (1.2 M, 6.0 ml) are added to 5-fluoro-1,2,3,4-tetrahydroquinoxalin-2-one (IV, EXAMPLE 24, 1.20 g) in THF (15 ml) at 0°. The ice bath is removed and the reaction is stirred for 2 hr, at which time additional diisopropylethylamine (0.2 ml) and phosgene (1.0 ml) are added. After 70 min, diisopropylethylamine (1.26 ml) and pyrrolidine (0.60 ml) are added. The reaction is stored in the freezer over the weekend and then stirred at 20°–25° for 8 hr. The reaction mixture is then partitioned between ethyl acetate and brine. The organic layers are dried over magnesium sulfate and concentrated. Chromatography on silica gel eluting with ethyl acetate/dichloromethane (3/7), pooling and concentrating the appropriate fractions gives the product. Crystallization from ethyl acetate/ethyl ether/hexane gives the title compound, mp 126°–132°; NMR (CDCl$_3$) 1.85, 3.28, 4.27, 6.68, 6.82, 7.04 and 8.41 δ.

EXAMPLE 30 tert-Butyl 6-Fluoro4,5-dihydro-5-[(pyrrolidino)carbonyl]-imidazo[1,5-a]quinoxaline-3-carboxylate (I)

Potassium tert-butoxide (1M, 3.8 ml) is added to 5-fluoro-1,2,3,4-tetrahydro-4-[(pyrrolidino)carbonyl]quinoxalin-2-one (XXXII, EXAMPLE 29, 0.908 g) at 0° in THF (20 ml). The mixture is stirred for 30 min and then diethylchlorophosphate (0.55 ml) is added. The reaction is stirred for 1 hr at 0°, then cooled at –78°. tert-butyl isocyanoacetate (0.58 g) is added, followed by potassium tert-butoxide (1 M, 4.14 ml). The reaction is stirred at –78° for 4 hr, then allowed to warm to 20°–25° over 1 hr. The mixture is then partitioned between ethyl acetate, water, and saline. The organic layers are dried over magnesium sulfate and concentrated. The crude product is chromatographed on silica gel (250 ml) eluting with a gradient of ethyl acetate/dichloromethane (20/80 to 40/60). The appropriate fractions are pooled, concentrated and crystallized from dichloromethane/hexane to give the title compound; mp 213.5–214.5°; MS (m/z) at 386; IR (mineral oil) 1689, 1677, 1217, 1363 and 1157 cm$^{-1}$; NMR (CDCl$_3$) 1.63, 1.88, 3.36, 5.08, 7.08, 7.20, 7.33 and 8.00 δ.

EXAMPLE 31

6-Fluoro-4,5-dihydro-3-(5-isopropyl-1,2,4-oxadiazol-3-yl)-5-[(pyrrolidino)carbonyl]imidazo[1,5-a]-quinoxaline (I)

Following the general procedure of EXAMPLE 30 and making non-critical variations but using 5-fluoro-1,2,3,4-tetrahydro-4-[(pyrrolidino)carbonyl]quinoxalin-2-one (XXXII, EXAMPLE 29, 0.978 g) and 3-isocyanomethyl-5-isopropyl-1,2,4-oxadiazole (0.673 g) are convened to the title compound, mp 169°–170°; MS (m/z) at 396; IR (mineral oil) 1657, 1495, 1216, 1614 and 785 cm$^{-1}$; NMR (CDCl$_3$) 1.47, 1.86, 3.30, 3.34, 5.13, 7.08, 7.22, 7.38 and 8.12 δ.

EXAMPLE 32

6-Fluoro-1,2,3,4-tetrahydro-3,3-dimethyl-4-[(pyrrolidino)carbonyl]quinoxalin-2-one (XXXII)

Phosgene in toluene (1.2M, 12.9 ml) is added to a mixture of 6-fluoro-1,2,3,4-tetrahydro-3,3-dimethylquinoxalin-2-one (IV, EXAMPLE 8, 1.001 g) and diisopropylethylamine (0.94 ml), and THF (10 ml) at 0°. After 45 min the reaction is allowed to warm to 20°–25°. After stirring for 3 hr, the reaction is again cooled to 0° and additional phosgene (4.2 ml) is added. The ice bath is removed and the reaction is stirred for 100 min, after which the excess phosgene and solvents are removed via a water aspirator. The mixture is then stirred with THF (10 ml) and of pyrrolidine (0.90 ml) are added. After stirring overnight, the reaction is concentrated mid the residue chromatographed on silica gel eluting with methanol/methylene chloride (2/98). The appropriate fractions are pooled and concentrated to give the title compound; MS (m/z) at 291; IR (mineral oil) 1681, 1660, 1396 and 1163 cm$^{-1}$; NMR (CDCl$_3$) 1.4–2.0, 3.15, 3.6, 6.43, 6.65, 6.76 and 8.32 δ.

EXAMPLE 33

7-Fluoro-4,5-dihydro-4,4-dimethyl-3-(5-isopropyl-1,2,4-oxadiazol-3-yl)-5-[(pyrrolidino)carbonyl]-imidazo[1,5-a]quinoxaline (I)

Following the general procedure for EXAMPLE 30 and making non-critical variation but starting with 6-fluoro-1,2,3,4-tetrahydro-3,3-dimethyl-4-[(pyrrolidino)carbonyl]quinoxalin-2-one (XXXII, EXAMPLE 32, 0.647 g) and 3-isocyanomethyl-5-isopropyl-1,2,4-oxadiazole (0.403 g) the title compound is obtained which is crystallized from methylene chloride/ethyl ether/hexane, mp 154.5°–155.5°; MS (m/z) at 424; IR (mineral oil) 1527, 1657, 1414, 1172 and 1395 cm$^{-1}$; NMR (CDCl$_3$) 1.45, 1.7–2.0, 3.0, 3.3, 3.33, 3.58, 6.55, 6.74, 7.45 and 8.06 δ.

EXAMPLE 34 tert-Butyl 7-fluoro-4,5-dihydro-4,4-dimethyl-5-[(pyrrolidino)-carbonyl]imidazo[1,5-a]quinoxaline-3-carboxylate (I)

Following the general procedure for EXAMPLE 30 and making non-critical variation but starting with 6-fluoro-1,2,3,4-tetrahydro-3,3-dimethyl-4-[(pyrrolidino)carbonyl]quinoxalin-2-one (XXXII, EXAMPLE 32, 0.750 g) and t-butyl isocyanoacetate (0.436 g) are converted to the title compound. After crystallization from ethyl ether/hexane, mp 168.5°–169.5°; MS (m/z) at 414; IR (mineral oil) 1713, 1668, 1520, 1181 and 1155 cm$^{-1}$; NMR (CDCl$_3$) 1.63, 1.8, 1.92, 2.08, 2.95, 3.23, 3.58, 6.52, 6.71 and 7.92 δ.

EXAMPLE 35

4-(tert-Butyloxycarbonyl)-1,2,3,4-tetrahydroquinoxalin-2-one (XXXII)

A mixture of 1,2,3,4-tetrahydroquinoxalin-2-one (IV, EXAMPLE 1, 1.08 g), di-tert-butyldicarbonate (1.59 g), potassium carbonate (1.01 g) and THF (10 ml) is stirred at 60° overnight. Additional di-tert-butyldicarbonate (0.93 g) and water (1 ml) are then added, and the reaction is stirred at 65° for 5.5 hr. After a final addition of di-tert-butyldicarbonate (0.24 g) and stirring for two more hours, the reaction is cooled, the solvent is removed under reduced pressure, and the residue is partitioned between dichloromethane and water, followed by a saline wash. The crude product is chromatographed on silica gel eluting with methanol/methylene chloride (2/98). The appropriate fractions are pooled and concentrated to give the title compound which is recrystallization from ethyl acetate and hexane, mp 143°–144°; NMR (CDCl$_3$) 1.54, 4.40, 6.88, 7.09, 7.63 and 8.58 δ.

EXAMPLE 36

5-(tert-Butyloxycarbonyl)-3-(5-cyclopropyl-1,2,4-oxadiazol-3-yl)4,5-dihydroimidazo[1,5-a]-quinoxaline (I)

Following the general procedure of EXAMPLES 30 and 40 and making non-critical variations but using 4-(tert-butyloxycarbonyl)-1,2,3,4-tetrahydro-quinoxalin-2-one (XXXII, EXAMPLE 35, 1.031 g) the title compound is obtained which is recrystallized from methanol/ethyl acetate/hexane, mp 203.5°–204.5°; MS (m/z) at 379; IR (mineral oil) 1706, 1509, 1574, 1308 and 1214 cm$^{-1}$; NMR (CDCl$_3$) 1.24, 1.37, 1.52, 2.28, 5.23, 7.29, 7.53, 7.76 and 8.10 δ.

EXAMPLE 37

4-Benzoyl-1,2,3,4-tetrahydroquinoxalin-2-one (XXXII)

A mixture of 1,2,3,4-tetrahydroquinoxalin-2-one (IV, EXAMPLE 1, 0.593 g) and triethylamine (0.725 ml) in THF (5 ml) is cooled at 0°. To this is added benzoyl chloride (0.56 ml). After the addition is complete, the ice bath is removed and additional THF (5 ml) is added. The reaction is stirred for 30 min and then partitioned between ethyl acetate, aq. sodium bicarbonate, and saline. The organic phases are separated and the organic phase is dried over magnesium sulfate and concentrated. The crude product is recrystallized from methanol/dichloromethane/hexane to give the title compound, mp 208.0°–208.5°; MS (m/z) at 252; IR (mineral oil) 1684, 1666, 1502, 757 and 1362 cm$^{-1}$; NMR (CDCl$_3$) 4.58, 6.7, 6.79, 6.98, 7.10, 7.34 and 7.40 δ.

EXAMPLE 38

5-Benzoyl-3-(5-cyclopropyl-1,2,4-oxadiazol-3-yl)4,5-dihydro-imidazo[1,5-a]quinoxaline (I)

Following the general procedure of EXAMPLE 40 and making non-critical variations but using 4-benzoyl-1,2,3,4-tetrahydroquinoxalin-2-one (IV, EXAMPLE 16, 0.6703 g) and DMF (0.25 ml) after the addition of diethyl chlorophosphate, the title compound is obtained, mp 198°–199° (from methylene chloride-ethyl acetate-hexane); MS (m/z) at 383; IR (mineral oil) 1663, 1506, 1574, 762 and 1481 cm$^{-1}$; NMR (CDCl$_3$) 1.25, 2.25, 5.40, 7.05, 7.3–7.45, 7.59 and 8.20 δ.

EXAMPLE 39

4-Acetyl-1,2,3,4-tetrahydroquinoxalin-2-one (XXXII)

Acetyl chloride (0.36 ml) is added to 1,2,3,4-tetrahydroquinoxalin-2-one (IV, EXAMPLE 1, 0.676 g) and triethylamine (0.76 ml) in THF (8 ml) at 0°. After stirring for 1 hr, the solvent is removed under reduced pressure and the residue is partitioned between dichloro-methane and aq. sodium bicarbonate. The layers are separated, the organic phase is filtered through sodium sulfate and concentrated. The concentrate is crystallized from methanol/methylene chloride/hexane to give the title compound, mp 164°–165°; NMR (CDCl$_3$) 2.28, 4.54, 7.00, 7.11, 7.21 and 9.19 δ.

EXAMPLE 40

5-Acetyl-3-(5-cyclopropyl-1,2,4-oxadiazol-3-yl)-4,5-dihydroimidazo[1,5-a]quinoxaline (I)

Potassium tert-butoxide (1M in THF, 2.92 ml) is added to 4-acetyl-1,2,3,4 -tetrahydroquinoxalin-2-one (XXXII, EXAMPLE 39, 0.5054 g) cooled at 0°. After the addition is complete the cooling bath is removed and the reaction is allowed to stir for 50 min, when it is again cooled in an ice/saline bath. Diethyl chlorophosphate (0.42 ml) is added. After 30 min, the ice/saline bath is removed. The reaction is stirred for an additional 15 min and then cooled at −78°. 5-Cyclopropyl-3-isocyanomethyl-1,2,4-oxadiazole (0.436 g) is added, followed by potassium tert-butoxide (1 M in THF, 2.92 ml). The reaction is stirred for 3 hr and then partitioned between ether and water and saline. The phases are separated, the organic phase is dried over magnesium sulfate, concentrated, and the residue chromatographed on silica gel (200 ml) eluting with ethyl acetate/methylene chloride (25/75). The appropriate fractions are pooled and concentrated to give the title compound which is recrystallized from methylene chloride/ethyl acetate/hexane, mp 187°–188°; MS (m/z) at 321; IR (mineral oil) 1576, 1654, 1505, 1387 and 1355 cm$^{-1}$; NMR (CDCl$_3$) 1.26, 1.38, 2.3, 5.30, 7.37, 7.60 and 8.13 δ.

EXAMPLE 41

4-(2-Furoyl)-1,2,3,4-tetrahydroquinoxalin-2-one (XXXII)

2-Furoyl chloride (0.49 ml) is added to a solution of the 1,2,3,4-tetrahydroquinoxalin-2 -one (IV, EXAMPLE 1, 710 mg), triethylamine (0.80 ml), and THF (20.0 ml) at 0°. The mixture is stirred for 1.5 hr at 0° and for 2 hr at 20°–25°. The mixture was diluted with aq. sodium bicarbonate and extracted with ethyl acetate and chloroform several times. The organic phases are combined, dried with magnesium sulfate, concentrated, and recrystallized from hot ethyl acetate to give the title compound, mp 229°–230°; IR (mineral oil) 2954, 2925, 1684, 1648, 1504, 1474, 1391, 1373 and 756 cm$^{-1}$; NMR (CDCl$_3$) 8.53, 7.39, 7.1–7.25, 6.85–7.05, 6.45 and 4.59 δ; MS (m/z) 242 and 95.

EXAMPLE 42

3-(5-Cyclopropyl-1,2,4-oxadiazol-3-yl)-5-(2-furoyl)-4,5-dihydro-imidazo[1,5-a]quinoxaline (I)

Following the general procedure of EXAMPLES 30 and 40 and making non-critical variations but using 4-(2-furoyl)-1,2,3,4-tetrahydroquinoxalin-2-one (XXXII, EXAMPLE 41,593 mg) the title compound is obtained, mp 190°–191°; IR (mineral oil) 2954, 2925, 1657, 1578, 1511, 1481, 1384, 1366, 1312, 1021 and 760 cm$^{-1}$; NMR (CDCl$_3$) 8.35, 7.66, 7.1–7.5, 7.02, 6.48, 5.43, 2.2–2.3 and 1.2–1.5 $\delta$; MS (m/z) 373, 278, 210 and 95.

EXAMPLE 43

4-(tert-Butyloxycarbonyl)-1,2,3,4-tetrahydro-5-methylquinoxalin-2-one (XXXII)

A solution of di-tert butyl dicarbonate (1.37 g) and THF (2.0 ml) is added to a solution of 5-methyl-1,2,3,4-tetrahydroquinoxalin-2-one (IV, EXAMPLE 18, 0.925 g) and THF (11.0 ml) at 0°. The solution is stirred at 0° for 15 min and after warming to 20°–25° is heated at reflux for 3 days. More di-tert butyl dicarbonate (0.390 ml) is added after 2 days. After cooling to 20°–25°, dilution with water, extraction with methylene chloride several times, drying with magnesium sulfate and purification by flash chromatography, eluting with hexane/ethyl acetate (3.5/1), pooling the appropriate fractions and concentration, the title compound is obtained, mp 175°–177°; IR (mineral oil) 2953, 2925, 2855, 1721, 1693, 1481, 1386, 1364, 1232 and 1156 cm$^{-1}$; NMR (CDCl$_3$) 7.10, 6.95, 6.80, 4.33, 2.29 and 1.48 $\delta$; MS (m/z) 262, 206, 162 and 133.

EXAMPLE 44

5-(tert-Butyloxycarbonyl)-3-(5-cyclopropyl-1,2,4-oxadiazol-3-yl)-4,5-dihydro-6-methylimidazo[1,5-a]quinoxaline (I)

Following the general procedure of EXAMPLES 30 and 40 and making non-critical variations but using 4-(tert-butyloxycarbonyl)-1,2,3,4-tetrahydro-5-methylquinoxalin-2-one (XXXII, EXAMPLE 43, 420 mg) the title compound from which an analytical sample is prepared by recrystallization from methylene chloride/hexane, mp 189°–192°; IR (mineral oil) 2954, 2924, 1697, 1577, 1499, 1458, 1421, 1369, 1241, 1159 and 772 cm$^{-1}$; NMR (CDCl$_3$) 8.14. 7.39, 7.15–7.35, 5.14, 2.38, 2.2–2.4, 1.41 and 1.1–1.5 $\delta$; MS (m/z) 393, 293 and 224.

EXAMPLE 45

7-Chloro-3-(5-cyclopropyl-1,2,4-oxadiazol-3-yl)-4,5-dihydro-5-[(pyrrolidino)carbonyl]imidazo[1,5-a]-quinoxaline (I)

Part A

Following the general procedure of EXAMPLES 29 and 32 and making non-critical variations but starting with 6-chloro-1,2,3,4-tetrahydroquinoxalin-2-one (IV, EXAMPLE 4), 6-chloro-1,2,3,4-tetrahydro-4-[(pyrrolidino)carbonyl]quinoxalin-2-one is produced.

Part B

Following the general procedure of EXAMPLES 36, 38, 40, 42 and 44 and making non-critical variations but starting with 6-chloro-1,2,3,4-tetrahydro-4-[(pyrrolidino)carbonyl] quinoxalin-2-one (XXXII, Part A) the title compound is obtained, mp 202°–204°: IR (mineral oil) 2953, 2924, 2855, 1679, 1660, 1576, 1503, 1406, 1390 and 1202 cm$^{-1}$; NMR (CDCl$_3$) 8.08, 7.46, 7.05–7.2, 5.02, 3.2–3.4, 2.2–2.35, 1.75–1.9 and 1.2–1.4 $\delta$; MS (m/z) 410, 340, 312, 272 and 98.

EXAMPLE 46

6-Chloro-4-[(dimethylamino)carbonyl]-1,2,3,4-tetrahydroquinoxalin-2-one (XXXII)

Part A

Phosgene (12.5% solution in toluene, 28 ml) is added to a solution of 6-chloro-1,2,3,4-tetrahydroquinoxalin-2-one (IV, EXAMPLE 4, 4.64 g), diisopropylethylamine (5.90 ml) and THF (100 ml) at 0°. The mixture is stirred for 1 hr at 0° and for 1 hr at 20°–25°. Dilution with water, extraction with ethyl acetate, drying with magnesium sulfate and concentration gives the carbamyl chloride of the starting material sufficiently pure to be used without further purification.

Part B

Diisopropylethylamine (11.4 ml) is added to a mixture of the crude carbamyl chloride (6.56 g), dimethylamine hydrochloride (2.50 g), and THF (130 ml) at 0°. The mixture is stirred for 1 hr at 0° and for 3 days at 20°–25°. Dilution with water, extraction with ethyl acetate several times, drying over magnesium sulfate, concentration, and trituration with hexane/ether/ethyl acetate gives the product, mp 242°–244°. The filtrate is concentrated and recrystallized from ethyl acetate to provide additional product, IR (mineral oil) 2953, 2923, 2855, 1677, 1654, 1502, 1392, 1376, 1205, 833 and 804 cm$^{-1}$; NMR (CDCl$_3$) 8.99, 6.99, 6.93, 6.85, 4.14, and 2.89 $\delta$; MS (m/z) 253 and 72.

EXAMPLE 47

7-Chloro-3-(5-cyclopropyl-1,2,4-oxadiazol-3-yl)-5-[(dimethylamino)carbonyl]-4,5-dihydroimidazo[1,5-a]quinoxaline (I)

Following the general procedure of EXAMPLE 44 and making non-critical variations but using 6-chloro-4-[(dimethylamino)carbonyl]-1,2,3,4-tetrahydroquinoxalin-2-one (XXXII, EXAMPLE 46, 275 mg), the title compound is obtained, mp 254.5°–255.5°; IR (mineral oil) 2955, 2924, 2855, 1676, 1666, 1633, 1496, 1457, 1446, 1397, 1382, 1359, 1201 and 1194 cm$^{-1}$; NMR (CDCl$_3$) 8.08.7.47, 7.14, 7.08, 4.98, 2.89, 2.2–2.35 and 1.2–1.4 $\delta$; MS (m/z) 384, 312, 272 and 72.

EXAMPLES 48–87

The process to produce the imidazol[1,5-a]quinoxalines (I) can be thought of as involving three steps. Step 1 is formation of the bicyclic amide (IV), step 2 is the addition of the exocyclic carbonyl-R$_5$ substituent at N$_5$, and step 3 is the formation of the imidazole ring with addition of the desired substituent at C$_3$.

The imidazol[1,5-a]quinoxaline (I) molecule has four different types of variable substituents. These are, in the order of their incorporation during the three steps discussed above are (1) W$_5$, W$_6$, W$_7$ and W$_8$ which are incorporated by definition when the starting material is chosen, (2) the R$_4$ substituent which is incorporated when the bicyclic amide (IV) is formed, (3) the exocyclic carbonyl-R$_5$ group which is added after formation of the bicyclic amide (IV, which has N$_5$=—NH—) and (4) the addition of the desired substituent at C$_3$ when the imidazole ring is formed. EXAMPLES 1, 2, (3 and 4), (5 and 6), (7 and 8), (9–12), (13–16), 17 and 18), (19–24) and (25–28) all exemplify step 1, formation of the bicyclic amide (IV) containing the desired $W_5$, $W_6$, $W_7$ and $W_8$ substituent (by starting with the appropriate starting material) and the desired $R_4$ substituent. EXAMPLES 29, 32, 35, 37, 39, 41, 43, 45 and 46 all exemplify step 2, the addition of the exocyclic carbonyl with the attached desired $R_5$ substituent. EXAMPLES 30, 31, 33, 34, 36, 38, 40, 42, 44, 45B and 47 exemplify step 3, the formation of the imidazole ring with the $R_3$ substituent. Following the general procedure of one or more of the above EXAMPLES (for each of steps 1, 2 and 3), making non-critical variations and starting with the appropriate starting material containing the desired $W_5$, $W_6$, $W_7$ and $W_8$ substituents, the compounds of the EXAMPLES below are formed:

EXAMPLE 48

5-(tert-Butyloxycarbonyl)-7-chloro-3-(5-cyclopropyl-1,2,4-oxadiazol-3-yl)-4,5-dihydroimidazo[1,5-a]-quinoxaline (I)

mp 218°–220°; IR (mineral oil) 2954, 2926, 1710, 1570, 1507, 1370, 1343, 1222 and 1213 cm$^{-1}$; NMR (CDCl$_3$) 8.08, 7.82, 7.47, 7.2–7.3, 5.22, 2.25–2.35, 1.54 and 1.2–1.4 δ; MS (m/z) 413, 313, 244 and 229.

EXAMPLE 49

7-Chloro-3-(5-cyclopropyl-1,2,4-oxadiazol-3-yl)-5-(2-furoyl)-4,5-dihydroimidazo[1,5-a]quinoxaline (I)

mp dec 190°: IR (mineral oil) 2954, 2925, 2855, 1671, 1577, 1510, 1468, 1366 and 1304 cm$^{-1}$; NMR (300 MHz, CDCl$_3$) 8.33, 7.58, 7.46, 7.32, 7.25, 7.15, 6.55, 5.44, 2.2–2.35 and 1.15–1.4 δ; MS (m/z) 407, 312 and 244.

EXAMPLE 50

5-Benzoyl-7-chloro-3-(5-cyclopropyl-1,2,4-oxadiazol-3-yl)-4,5-dihydro-imidazo[1,5-a]quinoxaline (I)

mp 228°–229°: IR (mineral oil) 2954, 2924, 2855, 1672, 1576, 1510, 1363, 1337 and 1207 cm$^{-1}$; NMR (CDCl$_3$) 8.41, 7.61, 7.2–7.6, 7.15, 5.35, 2.1–2.3 and 1.1–1.3 δ; MS (m/z) 417 348, 312 and 105.

EXAMPLE 51

5-(tert-Butyloxycarbonyl)-3-(5-cyclopropyl-1,2,4-oxadiazol-3-yl)-6-fluoro-4,5-dihydroimidazo-[1,5-a]quinoxaline (I)

mp 199°–200°; MS (m/z) at 397; IR (mineral oil) 1715, 1494, 1505, 1226 and 880 cm$^{-1}$; NMR (CDCl$_3$) 1.23, 1.36, 1.45, 2.27, 7.10, 7.32 and 8.12 δ.

EXAMPLE 52

5-Acetyl-7-chloro-3-(5-cyclopropyl-1,2,4-oxadiazol-3-yl)4,5-dihydro-imidazo[1,5-a]quinoxaline (I)

mp 191°–192: IR (mineral oil) 2954, 2925, 2855, 1663, 1575, 1504, 1386, 1211, 948 and 903 cm$^{-1}$; NMR (CDCl$_3$) 8.10, 7.53, 7.0–8.0, 7.37, 5,28, 2.34, 2.2–2.45 and 1.15–1.45 δ; MS (m/z) 355, 312, 272, 244 and 229.

EXAMPLE 53

7-Chloro-3-(5-cyclopropyl-1,2,4-oxadiazol-3-yl)-4,5-dihydro-5-propionylimidazo[1,5-a]quinoxaline (I)

mp 185°–186°; IR (mineral oil) 2954, 2927, 2855, 1688, 1583, 1506, 1382, 1315, 1201, 1192, 1169, 948, 898 and 817 cm$^{-1}$; NMR (CDCl$_3$) 8.09, 7.72, 7.52, 7.36, 5.27, 2.62, 2.2–2.35, 1.1–1.4 and 1.19 δ; MS m/z 370.

EXAMPLE 54 tert-Butyl 7-chloro-4,5-dihydro-5-[(pyrrolidino)carbonyl]-imidazo[1,5-a]quinoxaline-3-carboxylate (I)

mp 194°–196°; IR (mineral oil) 2954, 2925, 2855, 1725, 1661, 1507, 1406, 1383, 1370, and 1125 cm$^{-1}$; NMR (CDCl$_3$) 7.97, 7.43, 7.15, 7.12, 4.99, 3.2–3.4, 1.8–1.9, and 1.62 δ; MS m/z) 402, 346, 248, 231 and 98.

EXAMPLE 55 tert-Butyl 7-Chloro-5-[(dimethylamino)carbonyl]4,5-dihydro-imidazo[1,5-a]quinoxaline-3-carboxylate (I)

mp 210°–211.5°: IR (mineral oil) 2954, 2925, 2855, 1726, 1660, 1506, 1459, 1455, 1381, 1194, 1185, 1 150 and 1126 c$^{-1}$; NMR (CDCl$_3$) 7.97, 7.44, 7.12, 7.08, 4.94, 2.89 and 1.62 δ; MS (m/z) 376, 320, 248 and 230.

EXAMPLE 56

7-Chloro-4,5-dihydro-3-(5-isopropyl-1,2A-oxadiazol-3-yl)-5-[(pyrrolidino)carbonyl]imidazo-[1,5-a]quinoxaline (I)

mp 201°–201.5°: IR (mineral oil) 2954, 2923, 2855, 1659, 1566, 1505, 1464, 1451, 1410, 1389, 1364, 1309, 1282, 1192 and 949 cm$^{-1}$; NMR (CDCl$_3$) 8.09, 7.48, 7.1–7.2, 5.05, 3.2–3.4, 1.8–1.9 and 1.46 δ; MS (m/z) 412, 341, 314, 272 and 98.

EXAMPLE 57

7-Chloro-5-[(dimethylamino)carbonyl]-4,5-dihydro-3-(3-isopropyl-1,2,4-oxadiazol-5-yl)-imidazo[1,5-a]quinoxaline (I)

mp 189°–190.5°; IR (mineral oil) 3102, 2954, 2925, 2855, 1653, 1638, 1511, 1383, 1365 and 1198 cm$^{-1}$; NMR (300 MHz, CDCl$_3$) 8.11, 7.50, 7.16, 7.10, 5.04, 3.05–3.25, 2.91 and 1.40 δ; MS (m/z) 386, 314, 271 and 230.

EXAMPLE 58

7-Chloro-3-(5-ethyl-1,2,4-oxadiazol-3-yl)-4,5-dihydro-5-[(pyrrolidino)carbonyl]imidazo[1,5-a]quinoxaline (I)

mp 220°–221.5°; IR (mineral oil) 2966, 2961, 2953, 2926, 1654, 1623, 1570, 1508, 1391, 1385, 1380 and 1367 cm$^{-1}$; NMR (CDCl$_3$) 8.09, 7.47, 7.1–7.2, 5.05, 3.31, 2.97, 1.75–1.95 and 1.45 δ; MS (m/z) 398, 300, 272 and 98.

EXAMPLE 59

7-Chloro-5-[(dimethylamino)carbonyl]-3-(5-ethyl-1,2,4-oxadiazol-3 -yl)-4,5-dihydroimidazo-[1,5-a]quinoxaline (I)

mp 205°–207.5°; IR (mineral oil) 3100, 2953, 2925, 2868, 2855, 1666, 1577, 1507, 1485, 1473, 1383, 1363, 1310, 1281, 1271, 1205, 1188 and 1177 cm$^{-1}$; NMR (CDCl$_3$) 8.09, 7.48, 7.14, 7.08, 5.01, 2.97, 2.90 and 1.45 δ; MS (m/z) 372, 300, 272 and 72.

EXAMPLE 60 tert-Butyl 7-Fluoro4,5-dihydro-5 -[(pyrrolidino)carbonyl]imidazo[1,5-a]quinoxaline-3-carboxylate (I)

mp 115–116; IR (mineral oil) 1689, 1652, 1365, 1396 and 1519 cm–1; MS (m/z) 386; NMR (CDCl$_3$) 1.62, 1.86, 3.33, 4.99, 6.88, 7.45 and 7.95 δ.

EXAMPLE 61

7-Fluoro-4,5-dihydro-3-(5-isopropyl-1,2,4-oxadiazol-3-yl)-5-[(pyrrolidino)carbonyl]imidazo[1,5-a]quinoxaline (I)

mp 211–212.5; IR 1511, 1410, 1664, 1565 and 1393 cm–1; MS (m/z) 396; NMR (CDCl$_3$) 1.46, 1.85, 3.32, 5.04, 6.91, 7.50 and 8.07 δ.

EXAMPLE 62

7-Chloro-5-[(dimethylamino)carbonyl]4,5-dihydro-3-(5-isopropyl-1,2,4-oxadiazol-3-yl)imidazo-[1,5-a]quinoxaline (I)

mp 145°–146°: IR (mineral oil) 2953, 2925, 2855, 1662, 1563, 1508, 1503, 1458, 1380, 1187 and 821 cm$^{-1}$; NMR (CDCl$_3$) 8.09, 7.48, 7.05–7.2, 5.01, 3.2–3.4, 2.90 and 1.46 δ; MS m/z) 386, 314 and 272.

EXAMPLE 63 tert-Butyl 6-chloro4,5-dihydro-5-[(pyrrolidino)carbonyl]-imidazo[1,5-a]quinoxaline-3-carboxylate (I)

mp 246°–248°: IR (mineral oil) 2925, 1691, 1671, 1373, 1360, 1296, 1159 and 1080 cm$^{-1}$; NMR (CDCl$_3$) 8.00, 7.46, 7.36, 7.21, 5.06, 3.35–3.45, 1.85–1.95 and 1.63 δ; MS (m/z) 402, 346, 248, 231,203 and 98.

EXAMPLE 64

6-Chloro-4,5-dihydro-3-(5-isopropyl-1,2,4-oxadiazol-3-yl)-5-[(pyrrolidino)carbonyl]imidazo[1,5-a]-quinoxaline (I)

mp 233.5°–234.5°; IR (mineral oil) 2926, 1670, 1491, 1381 and 1187 cm$^{-1}$; NMR (CDCl$_3$) 8.13, 7.50, 7.37, 7.26, 5.11, 3.2–3.4, 1.8–1.95 and 1.47 δ; MS (m/z) 412, 377, 342, 314, 272 and 98.

EXAMPLE 65 tert-Butyl 6-chloro-5-[(dimethylamino)carbonyl]-4,5-dihydro-imidazo[1,5-a]quinoxaline-3-carboxylate (I)

mp 227°–228°; IR (mineral oil) 2925, 1694, 1681, 1381, 1374, 1370, 1154 and 1083 cm$^{-1}$; NMR (CDCl$_3$) 8.00, 7.46, 7.37, 7.22, 5.00, 3.02 and 1.63 δ; MS (m/z) 376, 320, 303, 248, 231, 203 and 72.

EXAMPLE 66

6-Chloro-3-(5-ethyl-1,2,4-oxadiazol-3-yl)-4,5-dihydro-5-[(pyrrolidino)carbonyl]imidazo[1,5-a]quinoxaline (I)

mp 245°–246°: IR (mineral oil) 2924, 1668, 1493, 1381, 1182 and 787 cm$^{-1}$; NMR (CDCl$_3$) 8.13, 7.50, 7.37, 7.23, 5.11, 3.3–3.45, 2.98, 1.8–1.95 and 1.46 δ; MS (m/z) 398, 363, 328, 300, 272 and 98.

EXAMPLE 67

6-Chloro-5-[(dimethylamino)carbonyl]4,5-dihydro-3-(5-isopropyl-1,2,4-oxadiazol-3-yl)imidazo[1,5-a]-quinoxaline (I)

mp 227.5°–228.5°; IR (mineral oil) 2924, 1672, 1492, 1464, 1387, 1184 and 780 cm$^{-1}$; NMR (CDCl$_3$) 8.13, 7.51, 7.37, 7.24, 5.06, 3.25–3.4, 3.00 and 1.47 δ; MS (m/z) 386, 341, 314, 298, 272 and 72.

EXAMPLE 68

6-Chloro-4,5-dihydro-3-(3-isopropyl-1,2,4-oxadiazol-5-yl)-5-[(pyrrolidino)carbonyl]imidazo[1,5-a]-quinoxaline (I)

mp 208°–209°; IR (mineral oil) 2926, 1655, 1393, 1072 and 779 cm$^{-1}$; NMR (CDCl$_3$) 8.15, 7.51, 7.41, 7.26, 5.15, 3.35–3.45, 3.1–3.25, 1.85–1.95 and 1.41 δ; MS (m/z) 412, 377, 342, 230 and 98.

EXAMPLE 69

6-Chloro-5-[(dimethylamino)carbonyl]-3-(5-ethyl-1,2,4-oxadiazol-3-yl)-4,5-dihydroimidazo[1,5-a]-quinoxaline (I)

mp 252°–254°; IR (mineral oil) 2925, 1668, 1494, 1389, 1180 and 780 cm$^{-1}$; NMR (CDCl$_3$) 8.12, 7.50, 7.38, 7.24, 5.05, 3.00, 2.99 and 1.46 δ; MS (m/z) 372, 328, 300, 272 and 72.

EXAMPLE 70

6-Chloro-5-[(dimethylamino)carbonyl]-4,5-dihydro-3-(3-isopropyl-1,2,4-oxadiazol-5-yl)imidazo[1,5-a]-quinoxaline (I)

mp 197.5°–198°; IR (mineral oil) 2925, 1678, 1492, 1466, 1385 and 780 cm$^{-1}$; NMR (CDCl$_3$) 8.15, 7.52, 7.41, 7.26, 5.09, 3.1–3.3, 3.02 and 1.41 δ; MS (m/z) 386, 351,342, 314, 230 and 72.

EXAMPLE 71

7-Chloro-3-(5-cyclopropyl-1,2,4-oxadiazol-3-yl)-4,5-dihydro-4,4-dimethyl-5-[(pyrrolidino)carbonyl]-imidazo[1,5-a]quinoxaline (I)

mp 207°–208°; IR (mineral oil) 3118, 2954, 2925, 2855, 1653, 1588, 1518, 1416, 1187 and 945 cm$^{-1}$; NMR (CDCl$_3$) 8.07, 7.41, 7.00, 6.80, 3.59, 2.8–3.4, 2.2–2.35, 1.5–2.2 and 1.15–1.45 δ; MS (m/z) 438, 423 and 98.

EXAMPLE 72

7-Chloro-3-(5-cyclopropyl-1,2,4-oxadiazol-3-yl)-5-[(dimethylamino)carbonyl]-4,5-dihydro-4,4-dimethyl-imidazo[1,5-a]quinoxaline (I)

mp 162°–165°, IR (mineral oil) 2953, 2924, 2855, 1675, 1570, 1511, 1474, 1379, 1325, 1196, 1187, 949 and 813 cm$^{-1}$; NMR (CDCl$_3$) 8.08, 7.41, 7.00, 6.70, 3.08, 2.75, 2.2–2.35, 1.95, 1.69 and 1.15–1.45 δ; MS (m/z) 412 and 397.

EXAMPLE 73

7-Chloro-4,5-dihydro-3-(5-isopropyl-1,2,4-oxadiazol-3-yl)4,4-dimethyl-5-[(pyrrolidino)carbonyl]imidazo-[1,5-a]quinoxaline (I)

mp 193°–195°; IR (mineral oil) 2953, 2925, 2855, 1654, 1518 and 1410 cm$^{-1}$; NMR (CDCl$_3$) 8.07, 7.42, 7.01, 6.80, 3.59, 2.8–3.4, 1.5–2.1 and 1.47 δ; MS (m/z) 440 and 425.

EXAMPLE 74

7-Chloro-5-[(dimethylamino)carbonyl]-4,5-dihydro-3-(5-isopropyl-1,2,4-oxadiazol-3-yl)4,4-dimethyl-imidazo-[1,5-a]quinoxaline (I)

mp 120°–121°; IR (mineral oil) 2953, 2925, 1659, 1567, 1519, 1513, 1384, 1333 and 1301 cm$^{-1}$; NMR (CDCl$_3$) 8.08, 7.43, 7.03, 6.72, 3.2–3.4, 3.10, 2.78, 1.99, 1.72 and 1.47 δ; MS (EI m/z) 414 and 399.

EXAMPLE 75 tert-Butyl 7-chloro-4,5-dihydro-4,4-dimethyl-5-[(pyrrolidino)-carbonyl]imidazo[1,5-a]quinoxaline-3-carboxylate (I)

mp 168°–169°; IR (mineral oil) 2973, 2953, 2925, 2855, 1711, 1661, 1513, 1411, 1383, 1367, 1288, 1180, 1147 and 970 cm$^{-1}$; NMR (CDCl$_3$) 7.93, 7.37, 6.98, 6.78, 3.5–3.7, 2.8–3.4, 1.5–2.2 and 1.63 δ; MS (EI m/z) 430, 415 and 244.

EXAMPLE 76 tert-Butyl 7-chloro-5-[(dimethylamino)carbonyl]-4,5-dihydro4,4-dimethylimidazo[1,5-a]quinoxaline-3-carboxylate (I)

mp 168°–169°; IR (mineral oil) 2954, 2925, 1725, 1718, 1672, 1511, 1277 and 1141 cm$^{-1}$; NMR (CDCl$_3$) 7.94, 7.38, 6.99, 6.70, 3.10, 2.77, 2.06, 1.68 and 1.63 δ; MS (EI m/z) 404, 389, 244.

EXAMPLE 77

7-Chloro-5-[(dimethylamino)carbonyl]4,5-dihydro-3-(3-isopropyl-1,2,4-oxadiazol-5-yl)-4,4-dimethyl-imidazo-[1,5-a]quinoxaline (I)

mp 122°–125°; IR (mineral oil) 2954, 2924, 2855, 1677, 1618, 1512, 1467, 1460, 1385 and 949 cm$^{-1}$; NMR (CDCl$_3$) 8.10, 7.44, 7.04, 6.74, 3.0–3.25, 3.11, 2.80, 2.10, 1.74 and 1.40 δ; MS (EI m/z) 414 and 399.

EXAMPLE 78

7-Chloro-3-(5-ethyl-1,2,4-oxadiazol-3-yl)-4,5-dihydro-4,4-dimethyl-5-[(pyrrolidino)carbonyl]imidazo-[1,5-a]quinoxaline (I)

mp 223°–224°; IR (mineral oil) 2953, 2925, 1654, 1577, 1517, 1410 and 1389 cm$^{-1}$; NMR (CDCl$_3$) 8.07, 7.42, 7.01, 6.81, 3.60, 3.00, 2.8–3.4, 1.4–2.2 and 1.46 δ MS (EI m/z) 426 and 411.

EXAMPLE 79

7-Chloro-5-[(dimethylamino)carbonyl]-3-(5-ethyl-1,2,4-oxadiazol-3-yl)-4,5-dihydro-4,4-dimethyl-imidazo-[1,5-a]quinoxaline (I)

mp 175.5°–177.5°; IR (mineral oil) 2953, 2925, 2855, 1668, 1568, 1514 and 1183 cm$^{-1}$; NMR (CDCl$_3$) 8.08, 7.43, 7.03, 6.72, 3.10, 3.00, 2.78, 1.99, 1.72 and 1.46 δ; MS (EI m/z) 400 and 385.

EXAMPLE 80 tert-Butyl 6-chloro-4,5-dihydro-4,4-dimethyl-5-[(pyrrolidino)-carbonyl]imidazo[1,5-a]quinoxaline-3-carboxylate (I)

IR (mineral oil) 2954, 2925, 2856, 1707, 1666, 1496, 1476, 1461, 1392, 1369, 1346, 1284, 1151 and 1050 cm$^{-1}$; NMR (CDCl$_3$) 8.02, 7.40, 7.30, 7.08, 3.3–3.7, 2.5–2.9, 1.92, 1.5–1.9 and 1.63 δ; MS (EI m/z) 430, 259, 244 and 98.

EXAMPLE 81

6-Chloro4,5-dihydro-3-(5-isopropyl-1,2,4-oxadiazol-3-yl)4,4-dimethyl-5-[(pyrrolidino)carbonyl]-imidazo[1,5-a]quinoxaline (I)

mp 147°–148°; IR (mineral oil) 2954, 2924, 2856, 1657, 1645, 1494, 1462, 1398 and 1386 cm$^{-1}$; NMR (CDCl$_3$) 8.12, 7.44, 7.31, 7.11, 3.2–3.6, 2.5–2.8, 1.89, 1.5–2.0 and 1.47 δ; MS (EI m/z 440, 425 and 98.

EXAMPLE 82

6-Chloro-5-[(dimethylamino)carbonyl]4,5-dihydro-3-(5-isopropyl-1,2,4-oxadiazol-3-yl)-4,4-dimethyl-imidazo-[1,5-a]quinoxaline (I)

mp 171°–172°; IR (mineral oil) 2960, 2925, 1660, 1496, 1467, 1375 and 1209 cm$^{-1}$; NMR (CDCl$_3$) 8.14, 7.45, 7.32, 7.13, 3.2–3.4, 2.79, 1.86 and 1.47 δ; MS (E m/z) 414 and 399.

EXAMPLE 83

6-Chloro-3-(5-ethyl-1,2,4-oxadiazol-3-yl)4,5-dihydro-4,4-dimethyl-5-[(pyrrolidino)carbonyl]imidazo-[1,5-a]quinoxaline (I)

mp 204°–206°; IR (mineral oil) 2954, 2926, 2856, 1653, 1645, 1498, 1461, 1399 and 1394 cm$^{-1}$; NMR (CDCl$_3$) 8.12, 7.44, 7.31, 7.11, 3.2–3.7, 3.00, 2.5–2.9, 1.89, 1.55–2.0 and 1.47 δ; MS (EI m/z) 426, 411 and 98.

EXAMPLE 84

6-Chloro-4,5-dihydro-3-(3-isopropyl-1,2,4-oxadiazol-5-yl)4,4-dimethyl-5-[(pyrrolidino)carbonyl]-imidazo[1,5-a]quinoxaline (I)

mp 175°–176°; IR (mineral oil) 2953, 2925, 2855, 1660, 1648, 1497, 1462, 1401 and 1390 cm$^{-1}$; NMR (CDCl$_3$) 8.14, 7.4.5, 7.34, 7.13, 3.3–3.7, 3.1–3.25, 2.6–3.0, 1.95, 1.6–1.9 and 1.40 δ; MS (EI m/z) 440, 425 and 98.

EXAMPLE 85 tert-Butyl 6-chloro-5-[(dimethylamino)carbonyl]-4,5-dihydro4,4-dimethylimidazo[1,5-a]quinoxaline-3-carboxylate (I)

mp 155°–158°; IR (mineral oil) 3113, 2953, 2923, 2855, 1710, 1668, 1541, 1502, 1488, 1478, 1466. 1453, 1375, 1368, 1349, 1331, 1296, 1287, 1206, 1193, 1168, 1161, 1147, 1133, 1057 and 774 cm$^{-1}$; NMR (CDCl$_3$) 7.98, 7.40, 7.30, 7.11, 2.82, 1.88 and 1.63 δ; MS (EI m/z) 404, 389, 333, 259 and 244.

EXAMPLE 86

6-Chloro-5-[(dimethylamino)carbonyl]-4,5-dihydro-3-(3-isopropyl-1,2,4-oxadiazol-5-yl)4,4-dimethyl-imidazo[1,5-a]quinoxaline (I)

mp 184.5°–185.5°; IR (mineral oil)2956, 2925, 2855, 1662, 1617, 1495, 1468, 1376, 1326, 1283, 1206 and 795 cm$^{-1}$; NMR (CDCl$_3$) 8.13, 7.46, 7.34, 7.16, 3.1–3.3, 2.87, 1.91 and 1.40 δ; MS (EI m/z) 414, 399 and 72.

EXAMPLE 87

6-Chloro-5-[(dimethylamino)carbonyl]-3-(5-ethyl-1,2,4-oxadiazol-3-yl)-4,5-dihydro-4,4-dimethyl-imidazo[1,5-a]quinoxaline (I)

mp 176°–177.5°; IR (mineral oil) 2953, 2925, 2855, 1671, 1584, 1503, 1488, 1463, 1380 and 1182 cm$^{-1}$; NMR (CDCl$_3$) 8.12, 7.45, 7.31, 7.13, 3.00, 2.79, 1.87 and 1.47 δ; MS (EI m/z) 400, 385, 300 and 72.

EXAMPLE 88

3-(5-Cyclopropyl-1,2,4-oxadiazol-3-yl)-45-dihydro-imidazo[1,5-a]quinoxaline (XXXIII)

A solution of the 1,2,3,4-tetrahydroquinoxalin-2-one (IV, 5.51 g) and THF (55 ml) is cooled to –40°, and potassium tert-butoxide (1.0 M in THF, 34.8 ml) is added dropwise over 5 min. The mixture is allowed to warm to –20° over 1 hr. DMF (10 ml) and THF (40 ml) are added to the resultant solid, allowing the mixture to stir. The mixture is cooled to –50°, and diethyl chlorophosphate (5.02 ml) is added dropwise over 5 min. The mixture is allowed to warm to –20° over 1 hr. The mixture is cooled to –78°, and the oxadiazole isocyanide (5.70 g) is added. Potassium tert-butoxide (34.8 ml) is added dropwise over 15 min, the mixture is allowed to warm slowly to 20°–25°, and is stirred for 3 days at 20°–25°. The mixture is quenched with water, filtered, washed with water and dried to provide the desired material as a solid. Additional solids that precipitated from the filtrate are filtered, triturated with ethyl acetate/hexane (20/80) and dried to give the title compound, mp 243°–245°; NMR (CDCl$_3$) 8.07, 7.47, 7.10, 6.8–6.9, 4.81, 4.08, 2.2–2.3 and 1.2–1.4 δ.

EXAMPLE 89

3-(5-Cyclopropyl-1,2,4-oxadiazol-3-yl)-4,5-dihydro-5-propionyl-imidazo[1,5-a]quinoxaline A mixture of 3-(5-cyclopropyl-1,2,4-oxadiazol-3-yl)-4,5-dihydroimidazo[1,5 -a]quinoxaline (XXXIII, EXAMPLE 88, 0.442 g), propionic anhydride (2 ml) and THF (1 ml) is stirred at 80° for 6 hr. The solvent is then removed under reduced pressure with heat and the residue is partitioned between ethyl acetate, aqueous sodium bicarbonate and saline. The phases are separated and the organic phase is dried over magnesium sulfate and concentrated. The crude product is chromatographed on silica gel eluting with ethyl acetate/dichloromethane (10/90). The appropriate fractions are pooled and concentrated to give a solid which is crystallized from dichloromethane and hexane to give the title compound, mp 175°–176°; MS (m/z) at 335; IR (mineral oil) 1491, 1671, 1509. 1202 and 1422 cm$^{631}$ $^1$; NMR (CDCl$_3$) 1.16, 1.24, 1.37, 2.28, 2.58, 5.30, 7.36, 7.60, and 8.12 δ.

EXAMPLE 90

3-(5-Cyclopropyl-1,2,4-oxadiazol-3-yl)-5-(ethoxyoxalyl)-4,5-dihydroimidazo[1,5-a]quinoxaline(I)

Triethylamine (0.11 ml) and DMF (4 ml) are added to 3-(5-cyclopropyl-1,2,4-oxadiazol- 3-yl)-4,5-dihydroimidazo[1,5a]quinoxaline (XXXIII, EXAMPLE 88, 0.20 g) in THF (6 ml). Ethyl oxalyl chloride (0.088 ml) is then added dropwise over about 5 min. The mixture is stirred for 1 hr, concentrated, and partitioned between dichloromethane and aqueous sodium bicarbonate. The phases are separated and the organic phase is dried over sodium sulfate and concentrated. The crude product is chromatographed on silica gel (90 ml) eluting with ethyl acetate/cyclohexane (60/40). The appropriate fractions are pooled and concentrated to give the title compound, mp 150°–151°; MS (m/z) at 379; IR (mineral oil) 1745, 1659, 1516, 1422, 1501 cm$^{-1}$; NMR (CDCl$_3$) 1.17, 1.28, 1.37, 4.20, 4.43, 5.20, 5.38, 7.31, 7.51, 7.63, 8.17 and 8.19 δ.

EXAMPLE 91

5-[(2-Chloro)benzoyl]-3-(5-cyclopropyl-1,2,4-oxadiazol-3-yl)-4,5-dihydroimidazo[1,5-a]quinoxaline (I)

A slurry consisting of 3-(5-cyclopropyl-1,2,4-oxadiazol-3-yl)-4,5-dihydroimidazo[1,5 -a]quinoxaline (XXXIII, EXAMPLE 88, 0.492 g), 2-chlorobenzoyl chloride (0.268 ml), dimethyl-aminopyridine (0.0538 g), diisopropylethylamine (0.368 g), and THF (9 ml) is stirred at 20°–25° for 1.5 hr. The mixture is then partitioned between ethyl acetate, aqueous sodium bicarbonate, and saline. The product is poorly soluble in both the organic and aqueous phases, filtration of the extraction solvents gives additional material. The crude product is then triturated with ethyl ether and dried to give the title compound, mp 254°–256°; MS (m/z)

EXAMPLE 92

3-(5-Cyclopropyl-1,2,4-oxadiazol-3-yl)-4,5-dihydro-
5-[(morpholino)-carbonyl]imidazo[1,5-a]quinoxaline
(I)

To a slurry consisting of 3-(5-cyclopropyl-1,2,4-oxadiazol-3-yl)4,5-dihydroimidazo[1,5 -a]quinoxaline (XXXIII, EXAMPLE 88, 0.499 g), diisopropylethylamine (0.81 ml) and THF (15 ml) is added phosgene (1.93 M in toluene, 1.20 ml). A slight exotherm ensues and the slurry becomes homogeneous. After 10 min, morpholine (0.20 ml) is added. The mixture is stirred for 2 hr and then partitioned between ethyl acetate, water, and saline. The phases are separated and the organic phase is dried over magnesium sulfate and concentrated. The crude product is chromatographed on silica gel (150 ml) eluting with methanol/dichloromethane (2/98). The appropriate fractions are pooled and concentrated to give the product. Recrystallization from dichloromethane and hexane gives the title compound, mp 198.0°–198.5°; MS (m/z) at 392; IR 1662, 1506, 1409, 1277, and 1579 cm$^{-1}$; NMR (CDCl$_3$) 1.24, 1.36, 2.27, 3.33, 3.64, 5.02, 7.21, 7.27, 7.55 and 8.11 δ.

EXAMPLE 93

3-(5-Cyclopropyl-1,2,4-oxadiazol-3-yl)-5-[(3,5-
dimethylpyrazolo)carbonyl]4,5-dihydroimidazo-
[1,5-a]quinoxaline (I)

Following the general procedure of EXAMPLE 92 and making non-critical variations but starting with 3-(5-cyclopropyl-1,2,4-oxadiazol-3-yl)-4,5-dihydroimidazo[1,5-a]quinoxaline (XXXIII, EXAMPLE 88, 0.501 g) and 3,5-dimethylpyrazole (0.426 g) the title compound is obtained, mp 85°–95° (decomp); MS (m/z) at 401; IR (mineral oil) 1388, 1702, 1355, 1414, and 1420 cm$^{-1}$; NMR (CDCl$_3$) 1.24, 2.19, 2.21, 2.43, 5.41, 5.99, 7.22, 7.32, 7.59, and 8.15 δ.

EXAMPLE 94

Ethyl
4,5-Dihydro-4,4-dimethylimidazo[1,5-a]quinoxaline-
3-carboxylate (XXXIII)

Potassium tert-butoxide (1M, 4.54 ml) is added to 1,2,3,4-tetrahydro-3,3 -dimethylquinoxalin-2-one (IV, EXAMPLE 2, 0.762 g) in THF (4 ml) at ice/saline temperature. The reaction is stirred for 40 min, at which time diethyl chlorophosphate (0.656 ml) is added. After stirring at ice-saline temperature for 2 hr, ethyl isocyanoacetate (0.562 g) is added, followed by potassium t-butoxide (1 M, 4.97 ml). The reaction is stirred for 3.5 hr, allowing it to slowly warm to 20°–25°. The reaction is then quenched with several drops of acetic acid and then partitioned between ethyl acetate, aqueous sodium bicarbonate and saline. The phases are separated and the organic phase is dried over magnesium sulfate, concentrated, and the resulting crude product chromatographed on silica gel (200 ml) eluting with methanol/ dichloromethane (2/98). The appropriate fractions are pooled and concentrated to give the title compound, mp 145°–149°; NMR (CDCl$_3$) 1.44, 1.74, 3.79, 4.40, 6.77, 6.82, 7.10, and 7.39 δ.

EXAMPLE 95

Ethyl
4,5-Dihydroimidazo[1,5-a]quinoxaline-3-carboxylate
(XXXIII)

Potassium tert-butoxide (1M in THF, 7.5 ml) is added to 1,2,3,4-tetrahydroquinoxalin-2-one (IV, EXAMPLE 1, 1.01 g) in THF (10 ml) cooled to 0°. A slurry formed after the addition is complete. Additional THF (5 ml) is added. The ice bath is removed and the reaction is stirred for 30 min, when it is cooled at –78°. Diethylchlorophosphate (1.08 ml) is added and the dry ice/acetone bath is replaced with an ice/water bath. The reaction is stirred for 1 hr, when it is again cooled at –78°. Ethyl isocyanoacetate (0.82 ml) is added, followed by potassium tert-butoxide (1M in THF, 7.5 ml) over 10 min. Ten minutes after the addition is complete, the dry ice bath is removed and the reaction is allowed to slowly warm to 20°–25°. When it has stirred for a total of 3 hr, aqueous ammonium chloride (about 1 ml) is added. The mixture is partitioned between a mixture of chloroform and dichloromethane and water. The phases are separated, the organic phase is filtered through sodium sulfate, concentrated, and the residue crystallized from methanol/dichloromethane/hexane to give the title compound, mp 248°–250°; MS (m/z) at 243; NMR (CDCl$_3$) 1.42, 4.08, 4.39, 4.83, 6.80, 6.85, 7.11, 7.39 δ.

EXAMPLE 96

3-(5-Cyclopropyl-1,2,4-oxadiazol-3-yl)-7-fluoro-
4,5-dihydroimidazo[1,5-a]quinoxaline (XXXIII)

Potassium tert-butoxide (1M in THF, 13.8 ml) is added to 7-fluoro-1,2,3,4 -tetrahydroquinoxalin-2-one (IV, EXAMPLE 6, 2.186 g) in THF (5 ml) and DMF (2 ml) cooled to 0°. The ice bath is removed and stirring improves as the reaction warms. After 15 min, the reaction is cooled in an ice/saline bath and diethylchlorophosphate (2.00 ml) is added. After 25 min 5 -cyclopropyl-3-isocyanomethyl-1,2, 4-oxadiazole (2.16 g) is added, followed by potassium tert-butoxide (14.5 ml). After stirring for 80 min, about 75 ml of water and ice is added. The solid is collected and washed several times with water, followed by small aliquots of ether. The solid is dried in under reduced pressure with heat over the weekend and then triturated with ether and with dichloromethane. The solid is collected and dried to give the title compound, mp 263°–265°; NMR (CDCl$_3$) 1.25, 1.32, 2.26, 4.78, 6.55, 7.38 and 8.07 δ.

EXAMPLE 97

3-(5-Cyclopropyl-1,2,4-oxadiazol-3-yl)-4,5-dihydro-4,4-
dimethylimidazo[1,5-a]quinoxaline (XXXIII)

Following the general procedure of EXAMPLES 88 and 94–96 and making non-critical variations but starting with 1,2,3,4-tetrahydroquinoxalin-2-one (IV, EXAMPLE 2), the title compound is obtained, mp 166°–169°; MS (m/z) at 307; NMR (CDCl$_3$) 1.23, 1.37, 2.27, 3.78, 6.79, 6.85, 7.10, 7.41 and 8.09 δ.

EXAMPLE 99

3-(3-Cyclopropyl-1,2,4-oxadiazol-5-yl)-4,5-dihydro-
4,4-dimethyl¹- imidazo[1,5-a]quinoxaline (XXXIII)

Potassium tert-butoxide (1M in THF, 1.95 ml) is added to cyclopropylcarboxamide oxime (0.195 g) in THF (7 ml) at 0°. After 10 min ethyl 4,5-dihydro-4,4-dimethylimidazo[1, 5-a]quinoxaline-3-carboxylate (XXXIII, EXAMPLE 94, 0.503 g) is added. The ice bath is removed after stirring for 10 min and the reaction is allowed to slowly warm to 20°–25°. After 2 hr DMF (4 ml) is added. When the reaction had stirred for a total of 7 hr, the solvents are removed under reduced pressure and the residue is partitioned between ethyl acetate and saline. The phases are separated, the organic phase is dried over magnesium sulfate and concentrated to give the title compound; mp 175°–179°; NMR (CDCl$_3$): 1.10, 1.76, 2.18, 3.83, 6.79, 6.85, 7.13, 7.42 and 8.10 δ.

EXAMPLE 100

5-Acetyl-3-(3-cyclopropyl-1,2,4-oxadiazol-5-yl)-4,5-dihydro-4,4-dimethylimidazo[1,5-a]quinoxaline (I)

A mixture of 3-(3-cyclopropyl-1,2,4-oxadiazol-5-yl)-4,5-dihydro-4,4-dimethylimidazo-[1,5-a]quinoxaline (XXXIII, EXAMPLE 99, 0.19 g) and acetic anhydride (3 ml) is stirred at 100° for 3 days. Excess acetic anhydride is then removed under reduced pressure and the residue is partitioned between dichloromethane and aqueous sodium bicarbonate. The phases are separated and the organic phase is filtered through sodium sulfate and concentrated. The crude product is chromatographed on silica gel (200 ml) eluting with ethyl acetate/dichloromethane (20/80). The appropriate fractions are pooled and concentrated to give the title compound, mp 169°–171°; MS (m/z) at 349; IR (mineral oil) 1666, 1613, 1327, 1281 and 1504 cm$^{-1}$; NMR (CDCl$_3$) 1.12, 1.94, 2.16, 2.18, 7.20, 7.33, 7.52 and 8.14 δ.

EXAMPLE 101

3-(3-Cyclopropyl-1,2,4-oxadiazol-5-yl)-4,5-dihydroimidazo[1,5-a]quinoxaline (XXXIII)

Sodium hydride (60% in oil, 0.142 g) is washed three times with pentane. THF (30 ml) is added, followed by cyclopropylcarboxamide oxime (0.356 g). After 10 min, Ethyl 4,5-dihydroimidazo[1,5-a]quinoxaline-3-carboxylate (XXXIII, EXAMPLE 95, 0.786 g) is added, followed by additional THF (5 ml). After an hour, DMP (14 ml) is added. The reaction is stirred an additional 4 hr, after which the solvents are removed under reduced pressure. Water is added to the residue and the solid is collected, washed with a small amount of ether, and dried under reduced pressure at 20°–25° to give the title compound, mp 248°–250°; NMR (CDCl$_3$) 1.07, 1.15, 1.93, 2.15, 4.83, 6.86, 7.14, 7.43 and 8.11 δ.

EXAMPLE 102

5-Acetyl-3-(3-cyclopropyl-1,2,4-oxadiazol-5-yl)-4,5-dihydroimidazo[1,5-a]quinoxaline (I)

A mixture of 3-(3-cyclopropyl-1,2,4-oxadiazol-5-yl)-4,5-dihydroimidazo[1,5-a]quinoxaline (XXXIII, EXAMPLE 101, 0.201 g) and acetic anhydride (3 ml) in THY (0.7 ml) is heated at 80° for 45 min. The reaction mixture is then cooled, concentrated, and partitioned between dichloromethane and aqueous sodium bicarbonate. The organic phase is separated and filtered through sodium sulfate and concentrated. The crude product is crystallized from dichloromethane and hexane to give the title compound, which is then recrystallized from ethyl ether/ethyl acetate/hexane. mp 202.0°–202.5°; MS (m/z) at 321; IR (mineral oil) 1674, 1639, 1501, 1358 and 1401 cm$^{-1}$; NMR (CDCl$_3$) 1.15, 2.18, 2.29, 5.32, 7.41.7.62 and 8.15 δ.

EXAMPLE 103

3-(5-Cyclopropyl-1,2,4-oxadiazol-3-yl)-6-fluoro-4,5-dihydroimidazo[1,5-a]quinoxaline (XXXIII)

A mixture of 5-(tert-butyloxycarbonyl)-3-(5-cyclopropyl-1,2,4-oxadiazol-3-yl)-6-fluoro-4,5-dihydroimidazo[1,5-a]quinoxaline (I, EXAMPLE 51, 3.39 g) and 50 ml of methanol saturated with HCl(g) is stirred at 20°–25° overnight. The solvent is then removed under reduced pressure and the residue is partitioned between dichloromethane and aqueous sodium bicarbonate. The organic phase is separated and dried over sodium sulfate and taken to dryness to give the title compound, NMR (CDCl$_3$) 1.23, 1.35, 2.26, 4.32, 4.86, 6.80, 6.95, 7.22 and 8.06 δ.

EXAMPLE 104

3-(5-Cyclopropyl-1,2,4-oxadiazol-3-yl)-5-[(dimethylamino)carbonyl]-6-fluoro-4,5-dihydroimidazo[1,5-a]-quinoxaline (I)

To 3-(5-cyclopropyl-1,2,4-oxadiazol-3-yl)-6-fluoro-4,5-dihydroimidazo[1,5-a]quinoxaline (XXXIII, EXAMPLE 103, 0.520 g) in THF (15 ml) is added diisopropylethylamine (0.305 ml) followed by phosgene (1.2M in toluene, 2.19 ml). After stirring for 3 hr, dimethylamine hydrochloride (0.285 g) is added followed by diisopropylethylamine (0.91 ml). The reaction is stirred for 3 hr, after which several ml of aqueous sodium bicarbonate is added. The reaction is concentrated under reduced pressure and the residue partitioned between dichloromethane, aqueous sodium bicarbonate and saline. The phases are separated, the organic phase is dried over sodium sulfate and concentrated. The solid is chromatographed on silica gel (150 ml) eluting with methanol/dichloromethane (2/98). The appropriate fractions are pooled and concentrated to give a solid, which is recrystallized from dichloromethane and hexane to give the title compound, mp 194°–195°; MS m/z at 368; IR (mineral oil) 1657, 1502, 1391, 786 and 1224 cm$^{-1}$; NMR (CDCl$_3$) 1.25, 1.36, 2.25, 2.94, 5.05, 7.08, 7.21, 7.37, 8.11 δ.

EXAMPLE 105

3-(5-Cyclopropyl-1,2,4-oxadiazol-3-yl)-6-fluoro-4,5-dihydro-5-[(pyrrolidino)carbonyl]-imidazo[1,5-a]-quinoxaline (I)

To 3-(5-cyclopropyl-1,2,4-oxadiazol-3-yl)-6-fluoro-4,5-dihydroimidazo[1,5-a]quinoxaline (XXXIII, EXAMPLE 103, 0.418 g) in THF (15 ml) is added diisopropylethylamine (0.245 ml) followed by phosgene (1.2M in toluene, 1.76 ml). The reaction is stirred for 3 hr, after which pyrrolidine (0.23 ml) and diisopropylethylamine (0.25 ml) are added. The reaction is stirred for 1 hr, then treated with several ml of water and concentrated. The residue is partitioned between dichloromethane, aqueous sodium bicarbonate, and saline. The phases are separated, the organic phase is dried over sodium sulfate and concentrated. The crude product is chromatographed on silica gel (150 ml) eluting with methanol/dichloromethane (2/98). The appropriate fractions are pooled and concentrated to give the product which is recrystallized from dichloromethane and hexane to give the title compound, mp 220.5°–221.5°; MS m/z at 394; IR (mineral oil) 1500, 1392, 1662, 1221, 793 and 1613 cm$^{-1}$; NMR (CDCl$_3$), 1.35, 1.86, 2.26, 3.33, 5.10, 7.08, 7.21, 7.37 and 8.11 δ.

EXAMPLE 106

5-Acetyl-3-(5-cyclopropyl-1,2,4-oxadiazol-3-yl)-6-fluoro-4,5-dihydroimidazo[1,5-a]quinoxaline (I)

A solution of 3-(5-cyclopropyl-1,2,4-oxadiazol-3-yl)-6-fluoro-4,5-dihydroimidazo[1,5-a]quinoxaline (XXXIII, EXAMPLE 103, 0.504 g), dimethylaminopyridine (0.03 g) and acetic anhydride (12 ml) is stirred at 100° for 1 hr. After cooling, excess acetic anhydride is removed under reduced pressure and the residue is partitioned between dichloromethane and aqueous sodium bicarbonate. The phases are separated and the organic phase is dried over sodium sulfate and concentrated. Chromatography on silica gel (320 ml) eluting with methanol/dichloromethane (2/98) gives a poor separation of the product from the imine byproduct. The imine impurily is successfully removed by taking up the mixture in dichloromethane and allowing the imine to precipitate out. The filtrate is collected, concentrated and the product crystallized from dichloromethane and hexane to give the title compound, mp 208.5°–210.0°; MS m/z at 339; IR (mineral oil) 1671, 1503, 1254, 879 and 1204 cm$^{-1}$; NMR (CDCl$_3$) 1.28, 2.38, 2.13, 2.29, 7.16, 7.41 and 8.13 δ.

EXAMPLE 107

5-Benzoyl-3-(5-cyclopropyl-1,2,4-oxadiazol-3-yl)-6-fluoro-4,5-dihydroimidazo[1,5-a]quinoxaline (I)

To 3-(5-cyclopropyl-1,2,4-oxadiazol-3-yl)-6-fluoro-4,5-dihydroimidazo[1,5-a]quinoxaline (XXXIII, EXAMPLE 103, 0.438 g), diisopropylethylamine (0.26 ml), and dimethylamino-pyridine (0.018 g) in THF (20 ml) is added benzoyl chloride (0.19 ml). After stirring for 5 hr, additional benzoyl chloride (0.20 ml) is added. The reaction is stirred at 20°–25° for 2 hr, then stored over the weekend in the freezer. It is then stirred again at 20°–25° for 24 hr, after which the THF solvent is removed under reduced pressure and replaced with dichloromethane. After stirring for a final 7 hr, the reaction is partitioned between dichloromethane and aqueous sodium bicarbonate. The phases are separated and the organic phase is filtered through sodium sulfate, concentrated, and the crude product chromatographed on silica gel (300 ml) eluting with ethyl acetate/dichloromethane (20/80). The appropriate fractions are pooled and concentrated to give the product which is recrystallized from dichloromethane and hexane to give the title compound, nip 234.5°–235.5°; MS m/z at 401; IR (mineral oil) 1660, 1502, 1366, 786 and 1247 cm$^{-1}$; NMR (CDCl$_3$) 1.21, 2.20, 5.32, 6.98, 7.3–7.5 and 8.19 δ.

EXAMPLES 108–148

There are a number of processes to produce the imidazo[1,5-a]quinoxalines (I). One process to produce the imidazol[1,5-a]quinoxalines (I) can be thought of as involving three steps. Step 1 is formation of the bicyclic amide (IV), step 2 is the formation of the imidazole ring with addition of the desired substituent at C$_3$ and step 3 is the addition of the R$_5$ substituent at N$_5$. It should be noted that steps 2 and 3 are reversed from EXAMPLES 48–87.

The imidazol[1,5-a]quinoxaline (I) molecule has four different types of variable substituents. These are, in the order of their incorporation during the three steps discussed above are (1) W$_5$, W$_6$, W$_7$ and W$_8$ which are incorporated by definition when the starting material is chosen, (2) the R$_4$ substituent which is incorporated when the bicyclic amide (IV) is formed, (3) the addition of the desired substituent at C$_3$ when the imidazole ring is formed and (4) the R$_5$ group which is added after formation of the bicyclic amide (IV, which has N$_5$=—NH—). EXAMPLES 1,2(3 and 4), (5 and 6), (7 and 8), (9–12), (13–16), (17 and 18), (19–24) and (25–28) all exemplify step 1, formation of the bicyclic amide (IV) containing the desired W$_5$, W$_6$, W$_7$ and W$_8$ substituent (by starting with the appropriate starting material) and the desired R$_4$ substituent. EXAMPLES 88–107 exemplify step 2, the formation of the imidazole ring with the R$_3$ substituent and step 3 the addition of the R$_5$ group. Following the general procedure of one or more of the above EXAMPLES (for each of steps 1, 2 and 3), making non-critical variations and starting with the appropriate starting material containing the desired W$_5$, W$_6$, W$_7$ and W$_8$ substituents, the compounds of the EXAMPLES below are formed:

EXAMPLE 108

5-Acetyl-3-(5-cyclopropyl-1,2,4-oxadiazol-3-yl)-7-fluoro-4,5-dihydroimidazo[1,5-a]quinoxaline (I)

mp 180.5–182.5°; MS (m/z) at 339; IR (mineral oil) 1512, 1577, 1669, 1221 and 1622 cm$^{-1}$; NMR (CDCl$_3$) 1.25, 2.36, 2.28, 2.35, 5.28, 7.09, 7.26, 7.58 and 8.08 δ.

EXAMPLE 109

3-(5-Cyclopropyl-1,2,4-oxadiazol-3-yl)-5-[(dimethylamino)carbonyl]-7-fluoro-4,5-dihydroimidazo[1,5-a]quinoxaline (I)

mp 227–228.5°; MS (m/z) at 368; IR (mineral oil) 1670, 1204, 1575, 1514 and 1364 cm$^{-1}$; NMR (CDCl$_3$) 1.23, 1.32, 2.27, 2.89, 4.98, 6.85, 7.50 and 8.06 δ.

EXAMPLE 110

3-(5-Cyclopropyl-1,2,4-oxadiazol-3-yl)-7-fluoro-4,5-dihydro-5-[(pyrrolidino)carbonyl]imidazo[1,5-a]quinoxaline (I)

mp 203°–204°; MS m/z at 394; IR (mineral oil) 1406, 1582, 1414, 1510, 1365, 1662 cm$^{-1}$; NMR (CDCl$_3$) 1.23, 1.35, 1.85, 2.25, 3.32, 5.02, 6.88, 7.50 and 8.06 δ.

EXAMPLE 111

5-Benzoyl-3-(5-cyclopropyl-1,2,4-oxadiazol-3-yl)-7-fluoro-4,5-dihydroimidazo[1,5-a]quinoxaline (I)

mp 190°–193°; MS m/z at 401; IR (mineral oil) 1367, 1672, 1515, 1499, 1577 cm$^{-1}$; NMR (CDCl$_3$) 1.24, 2.20, 5.35, 6.89, 7.00, 7.35–7.60 and 8.14 δ.

EXAMPLE 112

3-(5-Cyclopropyl-1,2,4-oxadiazol-3-yl)-7-fluoro-4,5-dihydro-5-[(1-imidazo)carbonyl]imidazo[1,5-a]quinoxaline (I)

mp 263°–265°; MS m/z at 391; IR (mineral oil) 1699, 1394, 1514, 1224, 1406 cm$^{-1}$; NMR (CDCl$_3$) 1.26, 1.33, 2.28, 5.36, 6.73, 7.08, 7.62, 7.83 and 8.17 δ.

EXAMPLE 113

3-(5-Cyclopropyl-1,2,4-oxadiazol-3-yl)-7-fluoro-4,5-dihydro-5-[(morpholino)carbonyl]imidazo[1,5-a]quinoxaline (I)

mp 224°–225°; MS m/z at 410; IR (mineral oil) 1662, 1504, 1423, 1578, 1280 cm$^{-1}$; NMR (CDCl$_3$) 1.25, 1.36, 2.28, 3.37, 3.67, 5.01, 6.92, 7.02, 7.53 and 8.07 δ.

EXAMPLE 114

5-Acetyl-3-(5-cyclopropyl-1,2,4-oxadiazol-3-yl)-4,5-dihydro-4,4-dimethylimidazo[1,5-a]quinoxaline (I)

mp 162°–163°; MS m/z at 349; NMR (CDCl$_3$) 1.26, 1.35, 1.90, 2.15, 2.27, 1.17, 7.32, 7.51 and 8.12 δ.

EXAMPLE 115

3-(5-Cyclopropyl-1,2,4-oxadiazol-3-yl)-4,5-dihydro-5-[(methoxy)carbonyl]-4,4-dimethylimidazo[1,5-a]-quinoxaline (I)

mp 183°–184°; MS: m/z at 365; IR (mineral oil) 1725, 1296, 1569, 1256, 1515 cm$^{-1}$; NMR (CDCl$_3$) 1.25, 1.36, 1.88, 2.28, 3.68, 7.28, 7.36, 7.48 and 8.09 δ.

EXAMPLE 116

3-(5-Cyclopropyl-1,2,4-oxadiazol-3-yl)-4,5-dihydro-5-[(isopropyloxy)carbonyl]-4,4-dimethylimidazo[1,5-a]-quinoxaline (I)

mp 172.5°–173.0°; MS m/z at 393; IR (mineral oil) 1716, 1252, 1288, 1510, 1291 cm$^{-1}$; NMR (CDCl$_3$) 1.23, 1.25, 1.35, 2.28, 4.98, 7.25, 7.38, 7.47 and 8.09 δ.

EXAMPLE 117

3-(5-Cyclopropyl-1,2,4-oxadiazol-3-yl)-5-[(ethoxy)-oxalyl]-4,5-dihydro-4,4-dimethylimidazo[1,5-a]-quinoxaline (I)

mp 157°–158°; MS m/z at 407; IR (mineral oil) 1672, 1576, 1517, 1198, 1743 and 1748 cm$^{-1}$; NMR (CDCl$_3$) 1.08, 1.27, 1.34, 1.98, 2.29, 4.09, 7.22, 7.25, 7.39, 7.55 and 8.16 δ.

EXAMPLE 118

3-(5-Cyclopropyl-1,2,4-oxadiazol-3-yl)-4,5-dihydro-4,4-dimethyl-5-[(phenoxy)carbonyl]imidazo[1,5-a]-quinoxaline (I)

mp 172.5°–174.5°; MS m/z at 427; IR (mineral oil) 1744, 1186, 1580, 1336 and 1514 cm$^{-1}$; NMR (CDCl$_3$) 1.25, 1.36, 1.95, 2.28, 7.08, 7.21, 7.32, 7.51, 7.58 and 8.15 δ.

EXAMPLE 119

3-(5-Cyclopropyl-1,2,4-oxadiazol-3-yl)-4,5-dihydro-4,4-dimethyl-5-[(pyrrolidino)oxalyl]imidazo[1,5-a]-quinoxaline (I)

mp 189.5°–190.5°; MS m/z at 432; IR (mineral oil) 1644, 1651, 1573, 1674 and 1516 cm$^{-1}$; NMR (CDCl$_3$) 1.28, 1.36, 1.75, 1.96, 2.28, 3.16, 3.29, 7.30, 7.40, 7.45, 7.53 and 8.14 δ.

EXAMPLE 120

6-Chloro-3-(5-cyclopropyl-1,2,4-oxadiazol-3-yl)-4,5-dihydro-5-[(pyrrolidino)carbonyl]imidazo[1,5-a]-quinoxaline (I)

mp 243°–244.5°: IR (mineral oil) 2924, 1651, 1497, 1407, 1395, 1380 and 781 cm$^{-1}$; NMR (CDCl$_3$) 8.11, 7.50, 7.36, 7.22, 5.08, 3.25–3.45, 2.2–2.35, 1.8–1.95 and 1.2–1.4 δ; MS (m/z) 410, 375, 340, 312, 272 and 98.

EXAMPLE 121

6-Chloro-3-(5-cyclopropyl-1,2,4-oxadiazol-3-yl)-5-[(dimethylamino)carbonyl]-4,5-dihydroimidazo[1,5-a]-quinoxaline (I)

mp 226°–228°; IR (mineral oil)2924, 1.661, 1600, 1495, 1389 and 1167 cm$^{-1}$; NMR (CDCl$_3$) 8.12, 7.50, 7.38, 7.2–7.3, 5.02, 3.00, 2.2–2.3 and 1.2–1.4 δ; MS (m/z) 384, 340, 312, 272 and 72.

EXAMPLE 122

6-Chloro-3-(5-cyclopropyl-1,2,4-oxadiazol-3-yl)-4,5-dihydro-5-[(methanethio)carbonyl]imidazo[1,5-a]-quinoxaline (I)

mp 212.5°–213.5°; IR (mineral oil) 2925, 1656, 1594, 1492, 1412, 1344 and 1152 cm$^{-1}$; NMR (CDCl$_3$) 8.13, 7.35–7.55, 6.1–6.5, 4.0–4.5, 2.33, 2.2–2.4 and 1.2–1.4 δ; MS (m/z) 387, 340, 312, 272, 244, 229 and 69.

EXAMPLE 123

3-(5-Cyclopropyl-1,2,4-oxadiazol-3-yl)-4,5-dihydro-5-(trifluoroacetyl)imidazo[1,5-a]quinoxaline (I)

mp 175°–177°; IR (mineral oil) 2954, 2925, 1707, 1604, 1512, 1498, 1459, 1432, 1424, 1419, 1283, 1218, 1211, 1205, 1194, 1163, 1154, 1087 and 768 cm$^{-1}$; NMR (CDCl$_3$)8.16, 7.88, 7.63, 7.35–7.55, 5.38, 2.2–2.4 and 1.2–1.4 δ; MS (m/z) 375, 306, 278 and 210.

EXAMPLE 124

3-(5-Cyclopropyl-1,2,4-oxadiazol-3-yl)-4,5-dihydro-5-[(1-imidazolyl)carbonyl]imidazo[1,5-a]quinoxaline (I)

mp 148°–150°; IR (mineral oil) 3121, 3110, 2954, 2926, 2855, 1704, 1577, 1509, 1502, 1406, 1390, 1334, 1287, 1246 and 746 cm$^{-1}$; NMR (CDCl$_3$) 8.26, 8.20, 7.65, 7.38, 7.1–7.3, 6.91, 5.34, 2.1–2.3 and 1.15–1.35 δ; MS (m/z) 373, 306, 277, 238, 210 and 195.

EXAMPLE 125

3-(5-Cyclopropyl-1,2,4-oxadiazol-3-yl)-4,5-dihydro-5-(2-pyridylcarbonyl)imidazo[1,5-a]quinoxaline (I)

mp 239°–240°; IR (mineral oil) 2954, 2925, 2855, 1660, 1590, 1513, 1499, 1448, 1411, 1376, 1290, 1153, 906, 773 and 765 cm$^{-1}$; NMR (CDCl$_3$) 8.56, 8.21, 7.83, 7.73, 7.60, 7.0–7.5, 5.45, 2.0–2.3 and 1.15–1.35; MS (m/z) 384, 278 and 210.

EXAMPLE 126

3-(5-Cyclopropyl-1,2,4-oxadiazol-3-yl)-4,5-dihydro-5-[(2-pyrrolyl)carbonyl]imidazo[1,5-a]quinoxaline (I)

IR (mineral oil) 3120, 2954, 2925, 2855, 1643, 1579, 1509, 1401, 1359, 1294, 1037 and 767 cm$^{-1}$; NMR (CDCl$_3$) 9.49, 8.15, 7.59, 7.2–7.4, 6.95, 6.30, 6.17, 5.49, 2.2–2.35 and 1.15–1.4 δ; MS (m/z) 372, 279, 210 and 195.

EXAMPLE 127

5-[(Anilino)carbonyl]-3-(5-cyclopropyl-1,2,4-oxadiazol-3-yl)-4,5-dihydroimidazo[1,5-a]quinoxaline (I)

mp 211–212.5°; IR (mineral oil) 2926, 2854, 1686, 1535, 1501, 1427, 1211 and 745 cm$^{-1}$; NMR (CDCl$_3$) 8.13, 7.55–7.7, 7.2–7.45, 7.0–7.15, 5.30, 2.1–2.35 and 1.2–1.4 δ; MS (m/z) 398, 279, 238, 210, 195 and 119.

EXAMPLE 128

3-(5-Cyclopropyl-1,2,4-oxadiazol-3-yl)-5-[(dimethylamino)carbonyl]-4,5-dihydroimidazo[1,5-a]-quinoxaline (I)

mp 196°–197°; IR (mineral oil) 2925, 2855, 1664, 1573, 1500, 1275, 1202 and 756 cm$^{-1}$; NMR (CDCl$_3$) 8.11, 7.54, 7.2–7.3, 7.05–7.2, 4.99, 2.85, 2.2–2.3 and 1.2–1.4 δ; MS (m/z), 350, 306, 278, 263, 238, 210. 195 and 72.

EXAMPLE 129

3-(5-Cyclopropyl-1,2,4-oxadiazol-3-yl)-4,5-dihydro-5-[(methylamino)carbonyl]imidazo[1,5-a]quinoxaline (I)

mp 214°–215°; IR (mineral oil) 3374, 3100, 2925, 2855, 1655, 1575, 1503 and 767 cm$^{-1}$; $^1$H NMR (CDCl$_3$) 8.10, 7.5–7.65, 7.2–7.4, 5.26, 5.06, 2.75–2.90, 2.2–2.3 and 1.15–1.4 δ; MS (m/z) 336, 279, 238, 210, 195 and 69.

EXAMPLE 130

5-[(2-Chlorophenylamino)carbonyl]-3-(5-cyclopropyl-1,2,4-oxadiazol-3-yl)-4,5-dihydroimidazo[1,5-a]-quinoxaline (I)

mp 209°–210°: IR (mineral oil) 3247, 2925, 2854, 1687, 1571, 1508, 1213 and 763 cm$^{-1}$; NMR (CDCl$_3$) 8.28, 8.21, 7.65–7.8, 7.4–7.5, 7.2–7.35, 7.00, 5.37, 2.2–2.35 and 1.2–1.4 δ; (m/z) 432, 279, 238, 210, 195 and 153.

EXAMPLE 131

3-(5-Cyclopropyl-1,2,4-oxadiazol-3-yl)-4,5-dihydro-5-[(isopropylamino)carbonyl]imidazo[1,5-a]quinoxaline (I)

mp 210°–211°; IR (mineral oil) 3268, 2924, 2855, 1682, 1672, 1580, 1505, 1334 and 750 cm$^{-1}$; NMR (CDCl$_3$) 8.11, 7.5–7.65, 7.2–7.4, 5.23, 4.87, 3.95–4.10, 2.2–2.35, 1.0–1.4 and 1.14 δ; MS (m/z) 364, 279, 238, 210 and 195.

EXAMPLE 132

3-(5-Cyclopropyl-1,2,4-oxadiazol-3-yl)-5-[(diethylamino)carbonyl]-4,5-dihydroimidro[1,5-a]-quinoxaline (I)

mp 173°–174°: IR (mineral oil) 3101, 2925, 2855, 1645. 1579, 1511, 1287 and 753 cm$^{-1}$; NMR (CDCl$_3$) 8.11.7.53, 7.1–7.3, 4.95, 3.26, 2.2–2.3, 1.2–1.4 and 1.13 δ; MS (m/z) 378, 306, 278, 238, 100 and 72.

EXAMPLE 133

3-(5-Cyclopropyl-1,2,4-oxadiazol-3-yl)-4,5-dihydro-5-[(pyrrolidino)carbonyl]imidazo[1,5-a]quinoxaline (I)

mp 181.5°–182.5°: IR (mineral oil) 3007, 2925, 2855, 1648, 1513, 1501, 1409, 1204, 760, 756 cm$^{-1}$; NMR (CDCl$_3$) 8.10, 7.54, 7.1–7.3, 5.04, 3.28, 2.2–2.3, 1.75–1.9 and 1.2–1.4 δ; MS (m/z) 376, 306, 278 and 238.

EXAMPLE 134

5-[(Benzenethio)carbonyl]-3-(5-cyclopropyl-1,2,4-oxadiazol-3-yl)-4,5-dihydroimidazo[1,5-a]-quinoxaline (I)

mp 222.5°–223.5°: IR (mineral oil) 2925, 2855, 1673, 1592, 1500, 1362, 1206, 751 cm$^{-1}$; NMR (CDCl$_3$) 8.16, 7.92, 7.61, 7.3–7.55, 5.38, 2.2–2.35 and 1.2–1.4 δ; MS (m/z) 415, 306, 278, 238 and 210.

EXAMPLE 135

3-(5-Cyclopropyl-1,2,4-oxadiazol-3-yl)-5-[(ethanethio)carbonyl]-4,5-dihydroimidazo[1,5-a]-quinoxaline (I)

mp 169°–170°: IR (mineral oil) 2925, 2855, 1657, 1579, 1491, 1207, 1177 and 765 cm$^{-1}$; NMR (CDCl$_3$) 8.12, 7.86, 7.58, 7.3–7.45, 5.33, 2.94, 2.2–2.35, 1.1–1.45, 1.29 δ; MS (m/z) 367, 306, 278, 238 and 195.

EXAMPLE 136

3-(5-Cyclopropyl-1,2,4-oxadiazol-3-yl)-5-[(ethylamino)carbonyl]-4,5-dihydroimidazo[1,5-a]-quinoxaline (I)

mp 189°–190°: IR (mineral oil) 2924, 2855, 1672, 1576, 1506. 1218 and 762 cm$^{-1}$; NMR (CDCl$_3$) 8.11, 7.5–7.65, 7.2–7.4, 5.25, 5.04, 3.25–3.4, 2.2–2.3, 1.2–1.4 and 1.12 δ; MS (m/z) 350, 279, 238, 210 and 195.

EXAMPLE 137

5-(Carbamoyl)-3-(5-cyclopropyl-1,2,4-oxadiazol-3-yl)-4,5-dihydroimidazo[1,5-a]quinoxaline (I)

mp 114°–115°; IR (mineral oil) 2924, 2855, 1695, 1579, 1513, 1387 and 759 cm$^{-1}$; NMR (CDCl$_3$) 8.16, 7.6–7.7, 7.2–7.45, 5.34, 5.24, 2.2–2.35 and 1.2–1.4 δ: MS (m/z) 322, 279 238, 210 and 195.

EXAMPLE 138

3-(5-Cyclopropyl-1,2,4-oxadiazol-3-yl)-4,5-dihydro-5-[(methanethio)carbonyl]imidazo[1,5-a]quinoxaline (I)

mp 176°–177°: IR (mineral oil) 2925, 2855, 1660. 1497, 1422, 1357, 1206 and 761 cm$^{-1}$; NMR (CDCl$_3$) 8.12, 7.85, 7.58, 7.3–7.45, 5.34, 2.36, 2.25–2.4 and 1.2–1.4 δ; MS (m/z) 353, 306, 278, 210 and 195.

EXAMPLE 139

3-(5-Cyclopropyl-1,2,4-oxadiazol-3-yl)-4,5-dihydro-4,4-dimethyl-5-](pyrrolidino)carbonyl]imidazo-[1,5-a]quinoxaline (I)

mp 200.5°–201.5°: IR (mineral oil) 3104, 2925, 2855, 1674, 1573, 1507, 1402 and 749 cm$^{-1}$; NMR (CDCl$_3$) 8.09, 7.48, 7.19, 7.04, 6.82, 3.55, 2.75–3.3, 2.2–2.35, 1.45–2.15 and 1.2–1.4 δ; MS (m/z) 404 and 389.

EXAMPLE 140

3-(5-Cyclopropyl-1,2,4-oxadiazol-3-yl)-5-[(dimethylamino)carbonyl]-4,5-dihydro-4,4-dimethylimidazo-[1,5-a]quinoxaline (I)

mp 160°–161°: IR (mineral oil) 3111, 2925, 2855, 1646, 1568, 1479, 1313 and 747 cm$^{-1}$; NMR (CDCl$_3$) 8.10, 7.49, 7.20, 7.05, 6.73, 3.07, 2.72, 2.2–2.35, 1.99, 1.70 and 1.15–1.45 δ; MS (m/z) 378, 363 and 295.

EXAMPLE 141

5-[(Benzenethio)carbonyl]-3-(5-cyclopropyl-1,2,4-oxadiazol-3-yl)-4,5-dihydro-4,4-dimethylimidazo-[1,5-a]quinoxaline (I)

mp 171°–172°: IR (mineral oil) 3098, 2925, 2855, 1695, 1590, 1510 and 1190 cm$^{-1}$; NMR (CDCl$_3$) 8.12, 7.72, 7.25–7.55, 2.2–2.3, 1.86 and 1.2–1.4 δ; MS (m/z) 443, 334 and 266.

EXAMPLE 142

5-(Carbamoyl)-3-(5-cyclopropyl-1,2,4-oxadiazol-3-yl)-4,5-dihydro-4,4-dimethylimidazo[1,5-a]-quinoxaline (I)

mp 168°–169°: IR (mineral oil) 3347, 2924, 2855, 1711, 1696, 1577, 1510 and 749 cm$^{-1}$; NMR (CDCl$_3$) 8.06, 7.48, 7.37, 7.2–7.3, 7.16, 5.15, 2.2–2.35, 1.89 and 1.2–1.4 δ; MS (m/z) 335, 307, 292, 224 and 209.

EXAMPLE 143

3-(5-Cyclopropyl-1,2,4-oxadiazol-3-yl)-5-[(diethylamino)carbonyl]-4,5-dihydro-4,4-dimethylimidazo-[1,5-a]quinoxaline (I)

mp 148°–149°: IR (mineral oil) 2925, 2855, 1671, 1572, 1508, 1302, 1264 and 749 cm$^{-1}$; NMR (CDCl$_3$) 8.10, 7.49, 7.18, 7.03, 6.84, 3.3–3.7, 3.0–3.3, 2.2–2.35. 1.98, 1.59, 1.1–1.4 and 0.89 δ; MS (m/z) 406, 391.

EXAMPLE 144

3-(5-cyclopropyl-1,2,4-oxadiazol-3-yl)-4,5-dihydro-4,4-dimethyl-5-[(methylamino)carbonyl]imidazo-[1,5-a]quinoxaline (I)

mp 126°–127°: IR (mineral oil) 2925, 2855, 1678, 1577, 1518, 1288 and 753 cm$^{-1}$; NMR (300 MHz, (CDCl$_3$) 7.92, 7.42, 7.15–7.3, 6.95–7.1, 5.70, 2.91, 2.2–2.3, 1.84 and 1.2–1.4 δ; MS (m/z) 364, 349, 292 and 224.

EXAMPLE 145

3-(5-Cyclopropyl-1,2,4-oxadiazol-3-yl)-5-[(ethylamino)carbonyl]-4,5-dihydro-4,4-dimethylimidazo-[1,5-a]quinoxaline (I)

mp 194°–195°: IR (mineral oil) 2925, 2855, 1677, 1577, 1279, 1263 and 755 cm$^{-1}$; NMR (CDCl$_3$) 7.98, 7.44, 7.21, 7.05, 5.63, 3.3–3.45, 2.2–2.3, 1.85, 1.1–1.4 and 1.19 δ; MS (m/z) 378, 363, 292 and 224.

EXAMPLE 146

3-(5-Cyclopropyl-1,2,4-oxadiazol-3-yl)-4,5-dihydro-5-[(methanethio)carbonyl]-4,4-dimethylimidazo[1,5-a]-quinoxaline (I)

mp 163°–164°: IR (mineral oil) 2924, 2855, 1687, 1573, 1507, 1290, 1195,763 and 731 cm$^{-1}$; NMR (CDCl$_3$) 8.12, 7.4–7.65, 7.25–7.35, 2.2–2.35, 2.17, 1.86 and 1.2–1.4 δ; MS (m/z) 381, 366, 338 and 266.

EXAMPLE 147

3-(5-Cyclopropyl-1,2,4-oxadiazol-3-yl)-5-[(ethanethio)carbonyl]-4,5-dihydro-4,4-dimethylimidazo-[1,5-a]quinoxaline (I)

mp 121°–122°: IR (mineral oil) 2924, 2855, 1683, 1578. 1508, 1194 and 764 cm$^{-1}$; NMR (CDCl$_3$) 8.12, 7.58, 7.45–7.55, 7.42, 7.2–7.35, 2.73, 2.2–2.35, 1.86, 1.1–1.4 and 1.18 δ; MS (m/z) 395, 380, 352, 320 and 266.

EXAMPLE 148

3-(5-Cyclopropyl-1,2,4-oxadiazol-3-yl)-5-formyl-4,5-dihydro-4,4-dimethylimidazo[1,5-a]-quinoxaline (I)

mp 117.5°–118.5°: IR (mineral oil) 2925, 2855, 1672, 1571, 1512, 1352, 1298 and 760 cm$^{-1}$; NMR (CDCl$_3$) 8.76, 8.12, 7.87, 7.5–7.6, 7.3–7.45, 2.25–2.35, 1.93 and 1.2–1.45 δ; MS (m/z) 335,320, 292, 252 and 224.

EXAMPLE 149

3-(5-Cyclopentyl-1,2,4-oxadiazol-3-yl)-4,5-dihydro-5-[(pyrrolidino)carbonyl]imidazo[1,5-a]quinoxaline (I)

mp 185°–8°; NMR (CDCl$_3$) 8.03, 7.45, 7.1–6.9, 4.8, 3.2, 3.09, 1.92, 1.81 and 1.6–1.4 δ.

EXAMPLE 150

4,5-Dihydro-3-(3-isopropyl-1,2,4-oxadiazol-5-yl)-4,4-dimethyl-5-[(pyrrolidino)carbonyl]imidazo[1,5-a]-quinoxaline (I)

mp 180°–3°; NMR (CDCl$_3$) 8.12, 7.50, 7.22, 7.05, 6.83, 3.60, 3.18, 3.10, 1.90, 1.77, 1.41 and 1.39 δ.

EXAMPLE 151

7-Chloro-4,5-dihydro-3-(3-isopropyl-1,2,4-oxadiazol-5-yl)-4,4-dimethyl-5-[(pyrrolidino)carbonyl]-imidazo[1,5-a]quinoxaline (I)

mp 210°–3°; NMR (CDCl$_3$) 8.10, 7.44, 7.02, 6.81, 3.61, 3.18, 3.10, 2.00, 1.94, 1.83, 1.41, 1.38 δ.

EXAMPLE 152 tert-Butyl 4,5-dihydro-4(S)-methyl-5-[(pyrrolidino)carbonyl]-imidazo[1,5-a]quinoxaline-3-carboxylate (I)

mp 178°–9°; NMR (CDCl$_3$) 7.85, 7.38, 7.2–6.9, 5.72, 3.04, 2.91, 1.62, 1.49, 1.39 and 1.15 δ.

EXAMPLE 153 tert-Butyl 4,5-dihydro-4(RS)-methyl-5-[(pyrrolidino)carbonyl]-imidazo[1,5-a]quinoxaline-3-carboxylate (I)

mp 177°–9°; NMR (CDCl$_3$) 7.98, 7.51, 7.3–7.1, 5.94, 3.26, 3.14, 1.85, 1.72, 1.63 and 1.37 δ.

EXAMPLE 154 tert-Butyl 4,5-dihydro-4(S)-methyl-7-methyl-5-[(pyrrolidino)-carbonyl]imidazo[1,5-a]quinoxaline-3-carboxylate (I)

mp 223°–4°; NMR (CDCl$_3$) 7.94, 7.37, 6.99, 6.95, 5.92, 3.25, 3.14, 2.37, 1.86, 1.70, 1.63 and 1.36 δ.

EXAMPLE 155

4,5-Dihydro-3-(5-isopropyl-1,2,4-oxadiazol-3-yl)-4(S)-methyl-5-[(pyrrolidino)carbonyl]imidazo-[1,5-a]quinoxaline (I)

mp 158°–61°; NMR (CDCl$_3$) 8.11, 7.41, 7.06, 6.86, 6.79, 5.36, 4.79, 3.28, 1.46, 1.43 and 1.29 δ.

EXAMPLE 156

4,5-Dihydro-3-(3-isopropyl-1,2,4-oxadiazol-5-yl)-4(S)-methyl-5-[(pyrrolidino)carbonyl]imidazo[1,5-a]-quinoxaline (I)

mp 149°–55°; NMR (CDCl$_3$) 8.11, 7.56, 7.3–7.1, 6.05, 3.27, 3.17, 3.15, 1.86, 1.76, 1.45 and 1.40 δ.

EXAMPLE 157 tert-Butyl 4,5-Dihydro-5-[2-(morpholino)acetyl]imidazo[1,5-a]-quinoxaline (I)

mp 182°–4°; NMR (CDCl$_3$) 8.01, 7.84, 7.55, 7.34, 5.33, 3.78, 2.17 and 1.64 δ.

EXAMPLE 158 tert-Butyl 4,5-Dihydro-7-methyl-5-[2-(morpholino)acetyl]-imidazo[1,5-a]quinoxaline (I)

mp 153°–5°; NMR (CDCl$_3$) 8.00, 7.46, 7.28, 3.52, 3.17, 2.37, 1.93 and 1.62 δ.

EXAMPLE 159

4,5-Dihydro-3-(3-isopropyl-1,2,4-oxadiazol-5-yl)-5-[(pyrrolidino)carbonyl]4-(spirocyclopentyl)imidazo-[1,5-a]quinoxaline (I)

mp 134°–6°; NMR (CDCl$_3$) 8.11, 7.50, 7.19, 7.04, 6.86, 3.29, 3.28, 2.29, 1.95, 1.80 and 1.46 δ.

EXAMPLE 160

7-Chloro-4,5-dihydro-3-(3-isopropyl-1,2,4-oxadiazol-5-yl)-5-[(pyrrolidino)carbonyl]imidazo [1,5-a]quinoxaline (I)

mp 193°–6°; NMR (CDCl$_3$) 8.11, 7.49, 7.18, 5.08, 3.33, 3.17, 1.86 and 1.39 δ.

EXAMPLE 161

7-Fluoro-4,5-dihydro-3-(3-isopropyl-1,2,4-oxadiazol-5-yl)-5-[(pyrrolidino)carbonyl]imidazo-[1,5-a]quinoxaline (I)

mp 202°–5°; NMR (CDCl$_3$) 8.10, 7.53, 6.92, 5.08, 3.34, 3.17, 1.86 and 1.39 δ.

EXAMPLE 162 tert-Butyl 4,5-Dihydro-5-[(pyrrolidino)carbonyl]4-(spirocyclopentyl)imidazo[1,5-a]quinoxaline (I)

mp 165°–7°; NMR (CDCl$_3$) 7.97, 7.47, 7.18, 7.04, 6.84, 2.25, 2.01 and 1.84 δ.

EXAMPLE 163 tert-Butyl 4,5-dihydro-5-[2-(pyrrolidino)acetyl]imidazo[1,5-a]-quinoxaline (I)

mp 178°–9°; NMR (CDCl$_3$) 8.01, 7.84, 7.56, 7.35, 5.32, 2.60, 2.18, 1.76 and 1.64 δ.

EXAMPLE 164

7-Fluoro-4,5-dihydro-4(S)-methyl-N-pyrrolidino-5-[(pyrrolidino)carbonyl]imidazo[1,5-a]quinoxaline-3-carboxamide (I)

mp 211°–14°; NMR (CDCl$_3$) 7.88, 7.48, 6.97, 6.86, 6.06, 4.12.4.01, 3.64, 3.33, 3.18, 1.98, 1.88, 1.74 and 1.44 δ.

EXAMPLE 165 tert-Butyl 4,5-Dihydro-4,4-dimethyl-5-[2-(pyrrolidino)acetyl]-imidazo[1,5-a]quinoxaline-3-carboxylate (I)

mp 235°–40°.

EXAMPLE 166

4,5-Dihydro-3-(5-isopropyl-1,2,4-oxadiazol-3-yl)-5-[(pyrrolidino)carbonyl]-4-(spirocyclo-pentyl)-imidazo[1,5-a]quinoxaline (I)

mp 133°–5°; NMR (CDCl$_3$) 8.13, 7.51, 7.23, 7.08, 6.88, 3.18, 2.44, 2.32, 2.00, 1.96, 1.83 and 1.39δ.

EXAMPLE 167

7-Fluoro-4,5-dihydro-3-(3-isopropyl-1,2,4-oxadiazol-5-yl)-4(S)-methyl-5-[(pyrrolidino)carbonyl]-imidazo[1,5-a]quinoxaline (I)

mp 191°–3°; NMR (CDCl$_3$) 8.07, 7.53, 6.98, 6.91, 6.01, 3.31, 3.20, 3.19, 1.89, 1.76, 1.47 and 1.40 δ.

EXAMPLE 168

7-Fluoro-4,5-dihydro-3-(5-isopropyl-1,2,4-oxadiazol-3-yl)-4(S)-methyl-5-[(pyrrolidino)carbonyl]imidazo-[1,5-a]quinoxaline (I)

mp 212°–4°; NMR (CDCl$_3$) 8.05, 7.52, 6.96, 6.87, 5.97, 3.32, 3.18, 1.88, 1.74, 1.46 and 1.43 δ.

EXAMPLE 169 tert-Butyl 7-fluoro-4,5-dihydro-4(S)-methyl-5-[(pyrrolidino)-carbonyl]imidazo[1,5-a]quinoxaline-3-carboxylate (I)

mp 188°–90°; NMR (CDCl$_3$) 7.93, 7.47, 6.94, 6.87, 5.91, 3.30, 3.18, 1.90, 1.76, 1.62 and 1.39 δ.

EXAMPLE 170 tert-Butyl 4,5-Dihydro-4(S)-isobutyl-5-[(pyrrolidino)carbonyl]-imidazo[1,5-a]quinoxaline-3-carboxylate (I)

mp 204°–8°; NMR (CDCl$_3$) 7.97, 7.51, 7.3–7.17, 6.01, 3.16, 3.05, 1.82, 1.70, 1.63, 1.60, 1.47, 1.32, 0.99 and 0.89 δ.

EXAMPLE 171 tert-Butyl 4(S)-Ethyl-4,5-dihydro-5-[(pyrrolidino)carbonyl]-imidazo[1,5-a]quinoxaline3-carboxylate (I)

mp 163°–6°; NMR (CDCl$_3$) 7.99, 7.50, 7.27, 7.16, 5.87, 3.20, 3.08, 1.83, 1.72, 1.63 and 0.93 δ.

EXAMPLE 172

4(S)-Ethyl-4,5-dihydro-3-(5-isopropyl-1,2,4-oxadiazol-3-yl)-5-[(pyrrolidino)carbonyl]imidazo[1,5-a]quinoxaline (I)

mp 150°–3°; NMR (CDCl$_3$) 8.10, 7.54, 7.27, 7.18, 5.93, 3.28, 3.18, 3.08, 1.81, 1.66, 1.46 and 0.92 δ.

EXAMPLE 173

4(S)-Ethyl-4,5-dihydro-3-(3-isopropyl-1,2,4-oxadiazol-5-yl)-5-[(pyrrolidino)carbonyl]imidazo[1,5-a]-quinoxaline (I)

mp 188°–91°; NMR (CDCl$_3$) 8.12, 7.56, 7.30, 7.19, 5.94, 3.24, 3.18, 3.08, 1.90, 1.66, 1.40 and 0.92 δ.

The product of EXAMPLES 174–181 is an amide, R$_3$ is —CO—NR$_{3-4}$R$_{3-5}$ which is produced by transformation from the corresponding ester, R$_3$ is —COO—R$_{3-1}$:

EXAMPLE 174

N-tert-Butylamino-4,5-dihydro-5-[(pyrrolidino)-carbonyl]imidazo[1,5-a]quinoxaline-3-carboxamide (I)

mp 185°–6°; NMR (CDCl$_3$) 7.89, 7.47, 7.2–7.0, 6.98, 5.08, 3.30, 1.81 and 1.48 δ.

EXAMPLE 175

N-tert-Butylamino-6-fluoro-4,5-dihydro-5-[(pyrrolidino)carbonyl]imidazo[1,5-a]quinoxaline-3-carboxamide (I)

mp 233°–6°; NMR (CDCl$_3$) 7.89, 7.30, 7.18, 7.05, 7.00, 5.13, 3.48, 1.92 and 1.48 δ.

EXAMPLE 176

N-tert-Butylamino-6-chloro-4,5-dihydro-5-[(pyrrolidino)carbonyl]imidazo[1,5-a]quinoxaline-3-carboxamide (I)

mp 291°–4°; NMR (CDCl$_3$) 7.89, 7.42, 7.34, 7.19, 6.99, 5.05, 3.54, 1.93 and 1.47 δ.

EXAMPLE 177

7-Chloro-4,5-dihydro-N-morpholino-5-[(pyrrolidino)-carbonyl]-imidazo[1,5-a]quinoxaline-3-carboxamide (I)

mp 275°–7°; NMR (CDCl$_3$) 7.93, 7.46, 7.36, 7.21, 5.04, 4.40, 3.78, 3.54 and 1.93 δ.

EXAMPLE 178

N-tert-Butylamino-7-chloro-4,5-dihydro-5-[(pyrrolidino)carbonyl]imidazo[1,5-a]quinoxaline-3-carboxamide (I)

mp 116°–9°; NMR (CDCl$_3$) 7.71, 7.26, 7.02, 6.93, 4.93, 3.20, 1.72 and 1.34 δ.

EXAMPLE 179

7-Chloro-N-cyclohexylamino-4,5-dihydro-5-[(pyrrolidino)carbonyl]imidazo[1,5-a]quinoxaline-3-carboxamide (I)

mp 213°–5°; NMR (CDCl$_3$) 8.05, 7.56, 7.34, 7.25, 7.12, 5.24, 4.10, 3.51, 2.14, 2.02, 1.90–1.78 and 1.60–1.30 δ.

EXAMPLE 180

N-tert-Butylamino-6-chloro-4,5-dihydro-5-(2-pyrrolidino-2-oxoethyl)imidazo[1,5-a]quinoxaline-3-carboxamide (I)

mp 200°–2°; NMR (CDCl$_3$) 7.92, 7.35, 7.23, 7.04, 4.63, 3.82, 3.28, 1.88, 1.68 and 1.53 δ.

EXAMPLE 181

N-tert-Butylamino-7-chloro-4,5-dihydro-5-(2-pyrrolidino-2-oxoethyl)imidazo[1,5-a]quinoxaline-3-carboxamide (I)

mp 131°–43°; NMR (CDCl$_3$) 7.93, 7.30, 6.79, 6.54, 4.87, 4.01, 3.53, 3.47, 2.06, 1.91 and 1.60 δ.

The product of EXAMPLE 181A is an alcohol, R$_3$ is —CH$_2$OH produced by transformation from the corresponding ester, R$_3$ is —COO—R$_{3-1}$:

EXAMPLE 181A 4,5-Dihydro-3-(hydroxymethyl)-5-[(pyrrolidino)-carbonyl]imidazo-[1,5-a]quinoxaline (I)
4,5-Dihydro-5-[(pyrrolidino)carbonyl]imidazo[1,5-a]quinoxaline-3-methanol (I)

mp 214°–5°; NMR (CDCl$_3$) 8.00, 7.47, 7.3–7.1, 4.73, 4.67, 3.26 and 1.81 δ.

Following the general procedure of EXAMPLES 48–87 and the EXAMPLES referenced therein are making non-critical variations the following compounds are produced:

EXAMPLE 182

3-(2-Benzoxazolyl)-7-fluoro-4,5-dihydro-5-[(pyrrolidino)carbonyl]imidazo[1,5-a]quinoxaline (I)

mp 256.5°–257.5°; MS m/z at 403; IR (mineral oil) 1513, 1660, 1637, 1395 and 1412 cm$^{-1}$; NMR (CDCl$_3$) 1.86, 3.35, 5.22, 6.86–6.96, 7.34, 7.53, 7.60, 7.74 and 8.11 δ.

EXAMPLE 183 tert- Butyl 4,5-dihydro-5-[(morpholino)carbonyl]imidazo[1,5-a]quinoxalin-3-carboxylate (I)

mp 205°–206°; MS m/z at 384; IR (mineral oil) 1685, 1653, 1506, 1113 and 1151 cm$^{-1}$; NMR (CDCl$_3$) 1.64, 3.33, 3.64, 4.99, 7.18, 7.28, 7.52 and 8.01 δ.

EXAMPLE 184

4,5-Dihydro-3-(5-isopropyl-1,2,4-oxadiazol-3-yl)-5-[(morpholino)carbonyl]imidazo[1,5-a]quinoxaline (I)

mp 207°–208°; MS m/z at 394; IR (mineral oil) 1668, 1277, 1505, 1566 and 1423 cm$^{-1}$; NMR (CDCl$_3$) 1.47, 3.30, 3.34, 3.64, 5.04, 7.20, 7.28, 7.56 and 8.13 δ.

EXAMPLE 185 tert-Butyl 5-[(di-n-propylamino)carbonyl]-4,5-dihydroimidazo-[1,5-a]quinoxaline-3-carboxylate (I)

mp 130°–131°; MS m/z at 398; IR (mineral oil) 1718, 1152, 1660, 1504 and 1283 cm$^{-1}$; NMR (CDCl$_3$) 0.82, 1.56, 1.62, 3.15, 4.91, 7.10–7.24, 7.50 and 8.01 δ.

EXAMPLE 186

5-[(Di-n-propylamino)carbonyl]-4,5-dihydro-3-(5-iso-propyl-1,2,4-oxadiazol-3-yl)imidazo[1,5-a]-quinoxaline (I)

mp 149°–152°; MS m/z at 408; IR (mineral oil) 1645, 1510, 751, 1427 and 1574 cm$^{-1}$; NMR (CDCl$_3$) 0.81, 1.46, 1.55, 3.15, 3.29, 4.98, 7.12–7.26, 7.54 and 8.12 δ.

EXAMPLE 187

7-Fluoro-4,5-dihydro-3-phenyl-5-[(pyrrolidino)-carbonyl]imidazo[1,5-a]quinoxaline (I)

mp 194.5°–196.5°; MS m/z at 362; NMR (CDCl$_3$) 1.82, 3.29, 4.91, 6.82–6.90, 7.30, 7.42–7.50, 7.66 and 8.04 δ.

EXAMPLE 188 tert-Butyl 5-(tert-butyloxycarbonyl)-4,5-dihydroimidro[1,5-a]quinoxaline-3-carboxylate (I)

mp 178°–180°; MS m/z at 371; IR (mineral oil) 1711, 1367, 1154, 1509 and 1300 cm$^{-1}$; NMR (CDCl$_3$) 1.54, 1.64, 5.17, 7.23–7.33, 7.50, 7.76 and 8.01 δ.

EXAMPLE 189 tert-Butyl 5-acetyl-4,5-dihydroimidazo[1,5-a]quinoxaline-3-carboxylate (I)

mp 150°–152°; MS m/z at 313; IR (mineral oil) 1691, 1669, 1502, 1154 and 1489 cm$^{-1}$; NMR (CDCl$_3$) 1.64, 2.28, 5.27, 7.37, 7.56 and 8.03 δ.

EXAMPLE 190

3-(2-Benzoxazolyl)-4,5-dihydro-5-[(pyrrolidino)-carbonyl]imidazo[1,5-a]quinoxaline (I)

mp 213°–214°; MS m/z at 385; IR (mineral oil) 1666, 1242. 1510, 747 and 1408 cm$^{-1}$; NMR (CDCl$_3$) 1.82, 3.31, 5.23, 7.15–7.37, 7.59, 7.74 and 8.15 δ.

EXAMPLE 191

3-(2-Benzoxazolyl)-7-fluoro-4,5-dihydro-5-[(pyrrolidino)carbonyl]imidazo[1,5-a]quinoxaline (I)

mp 256.5°–257.5°; MS m/z at 403; IR (mineral oil) 1513, 1660, 1637, 1395, 1412 and cm$^{-1}$; NMR (CDCl$_3$) 1.86, 3.35, 5.22, 6.86–6.96, 7.34, 7.53, 7.60, 7.74 and 8.11 δ.

EXAMPLE 192

7-Fluoro-3-(4-fluorophenyl)-4,5-dihydro-4,4-dimethyl-5-[(pyrrolidino)carbonyl]imidazo[1,5-a]quinoxaline (I)

mp 225°–226.5°; MS m/z at 408; IR (mineral oil) cm$^{-1}$; NMR (CDCl$_3$) 1.63, 1.79, 1.91, 2.9–3.4, 3.56, 6.54, 6.75, 7.10, 7.41–7.47 and 7.96 δ.

EXAMPLE 193

3-(5-tert-Butyl-1,2,4-oxadiazol-3-yl)-7-fluoro-4,5-dihydro-5-[(pyrrolidino)carbonyl]imidazo[1,5-a]-quinoxaline (I)

mp 241°–242°; MS m/z at 410; NMR (CDCl$_3$) 1.50, 1.85, 3.32, 5.04, 6.88, 6.93, 7.50 and 8.07 δ.

EXAMPLE 194

3-(5-tert-Butyl-1,2,4-oxadiazol-3-yl)-4,5-dihydro-5-[(morpholino)carbonyl]imidazo[1,5-a]quinoxaline (I)

mp 203°–204.5°; NMR (CDCl$_3$) 1.51, 3.33, 3.64, 5.04, 7.20, 7.29, 7.56 and 8.13 δ.

EXAMPLE 195

3-(5-tert-Butyl-1,2,4-oxadiazol-3-yl)-7-fluoro-4,5-dihydro-4,4-dimethyl-5-[(pyrrolidino)carbonyl]-imidazo-[1,5-a]quinoxaline (I)

mp 179°–180°; NMR (CDCl$_3$) 1.51, 1.7–2.1, 2.98, 3.23, 3.58, 6.55, 6.74, 7.45 and 8.06 δ.

EXAMPLE 196

3-(5-tert-Butyl-1,2,4-oxadiazol-3-yl)-6-fluoro-4,5-dihydro-5-[(pyrrolidino)carbonyl]imidazo-[1,5-a]quinoxaline (I)

mp 200°–202°; NMR (CDCl3) 1.50, 1.86, 3.35, 5.14, 7.07, 7.22, 7.37 and 8.12 δ.

EXAMPLE 197

5-[(Dimethylamino)carbonyl]-3-(5-ethyl-1,2,4-oxadiazol-3-yl)-4,5-dihydroimidazo[1,5-a]-quinoxaline (I)

mp 179°: IR (mineral oil) 3090, 2951, 2924, 2855, 1654, 1563, 1505, 1403, 1387 and cm$^{-1}$; NMR (CDCl$_3$) 8.12, 7.55, 7.2–7.35, 7.05–7.2, 5.02, 2.97, 2.86 and 1.45; MS (m/z) 338, 266, 238, 210, 195, 72 and 43.

EXAMPLE 198

5-[(Dimethylamino)carbonyl]-3-(5-ethyl-1,2,4-oxadiazol-3-yl)-4,5-dihydro-4,4-dimethylimidazo-[1,5-a]quinoxaline (I)

mp 201°–202°: IR (mineral oil) 3119, 2953, 2925, 2855, 1658, 1517, 1496, 1399, 1317, 1281 and 1186 cm$^{-1}$; NMR (CDCl$_3$) 8.12, 7.50, 7.1–7.25, 7.06, 6.74, 3.07, 3.00, 2.73, 2.00, 1.72 and 1.47; MS (m/z) 366, 351, 295, 266 and 72.

EXAMPLE 199

3-(5-Ethyl-1,2,4-oxadiazol-3-yl)-4,5-dihydro-4,4-dimethyl-5-[(pyrrolidino)carbonyl]imidazo-[1,5-a]quinoxaline (I)

mp 196.5°–197°: IR (mineral oil) 3106, 2951, 2925, 2871, 2855, 1656, 1585, 1511, 1499, 1409, 1314, 1184 and 750 cm$^{-1}$; NMR (CDCl$_3$) 8.11, 7.49, 7.1–7.25, 7.04, 6.82, 3.4–3.7, 2.8–3.3, 2.99, 1.6–2.1 and 1.46 δ; MS (m/z) 392, 378, 377, 266, 98 and 55.

EXAMPLE 200

3-(5-Ethyl-1,2,4-oxadiazol-3-yl)-4,5-dihydro-5-[(pyrrolidino)carbonyl]imidazo[1,5-a]quinoxaline (I)

mp 190.5°–191°: IR (mineral oil) 2957, 2926, 2883, 2866, 2856, 1647, 1572, 1509, 1410, 1400 and 771 cm$^{-1}$; NMR (CDCl$_3$) 8.12, 7.54, 7.1–7.3, 5.07, 3.28, 2.97, 1.7–1.9 and 1.45 δ; MS (EI, m/z) 364, 293, 266, 238, 210, 98 and 55.

EXAMPLE 201

4,5-Dihydro-3-(5-isopropyl-1,2,4-oxadiazol-3-yl)-5-[(piperidino)carbonyl]imidazo[1,5-a]quinoxaline (I)

mp 190°–191°: IR (mineral oil) 3095, 2953, 2925, 2856, 1644, 1571, 1508, 1430, 1355 and 1279 cm$^{-1}$; NMR (CDCl$_3$) 8.12, 7.54, 7.1–7.3, 5.01, 3.15–3.4, 1.4–1.7 and 1.46 δ; MS (m/z) 392, 307, 280, 238, 210, 112, 69 and. 40.

EXAMPLE 202 tert-Butyl 4,5-dihydro-5-[(piperidino)carbonyl]imidazo[1,5-a]-quinoxaline-3-carboxylate (I)

mp 167°: IR (mineral oil) 3098, 2947, 2924, 2856, 1697, 1669, 1510, 1426, 1377, 1301, 1288, 1262 and 1151 cm$^{-1}$; NMR (CDCl$_3$) 8.00, 7.49, 7.1–7.3, 4.95, 3.2–3.3, 1.45–1.7 and 1.63 δ; MS (m/z) 382, 326, 214, 197, 112, 69 and 40.

EXAMPLE 203

4,5-Dihydro-3-(3-isopropyl-1,2,4-oxadiazol-5-yl)-5-[(piperidino)carbonyl]imidazo[1,5-a]quinoxaline (I)

mp 173.5°–174.5°: IR (mineral oil) 3116, 2952, 2941, 2925, 2858, 1646, 1640, 1506, 1451 and 1420 cm$^{-1}$; NMR (CDCl$_3$) 8.14, 7.56, 7.1–7.35, 5.05, 3.2–3.35, 3.05–3.3, 1.4–1.7 and 1.40 δ; MS (m/z) 392, 280, 196, 112, 69 and 40.

EXAMPLE 204

3-(5-Ethyl-1,2,4-oxadiazol-3-yl)-4,5-dihydro-5-[(piperidino)carbonyl]imidazo[1,5-a]quinoxaline (I)

mp 191°–191.5°: IR (mineral oil) 2944, 2924, 2854, 1646, 1571, 1505, 1424, 1273, 1211 and 756 cm$^{-1}$; NMR (CDCl$_3$) 8.12, 7.54, 7.1–7.3, 5.02, 3.15–3.35, 2.97, 1.4–1.7 and 1.46 δ; MS (m/z) 378, 266, 238, 210, 112, 69 and 40.

EXAMPLE 205 tert-Butyl 4,5-dihydro-4,4-dimethyl-5-[(piperidino)carbonyl]-imidazo[1,5-a]quinoxaline-3-carboxylate (I)

mp 176°–177°: IR (mineral oil) 2926, 2856, 1720, 1654, 1514, 1367 and 1144 cm$^{-1}$; NMR (CDCl$_3$) 7.98, 7.44, 7.18, 6.95–7.05, 6.77, 3.8–4.2, 3.1–3.5, 2.8–3.1, 2.08, 1.2–1.8 and 1.63 δ; MS (m/z) 410, 395, 210 and 112.

EXAMPLE 206

4,5-Dihydro-3-(5-isopropyl-1,2,4-oxadiazol-3-yl)-4,4-dimethyl-5-[(piperidino)carbonyl]imidazo-[1,5-a]quinoxaline (I)

mp 190°–191°: IR (mineral oil) 2926, 2854, 1654, 1512, 1429, 1317 and 1267 cm$^{-1}$; NMR (CDCl$_3$) 8.12, 7.50, 7.1–7.25, 6.95–7.1, 6.79, 3.8–4.1, 3.1–3.4, 2.8–3.1, 1.2–2.1, 1.48 δ; (m/z) 420, 405, 113, 112 and 69.

EXAMPLE 207 tert-Butyl 5-[(dimethylamino)carbonyl]-4,5-dihydro-7-methyl-imidazo[1,5-a]quinoxaline-3-carboxylate (I)

mp 164°–165°: IR (mineral oil) 3113, 2925, 1684, 1656, 1521, 1491, 1353 and 1158 cm$^{-1}$; NMR (CDCl$_3$) 7.96, 7.38, 6.95, 6.89, 4.93, 2.86, 2.37 and 1.62 δ; MS (m/z) 356, 300, 228, 211, 210, 183 and 72.

EXAMPLE 208

5-[(Dimethylamino)carbonyl]-4,5-dihydro-3-(5-isopropyl-1,2,4-oxadiazol-3-yl)-7-methylimidazo-[1,5-a]quinoxaline (I)

mp 175°–176°: IR (mineral oil) 3100, 2925, 2855, 1654, 1566, 1515, 1492, 1355, 1284 and 1192 cm$^{-1}$; NMR (CDCl$_3$) 8.08, 7.42, 6.96, 6.90, 4.99, 3.2–3.35, 2.86, 2.38 and 1.45 δ; MS (m/z) 366, 294, 278, 252, 224, 209 and 72.

EXAMPLE 209 tert-Butyl 4,5-dihydro-7-methyl-5-[(pyrrolidino)carbonyl]-imidazo[1,5-a]quinoxaline-3-carboxylate (I)

mp 207.5°–208°: IR (mineral oil) 2954, 2925, 2869, 2856, 1692, 1641, 1518, 1410, 1394 and 1374 cm$^{-1}$; NMR (CDCl$_3$) 7.96, 7.37, 4.98, 3.2–3.4, 2.37, 1.75–1.9 and 1.62 δ; MS (m/z) 382, 326, 309, 228, 211, 210, 98 and 55.

EXAMPLE 210

4,5-Dihydro-3-(5-isopropyl-1,2,4-oxadiazol-3-yl)-7-methyl-5-[(pyrrolidino)carbonyl]imidazo-[1,5-a]quinoxaline (I)

mp 231°–231.5°: IR (mineral oil) 2955, 2925, 2873, 2855, 1653, 1566, 1412 and 1392 cm$^{-1}$; NMR (CDCl$_3$) 8.08, 7.42, 6.85–7.05, 5.03, 3.1–3.4, 2.38, 1.7–1.9 and 1.46 δ; MS (m/z) 392, 321, 294, 252, 224, 209, 98 and 55.

EXAMPLE 211

3-(5-tert-Butyl-1,2,4-oxadiazol-3-yl)-5-[(dimethylamino)carbonyl]-4,5-dihydroimidazo-[1,5-a]quinoxaline (I)

mp 219°–220°: NMR (CDCl$_3$) 8.12, 7.55, 7.05–7.35, 5.01, 2.86 and 1.50 δ.

EXAMPLE 212

3-(5-tert-Butyl-1,2,4-oxadiazol-3-yl)-5-[(dimethylamino)carbonyl]-4,5-dihydro-4,4-dimethylimidazo-[1,5-a]quinoxaline (I)

mp 160.5–162: NMR (CDCl$_3$) 8.12, 7.51, 7.15–7.25, 7.06, 6.74, 3.08, 2.73, 2.00, 1.72 and 1.51 δ.

EXAMPLE 213 tert-Butyl 4,5-dihydro-4,4-dimethyl-5-[(pyrrolidino)carbonyl]-imidazo[1,5-a]quinoxaline-3-carboxylate (I)

mp 124°–125°: IR (mineral oil) 2925, 1712, 1663, 1512, 1408, 1283 and 1155 cm$^{-1}$; NMR (CDCl$_3$) 7.97, 7.44, 7.1–7.25, 7.01, 6.80, 3.5–3.65, 2.8–3.35, 1.6–2.3 and 1.63 δ; MS (m/z) 396, 381, 210 and 98.

EXAMPLE 214 tert-Butyl 5-[(dimethylamino)carbonyl]-4,5-dihydro-4,4-dimethylimidazo-[1,5-a]quinoxaline-3-carboxylate (I)

mp 162°–163°: IR (mineral oil) 2925, 1712, 1670, 1662, 1510, 1489, 1386, 1269, 1186 and 1153 cm$^{-1}$; NMR (CDCl$_3$) 7.98, 7.45, 7.19, 7.03, 6.72, 3.08, 2.72, 2.08, 1.68 and 1.63 δ; MS (m/z) 370, 355, 210 and 72 δ.

EXAMPLE 215

4,5-Dihydro-3-(5-isopropyl-1,2,4-oxadiazol-3-yl)-4,4-dimethyl-5-[(pyrrolidino)carbonyl]imidazo-[1,5-a]quinoxaline (I)

mp 130°–132°: IR (mineral oil) 2925, 1665, 1566, 1403, 1308, 1288 and 752 cm$^{-1}$; NMR (CDCl$_3$) 8.11, 7.50, 7.20, 7.04, 6.83, 3.5–3.7, 3.25–3.4, 2.8–3.3, 1.6–2.1 and 1.47 δ; MS (m/z) 406, 391 and 98.

EXAMPLE 216

5-[(Dimethylamino)carbonyl]-4,5-dihydro-3-(5-isopropyl-1,2,4-oxadiazol-3-yl)-4,4-dimethyl-imidazo-[1,5-a]quinoxaline (I)

mp 171°–172°: IR (mineral oil) 2925, 1664, 1512. 1185 and 768 cm$^{-1}$; NMR (CDCl$_3$) 8.12, 7.51, 7.15–7.25, 7.06, 6.74, 3.2–3.4, 3.07, 2.73, 2.00, 1.72 and 1.48 δ; MS (m/z) 380, 365 and 72.

EXAMPLE 217 tert-Butyl 4,5-dihydro-5-[(pyrrolidino)carbonyl]imidazo[1,5-a]quinoxaline-3-carboxylate (I)

mp 127°–128°: IR (mineral oil) 2925, 1731, 1643, 1506, 1408, 1375 and 1149 cm$^{-1}$; NMR (CDCl$_3$) 8.00, 7.50, 7.1–7.3, 5.00, 3.2–3.35, 1.75–1.9 and 1.63 δ; MS (m/z) 368, 312, 214, 197 and 98.

EXAMPLE 218 tert-Butyl 5-[(dimethylamino)carbonyl]-4,5-dihydroimidazo-[1,5-a]quinoxaline-3-carboxylate (I)

mp 184°–186°: IR (mineral oil) 2925, 1691, 1680, 1509, 1379, 1153 and 774 cm$^{-1}$; NMR (CDCl$_3$) 8.00, 7.51, 7.2–7.35, 7.05–7.2, 4.96, 2.85 and 1.63 δ; MS (m/z) 342, 286, 269, 214, 196, 169 and 72.

EXAMPLE 219

5-[(Dimethylamino)carbonyl]-4,5-dihydro-3-(5-isopropyl-1,2,4-oxadiazol-3-yl)imidazo[1,5-a]-quinoxaline (I)

mp 190°–191°: IR (mineral oil) 2925, 1651, 1565, 1508, 1387, 1380, 1356, 1187 and 747 cm$^{-1}$; NMR (CDCl$_3$) 8.12, 7.55, 7.25–7.35, 7.05–7.2, 5.02, 3.2–3.4, 2.86 and 1.46 δ; MS (m/z) 352, 280, 264, 238, 210, 195 and 72.

EXAMPLE 220

4,5-Dihydro-4,4-dimethyl-5-[(pyrrolidino)carbonyl]-3-(p-tolyl)imidazo[1,5-a]quinoxaline (I)

mp 215°–216° C.: IR (mineral oil) 2926, 1650, 1522, 1505, 1407 and 745 cm$^{-1}$; NMR (CDCl$_3$) 8.02, 7.49, 7.37, 7.1–7.25, 7.0–7.1, 6.80, 3.5–3.7, 2.9–3.3, 2.40, 1.6–1.95 and 1.66 δ; MS (m/z) 386, 371 and 98.

EXAMPLE 221

5-[(Dimethylamino)carbonyl]-4,5-dihydro-4,4-dimethyl-3-(p-tolyl)imidazo[1,5-a]quinoxaline (I)

mp 248°–249°: IR (mineral oil) 2925, 1665, 1660, 1505, 1277, 1187, 1180 and 750 cm$^{-1}$; NMR (CDCl$_3$) 8.02, 7.50, 7.37, 7.1–7.25, 7.05, 6.71, 3.04, 2.74, 2.40 and 1.65 δ; MS (m/z) 360, 345, 316 and 72.

EXAMPLE 222

3-(4-Fluorophenyl)-4,5-dihydro-4,4-dimethyl-5-[(pyrrolidino)carbonyl]imidazo[1,5-a]quinoxaline (I)

mp 232°–233°: IR (mineral oil) 2925, 1648, 1501, 1407, 1215 and 748 cm$^{-1}$; NMR (CDCl$_3$) 8.02, 7.4–7.55, 7.0–7.2, 6.81, 3.5–3.65, 2.9–3.3, 1.6–1.95 and 1.64 δ; MS (m/z) 390, 375, 320 and 98.

EXAMPLE 223

5-[(Dimethylamino)carbonyl]-3-(4-fluorophenyl)-4,5-dihydro4,4-dimethylimidazo[1,5-a]-quinoxaline (I)

mp 248°–249°: IR (mineral oil) 2925, 1653, 1516, 1503, 1274, 1219 and 752 cm$^{-1}$; NMR (CDCl$_3$) 8.02, 7.4–7.55, 7.0–7.25, 6.72, 3.05, 2.74 and 1.64 δ; MS (m/z) 364, 349, 320 and 72.

EXAMPLE 224

4,5-Dihydro-3-phenyl-5-[(pyrrolidino)carbonyl]-imidazo[1,5-a]quinoxaline (I)

mp 205°–207°: IR (mineral oil) 2954, 2925, 2855, 1644, 1511, 1401, 1392, 1190, 763, 754, 701 and 697 cm$^{-1}$; NMR (CDCl$_3$) 8.09, 7.68, 7.53, 7.44, 7.1–7.35, 4.93, 3.25 and 1.65–1.85 δ; MS (m/z) 344, 246.

EXAMPLE 225

4,5-Dihydro-3-(5-isopropyl-1,2,4-oxadiazol-3-yl)-5-[(pyrrolidino)carbonyl]imidazo[1,5-a]quinoxaline (I)

mp 195°–196°: IR (mineral oil) 2954, 2924, 2855, 1644, 1572, 1509, 1407, 1394 and 1360 cm$^{-1}$; NMR (CDCl$_3$) 8.12, 7.54, 7.1–7.35, 5.06, 3.2–3.4, 1.7–1.9 and 1.46 δ; MS (m/z) 378, 307, 280, 238 and 98.

EXAMPLE 226

5-[(Dimethylamino)carbonyl]-4,5-dihydro-3-(3-isopropyl-1,2,4-oxadiazol-5-yl)imidazo[1,5-a]-quinoxaline (I)

mp 186°–187.5°: IR (mineral oil) 3104, 2954, 2925, 2855, 1655, 1652, 1625, 1561, 1505, 1486, 1466, 1458, 1389, 1349, 1276, 1259, 1171 and 750 cm$^{-1}$; NMR (CDCl$_3$) 8.14, 7.56, 7.05–7.35, 5.05, 3.05–3.25, 2.87 and 1.40 δ; MS (m/z) 352, 280, 196 and 72.

EXAMPLE 227

5-[(Dimethylamino)carbonyl]-4,5-dihydro-3-(3-isopropyl-1,2,4-oxadiazol-5-yl)-4,4-dimethylimidazo-[1,5-a]-quinoxaline (I)

mp 172°–173°; IR (mineral oil) 2961, 2953, 2925, 1668, 1626, 1510, 1388, 1384, 1291, 1281, 1269, 1188 and 768 cm$^{-1}$; NMR (CDCl$_3$) 8.13, 7.51, 7.2–7.3, 7.07, 6.75, 3.0–3.3, 3.09, 2.75, 2.11, 1.74 and 1.40 δ; MS (m/z) 380, 365 and 72.

EXAMPLE 228

5-[(Dimethylamino)carbonyl]-4,5-dihydro-4,4-dimethyl-3-phenylimidazo[1,5-a]quinoxaline (I)

mp 224°–225.5°: IR (mineral oil) 2954, 2924, 2855, 1650, 1518, 1497, 1383, 1274 and cm$^{-1}$; NMR (CDCl$_3$) 8.04, 7.25–7.6, 7.18, 7.06, 6.72, 3.04, 2.74 and 1.66 δ; MS (m/z) 346, 331, 302 and 72.

EXAMPLE 229

6-Chloro-5-[(dimethylamino)carbonyl]-4,5-dihydro-4,4-dimethyl-3-phenylimidazo[1,5-a]quinoxaline (I)

mp 194°–195°: IR (mineral oil) 2953, 2925, 2855, 1652, 1502, 1380, 785, 775 and 706 cm$^{-1}$; NMR (CDCl$_3$) 8.04, 7.2–7.5, 7.13, 2.78 and 1.65 δ; MS (m/z) 380, 365, 336 and 72.

EXAMPLE 230

7-Chloro-4,5-dihydro-4,4-dimethyl-3-phenyl-5-[(pyrrolidino)carbonyl]imidazo[1,5-a]quinoxaline (I)

mp 218.5°–219°: IR (mineral oil) 2951, 2925, 2869, 2855, 1662, 1508, 1401, 1388, 1324 and 955 cm$^{-1}$; NMR (CDCl$_3$) 7.99, 7.3–7.5, 7.01, 6.79, 3.4–3.6, 2.8–3.4, 1.65–2.0 and 1.65 δ; MS (m/z) 406, 391 and 98.

EXAMPLE 231

7-Chloro-5-[(dimethylamino)carbonyl]-4,5-dihydro-4,4-dimethyl-3-phenylimidazo[1,5-a]quinoxaline (I)

mp 172°–174°: IR (mineral oil) 2951, 2924, 2855, 1650, 1517, 1479, 1380, 1279 and 775 cm$^{-1}$; NMR (CDCl$_3$) 8.00, 7.3–7.5, 7.03, 6.70, 3.07, 2.79, 1.68 and 1.62 δ; MS (m/z) 380, 365 and 72.

EXAMPLE 232 tert-Butyl 4,5-dihydro-6-methyl-5-[(pyrrolidino)carbonyl]imidazo[1,5-a]quinoxaline-3-carboxylate (I)

mp 233°–234°: IR (mineral oil) 2967, 2953, 2924, 2872, 2855, 1689, 1666, 1510, 1374, 1359, 1299, 1213, 1158 and 1131 cm$^{-1}$; NMR (CDCl$_3$) 8.01, 7.3–7.4, 7.1–7.25, 5.09, 3.1–3.25, 2.21, 1.7–1.9 and, 1.63 δ; MS (m/z) 382, 326, 228, 211 and 98.

EXAMPLE 233

4,5-Dihydro-3-(5-isopropyl-1,2,4-oxadiazol-3-yl)-6-methyl-5-[(pyrrolidino)carbonyl]imidazo-[1,5-a]quinoxaline (I)

mp 220°–222°: IR (mineral oil) 2970, 2953, 2924, 2873, 1654, 1505, 1493, 1471, 1402, 1382 and 1371 cm$^{-1}$; NMR (CDCl$_3$) 8.12, 7.41, 7.1–7.3, 5.16, 3.2–3.4, 3.0–3.2, 2.23, 1.7–1.85 and 1.46 δ; MS (m/z) 392, 321, 294, 252, 98 and 55.

EXAMPLE 234 tert-Butyl 5-[(dimethylamino)carbonyl]-4,5-dihydro-6-methyl-imidazo[1,5-a]quinoxaline-3-carboxylate (I)

mp 214°–216°: IR (mineral oil) 2953, 2925, 2855, 1692, 1674, 1508, 1380, 1370, 1354, 1210, 1162 and 1153 cm$^{-1}$; NMR (CDCl$_3$) 8.00, 7.3–7.4, 7.1–7.3, 5.02, 2.90, 2.20 and 1.63 δ; MS (m/z) 356, 300, 228, 211 and 72.

EXAMPLE 235

5-[(Dimethylamino)carbonyl]-4,5-dihydro-3-(5-isopropyl-1,2,4-oxadiazol-3-yl)-6-methylimidazo-[1,5-a]quinoxaline (I)

mp 188°–189°: IR (mineral oil) 2952, 2924, 2855, 1668, 1498, 1494, 1471, 1380 and cm$^{-1}$; NMR (CDCl$_3$) 8.12, 7.42, 7.1–7.3, 5.07, 3.2–3.4, 2.88, 2.22 and 1.47 δ; MS (m/z) 366, 294, 278, 252 and 72.

EXAMPLE 236

3-(5-tert-Butyl-1,2,4-oxadiazol-3-yl)-4,5-dihydro-5-[(pyrrolidino)carbonyl]imidazo[1,5-a]quinoxaline (I)

mp 226°–227.5°: IR (mineral oil) 2925, 1642, 1557, 1508, 1411, 1396, 1360 and 748 cm$^{-1}$; NMR (CDCl$_3$) 8.11, 7.54, 7.1–7.3, 5.05, 3.28, 1.7–1.9 and 1.50 δ; MS (m/z) 392, 294, 264, 238, 210, 195, 98 and 55.

EXAMPLE 237

3-(5-tert-Butyl-1,2,4-oxadiazol-3-yl)-4,5-dihydro-4,4-dimethyl-5-[(pyrrolidino)carbonyl]imidazo-[1,5-a]quinoxaline (I)

mp 172°–173.5°: IR (mineral oil) 2925, 1660, 1516, 1404, 1315 and 1183 cm$^{-1}$; NMR (CDCl$_3$) 8.11, 7.49, 7.19, 7.04, 6.83, 3.5–3.7, 2.8–3.3, 1.6–2.1 and 1.51 δ; MS (m/z) 420, 405, 98 and 55.

EXAMPLE 238

3-(5-tert-Butyl-1,2,4-oxadiazol-3-yl)-7-chloro-4,5-dihydro-5-[(pyrrolidino)carbonyl]imidazo-[1,5-a]-quinoxaline (I)

mp 235°–236°: NMR (CDCl$_3$) 8.09, 7.47, 7.1–7.2, 5.04, 3.2–3.4, 1.8–1.95 and 1.50 δ.

EXAMPLE 239

3-(5-tert-Butyl-1,2,4-oxadiazol-3-yl)-7-chloro-5-[(dimethylamino)carbonyl]-4,5-dihydro-4,4-dimethyl-imidazo[1,5-a]quinoxaline (I)

mp 191°–192.5°: NMR (CDCl$_3$) 8.09, 7.48, 7.14, 7.09, 5.00, 2.90 and 1.49 δ.

EXAMPLE 240

3-(5-tert-Butyl-1,2,4-oxadiazol-3-yl)-7-chloro-5-[(dimethylamino)carbonyl]-4,5-dihydro-4,4-dimethyl-imidazo[1,5-a]quinoxaline (I)

mp 112°–113°: NMR (CDCl$_3$) 8.08, 7.43, 7.02, 6.72, 3.10, 2.78, 1.98, 1.72 and 1.51 δ.

EXAMPLE 241

3-(5-tert-Butyl-1,2,4-oxadiazol-3-yl)-6-chloro-4,5-dihydro-4,4-dimethyl-5-[(pyrrolidino)carbonyl]-imidazo[1,5-a]quinoxaline (I)

mp 185°–187°: NMR (CDCl3) 8.11, 7.44, 7.31, 7.11, 3.3–3.6, 2.5–2.8, 1.89, 1.6–1.9 and 1.51 δ.

EXAMPLE 242

3-(5-tert-Butyl-1,2,4-oxadiazol-3-yl)-6-chloro-5-[(dimethylamino)carbonyl]-4,5-dihydro-4,4-dimethyl-imidazo[1,5-a]quinoxaline (I)

mp 147°–148.5°: NMR (CDCl$_3$) 8.12, 7.45, 7.32, 7.13, 2.79, 1.86 and 1.51 δ.

EXAMPLE 243

3-(5-tert-Butyl-1,2,4-oxadiazol-3-yl)-6-chloro-4,5-dihydro-5-[(pyrrolidino)carbonyl]imidazo-[1,5-a]quinoxaline (I)

mp 246°–247°: NMR (CDCl$_3$) 8.13, 7.50, 7.37, 7.23, 5.12, 3.25–3.45, 1.75–1.95 and 1.50 δ.

EXAMPLE 244

3-(5-tert-Butyl-1,2,4-oxadiazol-3-yl)-6-chloro-5-[(dimethylamino)carbonyl]-4,5-dihydroimidazo[1,5-a]-quinoxaline (I)

mp 214°–215°: NMR (CDCl$_3$) 8.12, 7.51, 7.38, 7.24, 5.06, 3.01 and 1.51 δ.

EXAMPLE 245

5-tert-Butyl-3-(4-fluorophenyl)-4,5-dihydroimidazo-[1,5-a]quinoxalin-4-one (XXXIV)

Potassium tert-butoxide (1.0M in THF, 24.1 ml) is added to a mixture of 1-(tert-butyl)-tetrahydroquinoxalin-2,3-dione (XXXI, 5.00 g) and THF (54.0 ml) at −20°. The mixture is allowed to warm to 0° over 30 min. After cooling to 40°, diethyl chlorophosphate (3.53 ml) is added and the solution is allowed to warm to 20°–25° over 40 min. After cooling to −78°, a solution of 4-fluorobenzyl isocyanide (3.62 g) and THF (5.0 ml) is added. Potassium tert-butoxide (24.1 ml) is then added dropwise over several min. The mixture is stirred at -78° for 30 rain and is allowed to warm slowly to 20°–25° over 2 hr. Aqueous workup (ethyl acetate, magnesium sulfate) and purification by flash chromatography eluting with ethyl acetate/hexane (1/2), pooling the appropriate fractions and concentration gives the title compound, mp 135°–137°; IR (mineral oil) 2953, 2925, 2855, 1668, 1498, 1299 and 751 cm$^{-1}$; NMR (CDCl$_3$) 8.31, 8.22, 7.63, 7.55, 7.05–7.35 mid 1.76 δ; MS (m/z) 335, 279.

EXAMPLE 246

3-(4-fluorophenyl)-4,5-dihydroimidazo[1,5-a]-quinoxalin-4-one (XXXV)

Trifluoroacetic acid (50.0 ml) is added to a solution of 5-tert-butyl-3-(4 -fluorophenyl)-4,5-dihydroimidazo[1,5-a]quinoxalin-4-one (XXXIV, EXAMPLE 245, 4.01 g) and methylene chloride (50.0 ml) at 0°. The solution is stirred for 1 hr at 0° and is concentrated. The residue is triturated with water, filtered, washed with water (2×100 ml), ether (2×100 ml), and dried under reduced pressure to give the title compound, mp> 300°; IR (mineral oil) 2955, 2922, 2868, 2855, 1667, 1499, 1377 and 1366 cm$^{-1}$; NMR (d$_6$-DMSO) 11.45, 9.16, 8.3–8.45, 8.21 and 7.2–7.45 δ; MS (EI, m/z) 279, 251 and 223.

EXAMPLE 247

3-(4-Fluorophenyl)-4,5-dihydroimidazo[1,5-a]-quinoxaline (XXXVI)

Aluminum hydride (0.6M in THF, 80 ml) is added to 3-(4-fluorophenyl)-4,5 -dihydroimidazo[1,5-a]quinoxalin-4-one (XXXV, EXAMPLE 246, 3.21 g) and the resulting solution is heated at reflux for 36 hr. After 24 hr, lithium aluminum hydride (600 mg) is added as starting material is still present. After cooling to 20°–25°, methanol (12.1 ml) and sodium hydroxide (6N, 50.0 ml) are added successively and the resultant solution stirred for 30 min at 20°–25°. Aqueous workup (ethyl acetate, magnesium sulfate) and purification by flash chromatography eluting with hexane/ethyl acetate (2/1), pooling the appropriate fractions and concentration gives the title compound, IR (mineral oil) 3381, 2924, 1511, 1492, 1290, 1231, 838 and 741 cm$^{-1}$; NMR (CDCl$_3$) 8.04, 7.58, 7.42, 7.0–7.2, 6.8–6.95, 4.66 and 4.07 δ; MS (m/z) 265, 264, 237, 144 and 118.

EXAMPLE 248

3-(4-Fluorophenyl)-4,5-dihydro-5-[(pyrrolidino)-carbonyl]imidazo[1,5-a]quinoxaline (I)

Triphosgene (427 mg) is added to a mixture of 3-(4-fluorophenyl)-4,5 -dihydroimidazo[1,5-a]quinoxaline (XXXVI, EXAMPLE 247, 702 mg), methylene chloride (27.0 ml) and diisopropylethylamine (0.53 ml) at 0°. The resultant solution is stirred for 1 hr at 0° and for 2 hr at 20°–25°. The mixture is cooled to 0° and pyrrolidine (0.85 ml) is added. The mixture is maintained at 0° for 1 hr and is allowed to warm to 20°–25°. After stirring for 16 basic workup using sodium bicarbonate, methylene chloride and magnesium sulfate and purification by flash chromatography eluting with ethyl acetate/hexane (1/1), pooling the appropriate fractions and concentration gives the product. Recrystallization from hot ethyl acetate-hexane give the title compound, mp 217°–218°; IR (mineral oil) 2925, 1641, 1506, 1414 and 753 cm$^{-1}$; NMR (CDCl$_3$) 8.07, 7.64, 7.53, 7.05–7.3, 4.89, 3.25 and 1.7–1.85 δ; MS (m/z) 362, 264, 98 and 55.

Following the general procedure of EXAMPLES 245–248 and making non-critical variations but using various starting materials the products of EXAMPLES 249 thru 252 are obtained:

EXAMPLE 249

5-[(Dimethylamino)carbonyl]-3-(4-fluorophenyl)-4,5-dihydroimidazo [1,5-a]quinoxaline (I)

mp 192°–193.5°; IR (mineral oil) 2925, 1648, 1504, 1485, 1384, 1364, 1213 and 1205 cm$^{-1}$; NMR (CDCl$_3$) 8.07, 7.55–7.7, 7.54, 7.05–7.3, 4.84 and 2.83 δ; MS (m/z) 336, 264 and 72.

EXAMPLE 250

5-[(Dimethylamino)carbonyl]-4,5-dihydro-3-phenyl-imidazo[1,5-a]quinoxaline (I)

mp 225°–226°: IR (mineral oil) 2954, 2924, 2855, 1657, 1506, 1498, 1388, 1199, 752 and 702 cm$^{-1}$; NMR (CDCl$_3$) 8.09, 7.67, 7.54, 7.44, 7.05–7.35, 4.88 and 2.83 δ; MS (m/z) 318, 246 and 72.

EXAMPLE 251

4,5-Dihydro-3-phenyl-5-[(piperidino)carbonyl]-imidazo[1,5-a]quinoxaline (I)

mp 177°–180°: IR (mineral oil) 2953, 2930, 2853, 1651, 1410, 1213, 744 and 698 cm$^{-1}$; NMR (CDCl$_3$) 8.12, 7.68, 7.54, 7.45, 7.1–7.4, 4.88, 3.15–3.35 and 1.4–1.65 δ; MS (m/z) 358, 246, 112 and 69.

EXAMPLE 252

4,5-Dihydro-5-[(pyrrolidino)carbonyl]-3-(p-tolyl)-imidazo[1,5-a]quinoxaline (I)

mp 238.5°–239.5°: NMR (CDCl$_3$) 8.07, 7.45–7.65, 7.05–7.3, 4.91, 3.25, 2.39 and 1.65–1.85 δ.

Following the general procedure of EXAMPLES 48–87 and the EXAMPLES referenced therein and making non-critical variations the following compounds are produced:

EXAMPLE 253

5-Benzoyl-3-(3-cyclopropyl-1,2,4-oxadiazol-5-yl)-4,5-dihydroimidazo]1,5-a]quinoxaline (I)

mp 232°–233°.

EXAMPLE 254

3-(3-Cyclopropyl-1,2,4-oxadiazol-5-yl)-4,5-dihydro-5-propionylimidazo[1,5-a]quinoxaline (I)

mp 197°–198°.

EXAMPLE 255

3-(3-Cyclopropyl-1,2,4-oxadiazol-5-yl)-4,5-dihydro-5-(phenoxycarbonyl)imidazo[1,5-a]quinoxaline (I)

mp 212°–213°.

EXAMPLE 256

3-(3-Cyclopropyl-1,2,4-oxadiazol-5-yl)-4,5-dihydro-5-(ethoxycarbonyl)imidazo[1,5-a]quinoxaline (I)

mp 204°–205°.

EXAMPLE 257

3-(3-Cyclopropyl-1,2,4-oxadiazol-5-yl)-5-[(diethyl-amino)carbonyl]-4,5 -dihydroimidazo[1,2-a]quinoxaline (I)

mp 165°–166°.

EXAMPLE 258

3-(3-Cyclopropyl-1,2,4-oxadiazol-5-yl)-4,5-dihydro-5-(2-furoyl)imidazo[1,5-a]quinoxaline (I)

mp 197°–198°.

EXAMPLE 259 tert-Butylamino 7-fluoro-4,5-dihydro-4,4-dimethyl-5-[(pyrrolidino)carbonyl]imidazo[1,5-a]quinoxaline-3-carboxamide (I)

mp 196°–197°.

EXAMPLE 260

4,5-Dihydro-3-[5-[1-(2-methylpropyl)]-1,2,4-oxadiazol-3-yl]-5-[(pyrrolidino)carbonyl]imidazo-[1,5-a]quinoxaline (I)

mp 138°–40°.

EXAMPLE 261 tert-Butylamino 7-Fluoro-4,5-dihydro-5-[(pyrrolidino)carbonyl]imidazo[1,5-a]quinoxaline-3-carboxamide (I)

mp 243°–244°.

EXAMPLE 262

4,5-Dihydro-5-[(pyrrolidino)carbonyl]-3-[5-(3,3,3-trifluoropropyl)-1,2,4-oxadiazol-3-yl]imidazo-[1,5-a]quinoxaline (I)

mp 193°–4°.

EXAMPLE 263 tert-Butyl 6-fluoro-4,5-dihydro-5-(p-tolylsulfonyl)imidazo[1,5-a]quinoxaline-3-carboxylate mp 153°–5°.

EXAMPLE 264

7-Fluoro-4,5-dihydro-3-[5-(2-methylpropyl)-1,2,4-oxadiazol-3-yl]-5-[(pyrrolidino)carbonyl]imidazo-[1,5-a]quinoxaline (I)

mp 198°–9°.

EXAMPLE 265

7-Fluoro-4,5-dihydro-3-[5-(2-methyl-3,3,3-trifluoropropyl)-1,2,4-oxadiazol-3-yl]-5-[(pyrrolidino)-carbonyl]imidazo[1,5-a]quinoxaline (I)

mp 183°–4°.

EXAMPLE 266

4,5-Dihydro-3-[5-(2-methyl-3,3,3-trifluoropropyl)-1,2,4-oxadiazol-3-yl]-5-[(pyrrolidino)carbonyl]imidazo-[1,5-a]quinoxaline (I)

mp 142°–4°.

EXAMPLE 267

4,5-Dihydro-3-[5-(2-methyl-3,3,3-trifluoropropyl)-1,2,4-oxadiazol-3-yl]-5-[(morpholino)carbonylmethyl]-imidazo[1,5-a]quinoxaline (I)

mp 167°–71°.

EXAMPLE 268

3-[5-(Cyclopentyl)-1,2,4-oxadiazol-3-yl]-7-fluoro-4,5-dihydro-4(R)-methyl-5-[(morpholino)-carbonylmethyl]imidazo[1,5-a]quinoxaline (I)

mp 174°–50°.

EXAMPLE 269

7-Fluoro-4,5-dihydro-3-(5-isopropyl-1,2,4-oxadiazol-3-yl)-4(R)-methyl-5-[(pyrrolidino)carbonyl]-imidazo[1,5-a]quinoxaline (I)

mp 211°–2°.

EXAMPLE 270

3-(5-Cyclopentyl-1,2,4-oxadiazol-3-yl)-7-fluoro-4,5-dihydro-4(R)-methyl-5-[2-(morpholino)-acetyl]imidazo[1,5-a]quinoxaline (I)

mp 212°–3°.

EXAMPLE 271

3-(5-Cyclopentyl-1,2,4-oxadiazol-3-yl)-7-fluoro-4,5-dihydro-4(R)-methyl-5-[(piperidino)-carbonylmethyl]imidazo[1,5-a]quinoxaline (I)

mp 185°–6°.

EXAMPLE 272 tert-Butyl 7-fluoro-4,5-dihydro-4(R)-methyl-5-[(pyrrolidino)carbonyl]imidazo[1,5-a]quinoxaline-3-carboxylate (I)

mp 188°–9°.

EXAMPLE 273

3-(5-Cyclopentyl-1,2,4-oxadiazol-3-yl)-7-fluoro-4,5-dihydro-4(R)-methyl-5-[2-(pyrrolidino)acetyl]-imidazo[1,5-a]quinoxaline (I)

mp 146°–7°.

EXAMPLE 274 tert-Butyl 7-fluoro-4,5-dihydro-4(R)-methyl-5-(2-pyridylmethyl)imidazo[1,5-a]quinoxaline-3-carboxylate (LX)

mp 152°–3°.

EXAMPLE 275

3-(5-Cyclopentyl-1,2,4-oxadiazol-3-yl)-7-fluoro-4,5-dihydro-4(R)-methyl-5-[(pyrrolidino)carbonylmethyl]imidazo[1,5-a]quinoxaline (I)

mp 241°–2°.

EXAMPLE 276

7-Fluoro-4,5-dihydro-4(R)-methyl-3-[5-(1-methyl-cyclopropyl)-1,2,4-oxadiazol-3-yl]-5-(2-pyridylmethyl)-imidazo[1,5-a]quinoxaline (LX)

mp 147°–8°.

EXAMPLE 277

Cyclopropylmethylamino 7-Fluoro-4,5-dihydro-4(R)-methyl-5-(2-pyridylmethyl)imidazo-[1,5-a]quinoxaline-3-carboxamide (LX)

mp 145°–6°.

EXAMPLE 278

7-Fluoro-4,5-dihydro-4(R)-methyl-3-[5-(2-methyl-cyclopropyl)-1,2,4-oxidiazol-3-yl]-5-(2-pyridyl-methyl)imidazo[1,5-a]-quinoxaline (LX)

mp 97°–8°.

EXAMPLES 279–290 disclose the process to prepare the compounds of the present invention where $R_4$ and $R_5$ are cyclized to form a heterocyclic ring (I-$R_4$/$R_5$/$R_6$–1), via the 4,5 -cyclic amide (XXXIX) intermediate, see CHART J.

EXAMPLE 279

N-(2-Nitrophenyl)-DL-glutamic acid dimethyl ester (XI)

A mixture of 1-fluoro-2-nitrobenzene (VII, 4.80 g), DL-glutamic acid hydrate (XIIa, 5.62 g), potassium carbonate (8.00 g), ethanol (50 ml) and water (10 ml) is heated at 105° for hr. The reaction mixture is then stripped of solvents and the residue stirred in DMF with methyl iodide (4 ml). After about a week, the DMF is removed and the residue is partitioned between dichloromethane and water. Silica gel chromatography (500 ml) using ethyl acetate/hexane (30/70) gives the title compound, NMR (CDCl$_3$) 2.28, 2.51, 3.69, 3.79, 4.40, 6.73, 6.80, 7.45, 8.20 and 8.33 δ.

EXAMPLE 280

3,3a-Dihydropyrrolo[1,2-a]quinoxaline-1,4(2H,5H)-dione (IV)

To N-(2-nitrophenyl)-DL-glutamic acid dimethyl ester (XI, EXAMPLE 279, 5.09 g) in methanol (150 ml) is added p-toluenesulfonic acid (0.158 g) and palladium on carbon (10%, 0.495 g). The mixture is shaken under hydrogen at 37 psi for 2 hr; the mixture is then filtered and the filtrate is concentrated to about 70 ml. Additional p-toluenesulfonic acid (0.15 g) is added, and the solution is heated at 60° for 1 hr. After cooling, the solid is collected, washed with methanol, and dried to give the title compound, mp 231°–232°; NMR (CDCl$_3$) 2.65, 4.41, 6.93, 7.14, 8.10 and 8.55 δ.

EXAMPLE 281

1-(5-Cyclopropyl-1,2,4-oxadiazol-3-yl)-12,12a-dihydroimidazo[1,5-a]pyrrolo[2,1-a]quinoxalin-10(11H)-one (I)

3,3a Dihydropyrrolo[1,2-a]quinoxaline-1,4(2H, 5H)-dione (IV, EXAMPLE 280, 0.520 g) is stirred in DMF (6.5 ml) and cooled at 0°. To this is added potassium tert-butoxide in THF (1M, 2.70 ml). After 10 min the ice bath is removed. Ten minutes later an additional DMF (6 ml) is added. After 30 min had elapsed, the reaction mixture is cooled in an ice/methanol bath and diethylchlorophosphate (0.39 ml) is added. The reaction is stirred for 10 minutes, after which the ice/methanol bath is removed. After a total of 45 minutes, the reaction is cooled at –78° and 5-cyclopropyl-3-isocyanomethyl-1,2,4-oxadiazole (0.403 g) is added, followed by potassium tert-butoxide in THF (1M, 2.70 ml) dropwise over 10 minutes. The reaction is stirred at –78° for 1.5 hr, after which the cooling bath is removed. The reaction is allowed to warm to 20°–25° over about 30 min. Water is added and the reaction mixture is partitioned between ethyl acetate and water, followed with a saline wash. The organic layers are dried over magnesium sulfate and concentrated. The residue is chromatographed on silica gel (200 ml) eluting with ethyl acetate/hexane 75/25, the appropriate fractions are pooled and concentrated to give the title compound, which is recrystallized from dichloromethane/ethyl acetate/hexane, mp 180°–183° (decomp); MS (m/z) at 333; IR (mineral oil) 1701, 1574, 1509, 1477 and 766 cm$^{-1}$; NMR (CDCl$_3$) 1.26, 1.36, 2.27, 2.60, 2.78, 3.38, 5.30, 7.29, 7.35, 7.57, 8.17 and 8.38 δ.

EXAMPLE 282

(S)-1-(5-Cyclopropyl-1,2,4-oxadiazol-3-yl)-12,12a-dihydroimidazo[1,5-a]pyrrolo[2,1-c]quinoxalin-10(11H)-one (I)

Following the general procedure of EXAMPLES 279, 280 and 281 and making non-critical variations but using N-(2-nitrophenyl)-L-glutamic acid diethyl ester, the title compound is obtained, mp 181.5°–183° (decomp); MS (m/z) at 333; IR (mineral oil) 1708, 1511, 761, 1204, 1403 cm$^{-1}$; NMR (CDCl$_3$) 1.28, 1.38, 2.25, 2.6, 2.78, 3.36, 5.30, 7.28, 7.36, 7.55, 8.18, 8.38 δ; $[\alpha]_D$=–197° (0.98, CH$_2$Cl$_2$).

EXAMPLE 283

(R)-1-(5-Cyclopropyl-1,2,4-oxadiazol-3-yl)-12,12a-dihydroimidazo[1,5-a]pyrrolo[2,1-c]quinoxalin-10(11H)-one (I)

Following the general procedure of EXAMPLES 279, 280 and 281 and making non-critical variations but using N-(2-nitrophenyl)-D-glutamic acid diethyl ester, the title compound is obtained, mp 181.5°–183° (decomp); MS (m/z) at 333; IR (mineral oil) 1707, 1511, 1499, 761, 1403 cm$^{-1}$; NMR (CDCl$_3$) 1.27, 1.38, 2.27, 2.58, 2.77, 3.37, 5.30, 7.30, 7.36, 7.57, 8.17, 8.36 δ; $[\alpha]_D$=+154° (0.98, CH$_2$Cl$_2$).

EXAMPLE 284

(S)-1-(Benzoxazol-2-yl)-12,12a-dihydroimidazo-[1,5-a]pyrrolo[2,1-a]quinoxalin-10(11H)-one (I)

Following the general procedure of EXAMPLE 30 and making non-critical variations but starting with (S)-3,3a-dihydropyrrolo[1,2-a]quinoxaline-1,4(2H,5H)-dione (intermediate formed in EXAMPLE 282, 0.638 g) and 2-(isocyanomethyl)benzoxazole (0.599 g), the title compound is obtained, which after crystallization from methanol/dichloromethane/hexane, mp 270°–273°; MS (m/z) at 342; IR (mineral oil) 1705, 1510, 1271, 1690, 747, 1630 cm$^{-1}$; NMR (CDCl$_3$) 2.37–2.48, 2.57–2.66, 2.76–2.89, 3.62–3.72, 5.45, 7.30–7.42, 7.60, 7.64, 7.75, 8.22, 8.40 δ.

EXAMPLE 285 tert-Butyl (S)-12,12a-dihydroimidazo[1,5-a]pyrrolo[2,1-c]quinoxaline-1-carboxylate (I)

Following the general procedure of EXAMPLE 30 and making non-critical variations but starting with (S)-3,3a-dihydropyrrolo[1,2-a]quinoxaline-1,4(2H,5H)-dione (intermediate formed in EXAMPLE 282, 0.638 g) and tert-butyl isocyanoacetate (0.621 g), the title compound is obtained, mp 202°–207° (decomp); MS (m/z) at 325; IR (mineral oil) 1719, 1363, 1700, 1507, 1161, 1293 cm$^{-1}$; NMR (CDCl$_3$) 1.64, 2.25–2.40, 2.55–2.81, 3.31–3.41, 5.26, 7.23–7.29, 7.33, 7.52, 8.06, 8.34 δ; $[\alpha]_D$=–248° (0.96, methanol).

EXAMPLE 286

N-(2-Nitrophenyl)-DL-serine methyl ester (XI)

To 15.66 g of 1-fluoro-2-nitrobenzene (VII), 16.87 g of potassium carbonate, 100 ml of 95% ethanol, and 40 ml of water are added 11.66 g of DL-serine. The reaction is stirred at 90° overnight and then cooled. The solvents are removed trader vacuum and the residue is azeotroped with toluene to remove residual water. The resulting solid is washed with ether and toluene to remove unreacted 1-fluoro-2-nitrobenzene. The solid is then stirred for 18 hr at 20°–25° in 80 ml of DMF with 15.34 g of potassium carbonate and 24 ml of iodomethane. Excess iodomethane and DMF are then removed under vacuum and the residue is partitioned between a mixture of methylene chloride, chloroform and water. The organic layers are dried over sodium sulfate and concentrated. Ethyl ether and hexane are added to the residue and the solid is collected and dried to give the title compound, mp 138°–140°; NMR (CDCl$_3$) 2.15, 3.83, 4.10, 4.41, 6.73–6.81, 7.46, 8.22, 8.60 δ.

EXAMPLE 287

3-Hydroxymethyl-1,2,3,4-tetrahydroquinoxalin-2-one (IV)

A mixture of N-(2-nitrophenyl)-DL-serine methyl ester (XI, EXAMPLE 286, 0.506 g, 4.30 g), palladium on carbon (10%, 506 g) and 150 ml of methanol is shaken under hydrogen at 40 psi for 3.5 hr. The catalyst is then removed by filtration and the filtrate is concentrated under reduced pressure. The residue is then chromatographed on silica gel (400 ml) using eluting with methanol/methylene chloride (6/94), the appropriate fractions are pooled and concentrated to give the title compound, NMR (CDCl$_3$) 2.70, 3.90, 4.00–4.18, 6.75, 6.92, 8.23. δ.

EXAMPLE 288

3,3a,-Dihydro-1H-oxazolo[3,4-a]quinoxaline-1,4(5H)-dione (IV)

To 3-hydroxymethyl-1,2,3,4-tetrahydroquinoxalin-2-one (IV, EXAMPLE 286, 21.35 g), 1.00 g of carbonyldiimidazole, and 30 ml of THF are added 1.64. ml of triethylamine. The reaction is stirred at 20°–25° for 6 hr, then at 80° for 18 hr, at which time an additional 0.11 g carbonyldiimidazole are added. Heating is continued for another 6 hr, at which time the reaction mixture is cooled and the solvent is removed under reduced pressure. The residue is partitioned between methylene chloride and water, the organic layers are dried over sodium sulfate and concentrated. The residue is crystallized from methanol/dichloromethane to give the title compound, mp 230°–231°; MS (m/z) at 204; NMR (CDCl$_3$) 4.60, 4.78, 6.93, 7.19, 7.82 and 8.48 δ.

EXAMPLE 289

12-(5-Cyclopropyl-1,2,4-oxadiazol-3-yl)-1,12b-dihydroimidazo[1,5-a]oxazolo[-4,3-c]quinoxalin-3(3H)-one (I)

Following the general procedure of EXAMPLE 30 and making non-critical variations but starting with 3,3a,-dihydro-1H-oxazolo[3,4-a]quinoxaline-1,4(5H)-dione (IV, EXAMPLE 288, 0.485 g) and 0.425 g of 5-cyclopropyl-3-isocyanomethyl-1,2,4-oxadiazole, the title compound is obtained, mp 228°–230°; MS (m/z) at 335; IR (mineral oil) 1749, 1570, 1511, 1213, 761 cm$^{-1}$; NMR (CDCl$_3$) 1.27–1.40, 2.30, 4.63, 5.35, 5.57, 7.30, 7.40, 7.60, 8.19, 8.23 δ.

EXAMPLE 290

(S)-1-[5-(1,1-Dimethylethyl)-1,2,4-oxadiazol-3-yl]-12,12a-dihydroimidazo[1,5-a]pyrrolo[2,1-c]-quinoxalin-10(11H)-one (I)

Following the general procedure of EXAMPLE 30 and making non-critical variations but starting with 3,3a,-dihydro-1H-oxazolo[3,4-a]quinoxaline-1,4(5H)-dione (IV, EXAMPLE 288, 1.002 g) and 0.982 g of 5-(1,1-dimethyl-)ethyl-3-isocyanomethyl-1,2,4-oxadiazole, the title compound is obtained, mp 253°–257°; MS (m/z) at 349; IR (mineral oil) 1699, 1558, 1515, 755, 1300, 1573 cm$^{-1}$; NMR (CDCl$_3$) 1.52, 2.20–2.35, 2.55–2.64, 2.71–2.84, 3.34–3.44, 5.32, 7.28, 7.37, 7.58, 8.19, 8.37 δ; $[\alpha]_D$=–381° (0.89, CH$_2$Cl$_2$).

EXAMPLE 291

4-Benzoyl-1,2,3,4-tetrahydroquinoxalin-2-one (IV)

To 1,2,3,4-tetrahydroquinoxalin-2-one (IV, EXAMPLE 1, 4.425 g), 5.4 ml of triethylamine, and 40 ml of THF cooled at 0° are added dropwise over several minutes 4.2 ml of benzoyl chloride. After stirring for 35 min the ice bath is removed and after stirring an additional 25 min the reaction mixture is partitioned between ethyl acetate and aq. sodium bicarbonate and saline. The organic layers are dried over magnesium sulfate and concentrated. The product is crystallized from methanol/dichloromethane/hexane to give the title compound, mp 208°–209°; NMR (CDCl$_3$) 4.60, 6.75, 6.93, 7.10, 7.32, 7.42, 8.44 δ.

EXAMPLE 292

4-Benzoyl-6-fluoro-1,2,3,4-tetrahydroquinoxalin-2-one (IV)

To 6-fluoro-1,2,3,4-tetrahydroquinoxalin-2-one (IV, EXAMPLE 6, 2.65 g), 2.9 ml of triethylamine, and 20 ml of THF at 0° C. are added dropwise over several minutes 2.22 ml of benzoyl chloride. The reaction mixture is stirred for 35 min at 0°, at which time the ice bath is removed. After stirring an additional 25 min, the reaction mixture is partitioned between ethyl acetate and aq. sodium bicarbonate and saline. The organic layers are dried over magnesium sulfate and concentrated. The product is crystallized from methanol/dichloromethane/hexane to give the title compound, mp 226°–227°; NMR (CDCl$_3$) 4.55, 6.54, 6.80–6.92, 7.35–7.49, 8.54 δ.

EXAMPLE 293

4-(2-Chlorobenzoyl)-1,2,3,4-tetrahydroquinoxalin-2-one (IV)

To 1,2,3,4-tetrahydroquinoxalin-2-one (IV, EXAMPLE 1, 2.11 g), 2.58 ml of triethylamine, and 40 ml of THF at 0° are added 2.16 ml of 2-chlorobenzoyl chloride. After 15 min the ice bath is removed and the reaction is stirred for 20 min. Ether is added to the reaction mixture and the solid collected. TLC showed both solid and filtrate to contain product, so they are recombined and partitioned between dichloromethane and aq. sodium bicarbonate. The organic layers are filtered through sodium sulfate and concentrated. Ether is added to the crude product and the ether layer decanted from the crystalline product to give, after drying the title compound, mp 222.5°–224°; NMR (CDCl$_3$) 4.18, 4.48, 4.98, 6.50, 6.70, 7.2–7.5, 8.55 δ.

EXAMPLE 294

4-Methoxycarbonyl-1,2,3,4-tetrahydroquinoxalin-2-one (IV)

To 2.99 g of 1,2,3,4-tetrahydroquinoxalin-2-one (IV) in 30 ml of methyl tert-butyl ether are added 2.18 ml of methyl chloroformate. After stirring for 1 hr, 4.9 ml of diisopropylethylamine are added. The reaction is stirred an additional 30 min and then concentrated under reduced pressure. The residue is partitioned between dichloromethane and aq. sodium bicarbonate and the organic layers dried over sodium sulfate and concentrated. The crude product is crystallized from dichloromethane/hexane/ethyl ether to give the title compound, NMR (CDCl$_3$) 3.84, 4.45, 6.87, 7.11, 7.65, 8.27 δ.

EXAMPLE 295

3,3-Dimethyl-6-fluoro-4-methoxycarbonyl-1,2,3,4-tetrahydroquinoxalin-2-one (IV)

To 3.3-dimethyl-6-fluoro-1,2,3,4-tetrahydroquinoxalin-2-one (IV, EXAMPLE 8, 5.14 g), 4.84 ml of diisopropylethylamine, and 30 ml of THF at 0° are added 66 ml of 1.2M phosgene in toluene. After 25 min the ice bath is removed and the reaction is allowed to warm slowly to 20°–25° with stirring over 2.5 hr. The reaction mixture is stored overnight in the refrigerator and the next rooming concentrated and partitioned between dichloromethane, water, and aq. sodium bicarbonate. The organic layers are dried over sodium sulfate and concentrated. Ether and hexane are added to the crude product and the solid is collected. To 1.55 g of this material in 10 ml of methanol are added 1.3 g of sodium methoxide in methanol (25% by weight). After stirring for 1 hr the solvent is removed under reduced pressure and the residue is partitioned between dichloromethane and saline. The organic layers are dried over sodium sulfate and concentrated and the crude product chromatographed on silica gel (250 ml) eluting with ethyl acetate/methylene chloride (10/90), the appropriate fractions are pooled and concentrated to give the title compound which after crystallization from methylene chloride/hexane, mp 166°–168.5°; NMR (CDCl$_3$) 1.63, 3.77, 6.75–6.88, 7.00, 8.38 δ.

EXAMPLE 296

3,3-Dimethyl-4-[(1-methyl)ethyl]oxycarbonyl-1,2,3,4-tetrahydroquinoxalin-2-one (IV)

To 2.28 g of 4-chlorocarbonyl-3,3-dimethyl-1,2,3,4-tetrahydroquinoxalin-2-one (prepared by the method of Example 32 but using 3,3-dimethyl-1,2,3,4-tetrahydroquinoxalin-2-one rather than 6-fluoro-3,3-dimethyl-1,2,3,4-tetrahydroquinoxalin-2-one) in 25 ml of 2-propanol (the starting material is not all in solution) are added 0.694 g of lithium isopropoxide. After about 1.5 hr the reaction mixture became homogeneous and then again heterogeneous as the product precipitated out. After a total of 2 hr the solvent is removed under reduced pressure and the residue is partitioned between dichloromethane aid saline. The organic layers are dried over sodium sulfate and the filtrate is concentrated. Ether is added and the resulting solid is collected to give the title compound. NMR (CDCl$_3$) 1.28, 1.63, 5.01, 6.80, 6.98–7.11, 7.27, 7.96 δ.

EXAMPLE 297

5-Fluoro-4-methoxycarbonyl-1,2,3,4-tetrahydroquinoxalin-2-one (IV)

To 5-fluoro-1,2,3,4-tetrahydroquinoxalin-2-one (IV, EXAMPLE 24, 0.883 g) and 1.39 ml of diisopropylethylamine in 10 ml of THF are added 0.62 ml (7.97 mmol) of methyl chloroformate. The reaction mixture is stirred for 3 hr, when several mls of aqueous sodium bicarbonate are added to quench the unreacted methyl chloroformate. The mixture is then partitioned between ethyl acetate and aqueous sodium bicarbonate and saline. The organic layers are dried over magnesium sulfate and concentrated. The crude product is chromatographed on silica gel (120 ml) eluting with ethyl acetate/methylene chloride (20/80), the appropriate fractions are pooled and concentrated to give the title compound which after crystallization from dichloromethane/hexane, mp 170.5°–172°; NMR (CDCl$_3$) 3.83, 6.71, 6.87, 7.13–7.21, 8.72. δ.

EXAMPLE 298

4-[(Morpholino)carbonyl]-1,2,3,4-tetrahydroquinoxalin-2-one (IV)

A mixture of 4.79 g of 1,2,3,4-tetrahydroquinoxalin-2-one (IV, EXAMPLE 1) and 45 ml of THF is stirred at 0°. To this is added 6.66 ml of diisopropylethylamine, followed by 32.4 ml 1.2M phosgene in toluene. After stirring at 0° for 1.3 hr, an additional 6.76 ml of diisopropylethylamine is added, followed by 3.4 ml of morpholine. The reaction is stirred for 30 minutes and then the ice bath is removed and the reaction is allowed to warm to 20°–25° over 2 hr, at which time water is added and the mixture is partitioned between ethyl acetate and saline. The organic layers are dried over magnesium sulfate and concentrated under reduced pressure. The crude product is crystallized from ethyl acetate to give the title compound, mp 179.5°–180.5°; MS (m/z) at 261; IR (mineral oil) 1679, 1664, 1390, 1402, 761 cm$^{-1}$; NMR (CDCl$_3$) 3.32, 3.64, 4.20, 6.94, 7.06, 7.14, 8.90 δ.

EXAMPLE 299

N-(5-Fluoro-2-nitrophenyl)-2-methylalanine (II)

A mixture of 32.62 g of 2,4-difluoronitrobenzene, 24.2 g of 2-aminoisobutyric acid, 15.2 g of potassium carbonate, 100 ml of acetonitrile, and 100 ml of water is heated at 80° for 2 days (until TLC shows little or no starting material). The reaction is then cooled and acetonitrile is removed under reduced pressure. The pH is adjusted to 5 with 4N hydrochloric acid and the mixture is extracted with chloroform (3×300 ml). The organic layers are dried over sodium sulfate and concentrated. The material is used in the next step without further purification.

EXAMPLE 300

3,3-Dimethyl-6-fluoro-1,2,3,4-tetrahydroquinoxalin-2-one (IV)

N-(5-Fluoro-2-nitrophenyl)-2-methylalanine is taken up in approximately 1 L of ethanol and divided into two lots for reduction. The reductions are done with 1.7–1.9 g of palladium on carbon (10%) under hydrogen at initial pressures of 41 and 43 psi. After 4 hr the reaction is judged complete and the catalyst is filtered off. The filtrates are combined after concentration (with heating) to about 100 ml, then further concentrated. The crude product is chromatographed on silica gel (900 ml) eluting with ethyl acetate/dichloromethane (20/80), the appropriate fractions are pooled and concentrated to give the title compound which is crystallized from methanol/dichloromethane/hexane, mp 146°–148°.

EXAMPLE 301

3,3-Dimethyl-6-fluoro-4-[(pyrrolidino)carbonyl]-1,2,3,4-tetrahydroquinoxalin-2-one (IV)

To a mixture of 3,3-dimethyl-6-fluoro-1,2,3,4-tetrahydroquinoxalin-2-one (IV, EXAMPLE 300, 1.001 g) and 0.94 ml of diisopropylethylamine, and 10 ml of THF at 0° are added 12.9 ml of 1.2M phosgene in toluene. After 45 min the reaction is allowed to warm to 20°–25°. After stirring for 3 hr, the reaction is again cooled to 0° and additional 4.2 ml of phosgene are added. The ice bath is removed and the reaction is stirred for 100 min, after which the excess phosgene and solvents are removed via a water aspirator. The mixture is then stirred with 10 ml of THF and 0.90 ml of pyrrolidine are added. After stirring overnight, the reaction is concentrated and the residue chromatographed on silica gel using 2% methanol-98% dichloromethane. Recrystallization from dichloromethane/hexane gives the product; mp 199°–200°; MS (m/z) at 291; IR (mineral oil) 1681, 1660, 1396, 1163 cm$^{-1}$; NMR (CDCl$_3$) δ 1.4–2.0, 3.15, 3.6, 6.43, 6.65, 6.76, 8.32.

EXAMPLE 302

5-Fluoro-4-[(pyrrolidino)carbonyl]-1,2,3,4-tetrahydroquinoxalin-2-one (IV)

To 1.20 g of 5-fluoro-1,2,3,4-tetrahydroquinoxalin-2-one (EXAMPLE 24), 1.26 ml of diisopropylethylamine, and 15 ml of THF at 0° is added 6.0 ml of 1.2M phosgene in toluene. The ice bath is removed and the reaction is stirred for 2 h, at which time an additional 0.2 ml of diisopropylethylamine and 1.0 ml of phosgene solution are added. After an hour, 1.26 ml of diisopropylethylamine and 0.60 ml of pyrrolidine are added and the reaction is stored in the freezer over the weekend. The reaction is then partitioned between ethyl acetate and aq. sodium bicarbonate and saline. The organic layers are dried over magnesium sulfate and concentrated and the crude product is chromatographed on silica gel (250 ml) using ethyl acetate/dichloromethane (30/70) to give 1.47 g of product. Recrystallization from ethyl acetate/ethyl ether/hexane gives product in two crops; mp 186.5°–187.5°; MS (m/z) at 263; IR (mineral oil) 1692, 1658, 1407, 1604, 1623 cm$^{-1}$; NMR (CDCl$_3$) 1.85, 3.28, 4.27, 6.68, 6.82, 7.04, 8.41 δ.

EXAMPLE 303

4-[[4-(tert-Butyloxycarbonyl)piperazino]carbonyl]-1,2,3,4-tetrahydroquinoxalin-2-one (IV)

To 1,2,3,4-tetrahydroquinoxalin-2-one (IV, EXAMPLE 1, 2.13 g), 2.75 ml of diisopropylethylamine, and 20 ml of THF cooled at 0° are added 13.2 ml of 1.2M phosgene in toluene. The reaction is stirred at 0° for 1.5 hr and then allowed to warm to 20°–25°, at which time 2.75 ml of diisopropylethylamine and 2.94 g of tert-butyl 1-piperazinecarboxylate are added. The reaction is stirred for an additional 1.5 hr and then partitioned between a mixture of dichloromethane and chloroform and aq. sodium bicarbonate and saline. The organic layers are dried over sodium sulfate and concentrated. The addition of dichloromethane and ethyl ether gives a crystalline solid which is collected and washed with ether to give the title compound after drying, mp 166°–167°; MS (m/z) at 360; IR (mineral oil) 1685, 1646, 1698, 1419, 1499 cm$^{-1}$; $^1$H NMR (CDCl$_3$) δ 1.44, 3.28, 3.40, 4.20, 6.92, 7.01–7.08, 7.11, 8.76.

EXAMPLE 304

3,3-Dimethyl-4-[(morpholinyl)carbonyl]-1,2,3,4-tetrahydroquinoxalin-2-one (IV)

To 2.70 g of 4-(chlorocarbonyl)-3,3-dimethyl-1,2,3,4-tetrahydroquinoxalin-2-one (prepared from 3,3-dimethyl-1,2,3,4-tetrahydroquinoxalin-2-one (EXAMPLE 2) and phosgene) in 30 ml of dichloromethane are added 1.97 g of morpholine. After stirring for 30 min, the reaction mixture is partitioned between dichloromethane and saline. The organic layers are dried over sodium sulfate, concentrated, and crystallized from dichloromethane/hexane to give the title compound, mp 190.5°–193°; MS (m/z) at 289; IR (mineral oil) 1683, 1661, 1409, 1238, 1121, 1506 cm$^{-1}$; NMR (CDCl$_3$) δ 1.3–1.9, 3.0–4.1, 6.70, 6.84, 6.95–7.03, 8.31.

EXAMPLES 305–322

Following the general procedure of EXAMPLES 30, 31, 33, 34, 36, 38, 40, 42, 44, 45B and 47 and making non-critical variations but starting with the bicyclic amides (IV) of EXAMPLES of 23, 35, 291–298 and 301–304, the imidazo[1,5-a]quinoxalines (I) of the following EXAMPLES are obtained:

EXAMPLE 305

5-Benzoyl-4,5-dihydro-3-[5-[(1,1-dimethyl)ethyl]-1,2,4-oxadiazol-3-yl]imidazo[1,5-a]quinoxaline (I)

mp 201°–202°; MS (m/z) at 399; IR (mineral oil) 1497, 1659, 1670, 1240, 1392, 1604 cm$^{-1}$; NMR (CDCl$_3$) 1.46, 5.42, 7.08, 7.25–7.46, 7.60, 8.21 δ.

EXAMPLE 306

5-Benzoyl-4,5-dihydro-3-[5-[(1,1-dimethyl)ethyl]-2,4-oxadiazol-3-yl]-7-fluoroimidazo[1,5-a]-quinoxaline (I)

mp 187°–190°; MS (m/z) at 417; IR (mineral oil) 1366, 1499, 1674, 1668, 1239, 1514 cm$^{-1}$; NMR (CDCl$_3$) 1.44, 5.39, 6.95, 7.02, 7.36–7.51, 7.57, 8.16 δ.

EXAMPLE 307 tert-Butyl 5-benzoyl-4,5-dihydroimidazo[1,5-a]quinoxaline-3-carboxylate (I)

mp 218.5°–219.5°: MS (m/z) at 375; IR (mineral oil) 1713, 1509, 1141, 1157, 1339, 1242 cm$^{-1}$; NMR (CDCl$_3$) 1.56, 5.33, 7.08, 7.23–7.48.7.56 and 8.10 δ.

EXAMPLE 308 tert-Butyl 5-benzoyl-4,5-dihydro-7-fluoroimidazo[1,5-a]-quinoxaline-3-carboxylate (I)

mp 204°–205.5°; MS (m/z) at 393; IR (mineral oil) 1726, 1151, 1665, 1233, 1240, 1513 cm$^{-1}$; NMR (CDCl$_3$) 1.53, 5.29, 6.93, 7.00, 7.38–7.56, 8.05 δ.

EXAMPLE 309 tert-Butyl 5-(2-chlorobenzoyl)-4,5-dihydro-7-fluoroimidazo[1,5-a]quinoxaline-3-carboxylate (I)

mp 199°–200.5°; MS (m/z) at 409; IR (mineral oil) 1659, 1700, 1143, 1295, 1509, 1493 cm$^{-1}$; NMR (CDCl$_3$) 8.06 δ.

EXAMPLE 310 tert-Butyl 4,5-dihydro-6-fluoro-5-[(tert-butyloxy)carbonyl]-imidazo[1,5-a]quinoxalin-3-carboxylate (I)

mp 184°–186°; MS (m/z) at 389; IR (mineral oil) 1698, 1367, 1256, 1711, 1151, 1500 cm$^{-1}$; NMR (CDCl$_3$) 1.47, 1.64, 7.10, 7.31, 8.02 δ.

EXAMPLE 311

5-[(tert-Butyloxy)carbonyl]-4,5-dihydro-3-[(1,1-dimethyl)ethyl-1,2,4-oxadiazol-3-yl]imidazo-[1,5-a]quinoxaline (I)

mp 188°–190.5°; MS (m/z) at 395; IR (mineral oil) 1708, 1508, 1366, 1306, 1161, 752 cm$^{-1}$; NMR (CDCl$_3$) 1.51, 1.52, 5.26, 7.24–7.34, 7.54, 7.79, 8.12 δ.

EXAMPLE 312

5-[(tert-Butyloxy)carbonyl]-4,5-dihydro-3-[(1,1-dimethyl)ethyl-1,2,4-oxadiazol-3-yl]-6-fluoroimidazo-[1,5-a]quinoxaline (I)

mp 170°–171°; MS (m/z) at 413; IR (mineral oil) 1709, 1498, 1259, 1162, 1483, 1280 cm$^{-1}$ NMR (CDCl$_3$) 1.46, 1.51, 7.11, 7.31–7.38, 8.14 δ.

EXAMPLE 313

4,5-Dihydro-5-methoxycarbonyl-3-(benzoxazol-2-yl)-imidazo[1,5-a]quinoxaline (I)

mp 201°–203.5°; MS (m/z) at 346; IR (mineral oil) 1511, 1719, 1243, 750, 1638, 1448 cm$^{-1}$: NMR (CDCl$_3$) 3.86, 5.46, 7.30–7.40, 7.56–7.64, 7.77–7.80, 8.16 δ.

EXAMPLE 314 tert-Butyl 4,5-dihydro-4,4-dimethyl-7-fluoro-5-methoxycarbonylimidazo[1,5-a]quinoxalin-3-carboxylate (I)

mp 164°–165°; MS (m/z) at 375; IR (mineral oil) 1727, 1527, 1294, 1262, 1289, 1151, 1142, 1333 cm$^{-1}$; NMR (CDCl$_3$) 1.62, 1.92, 3.74, 6.96, 7.07, 7.39, 7.92 δ.

EXAMPLE 315 tert-Butyl 4,5-dihydro-4,4-dimethyl-5-[(1-methyl)ethoxycarbonylimidazo[1,5-a]quinoxalin-3-carboxylate (I)

mp 179°–180.5°; MS (m/z) at 385; IR (mineral oil) 1244, 1722, 1292, 1297, 1144, 755, 1108, 1706 cm$^{-1}$; NMR (CDCl$_3$) 1.25, 1.62, 1.92, 4.97, 7.20–7.24, 7.34, 7.40 and 7.96 δ.

EXAMPLE 316 tert-Butyl 4,5-dihydro-6-fluoro-5-methoxycarbonylimidazo[1,5-a]quinoxalin-3-carboxylate (I)

mp 174°–175°; MS (m/z) at 347; IR (mineral oil) 1717, 1709, 1142, 1496, 1504, 1279 cm$^{-1}$; NMR (CDCl$_3$) 1.64, 3.81, 7.13, 7.33, 8.02 δ.

EXAMPLE 317

4,5-Dihydro-3-[5-[(1,1-dimethyl)ethyl]-1,2,4-oxadiazol-3-yl]-5-[(morpholino)carbonyl]imidazo[1,5-a]-quinoxaline (I)

mp 203.0°–204.5°; MS (m/z) at 408; IR (mineral oil) 1647, 1424, 1510, 1557, 1281 cm$^{-1}$; NMR (CDCl$_3$) 1.51, 3.33, 3.64, 5.04, 7.20, 7.29, 7.56, 8.13 δ.

EXAMPLE 318

4,5-Dihydro-4,4-dimethyl-3-[5-[(1,1-dimethyl)ethyl]-1,2,4-oxadiazol-3-yl]-7-fluoro-5-[(pyrrolidino)-carbonyl]-imidazo[1,5-a]quinoxaline (I)

mp 179°–180°; MS (m/z) at 438; IR (mineral oil) 1681, 1521, 1172, 1285, 1560 cm$^{-1}$; NMR (CDCl$_3$) 1.51, 1.7–2.1, 2.9–3.4, 3.58, 6.55, 6.74, 7.45, 8.06 δ.

EXAMPLE 320

5-[[4-(tert-Butyloxycarbonyl)piperazino]carbonyl]-4,5-dihydro-3-[5-[(1,1-dimethyl)ethyl]-1,2,4-oxadiazol-3-yl]-imidazo[1,5-a]quinoxaline (I)

mp 147°–151° (softening), 176°–178°; MS (m/z) at 507; IR (mineral oil) 1700, 1670, 1692, 1416, 1403 cm$^{-1}$; NMR (CDCl$_3$) 1.44, 1.50, 3.29, 3.40, 5.04, 7.17–7.29, 7.56, 8.13 δ.

EXAMPLE 321 tert-Butyl 5-[[4-(tert-butyloxycarbonyl)piperazino]carbonyl]-4,5-dihydroimidazo[1,5-a]quinoxaline-3-carboxylate (I)

mp 140°–145°; MS (m/z) at 483; IR (mineral oil) 1696, 1687, 1657, 1424, 1435 cm$^{-1}$; NMR (CDCl$_3$) 1.44, 1.63, 3.29, 3.41, 5.00, 7.15–7.30, 7.52, 8.01 δ.

EXAMPLE 322 tert-Butyl 4,5-dihydro-4,4-dimethyl-5 -[(morpholino)carbonyl]imidazo[1,5-a]quinoxaline-3-carboxylate (I)

mp 181°–182°; MS (m/z) at 419; IR (mineral oil) 1668, 1274, 1239, 1112, 1699, 756 cm$^{-1}$; NMR (CDCl$_3$) 1.63, 1.7–2.2, 2.9–4.1, 6.78, 7.06, 7.21, 7.46, 7.98 δ.

EXAMPLE 323

4,5-Dihydro-5-[(pyrrolidino)carbonyl]imidazo[1,5-a]-quinoxaline-3-carboxylic acid (I)

To tert-butyl 4,5-dihydro-5-[(pyrrolidino)carbonyl]imidazo[1,5-a]quinoxaline-3 -carboxylate (I, EXAMPLE 217, 2.97 g) are added 20 ml of a solution of trifluoroacetic acid and dichloromethane (1/1). After stirring for 3.5 hr an additional 2 ml of the trifluoroacetic acid/dichloromethane solution are added, followed an hour later by another 2 ml and 30 min later with a final 2 ml of the trifluoroacetic acid/dichloromethane solution. The reaction is stirred additional hours and then concentrated under reduced pressure. Dichloromethane is added to the residue and the mixture is again concentrated to give the title compound, which is crystallized from methanol/dichloromethane, mp 197°–200°; MS (m/z) at 312; NMR (DMSO-d6) 1.72, 3.15, 4.86, 7.18–7.22, 7.33, 7.90, 8.70 δ.

EXAMPLE 324

Phenyl 4,5-Dihydro-5-[(pyrrolidino)carbonyl]imidazo[1,5-a]-quinoxaline-3-carboxylate (I)

To a mixture of 4,5-dihydro-5-[(pyrrolidino)carbonyl] imidazo[1,5-a]quinoxaline-3 -carboxylic acid (I, EXAMPLE 323, 0.543 g), 0.245 g of phenol, 0.48 ml of triethylamine, and 6 ml of dichloromethane are added 0.42 ml of diethyl cyanophosphonate. After stirring for 1 hr an additional 0.11 g of phenol are added. When the reaction had stirred another 2.5 hr an additional 0.11 g of phenol and 0.26 ml of diethyl cyanophosphonate are added. The reaction is stored overnight in the refrigerator and then stirred with 1 ml of aqueous sodium bicarbonate for about 30 min. The mixture is then partitioned between dichloromethane and aqueous sodium bicarbonate. The organic layers are dried over sodium sulfate, concentrated, and the residue chromatographed on silica gel (300 ml) eluting with methanol/methylene chloride (2/98), the appropriate fractions are pooled and concentrated to give the title compound, which is crystallized from dichloromethane/hexane, mp 196.5°–199°; MS (m/z) at 388; IR (mineral oil) 1648, 1199, 1723, 1502, 1410 cm$^{-1}$; $^1$H NMR (CDCl$_3$) 1.81, 3.31, 5.09, 7.15–7.33, 7.42, 7.55, 8.11 δ.

EXAMPLE 325

N-(Cyanomethyl)-4,5-dihydro-5-[(pyrrolidino)-carbonyl]imidazo[1,5-1,5-a]quinoxaline-3-carboxamide (I)

To a mixture of 4,5-dihydro-5-[(pyrrolidino)carbonyl] imidazo[1,5-a]quinoxaline-3 -carboxylic acid (I, EXAMPLE 323, 0.203 g), 0.060 g of aminoacetonitrile hydrochloride, and 3 ml of dichloromethane are added 0.23 ml of triethylamine and 0.15 ml of ethyl cyanophosphonate. A slight exotherm ensued. After about 45 min a precipitate formed and an additional 5 ml of dichloromethane are added. When the reaction had stirred for a total of 70 min it is partitioned between dichloromethane and aqueous sodium bicarbonate. The organic layers are dried over sodium sulfate and concentrated. The crude product is chromatographed on silica gel (125 ml) eluting with methanol/ methylene chloride (2/98), the appropriate fractions are pooled and concentrated to give the title compound, mp 241°–242.5°; MS (m/z) at 350; IR (mineral oil) 1641, 1506, 1658, 1409, 1417, 2237 (weak) cm$^{-1}$; NMR (CDCl$_3$) 1.83, 3.31, 4.36, 5.06, 7.12–7.30, 7.40, 7.49, 7.94 δ.

EXAMPLE 326

4,5-Dihydro-3-(oxazolin-2-yl)-5-[(pyrrolidino)-carbonyl]imidazo[1,5-a]quinoxaline (I)

To a mixture of 4,5-dihydro-5-[(pyrrolidino)carbonyl] imidazo[1,5-a]quinoxaline-3 -carboxylic acid (I, EXAMPLE 322, 1.03 g) and 25 ml of dichloromethane cooled at 0° in an ice bath are added 1.15 ml of triethylamine and 0.650 ml) of ethyl cyanophosphonate, followed immediately by 0.811 g of 2-bromoethylamine hydrobromide. The ice bath is then removed and the reaction is stirred for 40 min. Aqueous sodium bicarbonate is then added. The mixture is stirred for 10 min and then partitioned with dichloromethane. The organic layers are dried over sodium sulfate and concentrated. The resulting mixture is stirred in 20 ml of THF and 3.3 ml of 1M potassium tert-butoxide is added dropwise over 2–3 min and the reaction is stirred an additional 10 min, at which time the reaction mixture is partitioned between ethyl acetate, water, and saline. The organic layers are dried over magnesium sulfate and concentrated. The crude product is chromatographed on silica gel (300 ml) eluting with methanol/methylene chloride (4/96), the appropriate fractions are pooled and concentrated to give the title compound, mp 217°–220°; MS (m/z) at 337; IR (mineral oil) 1651, 1512, 1416, 1357, 1396 cm$^{-1}$; NMR (CDCl$_3$) 1.81, 3.27, 4.05, 4.42, 4.99, 7.11–7.18, 7.26, 7.51, 8.03 δ.

EXAMPLES 327–330

Following the general procedure of EXAMPLES 89–93, 100, 102, 104–107, 149–173 and making non-critical variations, the title compounds are obtained

EXAMPLE 327

4,5-Dihydro-3-(hydroxymethyl)imidazo[1,5-a]-quinoxaline (I)

mp 190°–2°

EXAMPLE 328

4,5-Dihydro-3-(benzoylmethyl)-5-(benzoyl)imidazo-[1,5-a]quinoxaline (I)

EXAMPLE 329

4,5-Dihydro-3-(benzoylmethyl)-5-(pyrrolidinyl)-carbonyl]imidazo[1,5 -a]quinoxaline (I)

mp 161°

EXAMPLE 330

4,5-Dihydro-3-(isopropyloxymethyl)-5-(pyrrolidinyl)carbonyl]imidazo[1,5-a]quinoxaline (I)

mp 104°–105°

EXAMPLES 331–332

Following the general procedure of EXAMPLES 48–87 (and the EXAMPLES referenced therein) and making noncritical variations, the title compounds are obtained:

EXAMPLE 331

3-(5-Cyclopropyl-1,2,4-oxadiazol-3-yl)-7-fluoro-4,5-dihydro-4(R)-methyl-5[(pyrrolidino)carbonyl]-imidazo[1,5-a]quinoxaline (I)

mp 242°–3°

EXAMPLE 332

7-Fluoro-4,5-dihydro-4(R)-methyl-3-[5-(1-methylcyclopropyl-1,2,4-oxadiazol-3-yl)-5[(pyrrolidino)-carbonyl]imidazo[1,5-a]quinoxaline (I)

mp 243°–5°

EXAMPLE 333

3-[3-Cyclopropyl-1,2,4-oxadiazol-5-yl ]-7-fluoro-4,5-dihydro-4-(morpholinocarbonyl)imidazo-[1,5-a]quinoxaline (I)

Following the general procedure of EXAMPLE 30 and making noncritical variation but using 6-fluoro-1,2,3,4-tetrahydroquinoxalin-2-one (IV, EXAMPLE 6, 1.023 g) and 5-isocyanomethyl-3-cyclopropyl-1,2,4-oxadiazole (0.616 g) are converted to the title compound, mp 240.5°–242°; MS (m/z) 410; IR (mineral oil) 1662, 1422, 1509, 1178, 1638 cm$^{-1}$; NMR (CDCl$_3$) 1.09, 1.17, 2.15, 3.39, 3.68, 5.03, 6.94, 7.03, 7.53, 8.08 δ.

EXAMPLE 334

3-(4-cyclopropylthiazol-2-yl)-4,5-dihydro-5-(morpholinocarbonyl)imidazo[1,5-a]quinoxaline (I)

Following the general procedure of EXAMPLE 323 and making noncritical variations 1.45 g of tert-butyl 4,5-dihydro-5-(morpholinylcarbonyl)imidazo[1,5-a]quinoxaline-3-carboxylate (I, EXAMPLE 183) is converted to 0.91 g of 4,5-dihydro-5-(morpholinocarbonyl)imidazo[1,5 -a]quinoxaline-3-carboxylic acid, mp 267°–267.5°; MS m/z 328; IR 1662, 1219, 1428, 1112, 1269 cm$^{-1}$; NMR (DMSO-d$_6$) 3.2, 3.5, 4.87, 7.20–7.25, 7.33, 7.91, 8.58 δ.

A mixture of 0.88 g of 4,5-dihydro-5-(morpholinocarbonyl)imidazo[1,5-a]quinoxaline-3 -carboxylic acid and excess thionyl chloride is stirred at reflux for 1 hr. Excess thionyl chloride is then removed under reduced pressure. Dichloromethane is added to the residue and then removed under reduced pressure to remove residual thionyl chloride. The residue is then added as a dichloromethane slurry to an ice-cooled solution of 30% ammonium hydroxide. After the addition the ice bath is removed and the reaction is stirred at 20°–25° for 2.5 hr. The mixture is then partitioned between dichloromethane, water, and saline. The organic layers are dried over sodium sulfate and concentrated to give product, which after crystallization from methanol/dichloromethane/hexane gives 0.52 g of 4,5-dihydro-5-(morpholinocarbonyl)imidazo[1,5-a]quinoxaline-3-carboxamide; mp 220°–221°; MS (m/z) 327; IR (mineral oil) 1680, 1668, 1417, 1509, 1223 cm$^{-1}$; NMR (CDCl$_3$) 3.36, 3.65, 5.07, 5.43, 6.94, 7.18, 7.24–7.32, 7.95 δ.

To 0.40 g of 4,5-dihydro-5-(morpholinocarbonyl)imidazo[1,5-a]quinoxaline-3 -carboxamide in THF (5 ml) is added 2,4-bis-(4-methoxyphenyl)-1,3-diathia-2,4-diphosphotane-2,4-disulfide (0.74 g). The mixture is stirred at reflux for 2 hr, then cooled and added directly to a silica gel column. Elution with a gradient of 100% dichloromethane to methanol/dichloromethane (8/92) gave product fractions which are combined, concentrated, and rechromatographed using methanol/dichloromethane (5/95) to give 0.293 g of 4,5-dihydro-5 -(morpholinocarbonyl)imidazo-[1,5-a]quinoxaline-3-thiocarboxamide; NMR (CDCl$_3$) δ 3.38, 3.68, 5.36, 7.12–1.30, 7.50, 7.94, 8.45.

A mixture of 4,5-dihydro-5-(morpholinocarbonyl)imidazo[1,5-a]quinoxaline-3 -thiocarboxamide (0.29 g) and 1-bromomethyl cyclopropyl ketone (0.165 g) in ethanol (10 ml) is stirred at 20°–25° for 1 day and then at 80° for 5.5 hr, after which it stirred at 20°–25° for an additional 20 hr. The mixture is then concentrated under reduced pressure and chromatographed on silica gel eluting with methanol/dichloromethane (2/98). The product fractions are combined and rechromatographed using ethyl acetate/dichloromethane (25/75) to give a solid. Crystallization from dichloromethane/hexane gives the title compound; mp 193°–194°; MS (m/z) 407; IR (mineral oil) 1511, 1669, 1115, 1392, 1227 cm$^{-1}$; NMR (CDCl$_3$) 0.98, 2.09, 3.35, 3.66, 5.09, 6.79, 7.19, 7.28, 7.53, 8.01 δ.

EXAMPLE 335

3-(Benzoxazol-2-yl)-4,5-dihydro-5-(morpholinocarbonyl)imidazo[1,5-a]quinoxaline (I)

Following the general procedure of EXAMPLE 30 and making noncritical variations but starting with the appropriate starting materials the title compound is obtained, mp 288°–290°; MS (m/z) 419; IR (mineral oil) 1671, 1519, 1270, 1636, 747 cm$^{-1}$; NMR (CDCl$_3$) 3.41, 3.68, 5.21, 6.94, 7.05, 7.36, 7.55, 7.62, 7.75, 8.11 δ.

EXAMPLE 336

3-(5-Cyclopropyl-1,2,4-oxadiazol-3-yl)-6-fluoro-4,5-dihydro-5-(morpholinylcarbonyl)imidazo[1,5-a]-quinoxaline (I)

Following the general procedure of EXAMPLE 104 and making noncritical variations but starting with the appropriate starting materials the title compound is obtained, mp 198.5°–201°; MS (m/z) 410; IR (mineral oil) 1235, 1419, 1501, 1660, 1213 cm$^{-1}$; NMR (CDCl$_3$) 1.27, 1,35, 2.27, 3.43, 3.73, 5.07, 7.09, 7.24, 7.38, 8.12 δ.

EXAMPLE 337

3-tert-Butyl 5-methyl-7-fluoro-4,5-dihydroimidazo[1,5-a]-quinoxaline-3,5(4H)-dicarboxylate (I)

To a mixture of 1.97 g of 6-fluoro-1,2,3,4-tetrahydroquinoxalin-2-one (EXAMPLE 6), 3.1 ml of diisopropylethylamine, and 11 ml of THF is added 1.4 ml of methyl chloroformate. The reaction is cooled with cool tap water as an exotherm ensued. After 35 min, the mixture is partitioned between ethyl acetate, aq. sodium bicarbonate, and saline. The organic layers are dried over magnesium sulfate, concentrated, and the crude product is crystallized from dichloromethane/methanol/ethyl acetate to give 2.06 g of methyl 6-fluoro-1,2,3,4-tetrahydro4 -(methoxycarbonyl)quinoxaline-2-one; mp 206.5°–207.5°; NMR (CDCl$_3$) 3.86, 4.43, 6.84, 7.48, 8.67 δ.

Following the general procedure of EXAMPLE 30 and making noncritical variations methyl 6-fluoro-1,2,3,4-tetrahydro-4-(methoxycarbonyl)quinoxaline-2-one is converted to the title compound; mp 130.5°–132°; MS (m/z) 347; NMR (CDCl$_3$) 1.66, 3.87, 5.26, 7.01, 7.49, 7.62, 7.98 δ.

EXAMPLE 338

3-(5-Cyclopropyl-1,2,4-oxadiazol-3-yl)-5-[(3,5-dimethyl)-morpholinocarbonyl]-7-fluoro-4,5-dihydroimidazo[1,5-a]quinoxaline (I)

Following the general procedure of EXAMPLE 104 and making noncritical variations but starting with the appropriate starting materials the title compound is obtained, mp 143°–146°; MS (m/z) 438; IR (mineral oil) 1515, 1665, 1409, 1575, 1363 cm$^{-1}$; NMR (CDCl$_3$) 1.1–1.4, 2.27, 2.8–5.4, 6.93, 7.24, 7.52, 8.08 δ.

EXAMPLES 339–352

Following the general procedure of EXAMPLE 30 and making non-critical variations but starting with the appropriate starting materials, the title compounds are obtained:

EXAMPLE 339

3-(5-tert-butyl-1,2,4-oxadiazol-3-yl)-4,5-dihydro-6-methyl-5-(pyrrolidinocarbonyl)imidazo[1,5-a]-quinoxaline (I)

mp 231°–233°; MS (m/z) at 406, 336, 308, 278, 98; IR (mineral oil) 1695, 1505, 1499, 1493, 1473, 1402, 1385, 1186 cm$^{-1}$; NMR (CDCl$_3$) 8.12, 7.4–7.45, 7.15–7.3, 5.14, 3.15, 2.23, 1.7–1.85, 1.50 δ.

EXAMPLE 340

3-(5-tert-butyl-1,2,4-oxadiazol-3-yl)-4,5-dihydro-5-(piperidinocarbonyl)imidazo[1,5-a]quinoxaline (I)

mp 209°–211°; MS (m/z) at 406, 294, 112; IR (mineral oil) 3098, 1645, 1558, 1516, 1431, 1286, 1274, 745 cm$^{-1}$; NMR (CDCl$_3$) δ 8.12, 7.55, 7.1–7.3, 5.01, 3.2–0.35, 1.45–1.7, 1.50.

EXAMPLE 341

3-(5-tert-butyl-1,2,4-oxadiazol-3-yl)-5-(3-fluorobenzoyl)-4,5-dihydroimidazo[1,5-a]quinoxaline (I)

mp 164°–165°; MS (m/z) at 417, 360, 294, 123, 95; IR (mineral oil) 1660, 1498, 1408, 1376, 748; NMR (CDCl$_3$) δ 8.21, 7.62, 7.25–7.4, 7.0–7.25, 5.40, 1.46.

EXAMPLE 342

Methyl 3-(5-tert-butyl-1,2,4-oxadiazol-3-yl)-4,5-dihydroimidazo[1,5-a]quinoxaline-5-carboxylate (I)

mp 154°–155°; MS (m/z) at 353, 294, 268, 209, 195; IR (mineral oil) 1711, 1514, 1503, 1471, 1442, 1402, 1372, 1303, 1293, 1257, 1221, 765, 756 cm$^{-1}$; NMR (CDCl$_3$) δ 8.13, 7.7–7.85, 7.5–7.6, 7.2–7.4, 5.30, 3.84, 1.52.

EXAMPLE 343

Methyl 3-(5-tert-butyl-1,2,4-oxadiazol-3-yl)-7-chloro-4,5-dihydroimidro[1,5-a]quinoxaline-5-carboxylate (I)

mp 175°–176.5°; MS (m/z) at 387, 328, 302, 243, 229; IR (mineral oil) 3094, 1719, 1559, 1511, 1449, 1441, 1379, 1365, 1344, 1305, 1288, 1251, 1218, 1203, 819 cm$^{-1}$; NMR (CDCl$_3$) 8.10, 7.86, 7.49, 7.207.3, 5.30, 3.86, 1.51 δ.

EXAMPLE 344

3-(5-tert-butyl-1,2,4-oxadiazol-3-yl)-5-benzoyl-4,5-dihydroimidazo[1,5-a]quinoxaline (I)

mp 202.5°–204°; MS (m/z) at 433, 376, 105, 77; IR (mineral oil) 1661, 1364, 1237, 812 cm$^{-1}$; NMR (CDCl$_3$) δ 8.17, 7.35–7.6, 7.15–7.3, 5.38, 1.43.

EXAMPLE 345

Methyl 3-(5-tert-butyl-1,2,4-oxadiazol-3-yl)-7-chloro-4,4-dimethylimidazo[1,5-a]quinoxaline-5-carboxylate (I)

mp 63°–67°; MS (m/z) at 415, 400, 316, 257; IR (mineral oil) 1724, 1511, 1443, 1331, 1282, 1253, 1248, 1184 cm$^{-1}$; NMR (CDCl$_3$) δ 8.08, 7.42, 7.37, 7.26, 3.72, 1.51.

EXAMPLE 346

3-(5-tert-butyl-1,2,4-oxadiazol-3-yl)-7-chloro-4,4-dimethyl-5-(4-morpholinylcarbonyl)imidazo-[1,5-a]quinoxaline (I)

mp 219°–220°; MS (m/z) at 470, 455, 114; IR (mineral oil) 1650, 1519, 1512, 1416, 1243, 1122 cm$^{-1}$; NMR (CDCl$_3$) δ 8.09, 7.44, 7.05, 6.80, 3.0–4.1, 1.6–2.1, 1.51.

EXAMPLE 347

3-(5-tert-butyl-1,2,4-oxadiazol-3-yl)-6-chloro-4,4-dimethyl-5-(4-morpholinylcarbonyl)imidazo-[1,5-a]quinoxaline (I)

mp 132°–136°; MS (m/z) at 470, 455, 114; IR (mineral oil) 1652, 1498, 1414, 1272, 117 cm$^{-1}$; NMR (CDCl$_3$) δ 8.13, 7.46, 7.33, 7.17, 3.4–3.6, 3.28, 1.87, 1.51.

EXAMPLE 348

3-(3-tert-butyl-1,2,4-oxadiazol-5-yl)-4,5-dihydro-5-(pyrrolidinocarbonyl)imidazo[1,5-a]quinoxaline (I)

mp 207.5°–208.5°; MS (m/z) at 350, 308, 293, 267, 252, 212; IR (mineral oil) 2961, 1925, 1657, 1508, 1466, 1392, 1343, 1307, 1304; NMR (CDCl$_3$) δ 8.06, 7.52, 7.1–7.3, 6.53, 5.04, 3.2–3.4, 1.75–1.85, 1.38.

EXAMPLE 349

3-(5-tert-butyl-1,2,4-oxadiazol-3-yl)-4,5-dihydro-5-(4-nitrobenzoyl)imidazo[1,5-a]quinoxaline (I)

mp 243°–245°; MS (m/z) at 444, 387, 294, 150; IR (mineral oil) 1662, 1551, 1528, 1508, 1344, 1278, 767 cm$^{-1}$; NMR (CDCl$_3$) δ 8.24, 8.20, 7.65, 7.59, 7.0–7.2, 5.42, 1.45.

EXAMPLE 350

3-(5-tert-butyl-1,2,4-oxadiazol-3-yl)-5-(4-fluoro-benzoyl)-4,5-dihydroimidazo[1,5-a]quinoxaline (I)

mp 182°–183°; MS (m/z) at 417, 360, 294, 123; IR (mineral oil) 1657, 1505, 1240, 1191, 1154, 752; NMR (CDCl$_3$) δ 8.21, 7.61, 7.4–7.5, 7.25–7.35, 6.95–7.15, 5.41, 1.47.

EXAMPLE 351

3-(5-tert-butyl-1,2,4-oxadiazol-3-yl)-5-(3-chloro-benzoyl)-4,5-dihydroimidazo[1,5-a]quinoxaline (I)

mp 209°–211°; MS (m/z) at 433, 376, 294, 139; IR (mineral oil) 1670, 1500, 1343, 1243 cm$^{-1}$; NMR (CDCl$_3$) δ 8.22, 7.2–7.35, 7.05–7.2, 5.39, 1.46.

EXAMPLE 352

3-(5-tert-butyl-1,2,4-oxadiazol-3-yl)-5-(2-fluoro-benzoyl)-4,5-dihydroimidro[1,5-a]quinoxaline (I)

mp 213.5°–214.5°; MS (m/z) at 417, 360, 294, 123; IR (mineral oil) 1660, 1512, 1501, 1493, 1398, 1285, 1210, 766 cm$^{-1}$; NMR (CDCl$_3$) δ 8.19, 7.60, 6.7–7.55, 5.0–5.7, 1.44.

EXAMPLE 353

4,5-Dihydro-5-dimethylamino-3-(4-methylphenyl)-imidazo[1,5-a]quinoxaline (I)

Following the general procedure of EXAMPLE 248 and making noncritical variations but starting with the appropriate starting materials the title compound is obtained, mp 204°–205°; IR (mineral oil) 2925, 1653, 1507, 1393, 1271, 752 cm$^{-1}$; NMR (CDCl$_3$) δ 8.07, 7.5–7.6, 7.05–7.3, 4.86, 2.82, 2.39; MS (m/z) at 332, 260, 72.

EXAMPLE 354

3-(4-Fluorophenyl)-4,5-dihydro-5-(4-morpholinocarbonyl)imidazo[1,5-a]quinoxaline (I)

Following the general procedure of EXAMPLE 248 and making noncritical variations but starting with the appropriate starting materials the title compound is obtained, mp 193°–194°; MS (m/z) at 378, 264, 114; IR (mineral oil) 1660, 1506, 1423, 1272, 1265, 755 cm$^{-1}$; NMR (CDCl$_3$) δ 8.08, 7.55–7.7, 7.55, 7.1–7.3; 4.87, 3.55–3.65, 3.2–3.35.

EXAMPLE 355

3-(4-Fluorophenyl)-5-(3-fluorobenzoyl)-4,5-dihydro-imidazo[1,5-a]quinoxaline (I)

Following the general procedure of EXAMPLE 107 and making noncritical variations but starting with the appropriate starting materials the title compound is obtained, mp 176°–177°; MS (m/z) at 387, 264, 123, 95; IR (mineral oil) 1663, 1588, 1507, 1445, 1369, 1345, 1283, 1274, 1210, 844, 750 cm$^{-1}$; NMR (CDCl$_3$) δ 8.18, 7.55–7.75, 7.0–7.35, 7.01, 6.75–6.9, 5.25.

EXAMPLE 356

Methyl 3-(4-Fluorophenyl)-4,5-dihydroimidazo[1,5-a]quinoxaline-5-carboxylate (I)

Following the general procedure of EXAMPLE 250 and making noncritical variations but starting with the appropriate starting materials the title compound is obtained, mp 156°–160°; MS (m/z) at 323, 308, 264, 236; IR (mineral oil) 1709, 1505, 1438, 1368, 1223 cm$^{-1}$; NMR (CDCl$_3$) δ 8.07, 7.6–7.8, 7.65, 7.5–7.6, 7.25–7.35, 7.16, 5.11, 3.81.

EXAMPLE 357

5-(tert-Butylaminocarbonyl)-3-(4-fluorophenyl)-4,5-dihydroimidazo[1,5-a]quinoxaline (I)

Following the general procedure of EXAMPLE 250 and making noncritical variations but starting with the appropriate starting materials the title compound is obtained, mp 241°–243.5°; MS (m/z) at 364, 264; IR (mineral oil) 1673, 1532, 1506, 1223, 749 cm$^{-1}$; NMR (CDCl$_3$) δ 8.08, 7.55–7.75, 7.45–7.55, 7.25–7.35, 7.13, 5.07, 4.99, 1.33.

EXAMPLE 358

3-(4-Fluorophenyl)-4,5-dihydro-5-(4-trifluoromethyl-benzoyl)imidazo[1,5-a]quinoxaline (I)

Following the general procedure of EXAMPLE 107 and making noncritical variations but starting with the appropriate starting materials the title compound is obtained, mp 211°–212°; MS (m/z) at 437, 264, 173, 145; IR (mineral oil) 1673, 1505, 1397, 1329, 1172, 1149, 1112, 837, 759; NMR (CDCl$_3$) δ 8.20, 7.4–7.75, 7.2–7.35, 7.16, 7.01, 6.65–6.85, 5.27.

EXAMPLE 359

5-(Aminocarbonyl)-3-(4-fluorophenyl)-4,5-dihydro-imidazo[1,5-a]quinoxaline (I)

Following the general procedure of EXAMPLE 248 and making noncritical variations but starting with the appropriate starting materials the title compound is obtained, mp 222°–223°; IR (mineral oil) 3120, 1673, 1506, 1415, 1405, 1227 cm$^{-1}$; MS (m/z) at 308, 264; NMR (CDCl$_3$) δ 8.13, 7.55–7.7, 7.3–7.45, 7.15, 5.33, 5.11.

EXAMPLE 360

5-(Ethylaminocarbonyl)-3-(4-fluorophenyl)-4,5-dihydroimidazo[1,5-a]quinoxaline (I)

Following the general procedure of EXAMPLE 248 and making noncritical variations but starting with the appropriate starting materials the title compound is obtained, mp 196°–200°; IR (mineral oil) 1670, 1550, 1507, 1225, 759; NMR (CDCl$_3$) δ 8.08, 7.5–7.75, 7.25–7.4, 7.13, 5.12, 4.95–5.1, 3.2–3.35, 1.12; MS (m/z) at 336, 264.

EXAMPLE 361

Isopropyl 3-(4-Fluorophenyl)-4,5-dihydroimidazo[1,5-a]-quinoxaline-5-carboxylate (I)

Following the general procedure of EXAMPLE 248 and making noncritical variations but starting with the appropriate starting materials the title compound is obtained, mp 160°–160.5°; MS (m/r) at 351, 308, 264, 236; IR (mineral oil) 1701, 1506, 1403, 1284, 1225, 753; NMR (CDCl$_3$) δ 8.07, 7.5–7.75, 7.2–7.35, 7.15, 5.10, 4.9–5.1, 1.29.

EXAMPLE 362

3-(4-Fluorophenyl)-5-(4-fluorobenzoyl)-4,5-dihydroimidazo[1,5-a]quinoxaline (I)

Following the general procedure of EXAMPLE 107 and making noncritical variations but starting with the appropriate starting materials the title compound is obtained, mp 230°–231°; IR (mineral oil) 1647, 1600, 1506, 1367, 1232, 1222, 846, 753 cm$^{-1}$; MS (m/z) at 387, 264, 123, 95; NMR (CDCl$_3$) δ 8.17, 7.55–7.75, 7.35–7.45, 7.1–7.3, 6.9, 7.05, 6.78, 5.25.

EXAMPLE 363

3-(5-Cyclopropyl-1,2,4-oxadiazol-3-yl)-3a,4,4a,5,6,10b-hexahydro-7H-imidazo[5,1-f]-7-oxa-4a,10b-diazaphenalen-5-one (I)

A mixture of 2-amino-3-nitrophenol (LVI, 1.00 g, 6.49 mmol), diisopropylethylamine (1.60 ml, 9.19 mmol), and ethyl bromoacetate (2.00 ml, 18.0 retool) is heated at reflux for 5.5 hr. The resultant solution is allowed to cool to 20°–25°. Aqueous workup (chloroform and magnesium sulfate) and purification by flash chromatography, eluting with hexane/ethyl acetate (3/1), pooling and concentration of the appropriate fractions gives a mixture.

The crude material was combined with ethanol (75 ml) and a solution of sodium ethoxide (20.0 ml of ethanol and 69 mg of sodium). The mixture is heated at reflux for 72 hr. Potassium carbonate (57.0 mg, 0.41 mmol) is added after 24 hr. After cooling to 20°–25°, concentration, and aqueous workup (chloroform and magnesium sulfate) the cyclized amide (LVII) is obtained and is recrystallized from ethyl acetate/hexane, mp 82°–85°; IR (mineral oil) 3293, 2954, 2925, 2855, 1731, 1538, 1532, 1490, 1344, 1302, 1249, 1180, 735 cm$^{-1}$; NMR (300 MHz, CDCl$_3$) 10.07, 7.94, 7.32, 7.09, 4.71; MS (EI) m/e 194.

A mixture of the cyclized amide (LVII, 533 mg, 2.75 mmol), 10% Palladium on carbon (175 mg), and ethanol (75 ml) is hydrogenated (48 psi) at 20°–25° for 16 hr. The mixture is filtered, the residue washed with ethanol several times, and the combined filtrates concentrated to provide an amino cyclic amide, mp 213°–215°; IR (mineral oil) 3448, 3350, 3217, 2954, 2925, 1698, 1687, 1650, 1614, 1451, 1412, 723 cm$^{-1}$; NMR (300 MHz, CDCl$_3$) 6.80, 6.44, 4.54; MS (EI) m/e 164, 135.

Chloroacetyl chloride (0.28 ml, 3.5 mmol) was added to a partial solution of the amino cyclic amide (514 mg, 3.13 mmol), THF (40.0 ml), and diisopropylethylamine (1.36 ml, 7.81 mmol) at 0°. The mixture is stirred for 1 hr at 0° and for 16 hr at 20°–25°. Basic workup (ethyl acetate, sodium bicarbonate and magnesium sulfate) gives a 1/1 mixture of the intermediate chloride and bis-amide sufficiently pure to be carried on crude. Spectral features for the chloride are NMR (300 MHz, d$_6$-acetone) 6.8–7.1, 4.54 and 4.35.

Potassium tert-butoxide (7.14 ml, 7.14 mmol, 1.0M in THF) is added to a mixture of the intermediate chloride and bis-amide (1.70 g, ca 8.6 mmol), and THF (120 ml) at 0°. The mixture is stirred for 1 hr at 0° and for 16 hr at 20°–25°. Aqueous workup (ethyl acetate, magnesium sulfate) and trituration of the residue several times with ethyl acetate provides the bis-amide, homogeneous by TLC analysis, mp 285°–287°; IR (mineral oil) 2953, 2924, 1691, 1674, 1616, 1506, 1400, 1390, 1240 cm$^{-1}$; NMR (300 MHz, d$_6$-acetone) 9.77, 6.95, 6.71, 6.66, 4.66 and 4.43; MS (EI) m/e 204, 175 and 147.

Potassium tert-butoxide (2.50 ml, 2.50 mmol, 1.0M in THF) is added to a mixture of the bis-amide (467 mg, 2.29 mmol), THF (4.0 ml), and DMF (4.0 ml) at 0°. The mixture is allowed to warm to 20°–25° and is stirred for 30 min. After cooling to −20°, diethyl chlorophosphate (0.430 ml, 2.98 mmol) was added and the mixture is allowed to warm to 20°–25°. The resultant solution is stirred at 20°–25° for 40 min and was then cooled to −78°. A solution of the isocyanide (372 mg, 2.49 mmol) and THF (0.80 ml) is added. Potassium tert-butoxide (2.50 ml, 2.50 mmol) is then added dropwise over several minutes to form a mixture. This mixture is stirred at −78° for 30 min, and was allowed to warm to 20°–25° over 1.5 hr. After stirring for an additional 3 hr at 20°–25°, the reaction is quenched with aqueous ammonium chloride. Aqueous workup (ethyl acetate and then chloroform and magnesium sulfate) and purification by flash chromatography, eluting with chloroform/acetone (10/1), pooling and concentrating the appropriate fractions gives the title compound which is purified by recrystallization from methanol/ether, mp 267°–268°; IR (mineral oil) 2954, 2924, 2855, 1689, 1519, 1507, 1424, 1415, 1402, 1207 cm$^{-1}$; NMR (300 MHz, CDCl$_3$) 8.24, 7.28, 7.12, 6.95, 5.40, 4.71, 2.15–2.35, 1.2–1.4.

EXAMPLE 364

3-(5-cyclopropyl-1,2,4-oxadiazol-3-yl)-3a,4,4a,5,6,10b-hexahydro-7H-imidazo[5,1-f]-6-oxa-4a,10b-diazaphenalen-5-one (I)

A solution of 2-chloro-3-nitrobenzoic acid (5.00 g, 24.8 mmol), ammonium hydroxide (25.0 ml) and copper (1) chloride (50 mg) is heated hi a bomb at 125° for 20 hr and is then allowed to cool to 20°–25°. The solid residue is dissolved in water and the solution acidified with 3 N hydrochloric acid. The resultant mixture is filtered, washed, and dried to provide the 2-amino-3-nitrobenzoic acid, mp 201°–203; IR (mineral oil) 3478, 3345, 2954, 2925, 2855, 1692, 1677, 1571, 1559, 1520, 1512, 1442, 1271, 1259, 1130 cm$^{-1}$; NMR (300 MHz, CDCl$_3$-MeOD) 8.38, 8.30, 6.66; MS (EI) m/e 182, 164.

Borane-methyl sulfide complex (1.20 ml, 12.0 mmol, 10.0M) is added to a mixture of the 2-amino-3-nitrobenzoic acid (1.05 g, 5.76 mmol), and THF (17.4 ml). The mixture is stirred for 3 hr at 20°–25° and 16 hr at reflux. After cooling to 20°–25°, the mixture is quenched with 10% hydrochloric acid. Basic workup (methylene chloride, sodium bicarbonate and magnesium sulfate) gives the 2-amino-3-nitrobenzyl alcohol (LI), mp 100°–101°; IR (mineral oil) 3488, 3466, 3365, 3346, 2953, 2925, 1641, 1515, 1428, 1250, 1015, 745 cm$^{-1}$; NMR (300 MHz, CDCl$_3$) 8.13, 7.30, 6.85, 6.65), 4.78; MS (EI) m/e 168, 150.

A solution of the 2-amino-3-nitrobenzyl alcohol (LI, 1.70 g, 10.1 mmol), THF (86.0 ml) and 1,1'-carbonyldiimidazole (1.81 g, 11.2 mmol) is heated at reflux for 48 hr. After cooling to 20°–25°, aqueous workup (methylene chloride and magnesium sulfate) provides the cyclic amide (LII) as a solid. Recrystallization from ethyl acetate/hexane (2 lots) gives the cyclic amide (LII), mp 181°–182.5°; IR (mineral oil) 3314, 2925, 1779, 1765, 1619, 1530, 1466, 1351, 1243, 1228, 1061, 765, 736 cm$^{-1}$; NMR (300 MHz, CDCl$_3$) 9.68, 8.22, 7.46, 7.19, 5.37; MS (EI) m/e 194, 150.

A mixture of the cyclic amide (LII, 195 mg, 1.00 mmol), ethanol (20.0 ml), and 10% Palladium on carbon is hydrogenated (44 psi) at 20°–25°. The mixture is filtered, the residue washed with ethanol, methanol, and methylene chloride and the combined filtrates concentrated to provide the amino cyclic amide (LIII), mp 198–200; IR (mineral oil) 3465, 2953, 2925, 1713, 1697, 1633, 14:14, 1289, 1048 cm$^{-1}$; NMR (300 MHz, CDCl$_3$) 9.13, 6.89, 6.72, 6.57, 5.29; MS (EI) m/e 164, 120, 105, 93.

Chloroacetyl chloride (0.39 ml, 4.9 mmol) is added to a solution of the amino cyclic amide (LIII, 708 mg, 4.31 mmol), diisopropylethylamine (1.71 ml, 9.82 mmol), and THF (50.0 ml) at 0°. The mixture is stirred at 0° for 1 hr and 16 hr at 20°–25°. The mixture is filtered and the solids washed several times with water and ethyl acetate to give the chloride intermediate. Aqueous workup (ethyl acetate, magnesium sulfate) of the filtrate provides additional intermediate chloride, mp 255–257; IR (mineral oil) 2954, 2924, 2855, 1715, 1704, 1679, 1555, 1475, 1459, 1267, 1062, 780 cm$^{-1}$; NMR (300 MHz, d$_6$-DMSO) 9.69, 7.27, 7.10, 7.02, 5.29, 4.29; MS (EI) m/e 240, 191, 147.

Potassium tert-butoxide (3.50 ml, 3.50 mmol, 1.0M in THF) is added to a mixture of the intermediate chloride (822 mg, 3.42 mmol) and THF (70.0 ml) at 0°. The mixture is stirred for 1 hr at 0° and 16 hr at 20°–25°. The mixture is then quenched with aqueous ammonium chloride. Aqueous workup (ethyl acetate, magnesium sulfate) and trituration of the resultant solid with ether provides the bis-amide (LIV), mp 255°–256°; IR (mineral oil) 2954, 2924, 1705, 1630, 1504, 1410, 1271 cm$^{-1}$; NMR (300 MHz, d$_6$-acetone) 9.80, 7.05, 6.98, 6.92, 5.32, 4.48; MS (EI) m/e 204, 160, 131.

Potassium tert-butoxide (2.30 ml, 2.30 mmol, 1.0M in THF) is added to a mixture of the bis-amide (LIV, 425 mg, 2.08 mmol), THF (2.10 ml), and DMF (1.30 ml) at 0°. The resultant mixture is allowed to warm to 20°–25° and is stirred for 30 min. After cooling to −20°, diethyl chlorophosphate (0.39 ml, 2.7 mmol) is added and the mixture allowed to warm to 20°–25°. THF (4.0 ml) and DMF (1.0 ml) are added to the mixture to form a solution which is stirred at 20°–25° for 45 min. After cooling to −78° a solution of the isocyanide (339 mg, 2.27 mmol) and THF (0.80 ml) is added followed by dropwise addition of potassium tert-butoxide (2.30 ml, 2.30 mmol) over 5 min. The mixture is stirred at −78° for 30 min and is allowed to warm to 20°–25° over 2 hr. After stirring at 20°–25° for an additional 2 hr the mixture is quenched with aqueous ammonium chloride. Aqueous workup (ethyl acetate, magnesium sulfate) and purification by flash chromatography eluting with ethyl acetate gives the title compound. An analytical sample is prepared by recrystallization from ethyl acetate, mp 235°–237°; IR (mineral oil) 2954, 2924, 2855, 1710, 1574, 1510, 1456, 1419, 1399, 1377, 1293, 1201, 725 cm$^{-1}$; NMR (300 MHz, CDCl$_3$) 8.32, 7.58, 7.22, 7.09, 5.48, 5.34, 2.2–2.4, 1.2–1.4; MS (EI) m/e 335, 291, 266, 222, 207; Anal. Calcd for C$_{17}$H$_{13}$N$_5$O$_3$·(C$_4$H$_8$O$_2$)$_{1/2}$·(H$_2$O)$_{1/4}$: C, 59.45; H, 4.60; N, 18.24; found: C, 59.54; H, 4.22; N, 18.49.

EXAMPLE 365

3-(5-Cyclopropyl-1,2,4-oxadiazol-3-yl)-3a,4,4a,5,6, 10b-hexahydro-7H-6-(1-methylethyl)imidazo-[5,1-f]4a,6,10b-triazaphenalen-5-one (I)

A solution of methanesulfonyl chloride (69.0 mg, 0.602 mmol) and THF (0.50 ml) is added to a solution of 2-amino-3-nitrobenzyl alcohol (100 mg, 0.595 mmol), diisopropylethylamine (0.12 ml, 0.69 mmol), and THF (4.0 ml) at 0°. After 2.5 hr at 0°, isopropylamine (0.51 ml, 6.0 mmol) is added. The solution is stirred for an additional hour at 0° and is allowed to warm to 20°–25°. After 24 hr, basic workup (ethyl acetate, sodium bicarbonate and magnesium sulfate) and purification by flash chromatography eluting with hexane/ethyl acetate (2/1), pooling and concentrating the appropriate fractions gives nitro compound (LI), IR (neat) 3451, 3230, 2966, 1622, 1576, 1518, 1453, 1440, 1355, 1333, 1257, 743 cm$^{-1}$; NMR (300 MHz, CDCl$_3$) 8.07, 7.72, 7.23, 6.57, 3.90, 2.7–2.9, 1.12; MS (EI) m/e 209, 192, 162, 151.

A solution of the nitro compound (LI, 780 mg, 3.73 mmol), toluene (33.0 ml), and 1,1′-carbonyldiimidazole (CDI, 589 mg, 3.63 mmol) is heated at reflux for 6 days. After 2 days additional CDI (300 mg, 1.85 mmol) is added. After cooling to 20–250, concentration and aqueous workup (methylene chloride and magnesium sulfate) gives a solid which is a mixture of the desired product and starting material. Resubmission of the crude to the above reaction conditions (1.19 g of CDI, 6 days at reflux) provides (after workup as described above) cyclic amide (LI) as a solid, homogeneous by TLC analysis, IR (mineral oil) 3400, 2962, 2925, 1693, 1683, 1620, 1593, 1530, 1471, 1454, 1342, 1265, 1204 cm$^{-1}$; NMR (300 MHz, CDCl$_3$) 9.33, 8.14, 7.39, 7.02, 4.7–4.9, 4.38, 1.24; MS (EI) m/e 235, 220, 192, 177.

A mixture of the cyclic amide (LII, 842 mg, 3.58 mmol), ethanol (66.0 ml) and 10% palladium on carbon (132 mg) is hydrogenated (38 psi) at 20°–25° for 16 hr. The mixture is filtered, and the residue washed with ethanol, chloroform and methanol successively. The combined filtrates are concentrated to provide amino cyclic amide (LIII), mp 148°–150°; IR (mineral oil) 3370, 2954, 2925, 2855, 1676, 1631, 1506, 1455, 1447, 1295 cm$^{-1}$; MS (EI) m/e 205, 190, 162, 147, 120.

Chloroacetyl chloride (0.29 ml, 3.6 mmol) is added to a solution of amino cyclic amide (LII, 660 mg, 3.21 mmol), THF (37.0 ml), and diisopropylethylamine (1.28 ml, 7.35 mmol) at 0°. The solution is allowed to stir for 1 hr at 0° and for 16 hr at 20°–25°. Aqueous workup (ethyl acetate, magnesium sulfate) of the mixture provides a solid which is purified by flash chromatography eluting with ethyl acetate/hexane (2/1) to give the chloro intermediate, mp 173°–174°; IR (mineral oil) 3329, 2954, 2925, 2855, 1702, 1663, 1552, 1472, 1459, 1453, 754 cm$^{-1}$; MS (EI) m/e 281, 266, 223, 147.

Potassium tert-butoxide (2.35 ml, 2.35 mmol, 1.0M in THF) is added to a solution of the chloro intermediate (644 mg, 2.29 mmol) and THF (47.0 ml) at 0°. The solution is stirred for 1 hr at 0° and for 16 hr at 20°–25°. After quenching with aqueous ammonium chloride, aqueous workup (ethyl acetate, magnesium sulfate), and trituration of the residue with ethyl acetate/ether provides the bis-amide (LIV), mp 244°–247°; IR (mineral oil) 2954, 2924, 2855, 1681, 1637, 1617, 1505, 1447, 1409, 786 cm$^{-1}$; MS (EI) m/e 245,230, 202, 160, 131.

Potassium tert-butoxide (1.80 ml, 1.80 mmol, 1.0M in THF is added to a solution of the bis-amide (LIV, 400 mg, 1.63 mmol), THF (2.50 ml), and DMF (0.33 ml) at 0°. The mixture is allowed to warm to 20°–25° and is stirred for 30 min. After cooling to −20°, diethyl chlorophosphate (0.31 ml, 2.15 mmol) is added and mixture is allowed to war to 20°–25°. After stirring for 45 min at 20°–25°, the resultant solution is cooled to −78°. A solution of the isocyanide (266 mg, 1.78 mmol) and THF (0.60 ml) is added followed by the addition of potassium tert-butoxide (1.80 ml, 1.80 mmol) dropwise over several min. The mixture is stirred for 1.5 hr at −78°, and is allowed to warm to 20°–25° over 1.5 hr. After stirring at 20°–25° for 1.5 hr the mixture is quenched with aqueous ammonium chloride. Aqueous workup (ethyl acetate and then chloroform, magnesium sulfate), purification by flash chromatography eluting with ethyl acetate, pooling and concentration of the appropriate fractions, and trituration of the isolated material with ether gives the title compound, mp 191°–193°; IR (mineral oil) 2955, 2927, 2855, 1652, 1572, 1511, 1466, 1458, 1446, 1396, 1384, 1378, 1294, 1215, 1035 cm$^{-1}$; NMR (300 MHz, CDCl$_3$) 8.10, 7.43, 6.95–7.10, 5.43, 4.7–4.85, 4.35, 2.2–2.35, 1.1–1.4, 1.24; MS (EI) m/e 376, 307, 222, 207; Anal. Calcd for C$_{20}$H$_{18}$N$_6$O$_2$·(H$_2$O)$_{1/2}$; C, 62.65; H, 5.00; N, 21.92, found: C, 62.55; H, 5.42; N, 21.70.

EXAMPLE 366

3-(5-Cyclopropyl-1,2,4-oxadiazol-3-yl)-3a,4,4a,5,6,10b-hexahydro-7H-6-methylimidazo[5,1-f]-4a,6,10b-triazaphenalen-5-one (I)

Methanesulfonyl chloride (0.36 ml, 4.7 mmol) is added to a solution of the 2-amino-3-nitrobenzyl alcohol (783 mg, 4.66 mmol), THF (31.0 ml), and diisopropylethylamine (0.94 ml, 5.4 mmol) at 0°. The mixture is stirred at 0° for 4 hr. Aqueous methylamine (40%, 4.0 ml, 46 mmol) is added and the mixture stirred for an additional hour at 0° and for 24 hr at 20°–25°. Acidic workup (ether, methylene chloride, magnesium sulfate) provides the nitro compound (LI), homogeneous by TLC analysis, IR (neat) 3449, 2847, 1621, 1575, 1516, 1451, 1350, 1331, 1254, 743 cm$^{-1}$; NMR (300 MHz, CDCl$_3$) 8.08, 7.67, 7.23, 6.58, 3.87, 2.42, 1.2–1.5; MS (EI) m/e 181, 164, 134, 105.

A solution of the nitro compound (LI, 1.74 g, 9.60 mmol), THF (75.0 ml), and CDI (2.33 g, 14.4 mmol) is heated at reflux for 6 days. After 3 days additional CDI (1.16 g, 7.15 mmol) is added. After cooling to 20°–25°, the mixture is diluted with ethyl acetate and the organic layer is washed with water, 5% hydrochloric acid, sodium bicarbonate, and saline. The organic layer is dried (magnesium sulfate), filtered and concentrated. Recrystallization of the residue from ethyl acetate/hexane gives the cyclic amide (LII), mp 155°–157°. The filtrate is concentrated and purified by flash chromatography (ethyl acetate) to provide an additional product, IR (mineral oil) 3396, 2954, 2925, 2855, 1700, 1620, 1591, 1529, 1483, 1464, 1339, 1271, 1233, 1216, 753, 747 cm$^{-1}$; MS (EI) m/e 207, 160.

A mixture of the cyclic amide (LII, 1.38 g, 6.66 mmol), 10% palladium on carbon (250 mg), and ethanol (132 ml) is hydrogenated (50 psi) at 20°–25° in a Parr flask. After 16 hr, the mixture is filtered and the remaining solids washed with ethanol, chloroform and methanol. The combined filtrates are concentrated. Trituration (ether) of the crude provides the amino cyclic amide (LIII), mp 229°–231°; IR (mineral oil) 3298, 2953, 2925, 2855, 1677, 1515, 1443, 1406, 1299, 1278 cm$^{-1}$.

Chloroacetyl chloride (0.54 ml, 6.8 mmol) is added to a mixture of the cyclic amide (LIII, 1.07 g, 6.04 mmol), THF (70 ml), and diisopropylethylamine (2.40 ml, 13.8 mmol) at 0°. The solution is stirred for 1 hr at 0° and for 16 hr at 20°–25°. Aqueous workup (ethyl acetate, magnesium sulfate) and trituration with ethyl acetate gives the chloro intermediate, mp 197°–199°. The filtrate is concentrated and the residue purified by flash chromatography eluting with ethyl acetate to provide additional chloro intermediate, IR (mineral oil) 3256, 2954, 2925, 2855, 1701, 1648, 1527, 1458, 1270 cm$^{-1}$; MS (EI) m/e 253, 204, 176, 147.

Potassium tert-butoxide (4.8 ml, 4.8 mmol, 1.0M in THF) is added to a mixture of the chloro intermediate (1.19 g, 4.69 mmol) and THF (96 ml) at 0°. The mixture is stirred for 1 hr at 0°, 16 hr at 20°–25°, and is then quenched with aqueous ammonium chloride. Aqueous workup (ethyl acetate, chloroform/methanol, magnesium sulfate) and trituration of the residue with ethyl acetate gives the bis-amide (LIV), mp 238°–241°. The filtrate is concentrated and after trituration with ethyl acetate provides additional bis-amide (LIV), IR (mineral oil) 3359, 2954, 2925, 1693, 1649, 1505, 1448, 1268 cm$^{-1}$; NMR (300 MHz, CDCl$_3$-MeOD) 6.94, 6.76, 4.52, 4.46, 3.04.

Potassium tert-butoxide (1.90 ml, 1.90 mmol, 1.0M in THF) is added to a mixture of the bis-amide (LIV, 380 mg, 1.75 mmol), and DMF (8.0 ml) at 0°. The mixture is allowed to warm to 20°–25° and is stirred for 30 min. After cooling to 0°, diethyl chlorophosphate (0.29 ml, 2.0 mmol) is added and mixture is allowed to warm to 20°–25°. After stirring for 30 min at 20°–25° the resultant solution is cooled to 40°. A solution of the isocyanide (286 mg, 1.92 mmol) and THF (1.0 ml) is added followed by the addition of potassium tert-butoxide (1.90 ml, 1.90 mmol) dropwise over several min. The mixture is stirred for 30 min at −30°, and is then allowed to warm to 20°–25°. After stirring at 20°–25° for 3 hr the mixture is quenched with aqueous ammonium chloride. Aqueous workup (ethyl acetate, magnesium sulfate), and purification by flash chromatography eluting with ethyl acetate gives the title compound. An analytical sample is prepared by recrystallization from ethyl acetate, mp 215°–217°; IR (mineral oil) 2954, 2925, 2855, 1659, 1583, 1517, 1501, 1478, 1444, 1410, 1270, 891, 783 cm$^{-1}$; NMR (300 MHz, CDCl$_3$) 8.10, 7.43, 7.05, 6.97, 5.39, 4.49, 3.08, 2.2–2.35, 1.2–1.4; MS (FAB) m/e 349 [M+H]$^+$, 348, 281, 162; Anal. Calcd for C$_{18}$H$_{16}$N$_6$O$_2$: C, 62.06; H, 4.63; N, 24.13, found: C, 61.87; H, 4.55; N, 24.17.

EXAMPLES 367–393

Following the general procedure of EXAMPLES 48–87 (R$_5$ then R$_3$) and making non-critical variations but starting with the appropriate starting materials, the compounds of EXAMPLES 367 thru 393 are obtained:

EXAMPLE 367

3-(5-tert-Butyl-1,2,4-oxadiazol-3-yl)-4,5-dihydro-6-methyl-5-[(pyrrolidino)carbonyl]imidazo-[1,5-a]quinoxaline (I)

mp 231°–233°: IR (mineral oil) 1659, 1505, 1499, 1493, 1473, 1402, 1385, 1186 cm$^{-1}$; NMR (CDCl$_3$) 8.12, 7.4–7.45, 7.15–7.3, 5.14, 3.15, 2.23, 1.7–1.85, 1.50; MS (EI) m/e 406, 336, 308, 278, 98.

EXAMPLE 368 tert-Butyl 7-chloro-4,5-dihydro-5-[(methoxy)carbonyl]-4,4-dimethylimidazo[1,5-a]quinoxaline-3-carboxylate (I)

mp 162.5°–164.5°: IR (mineral oil) 1716, 1690, 1512, 1326, 1282, 1240, 1159, 1144 cm$^{-1}$; NMR (CDCl$_3$) 7.93, 7.3–7.4, 7.22, 3.74, 1.92, 1.62; MS (EI) m/e 391, 376, 320, 276, 244.

EXAMPLE 369 tert-Butyl 5-benzoyl-7-chloro-4,5-dihydroimidazo[1,5-a]-quinoxaline-3-carboxylate (I)

mp 244–244.5°: IR (mineral oil) 1724, 1660, 1505, 1381, 1370, 1362, 1330, 1236, 1153, 1141, 729 cm$^{-1}$; NMR (CDCl$_3$) 8.06, 7.35–7.55, 7.15–7.3, 5.28, 1.52; MS (EI) m/e 409, 353, 336, 248, 231, 105.

EXAMPLE 370 tert-Butyl 7-chloro-4,5-dihydro-5-[(methoxy)carbonyl]imidazo-[1,5-a]quinoxaline-3-carboxylate (I)

mp 176°–177°: IR (mineral oil) 1725, 1717, 1700, 1513, 1433, 1377, 1370, 1338, 1299, 1226, 1158, 1131, 1063 cm$^{-1}$; NMR (CDCl$_3$) 7.98, 7.85, 7.45, 7.2–7.3, 5.25, 3.87, 1.64; MS (EI) m/e 363, 307, 289, 261, 248, 230.

EXAMPLE 371 tert-Butyl 4,5-dihydro-5-[(4-trifluoromethyl)benzoyl]imidazo-[1,5-a]quinoxaline-3-carboxylate (I)

mp 233°–234°: IR (mineral oil) 1694, 1672, 1517, 1324, 1298, 1169, 1141, 965, 756 cm$^{-1}$; NMR (CDCl$_3$) 8.11, 7.5–7.7, 7.2–7.4, 6.9–7.2, 5.32, 1.56; MS (ED m/e 443, 387, 370, 214, 196, 173, 145.

EXAMPLE 372 tert-Butyl 5-[(4-dimethylamino)benzoyl]-4,5-dihydroimidazo[1,5-a]quinoxaline-3-carboxylate (I)

mp 152°–153°: IR (mineral oil) 1696, 1650, 1604, 1593, 1505, 1365, 1352, 1341, 1298, 1288, 1191, 1160, 758 cm$^{-1}$; NMR (CDCl$_3$) 8.09, 7.54, 7.34, 7.15–7.25, 6.95–7.15, 6.53, 5.32, 3.00, 1.60; MS (EI) m/e 418, 345, 148.

EXAMPLE 373 tert-Butyl 5-benzoyl-4,5-dihydro-4,4-dimethylimidazo[1,5-a]-quinoxaline-3-carboxylate (I)

mp 198°–200°: IR (mineral oil) 1714, 1675, 1513, 1367, 1332, 1304, 1284, 1262, 1153, 1141, 1032, 764, 717 cm$^{-1}$; NMR (CDCl$_3$) 8.08, 7.55, 7.35–7.5, 7.2–7.35, 7.06, 6.88, 6.61, 2.06, 1.65; MS (EI) m/e 403, 388, 210, 105.

EXAMPLE 374 tert-Butyl 4,5-dihydro-5-[(isopropoxy)carbonyl]imidazo[1,5-a]quinoxaline-3-carboxylate (I)

mp 201°–202°: IR (mineral oil) 1708, 1694, 1511, 1380, 1294, 1119 cm$^{-1}$; NMR (CDCl$_3$) 8.01, 7.79, 7.52, 7.2–7.4, 5.22, 5.0–5.15, 1.64, 1.33; MS (EI) m/e 357, 301, 283, 241, 214, 196, 169.

EXAMPLE 375 tert-Butyl 7-chloro-4,5-dihydro-4,4-dimethyl-5-[(morpholino)carbonyl]imidazo[1,5-a]quinoxaline-3-carboxylate (I)

mp 193°–194°: IR (mineral oil) 1704, 1647, 1529, 1515, 1420, 1288, 1271, 1241, 1148, 1125, 969 cm$^{-1}$; NMR (CDCl$_3$) 7.94, 7.39, 7.02, 6.78, 3.0–4.1, 1.5–2.2, 1.63; MS (EI) m/e 446, 431, 244, 114.

EXAMPLE 376 tert-Butyl 4,5-dihydro-5-[(methoxy)carbonyl]-4,4-dimethylimidazo[1,5-a]quinoxaline-3-carboxylate (I)

mp 212°–212.5°: IR (mineral oil) 3103, 1724, 1707, 1518, 1333, 1295, 1292, 1258, 1156, 1145, 760 cm$^{-1}$; NMR (CDCl$_3$) 7.96, 7.2–7.5, 3.70, 1.92, 1.63; MS (EI) m/e 357, 342, 286, 242, 210.

EXAMPLE 377 tert-Butyl 5-[(tert-butyloxy)carbonyl]-7-chloro-4,5-dihydro-4,4-dimethylimidazo[1,5-a]quinoxaline-3-carboxylate (I)

mp 157°–158°: IR (mineral oil) 1731, 1727, 1706, 1517, 1372, 1366, 1294, 1286, 1244, 1156, 1145, 971 cm$^{-1}$; NMR (CDCl$_3$) 7.92, 7.3–7.4, 7.14, 1.92, 1.62, 1.50; MS (EI) m/e 433, 377, 362, 318, 306, 277, 262, 244.

EXAMPLE 378

3-(3-tert-Butyl-5-isoxazolyl)-4,5-dihydro-5-[(pyrrolidino)carbonyl]imidazo[1,5-a]quinoxaline (I)

mp 207.5°–208.5°: IR (mineral oil) 2961, 2925, 1657, 1508, 1466, 1392, 1343, 1307, 1304, 745 cm$^{-1}$; NMR (CDCl$_3$) 8.06, 7.52, 7.1–7.3, 6.53, 5.00, 3.2–3.4, 1.75–1.85, 1.38; MS (EI) m/e 350, 308, 293, 267, 252, 212.

EXAMPLE 379 tert-Butyl 6-chloro-4,5-dihydro-5-[(methoxy)carbonyl]imidazo-[1,5-a]quinoxaline-3-carboxylate (I)

mp 203°–204°: IR (mineral oil) 1717, 1705, 1492, 1441, 1214, 1135 cm$^{-1}$; $^1$H NMR (CDCl$_3$) 8.02, 7.4–7.5, 7.3–7.4, 6.05–6.35, 4.0–4.4, 3.78, 1.64; MS (EI) m/e 363, 307, 289, 248, 230.

EXAMPLE 380 tert-Butyl 5-benzoyl-7-chloro-4,5-dihydro-4,4-dimethylimidazo-[1,5-a]quinoxaline-3-carboxylate (I)

mp 195.5°–196.5°: IR (mineral oil) 1709, 1680, 1510, 1286, 1279, 1248, 1154, 968 cm$^{-1}$; NMR (CDCl$_3$) 8.00, 7.5–7.6, 7.4–7.5, 7.25–7.4, 7.02, 6.59, 2.05, 1.64; MS (EI) m/e 437, 422, 259, 244, 105.

EXAMPLE 381 tert-Butyl 5-[(3-fluoro)benzoyl]-4,5-dihydro-4,4-dimethylimidazo-[1,5-a]quinoxaline-3-carboxylate (I)

mp 214°–215.5°: IR (mineral oil) 1706, 1672, 1518, 1440, 1295, 1291, 1268, 1144, 752 cm$^{-1}$; NMR (CDCl$_3$) 8.08, 7.45, 7.15–7.35, 7.05–7.15, 6.92, 6.62, 2.05, 1.65; MS (EI) m/e 421, 406, 210, 123.

EXAMPLE 382 tert-Butyl 5-[(3-fluoro)benzoyl]-7-chloro-4,5-dihydro-4,4-dimethylimidazo[1,5-a]quinoxaline-3-carboxylate (I)

mp 187°–187.5°: IR (mineral oil) 1713, 1684, 1511, 1480, 1444, 1324, 1285, 1282, 1261, 1153, 1141, 968 cm$^{-1}$; NMR (CDCl$_3$) 8.04, 7.39, 7.25–7.35, 7.10–7.25, 7.07, 6.59, 2.04, 1.64; MS (EI) m/e 455, 440, 244, 123.

EXAMPLE 383 tert-Butyl 6-chloro-4,5-dihydro-4,4-dimethyl-5-[(morpholino)carbonyl]imidazo[1,5-a]quinoxaline-3-carboxylate (I)

mp effr 73°–76°: IR (mineral oil) 1707, 1670, 1496, 1476, 1412, 1367, 1290, 1274, 1248, 1229, 1160, 1151, 1117, 1051 cm$^{-1}$; NMR (CDCl$_3$) 7.99, 7.40, 7.32, 7.14, 3.45–3.6, 3.30, 1.89, 1.63; MS (EI) m/e 446, 431, 244, 114.

EXAMPLE 384 tert-Butyl 6-chloro-4,5-dihydro-5-[(methoxy)carbonyl]-4,4-dimethylimidazo[1,5-a]quinoxaline-3-carboxylate (I)

mp 108°–109°: IR (mineral oil) 1752, 1710, 1503, 1439, 1330, 1285, 1257, 1229, 1146, 1050, 783 cm$^{-1}$; NMR (CDCl$_3$) 7.95, 7.25–7.45, 3.60, 1.89, 1.63; MS (EI) m/e 391, 376, 320, 302, 244.

EXAMPLE 385 tert-Butyl 7-chloro-4,5-dihydro-5-[(isopropoxy)carbonyl]-4,4-dimethylimidazo[1,5-a]quinoxaline-3-carboxylate (I)

mp 126°–127°: IR (mineral oil) 1722, 1708, 1517, 1291, 1242, 1144, 1111, 971 cm$^{-1}$; $^1$H NMR (CDCl$_3$) 7.93, 7.3–7.4, 7.17, 4.9–5.1, 1.93, 1.63, 1.29; MS (EI) m/e 419, 404, 262, 244.

EXAMPLE 386 tert-Butyl 7-Chloro-5-[(4-dimethylamino)benzoyl]-4,5-dihydroimidazo[1,5-a]quinoxaline-3-carboxylate (I)

mp 135°–137°

EXAMPLE 387 tert-Butyl 7-chloro-4,5-dihydro-4,4-dimethyl-5-[(3,5-dimethylmorpholino)carbonyl]imidazo[1,5-a]-quinoxaline-3-carboxylate (I)

mp 187.5°–188°

EXAMPLE 388

7-Chloro-3-(5-cyclopropyl-1,2,4-oxadiazol-3-yl)-4,5-dihydro-5-[(morpholino)carbonyl]imidazo-[1,5-a]quinoxaline (I)

mp 209°–210°

EXAMPLE 389

7-Chloro-3-(3-cyclopropyl-1,2,4-oxadiazol-5-yl)-4,5-dihydro-5-[carbonyl]imidazo[1,5-a]quinoxaline (I)

mp 244°∝246°

EXAMPLE 390

7-Chloro-3-(5-cyclopropyl-1,2,4-oxadiazol-3-yl)-4,5-dihydro-5-[(1-(4-methyl)piperazino)carbonyl]imidazo-[1,5-a]quinoxaline (I)

mp 189°–191°

EXAMPLE 391

7-Chloro-3-(5-cyclopropyl-1,2,4-oxadizol-3-yl)-4,5-dihydro-5-[(4-(3,5 -dimethyl)morpholino)-carbonyl]imidazo[1,5-a]quinoxaline (I)

mp 139°–145°

EXAMPLE 392

7-Chloro-3-(3-cyclopropyl-1,2,4-oxadiazol-5-yl)-4,5-dihydro-5-[(1-(4-methyl)piperazino)carbonyl]-imidazo[1,5-a]quinoxaline (I)

mp 187°–189°

EXAMPLE 393

7-Chloro-3-(3-cyclopropyl-1,2,4-oxadizol-5-yl)-4,5-dihydro-5-[(isopropoxy)carbonyl]-imidazo[1,5-a]quinoxaline (I)

mp 204°–205°

EXAMPLES 394–423

Following the general procedure of EXAMPLES 108–148 (R$_3$ then R$_5$) and making non-critical variations but starting with the appropriate starting materials, the compounds of EXAMPLES 394 thru 423 are obtained:

EXAMPLE 394 tert-Butyl 5-[(ethylamnino)carbonyl]-4,5-dihydroimidazo[1,5-a]quinoxaline-3-carboxylate (I)

mp 193°–194°: IR (mineral oil) 2926, 1726, 1662, 1508, 1381, 1367, 1282, 1149 cm$^{-1}$; $^1$H NMR (CDCl$_3$) 8.01, 7.5–7.65, 7.25–7.4, 5.22, 5.0–5.1, 3.25–3.4, 1.64, 1.15; MS (EI) m/e 342, 286, 269, 214, 196, 169.

EXAMPLE 395 tert-Butyl 5-[(tert-butylamino)carbonyl]-4,5-dihydmimidazo[1,5-a]quinoxaline-3-carboxylate (I)

mp 194°–195°: IR (mineral oil) 2925, 1699, 1678, 1505, 1281, 1133 cm$^{31\ 1}$; $^1$H NMR (CDCl$_3$) 8.02, 7.5–7.6, 7.25–7.4, 5.14, 4.94, 1.64, 1.36; MS (EI) m/e 370, 314, 297, 214, 197, 169.

EXAMPLE 396 tert-Butyl 5-carbamoyl-4,5-dihydro4,4-dimethylimidazo[1,5-a]quinoxaline-3-carboxylate (I)

mp 172°–173°: IR (mineral oil) 3429, 2954, 2925, 1702, 1691, 1516, 1300, 1286, 1163, 1149 cm$^{-1}$; $^1$H NMR (CDCl$_3$) 7.78, 7.3–7.4, 7.2–7.3, 7.05–7.15, 5.44, 1.91, 1.62; MS (EI) m/e 342, 327. 299, 284, 271, 228, 184.

EXAMPLE 397 tert-Butyl 5-[(tert-butylamino)carbonyl]-4,5-dihydro4,4-dimethylimidazo[1,5-a]quinoxaline-3-carboxylate (I)

mp 189°–191°): IR (mineral oil) 2925, 1703, 1686, 1541, 1509, 1365, 1361, 1280, 1268, 1155, 973,744 cm$^{-1}$; $^1$H NMR (CDCl$_3$) 7.85, 7.37, 7.15–7.25, 6.95–7.1, 5.68, 1.87, 1.62, 1.42; MS (EI) m/e 398, 383, 325, 299, 284, 228, 210, 184.

EXAMPLE 398 tert- Butyl 5-[(ethylamino)carbonyl]-4,5-dihydro-4,4-dimethyl-imidazo[1,5-a]quinoxaline-3-carboxylate (I)

mp 198°–199°): IR (mineral oil) 2953, 2926, 1708, 1681, 1544, 1311, 1283, 1262, 1157, 974, 748 cm$^{-1}$; $^1$H NMR (CDCl$_3$) 7.80, 7.36, 7.15–7.25, 6.95–7.1, 5.75–5.85, 3.3–3.45, 1.88, 1.62, 1.21; MS (EI) m/e 370, 355,297, 284, 228, 210, 184.

EXAMPLE 399 tert-Butyl 5-carbmnoyl-7-chloro-4,5-dihydro-4,4-dimethyl-imidazo[1,5-a]quinoxaline-3-carboxylate (I)

mp 229°–231°: IR (mineral oil) 3433, 1719, 1602, 1538, 1516, 1513, 1356, 1333, 1325, 1278, 1183, 1150, 1050, 972, 799 cm$^{-1}$; $^1$H NMR (CDCl$_3$) 7.84, 7.25–7.35, 7.05, 5.72, 1.91, 1.61; MS (EI) m/e 376, 361, 305, 262, 218.

EXAMPLE 400 tert-Butyl 7-chloro-5-[(ethylarnino)carbonyl]-4,5-dihydro-4,4-dimethylimidazo[1,5-a]quinoxaline-3-carboxylate (I)

mp 228°–230°: IR (mineral oil) 1712, 1680, 1515, 1288, 1260, 972 cm$^{-1}$; $^1$H NMR (CDCl$_3$) 7.84, 7.32, 6.95–7.05, 5.6–5.75, 3.3–3.5, 1.88, 1.62, 1.24; MS (EI) m/e 404, 389, 318, 262, 244, 218.

EXAMPLE 401

3-(5-Cyclopropyl-1,2,4-oxadiazol-3-yl)-4,5-dihydro-5-[(2-(4-morpholinyl)ethylamino)carbonyl]-imidazo[1,5-a]quinoxaline (I)

mp 188°–189°

EXAMPLE 402

3-(5-cyclopropyl-1,2,4-oxadiazol-3-yl)-5-[(2-(diethylamino)ethylamino)carbonyl]-4,5-dihydro-imiclazo[1,5-a]quinoxaline (I)

mp 155°–156°

EXAMPLE 403

3-(5-cyclopropyl-1,2,4-oxadiazol-3-yl)-4,5-dihydro-5-[(2-(methoxy)ethylamino)carbonyl]imidazo-[1,5-a]quinoxaline (I)

mp 166.5°–167.5°

EXAMPLE 404

3-(5-cyclopropyl-1,2,4-oxadiazol-3-yl)-4,5-dihydro-5-[(1-(3,5-dimethyl)piperazino)caxbonyl]imidazo-[1,5-a]quinoxaline (I)

mp 201.5°–202.5°

EXAMPLE 405

3-(5-cyclopropyl-1,2,4-oxadiazol-3-yl)-4,5-dihydro-5-[(2-methoxyethoxy)carbonyl]imidazo-[1,5-a]quinoxaline (I)

mp 119°–120°

EXAMPLE 406

7-chloro-3-(5-cyclopropyl-1,2,4-oxadiazol-3-yl)-5-[(ethylamino)carbonyl]-4,5-dihydroimidazo[1,5-a]-quinoxaline (I)

mp 248.5°–250°

EXAMPLE 407

5-(carbamoyl)-7-chloro-3-(5-cyclopropyl-1,2,4-oxadiazol-3-yl)-4,5-dihydroimidazo[1,5-a]-quinoxaline (I)

mp 228°–229°

EXAMPLE 408

3-(3-cyclopropyl-1,2,4-oxadiazol-5-yl)-4,5-dihydro-5-[(isopropoxy)carbonyl]-7-methylimidazo[1,5-a]-quinoxaline (I)

mp 19 1.5°–192°

EXAMPLE 409

3-(3-cyclopropyl-1,2,4-oxadiazol-5-yl)-4,5-dihydro-7-methyl-5-[(morpholino)carbonyl]imidazo-[1,5-a]quinoxaline (I)

mp 227°–228°

EXAMPLE 410

3-(3-cyclopropyl-1,2,4-oxadiazol-5-yl)-4,5-dihydro-5-[(1-(3,5-dimethyl)piperazino)carbonyl]-7-methylimidazo[1,5-a]quinoxaline (I)

mp 237°–238°

EXAMPLE 411

5-(carbamoyl)-3-(3-cyclopropyl-1,2,4-oxadiazol-5-yl)-4,5-dihydro-7-methylimidazo[1,5-a]quinoxaline (I)

mp 205°–207°

EXAMPLE 412

3-(5-cyclopropyl-1,2,4-oxadiazol-3-yl)-4,5-dihydro-5-[(1-(3,4,5-trimethyl)piperazino)carbonyl]imidazo-[1,5-a]quinoxaline (I)

mp 189.5°–190.5°

EXAMPLE 413

3-(5-cyclopropyl-1,2,4-oxadiazol-3-yl)-4,5-dihydro-5-
[((2-dimethylamino)ethoxy)carbonyl]imidazo-
[1,5-a]quinoxaline (I)

mp 165.5°–167°

EXAMPLE 414

3-(3-cyclopropyl-1,2,4-oxadiazol-5-yl)-5-[(ethyl-
amino)carbonyl]-4,5-dihydro-7-methyl-
imidazo[1,5-a]-quinoxaline (I)

mp 240°–241°

EXAMPLE 415

3-(3-cyclopropyl-1,2,4-oxadiazol-5-yl)-4,5-dihydro-
7-methyl-5-[(1-(4-methyl)piperazino)carbonyl]-
imidazo-[1,5-a]quinoxaline (I)

mp 191.5°–192°

EXAMPLE 416

7-chloro-3-(3-cyclopropyl-1,2,4-oxadiazol-5-yl)-4,5-
dihydro-5-[(1-(3,5-dimethyl)piperazino)carbonyl]-
imidazo-[1,5-a]quinoxaline (I)

mp 223°–224°

EXAMPLE 417

3-(5-cyclopropyl-1,2,4-oxadiazol-3-yl)-
4,5-dihydro-6-methyl-5-[(morpholino)carbonyl]-
imidazo[1,5-a]-quinoxaline (I)

mp 265°–265.5°

EXAMPLE 418

3-(5-cyctopropyl-1,2,4-oxadiazol-3-yl)-4,5-dihydro-6-
methyl-5-[(1-(4-methyl)piperazino)carbonyl]-
imidazo[1,5-a]quinoxaline (I)

mp 192–193°

EXAMPLE 419

7-chloro-3-(3-cyclopropyl-1,2,4-oxadiazol-5-yl)-4,5-
dihydro-5-[(1-(3,4,5-trimethyl)piperazino)-
carbonyl]-imidazo[1,5-a]quinoxaline (I)

25728-EJJ-149A mp 231°–234°

EXAMPLE 420

5-[(2-fluoro)benzoyl]-3-(4-fluorophenyl)-4,5-dihydro-
imidazo[1,5-a]quinoxaline (I)

mp 185°–189°

EXAMPLE 421

3-(4-fluorophenyl)-4,5-dihydro-5-[(3-
trifluoromethyl)benzoyl]imidazo[1,5-a]-
quinoxaline (I)

mp 176°–178°

EXAMPLE 422

7-fluoro-3-(4-fluorophenyl)-4,5-dihydro-5-
[(morpholino)carbonyl]imidazo[1,5-a]quinoxaline
(I)

mp 180°–181.5°

EXAMPLE 423

7-chloro-3-(4-fluorophenyl)-4,5-dihydro-5-
[(morpholino)carbonyl]imidazo[1,5-a]quinoxaline
(I)

mp 142°–144°

EXAMPLES 424–430

Following the general procedure of EXAMPLE 30 and making non-critical variations but starting with the appropriate starting materials, the compounds of EXAMPLES 424 thru 430 are obtained:

EXAMPLE 424

3-(5-Cyclopropyl-1,2,4-oxadiazol-3-yl)-7-fluoro-4,5-
dihydro-5-[bis-(2-methoxyethyl)aminocarbonyl]-
imidazo-[1,5-a]quinoxaline (I)

mp 124.5°–125.0°; MS (m/z) 456; IR (mineral oil) 1673, 1203, 1517, 1417, 1498 cm$^{-1}$; NMR (CDCl$_3$) δ 1.24, 1.34, 2.25, 3.29, 3.48, 4.94, 6.84, 7.32, 7.47, 8.05.

EXAMPLE 425 tert-Butyl
7-fluoro-4,4-dimethyl-5-(morpholino)carbonylimidazo-
[1,5-a]quinoxaline-3-carboxylate (I)

mp 167°–191°; MS (m/z) 430; IR (mineral oil) 1652, 1705, 1531, 1124, 1524 cm$^{-1}$; NMR (CDCl$_3$) δ 1.63, 1.70, 2.08, 3.1–4.1, 6.51, 6.75, 7.42, 7.93.

EXAMPLE 426 tert-Butyl
7-fluoro-5-[bis(2-methoxyethyl)aminocarbonyl]-4,4-
dimethylimidazo[1,5-a]quinoxaline-3-carboxylate
(I)

mp 144°–145°; MS (m/z) 476; IR (mineral oil) 1707, 1282, 1153, 1658, 1666 cm$^{-1}$; NMR (CDCl3) δ 1.63, 1.67, 2.09, 3.16, 3.43, 3.2–3.4, 3.61, 3.72, 4.1, 6.73, 6.88, 7.38, 7.92.

EXAMPLE 427 tert-Butyl
7-fluoro4,5-dihydro-5-(isopropyloxycarbonyl)imidazo-
[1,5-a]quinoxaline-3-carboxylate (I)

mp 182°–183°; MS (m/z) 375; IR (mineral oil) 1710, 1519, 1302, 1696, 1227 cm$^{-1}$; NMR (CDCl$_3$) δ 1.35, 1.64, 5.08, 5.22, 6.99, 7.48, 7.61, 7.97.

EXAMPLE 428

3-(3-cyclopropyl-1,2,4-oxadiazol-5-yl)-7-fluoro-4,5-dihydro-5-(isopropyloxycarbonyl)imidazo-[1,5-a]quinoxaline (I)

mp 203.5°–205°; MS (m/z) 383; IR (mineral oil) 1710, 1512, 1234, 1640, 1254 cm$^{-1}$; NMR (CDCl$_3$) δ 1.09, 1.16, 1.35, 2.18, 5.07, 5.30, 7.03, 7.52, 7.63, 8.08.

EXAMPLE 429

3-(5-cyclopropyl-1,2,4-oxadiazol-3-yl)-7-fluoro-4,5-dihydro-5-(piperazinylcarbonyl)imidazo-[1,5-a]quinoxaline hydrochloride (I)

mp 216°–220°; MS (m/z) 409; IR (mineral oil) 1421, 1671, 1660, 1199, 1477 cm$^{-1}$; NMR (CDCl$_3$) δ 1.25, 1.35, 1.45, 2.26, 3.33, 3.42, 5.01, 6.91, 6.99, 7.52, 8.07.

EXAMPLE 430

3-(5-cyclopropyl-1,2,4-oxadiazol-3-yl)-6-fluoro-4,5-dihydro-5-(piperazinylcarbonyl)imidazo-[1,5-a]quinoxaline hydrochloride (I)

mp 240°–248°; MS (m/z) 409; IR (mineral oil) 1663, 1425, 1420, 1583, 1247 cm$^{-1}$; NMR (CDCl$_3$) δ 1.18, 1.30, 2.44, 3.09, 3.55, 5.08, 7.28, 7.39, 7.85, 8.76, 9.30.

EXAMPLE 431 t-Butyl 7-fluoro-4,5-dihydro-5-(morpholinocarbonyl)-imidazo[1,5-a]quinoxaline-3-carboxylate (I)

Following the general procedure of EXAMPLES 48–87 (R$_5$ then R$_3$) and making non-critical variations but starting with the appropriate starting material, the title compound is obtained, mp 195.5°–196.5°.

EXAMPLES 432–560

Following the general procedure of EXAMPLES 48–87 (R$_5$ then R$_3$) or of EXAMPLES 108–148 (R$_3$ then R$_5$) and making non-critical variations but starting with the appropriate starting materials, the compounds of EXAMPLES 432 thru 560 are obtained:

EXAMPLE 432

3-(3-cyclopropyl-1,2,4-oxadiazol-5-yl)-4,5-dihydro-5-[(1-(4-methyl)piperazino)carbonyl]imidazo-[1,5-a]quinoxaline (I)

EXAMPLE 433

3-(3-cyclopropyl-1,2,4-oxadiazol-5-yl)-7-fluoro-4,5-dihydro-5-[(1-(4-methyl)piperazino)carbonyl]-imidazo-[1,5-a]quinoxaline (I)

EXAMPLE 434

3-(3-cyclopropyl-1,2,4-oxadiazol-5-yl)-6-fluoro-4,5-dihydro-5-[(1-(4-methyl)piperazino)carbonyl]-imidazo]1,5-a]quinoxaline (I)

EXAMPLE 435

3-(3-cyclopropyl-1,2,4-oxadiazol-5-yl)-4,5-dihydro-7-methyl-5-[(1-(4-methyl)piperazino)carbonyl]-imidazo-[1,5-a]quinoxaline (I)

EXAMPLE 436

3-(5-cyclopropyl-1,2,4-oxadiazol-3-yl)-4,5-dihydro-5-[(1-(4-methyl)piperazino)carbonyl]-imidazo[1,5-a]quinoxaline (I)

EXAMPLE 437

3-(5-cyclopropyl-1,2,4-oxadiazol-3-yl)-7-fluoro-4,5-dihydro-5-[(1-(4-methyl)piperazino)carbonyl]-imidazo[1,5-a]quinoxaline (I)

EXAMPLE 438

3-(5-cyclopropyl-1,2,4-oxadiazol-3-yl)-6-fluoro-4,5-dihydro-5-[(1-(4-methyl)piperazino)carbonyl]-imidazo-[1,5-a]quinoxaline (I)

EXAMPLE 439

3-(5-cyclopropyl-1,2,4-oxadiazol-3-yl)-4,5-dihydro-7-methyl-5-[(1-(4-methyl)piperazino)carbonyl]-imidazo-[1,5-a]quinoxaline (I)

EXAMPLE 440

3-(4-fluorophenyl)-4,5-dihydro-5-[(1-(4-methyl)piperazino)carbonyl]imidazo[1,5-a]quinoxaline (I)

EXAMPLE 441

7-chloro-3-(4-fluorophenyl)-4,5-dihydro-5-[(1-(4-methyl)piperazino)carbonyl]imidazo[1,5-a]quinoxaline (I)

EXAMPLE 442

7-fluoro-3-(4-fluorophenyl)-4,5-dihydro-5-[(1-(4-methyl)piperazino)carbonyl]imidazo[1,5-a]quinoxaline (I)

EXAMPLE 443

3-(4-fluorophenyl)-4,5-dihydro-7-methyl-5-[(1-(4-methyl)piperazino)carbonyl]imidazo[1,5-a]quinoxaline (I)

EXAMPLE 444

3-(4-cyclopropylthiazol-2-yl)-4,5-dihydro-5-[(1-(4-methyl)piperazino)carbonyl]imidazo[1,5-a]quinoxaline (I)

EXAMPLE 445

7-chloro-3-(4-cyclopropylthiazol-2-yl)-4,5-dihydro-5-[(1-(4-methyl)piperazino)carbonyl]imidazo-[1,5-a]quinoxaline (I)

EXAMPLE 446

3-(4-cyclopropylthiazol-2-yl)-7-fluoro-4,5-dihydro-5-[(1-(4-methyl)piperazino)carbonyl]imidazo-[1,5-a]quinoxaline (I)

EXAMPLE 447

3-(4-cyclopropylthiazol-2-yl)-6-fluoro-4,5-dihydro-5-[(1-(4-methyl)piperazino)carbonyl]imidazo-[1,5-a]quinoxaline (I)

EXAMPLE 448

3-(4-cyclopropylthiazol-2-yl)-4,5-dihydro-7-methyl-5-[(1-(4-methyl)piperazino)carbonyl]imidazo-[1,5-a]quinoxaline (I)

EXAMPLE 449

7-chloro-3-(3-cyclopropyl-1,2,4-oxadiazol-5-yl)-4,5-dihydro-5-[(1-(3,4,5-trimethyl)piperazino)-carbonyl]imidazo[1,5-a]quinoxaline (I)

EXAMPLE 450

3-(3-cyclopropyl-1,2,4-oxadiazol-5-yl)-7-fluoro-4,5-dihydro-5-[(1-(3,4,5-trimethyl)piperazino)-carbonyl]imidazo[1,5-a]quinoxaline (I)

EXAMPLE 451

3-(3-cyclopropyl-1,2,4-oxadiazol-5-yl)-6-fluoro-4,5-dihydro-5-[(1-(3,4,5-trimethyl)piperazino)-carbonyl]imidazo[1,5-a]quinoxaline (I)

EXAMPLE 452

3-(3-cyclopropyl-1,2,4-oxadiazol-5-yl)4,5-dihydro-7-methyl-5-[(1-(3,4,5-trimethyl)piperazino)-carbonyl]imidazo[1,5-a]quinoxaline (I)

EXAMPLE 453

3-(5-cyclopropyl-1,2,4-oxadiazol-3-yl)-4,5-dihydro-5-[(1-(3,4,5-trimethyl)piperazino)carbonyl]-imidazo[1,5-a]quinoxaline (I)

EXAMPLE 454

3-(5-cyclopropyl-1,2,4-oxadiazol-3-yl)-7-fluoro-4,5-dihydro-5-[(1-(3,4,5-trimethyl)piperazino)-carbonyl]imidazo[1,5-a]quinoxaline (I)

EXAMPLE 455

3-(5-cyclopropyl-1,2,4-oxadiazol-3-yl)-6-fluoro-4,5-dihydro-5-[(1-(3,4,5-trimethyl)piperazino)-caxbonyl]imidazo[1,5-a]quinoxaline (I)

EXAMPLE 456

3-(5-cyclopropyl-1,2,4-oxadiazol-3-yl)-4,5-dihydro-7-methyl-5-[(1-(3,4,5-trimethyl)piperazino)-carbonyl]imidazo[1,5-a]quinoxaline (I)

EXAMPLE 457

3-(4-fluorophenyl)-4,5-dihydro-5-[(1-(3,4,5-trimethyl)piperazino)carbonyl]imidazo[1,5-a]-quinoxaline (I)

EXAMPLE 458

7-chloro-3-(4-fluorophenyl)-4,5-dihydro-5-[(1-(3,4,5-trimethyl)piperazino)carbonyl]imidazo[1,5-a]-quinoxaline (I)

EXAMPLE 459

7-fluoro-3-(4-fluorophenyl)-4,5-dihydro-5-[(1-(3,4,5-trimethyl)piperazino)carbonyl]imidazo[1,5-a]-quinoxaline (I)

EXAMPLE 460

3-(4-fluorophenyl)-4,5-dihydro-7-methyl-5-[(1-(3,4,5-trimethyl)piperazino)carbonyl]imidazo[1,5-a]-quinoxaline (I)

EXAMPLE 461

3-(4-cyclopropylthiazol-2-yl)-4,5-dihydro-5-[(1-(3,4,5-trimethyl)piperazino)carbonyl]imidazo[1,5-a]-quinoxaline (I)

EXAMPLE 462

7-chloro-3-(4-cyclopropylthiazol-2-yl)-4,5-dihydro-5-[(1-(3,4,5-trimethyl)piperazino)carbonyl]-imidazo[1,5-a]quinoxaline (I)

EXAMPLE 463

3-(4-cyclopropylthiazol-2-yl)-7-fluoro-4,5-dihydro-5-[(1-(3,4,5-trimethyl)piperazino)carbonyl]-imidazo[1,5-a]quinoxaline (I)

EXAMPLE 464

3-(4-cyclopropylthiazol-2-yl)-6-fluoro-4,5-dihydro-5-[(1-(3,4,5-trimethyl)piperazino)carbonyl]-imidazo[1,5-a]quinoxaline (I)

EXAMPLE 465

3-(4-cyclopropylthiazol-2-yl)-4,5-dihydro-7-methyl-5-[(1-(3,4,5-trimethyl)piperazino)carbonyl]-imidazo[1,5-a]quinoxaline (I)

EXAMPLE 466

7-chloro-3-(3-cyclopropyl-1,2,4-oxadiazol-5-yl)-4,5-dihydro-5-[(1-(3,5-dimethyl)piperazino)carbonyl]imidazo[1,5-a]-quinoxaline (I)

EXAMPLE 467

3-(3-cyclopropyl-1,2,4-oxadiazol-5-yl)-7-fluoro-4,5-dihydro-5-[(1-(3,5-dimethyl)piperazino)carbonyl]-imidazo[1,5-a]quinoxaline (I)

EXAMPLE 468

3-(3-cyclopropyl-1,2,4-oxadiazol-5-yl)-6-fluoro-4,5-dihydro-5-[(1-(3,5-dimethyl)piperazino)carbonyl]-imidazo[1,5-a]quinoxaline (I)

EXAMPLE 469

3-(3-cyclopropyl-1,2,4-oxadiazol-5-yl)4,5-dihydro-7-methyl-5-[(1-(3,5-dimethyl)piperazino)-carbonyl]imidazo[1,5-a]quinoxaline (I)

EXAMPLE 470

3-(5-cyclopropyl-1,2,4-oxadiazol-3-yl)-4,5-dihydro-5[(1-(3,5-dimethyl)piperazino)carbonyl]-imidazo[1,5-a]quinoxaline (I)

EXAMPLE 471

3-(5-cyclopropyl-1,2,4-oxadiazol-3-yl)-7-fluoro-4,5-dihydro-5-[(1-(3,5-dimethyl)piperazino)-carbonyl]imidazo[1,5-a]quinoxaline (I)

EXAMPLE 472

3-(5-cyclopropyl-1,2,4-oxadiazol-3-yl)-6-fluoro-4,5-dihydro-5-[(1-(3,5-dimethyl)piperazino)-carbonyl]imidazo[1,5-a]quinoxaline (I)

EXAMPLE 473

3-(4-fluorophenyl)4,5-dihydro-5-[(1-(3,5-dimethyl)piperazino)carbonyl]imidazo[1,5-a]-quinoxaline (I)

EXAMPLE 474

7-chloro-3-(4-fluorophenyl)-4,5-dihydro-5-[(1-(3,5-dimethyl)piperazino)carbonyl]imidazo[1,5-a]-quinoxaline (I)

EXAMPLE 475

7-fluoro-3-(4-fluorophenyl)-4,5-dihydro-5-[(1-(3,5-dimethyl)piperazino)carbonyl]imidazo[1,5-a]-quinoxaline (I)

EXAMPLE 476

3-(4-fluorophenyl)-4,5-dihydro-7-methyl-5-[(1-(3,5-dimethyl)piperazino)carbonyl]imidazo[1,5-a]-quinoxaline (I)

EXAMPLE 477

3-(4-cyclopropylthiazol-2-yl)-4,5-dihydro-5-[(1-(3,5-dimethyl)piperazino)carbonyl]imidazo[1,5-a]-quinoxaline (I)

EXAMPLE 478

7-chloro-3-(4-cyclopropylthiazol-2-yl)-4,5-dihydro-5-[(1-(3,5-dimethyl)piperazino)carbonyl]-imidazo[1,5-a]quinoxaline (I)

EXAMPLE 479

3-(4-cyclopropylthiazol-2-yl)-7-fluoro-4,5-dihydro-5-[(1-(3,5-dimethyl)piperazino)carbonyl]-imidazo[1,5-a]quinoxaline (I)

EXAMPLE 480

3-(4-cyclopropylthiazol-2-yl)-6-fluoro-4,5-dihydro-5-[(1-(3,5-dimethyl)piperazino)carbonyl]-imidazo[1,5-a]quinoxaline (I)

EXAMPLE 481

3-(4-cyclopropylthiazol-2-yl)-4,5-dihydro-7-methyl-5-[(1-(3,5-dimethyl)piperazino)carbonyl]-imidazo[1,5-a]quinoxaline (I)

EXAMPLE 482

3-(3-cyclopropyl-1,2,4-oxadiazol-5-yl)4,5-dihydro-5-[(1-(2,4,6-trimethyl)piperazino)-carbonyl]imidazo[1,5-a]quinoxaline (I)

EXAMPLE 483

7-chloro-3-(3-cyclopropyl-1,2,4-oxadiazol-5-yl)-4,5-dihydro-5-[(1-(2,4,6-trimethyl)piperazino)-carbonyl]imidazo[1,5-a]quinoxaline (I)

EXAMPLE 484

3-(3-cyclopropyl-1,2,4-oxadiazol-5-yl)-7-fluoro-4,5-dihydro-5-[(1-(2,4,6-trimethyl)piperazino)-carbonyl]imidazo[1,5-a]quinoxaline (I)

EXAMPLE 485

3-(3-cyclopropyl-1,2,4-oxadiazol-5-yl)-6-fluoro-4,5-dihydro-5-[(1-(2,4,6-trimethyl)piperazino)-carbonyl]imidazo[1,5-a]quinoxaline (I)

EXAMPLE 486

3-(3-cyclopropyl-1,2,4-oxadiazol-5-yl)-4,5-dihydro-7-methyl-5-[(1-(2,4,6-trimethyl)piperazino)-carbonyl]imidazo[1,5-a]quinoxaline (I)

EXAMPLE 487

3-(5-cyclopropyl-1,2,4-oxadiazol-3-yl)-4,5-dihydro-5-[(1-(2,4,6-trimethyl)piperazino)-carbonyl]imidazo[1,5-a]quinoxaline (I)

EXAMPLE 488

7-chloro-3-(5-cyclopropyl-1,2,4-oxadiazol-3-yl)-4,5-dihydro-5-[(1-(2,4,6-trimethyl)piperazino)-carbonyl]imidazo[1,5-a]quinoxaline (I)

EXAMPLE 489

3-(5-cyclopropyl-1,2,4-oxadiazol-3-yl)-7-fluoro-4,5-dihydro-5-[(1-(2,4,6-trimethyl)piperazino)-carbonyl]imidazo[1,5-a]quinoxaline (I)

EXAMPLE 490

3-(5-cyclopropyl-1,2,4-oxadiazol-3-yl)-6-fluoro-4,5-dihydro-5-[(1-(2,4,6-trimethyl)piperazino)-carbonyl]imidazo[1,5-a]quinoxaline (I)

EXAMPLE 491

3-(5-cyclopropyl-1,2,4-oxadiazol-3-yl)-4,5-dihydro-7-methyl-5-[(1-(2,4,6-trimethyl)piperazino)-carbonyl]imidazo[1,5-a]quinoxaline (I)

EXAMPLE 492

3-(4-fluorophenyl)-4,5-dihydro-5-[(1-(2,4,6-trimethyl)piperazino)carbonyl]imidazo[1,5-a]-quinoxaline (I)

EXAMPLE 493

7-chloro-3-(4-fluorophenyl)-4,5-dihydro-5-[(1-(2,4,6-trimethyl)piperazino)carbonyl]imidazo[1,5-a]-quinoxaline (I)

EXAMPLE 494

7-fluoro-3-(4-fluorophenyl)-4,5-dihydro-5-[(1-(2,4,6-trimethyl)piperazino)carbonyl]imidazo[1,5-a]-quinoxaline (I)

EXAMPLE 495

3-(4-fluorophenyl)-4,5-dihydro-7-methyl-5-[(1-(2,4,6-trimethyl)piperazino)carbonyl]imidazo[1,5-a]-quinoxaline (I)

EXAMPLE 496

3-(4-cyclopropylthiazol-2-yl)-4,5-dihydro-5-[(1-(2,4,6-trimethyl)piperazino)carbonyl]imidazo[1,5-a]-quinoxaline (I)

EXAMPLE 497

7-chloro-3-(4-cyclopropylthiazol-2-yl)-4,5-dihydro-5-[(1-(2,4,6-trimethyl)piperazino)-carbonyl]imidazo[1,5-a]quinoxaline (I)

EXAMPLE 498

3-(4-cyclopropylthiazol-2-yl)-7-fluoro-4,5-dihydro-5-[(1-(2,4,6-trimethyl)piperazino)-carbonyl]imidazo[1,5-a]quinoxaline (I)

EXAMPLE 499

3-(4-cyclopropylthiazol-2-yl)-6-fluoro-4,5-dihydro-5-[(1-(2,4,6-trimethyl)piperazino)-carbonyl]imidazo[1,5-a]quinoxaline (I)

EXAMPLE 500

3-(4-cyclopropylthiazol-2-yl)-4,5-dihydro-7-methyl-5-[(1-(2,4,6-trimethyl)piperazino)-carbonyl]imidazo[1,5-a]quinoxaline (I)

EXAMPLE 501

3-(3-cyclopropyl-1,2,4-oxadiazol-5-yl)-4,5-dihydro-5-[(1-(2,6-dimethyl)piperazino)-carbonyl]imidazo[1,5-a]quinoxaline (I)

EXAMPLE 502

7-chloro-3-(3-cyclopropyl-1,2,4-oxadiazol-5-yl)-4,5-dihydro-5-[(1-(2,6-dimethyl)piperazino)-carbonyl]imidazo[1,5-a]quinoxaline (I)

EXAMPLE 503

3-(3-cyclopropyl-1,2,4-oxadiazol-5-yl)-7-fluoro-4,5-dihydro-5-[(1-(2,6-dimethyl)piperazino)-carbonyl]imidazo[1,5-a]quinoxaline (I)

EXAMPLE 504

3-(3-cyclopropyl-1,2,4-oxadiazol-5-yl)-6-fluoro-4,5-dihydro-5-[(1-(2,6-dimethyl)piperazino)-carbonyl]imidazo[1,5-a]quinoxaline (I)

EXAMPLE 505

3-(3-cyclopropyl-1,2,4-oxadiazol-5-yl)-4,5-dihydro-7-methyl-5-[(1-(2,6-dimethyl)piperazino)-carbonyl]imidazo[1,5-a]quinoxaline (I)

EXAMPLE 506

3-(5-cyclopropyl-1,2,4-oxadiazol-3-yl)-4,5-dihydro-5-[(1-(2,6-dimethyl)piperazino)-carbonyl]imidazo[1,5-a]quinoxaline (I)

EXAMPLE 507

7-chloro-3-(5-cyclopropyl-1,2,4-oxadiazol-3-yl)-4,5-dihydro-5-[(1-(2,6-dimethyl)piperazino)-carbonyl]imidazo[1,5-a]quinoxaline (I)

EXAMPLE 508

3-(5-cyclopropyl-1,2,4-oxadiazol-3-yl)-7-fluoro-4,5-dihydro-5-[(1-(2,6-dimethyl)piperazino)-carbonyl]imidazo[1,5-a]quinoxaline (I)

EXAMPLE 509

3-(5-cyclopropyl-1,2,4-oxadiazol-3-yl)-6-fluoro-4,5-dihydro-5-[(1-(2,6-dimethyl)piperazino)-carbonyl]imidazo[1,5-a]quinoxaline (I)

EXAMPLE 510

3-(5-cyclopropyl-1,2,4-oxadiazol-3-yl)-4,5-dihydro-7-methyl-5-[(1-(2,6-dimethyl)piperazino)carbonyl]-imidazo[1,5-a]quinoxaline (I)

EXAMPLE 511

3-(4-fluorophenyl)-4,5-dihydro-5-[(1-(2,6-dimethyl)piperazino)carbonyl]imidazo[1,5-a]-quinoxaline (I)

EXAMPLE 512

7-chloro-3-(4-fluorophenyl)-4,5-dihydro-5-[(1-(2,6-dimethyl)piperazino)carbonyl]imidazo[1,5-a]-quinoxaline (I)

EXAMPLE 513

7-fluoro-3-(4-fluorophenyl)-4,5-dihydro-5-[(1-(2,6-dimethyl)piperazino)carbonyl]imidazo[1,5-a]-quinoxaline (I)

EXAMPLE 514

3-(4-fluorophenyl)-4,5-dihydro-7-methyl-5-[(1-(2,6-dimethyl)piperazino)carbonyl]imidazo[1,5-a]-quinoxaline (I)

EXAMPLE 515

3-(4-cyclopropylthiazol-2-yl)-4,5-dihydro-5-[(1-(2,6-dimethyl)piperazino)carbonyl]imidazo[1,5-a]-quinoxaline (I)

EXAMPLE 516

7-chloro-3-(4-cyclopropylthiazol-2-yl)-4,5-dihydro-5-[(1-(2,6-dimethyl)piperazino)carbonyl]-imidazo[1,5-a]quinoxaline (I)

EXAMPLE 517

3-(4-cyclopropylthiazol-2-yl)-7-fluoro-4,5-dihydro-5-[(1-(2,6-dimethyl)piperazino)carbonyl]-imidazo[1,5-a]quinoxaline (I)

EXAMPLE 518

3-(4-cyclopropylthiazol-2-yl)-6-fluoro-4,5-dihydro-5-[(1-(2,6-dimethyl)piperazino)carbonyl]-imidazo[1,5-a]quinoxaline (I)

EXAMPLE 519

3-(4-cyclopropylthiazol-2-yl)4,5-dihydro-7-methyl-5-[(1-(2,6-dimethyl)piperazino)carbonyl]-imidazo[1,5-a]quinoxaline (I)

EXAMPLE 520 tert-butyl
4,5-dihydro-4,4-dimethyl-5-[(1-(3,4,5-trimethyl)-piperazino)-carbonyl]imidazo[1,5-a]-quinoxaline-3-carboxylate (I)

EXAMPLE 521 tert-butyl
7-chloro-4,5-dihydro-4,4-dimethyl-5-[(1-(3,4,5-trimethyl)-piperazino)carbonyl]imidazo[1,5-a]-quinoxaline-3-carboxylate (I)

EXAMPLE 522 tert-butyl
7-fluoro-4,5-dihydro-4,4-dimethyl-5-[(1-(3,4,5-trimethyl)-piperazino)carbonyl]imidazo[1,5-a]-quinoxaline-3-carboxylate (I)

EXAMPLE 523 tert-butyl
6-fluoro-4,5-dihydro-4,4-dimethyl-5-[(1-(3,4,5-trimethyl)-piperazino)carbonyl]imidazo[1,5-a]quinoxaline-3-carboxylate (I)

EXAMPLE 524 tert-butyl
4,5-dihydro-7-methyl-4,4-dimethyl-5-[(1-(3,4,5-trimethyl)-piperazino)carbonyl]imidazo[1,5-a]-quinoxaline-3-carboxylate (I)

EXAMPLE 525 tert-butyl
5-[(1-(3,5-dimethyl)piperazino)carbonyl]-4,5-dihydro-4,4-dimethylimidazo[1,5-a]-quinoxaline-3-carboxylate (I)

EXAMPLE 526 tert-butyl
7-chloro-5-[(1-(3,5-dimethyl)piperazino)carbonyl]-4,5-dihydro-4,4-dimethylimidazo[1,5-a]-quinoxaline-3-carboxylate (I)

EXAMPLE 527 tert-butyl
5-[(1-(3,5-dimethyl)piperazino)carbonyl]-7-fluoro-4,5-dihydro-4,4-dimethylimidazo[1,5-a]-quinoxaline-3-carboxylate (I)

EXAMPLE 528 tert-butyl
5-[(1-(3,5-dimethyl)piperazino)carbonyl]-6-fluoro-4,5-dihydro-4,4-dimethylimidazo[1,5-a]-quinoxaline-3-carboxylate (I)

EXAMPLE 529 tert-butyl
5-[(1-(3,5-dimethyl)piperazino)carbonyl]-4,5-dihydro-
7-methyl-4,4-dimethylimidazo[1,5-a]-
quinoxaline-3-carboxylate (I)

EXAMPLE 530 tert-butyl
4,5-dihydro-4,4-dimethyl-5-[(1-(2,4,6-trimethyl)-
piperazino)-carbonyl]imidazo[1,5-a]-
quinoxaline-3-carboxylate (I)

EXAMPLE 531 tert-butyl
7-chloro-4,5-dihydro-4,4-dimethyl-5-[(1-(2,4,6-
trimethyl)-piperazino)carbonyl]imidazo[1,5-a]-
quinoxaline-3-carboxylate (I)

EXAMPLE 532 tert-butyl
7-fluoro-4,5-dihydro-4,4-dimethyl-5-[(1-(2,4,6-
trimethyl)-piperazino)carbonyl]imidazo[1,5-a]-
quinoxaline-3-carboxylate (I)

EXAMPLE 533 tert-butyl
6-fluoro-4,5-dihydro-4,4-dimethyl-5-[(1-(2,4,6-
trimethyl)-piperazino)carbonyl]imidazo[1,5-a]-
quinoxaline-3-carboxylate (I)

EXAMPLE 534 tert-butyl
4,5-dihydro-7-methyl-4,4-dimethyl-5-[(1-(2,4,6-
trimethyl)-piperazino)carbonyl]imidazo[1,5-a]-
quinoxaline-3-carboxylate (I)

EXAMPLE 535 tert-butyl
5-[(1-(2,6-dimethyl)piperazino)carbonyl]-4,5-
dihydro-4,4-dimethylimidazo[1,5-a]-
quinoxaline-3-carboxylate (I)

EXAMPLE 536 tert-butyl
7-chloro-5-[(1-(2,6-dimethyl)piperazino)carbonyl]-
4,5-dihydro-4,4-dimethylimidazo[1,5-a]-
quinoxaline-3-carboxylate (I)

EXAMPLE 537 tert-butyl
5-[(1-(2,6-dimethyl)piperazino)carbonyl]-7-fluoro-
4,5-dihydro-4,4-dimethylimidazo[1,5-
a]quinoxaline-3-carboxylate (I)

EXAMPLE 538 tert-butyl
5-[(1-(2,6-dimethyl)piperazino)carbonyl]-6-fluoro-
4,5-dihydro-4,4-dimethylimidazo[1,5-a]-
quinoxaline-3-carboxylate (I)

EXAMPLE 539 tert-butyl
5-[(1-(2,6-dimethyl)piperazino)carbonyl]-4,5-dihydro-
7-methyl-4,4-dimethylimidazo[1,5-a]-
quinoxaline-3-carboxylate (I)

EXAMPLE 540 tert-butyl
4,5-dihydro-5-[(1-(3,4,5-trimethyl)piperazino)-
carbonyl]imidazo[1,5-a]quinoxaline-3-carboxylate
(I)

EXAMPLE 541 tert-butyl
7-chloro-4,5-dihydro-5-[(1-(3,4,5-trimethyl)piperazino)-
carbonyl]imidazo[1,5-a]quinoxaline-3-carboxylate
(I)

EXAMPLE 542 tert-butyl
7-fluoro-4,5-dihydro-5-[(1-(3,4,5-trimethyl)piperazino)-
carbonyl]imidazo[1,5-a]quinoxaline-3-carboxylate
(I)

EXAMPLE 543 tert-butyl
6-fluoro-4,5-dihydro-5-[(1-(3,4,5-trimethyl)piperazino)-
carbonyl]imidazo[1,5-a]quinoxaline-3-carboxylate
(I)

EXAMPLE 544 tert-butyl
4,5-dihydro-7-methyl-5-[(1-(3,4,5-trimethyl)piperazino)-
carbonyl]imidazo[1,5-a]quinoxaline-3-carboxylate
(I)

EXAMPLE 545 tert-butyl
5-[(1-(3,5-dimethyl)piperazino)carbonyl]-4,5-
dihydroimidazo[1,5-a]quinoxaline-3-carboxylate (I)

EXAMPLE 546 tert-butyl
7-chloro-5-[(1-(3,5-dimethyl)piperazino)carbonyl]-4,5
-dihydroimidazo[1,5-a]quinoxaline-3-carboxylate (I)

EXAMPLE 547 tert-butyl
5-[(1-(3,5-dimethyl)piperazino)carbonyl]-7-fluoro-4,5-
dihydroimidazo[1,5-a]quinoxaline-3-carboxylate (I)

EXAMPLE 548 tert-butyl
5-[(1-(3,5-dimethyl)piperazino)carbonyl]-6-fluoro-4,5-
dihydroimidazo[1,5-a]quinoxaline-3-carboxylate (I)

EXAMPLE 549 tert-butyl
5-[(1-(3,5-dimethyl)piperazino)carbonyl]-4,5-dihydro-7-
methylimidazo[1,5-a]quinoxaline-3-carboxylate (I)

EXAMPLE 550 tert-butyl
4,5-dihydro-5-[(1-(2,4,6-trimethyl)piperazino)-
carbonyl]-imidazo[1,5-a]quinoxaline-3-carboxylate
(I)

EXAMPLE 551 tert-butyl
7-chloro-4,5-dihydro-5-[(1-(2,4,6-trimethyl)piperazino)-
carbonyl]imidazo[1,5-a]quinoxaline-3-carboxylate
(I)

EXAMPLE 552 tert-butyl
7-fluoro-4,5-dihydro-5-[(1-(2,4,6-trimethyl)piperazino)-
carbonyl]imidazo[1,5-a]quinoxaline-3-carboxylate
(I)

EXAMPLE 553 tert-butyl
6-fluoro-4,5-dihydro-5-[(1-(2,4,6-trimethyl)piperazino)-
carbonyl]imidazo[1,5-a]quinoxaline-3-carboxylate
(I)

EXAMPLE 554 tert-butyl 4,5-dihydro-7-methyl-5-[(1-(2-
,4,6-trimethyl)piperazino)-
carbonyl]imidazo[1,5-a]quinoxaline-3-carboxylate
(I)

EXAMPLE 555 tert-butyl
5-[(1-(2,6-dimethyl)piperazino)carbonyl]-4,5-
dihydroimidazo[1,5-a]quinoxaline-3-carboxylate (I)

EXAMPLE 556 tert-butyl
7-chloro-5-[(1-(2,6-dimethyl)piperazino)carbonyl]4,5-
dihydroimidazo[1,5-a]quinoxaline-3-carboxylate (I)

EXAMPLE 557 tert-butyl
5-[(1-(2,6-dimethyl)piperazino)carbonyl]-7-fluoro-4,5-
dihydroimidazo[1,5-a]quinoxaline-3-carboxylate (I)

EXAMPLE 558 tert-butyl
5-[(1-(2,6-dimethyl)piperazino)carbonyl]-6-fluoro-4,5-
dihydroimidazo[1,5-a]quinoxaline-3-carboxylate (I)

EXAMPLE 559 tert-butyl
5-[(1-(2,6-dimethyl)piperazino)carbonyl]-4,5-dihydro-7-
methylimidazo[1,5-a]quinoxaline-3-carboxylate (I)

EXAMPLE 560 tert-butyl
7-trifluoromethyl-5-[(1-(3,5-dimethyl)piperazino)-
carbonyl]-4,5-dihydroimidazo[1,5-a]quinoxaline-
3-carboxylate (I)

CHART A

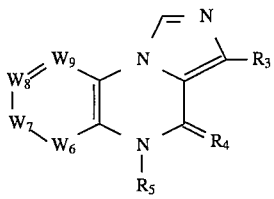

(I)

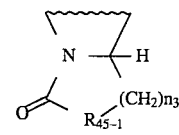

($R_4$/$R_5$/$R_6$-1))

-continued
CHART A
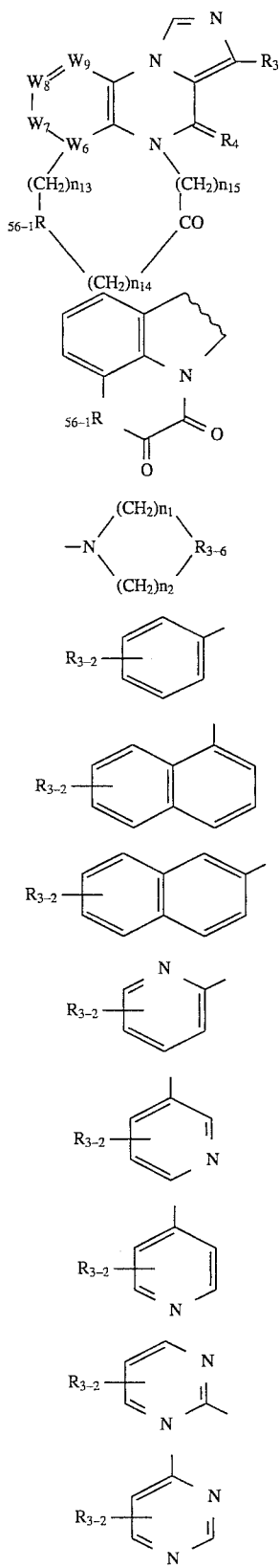
(R4/R5/R6-2a)
(R4/R5/R6-2b)
(C3-1a)
(F-Aryl-I)
(F-Aryl-II)
(F-Aryl-III)
(F-Aryl-IV)
(F-Aryl-V)
(F-Aryl-VI)
(F-Aryl-VII)
(F-Aryl-VIII)
-continued
CHART A
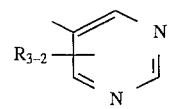 (F-Aryl-IX)
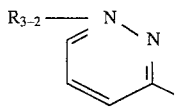 (F-Aryl-X)
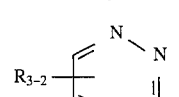 (F-Aryl-XI)
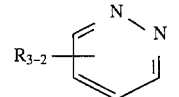 (F-Aryl-XII)
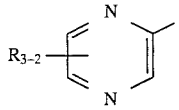 (F-Aryl-XIII)
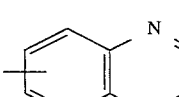 (F-Aryl-XIV)
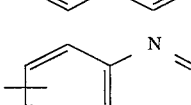 (F-Aryl-XV)
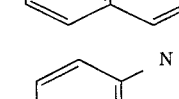 (F-Aryl-XVI)
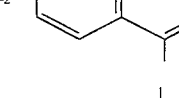 (F-Aryl-XVII)
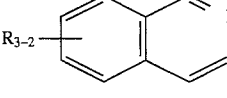 (F-Aryl-XVIII)
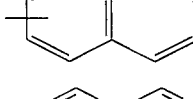 (F-Aryl-XIX)
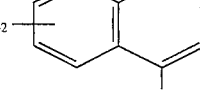 (F-Aryl-XX)
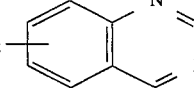 (F-Aryl-XXI)

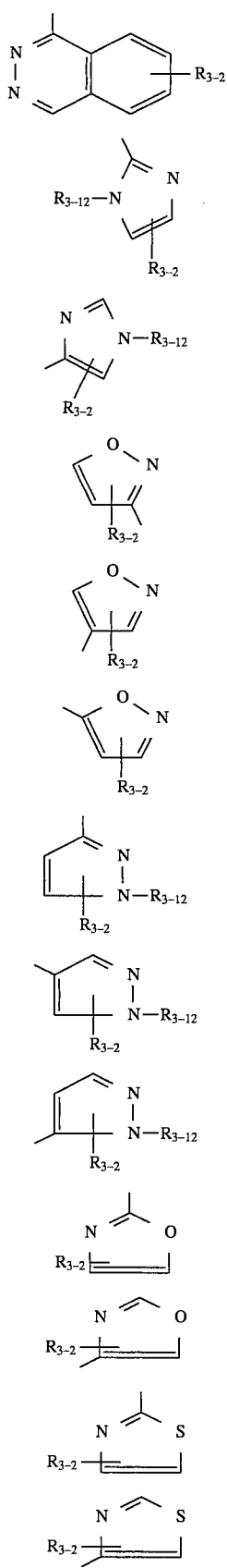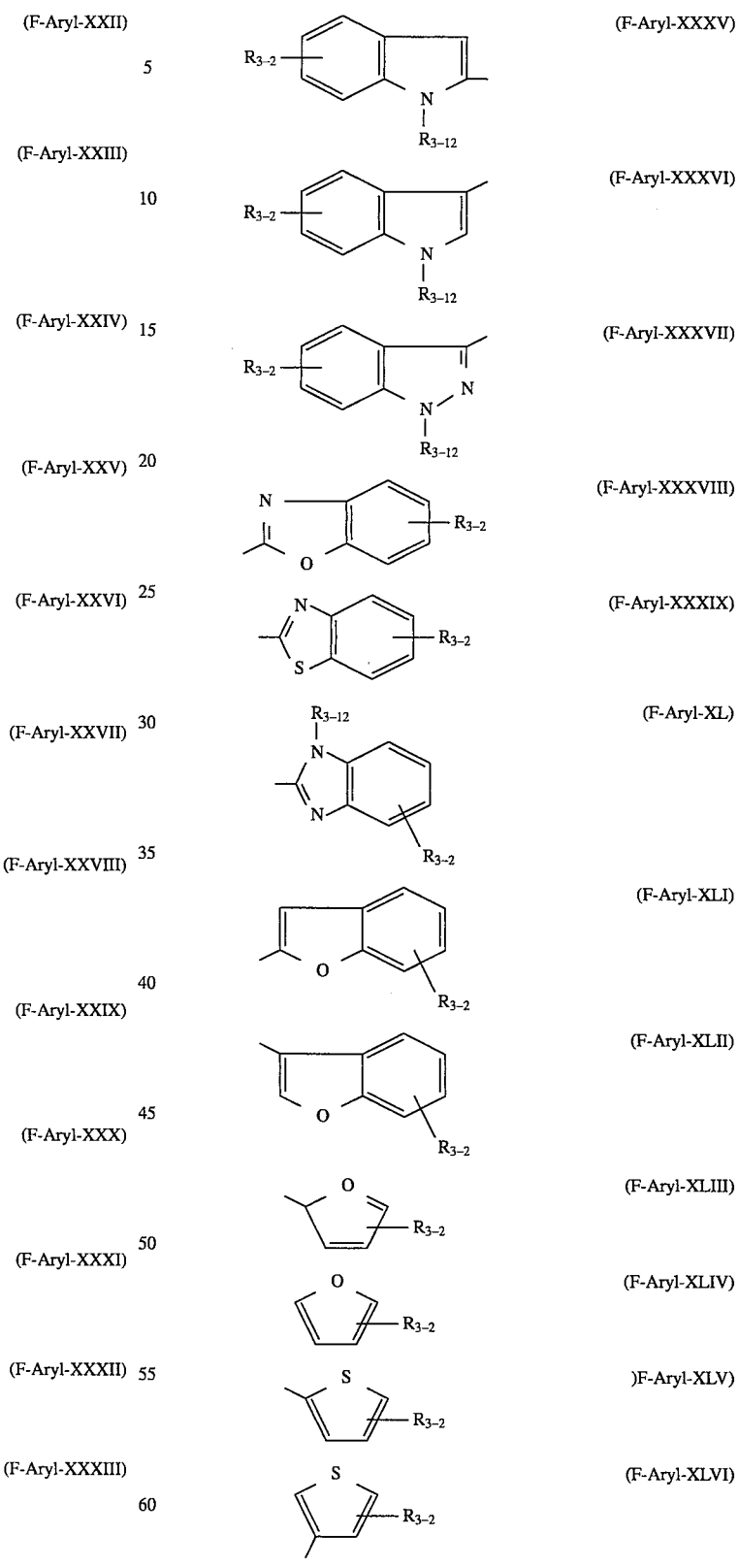

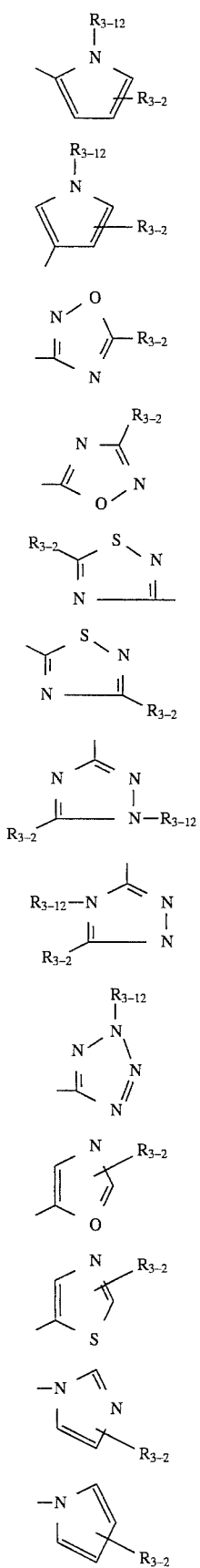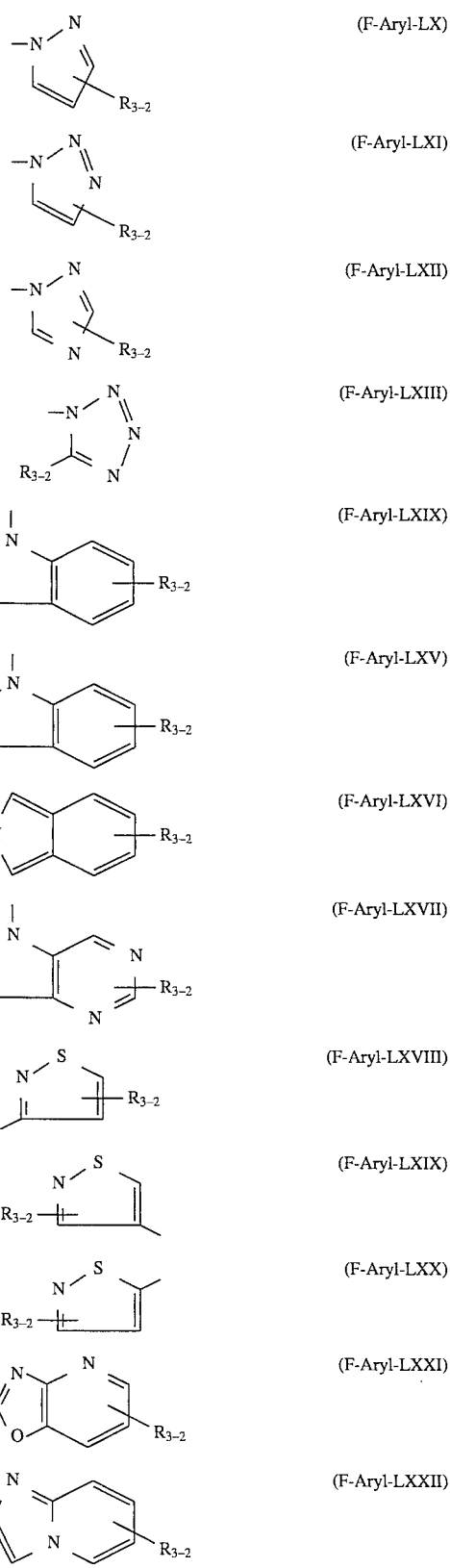

5,541,324
127
CHART B
128
-continued
CHART C
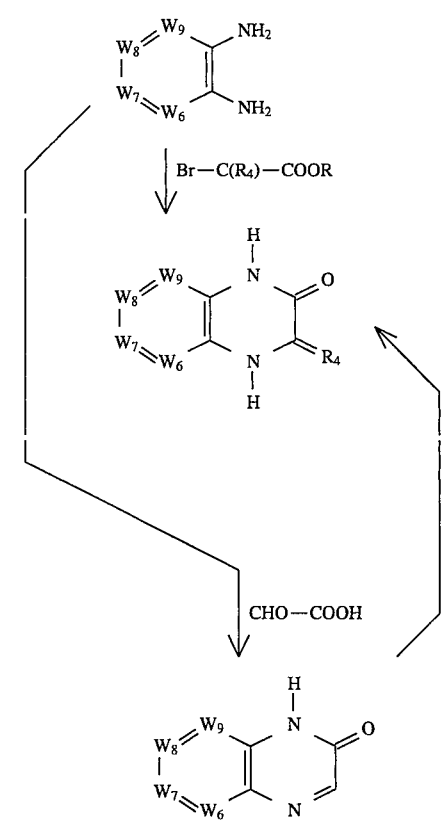
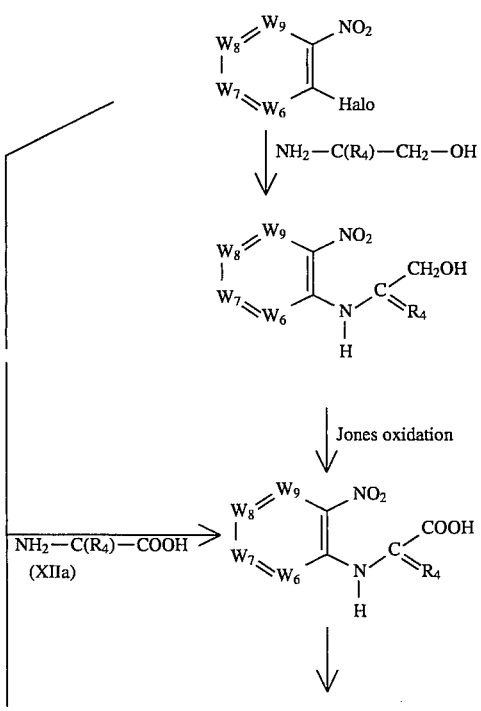
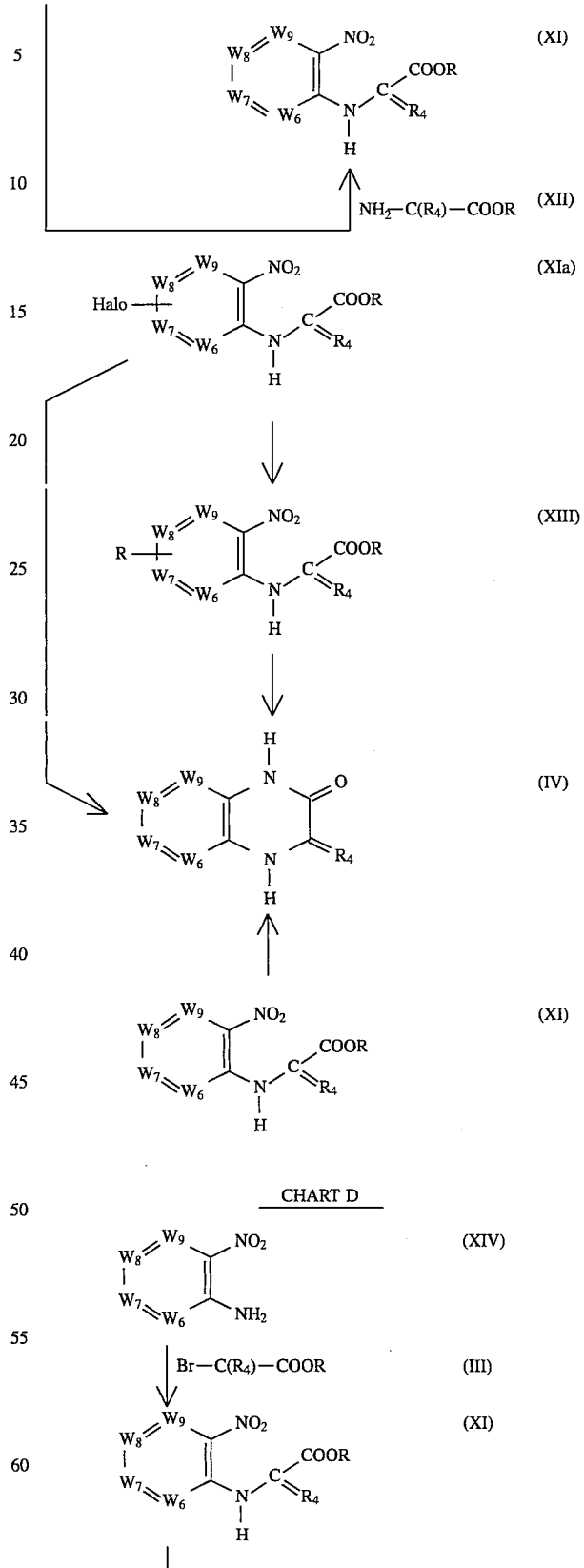

-continued
CHART D
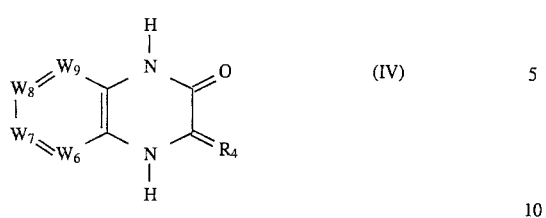
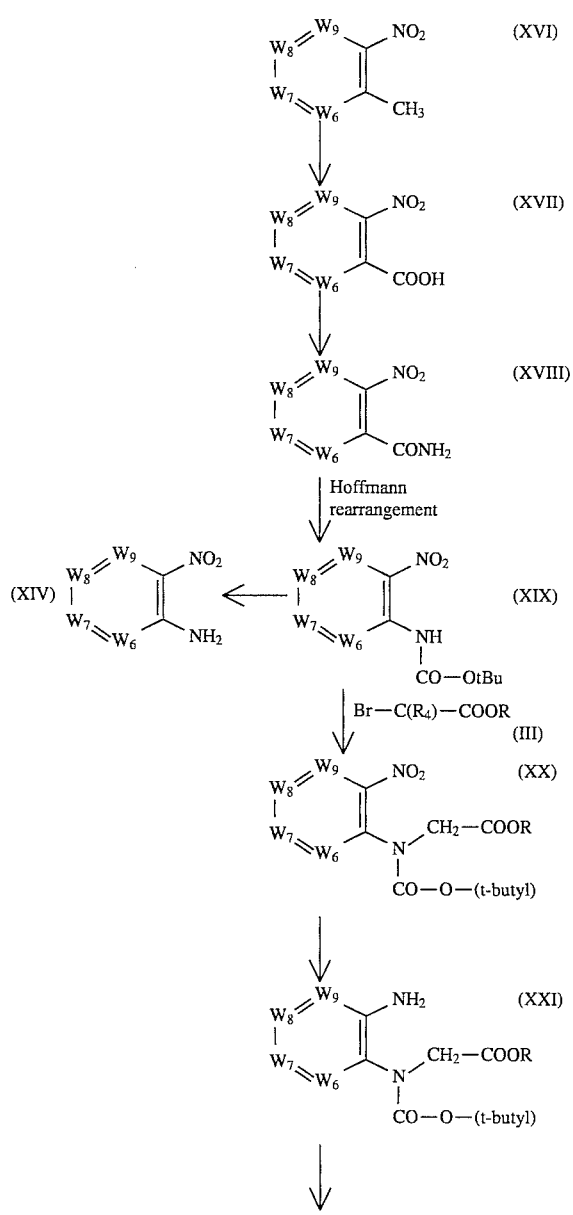

-continued
CHART E
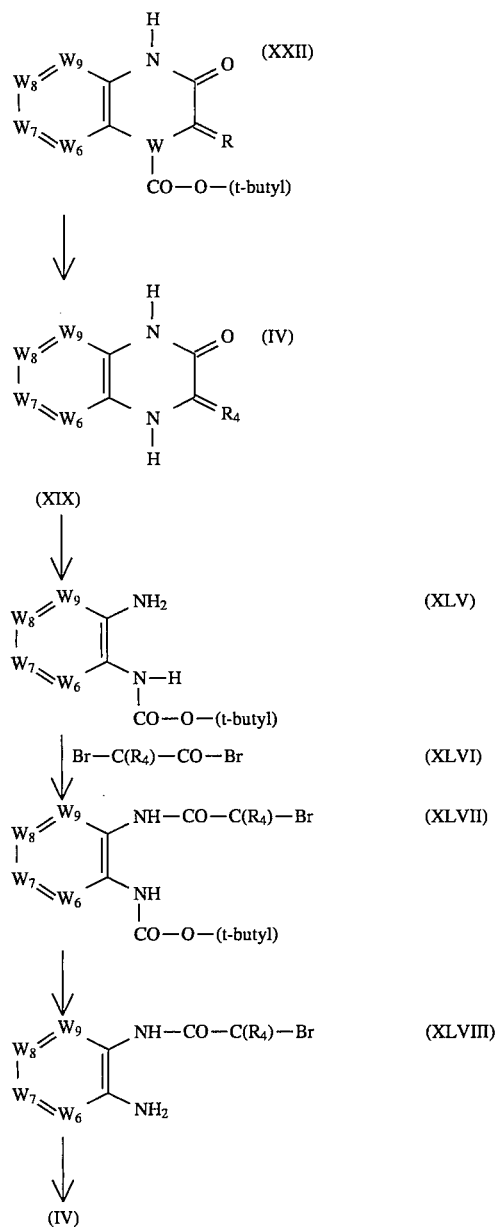
CHART F
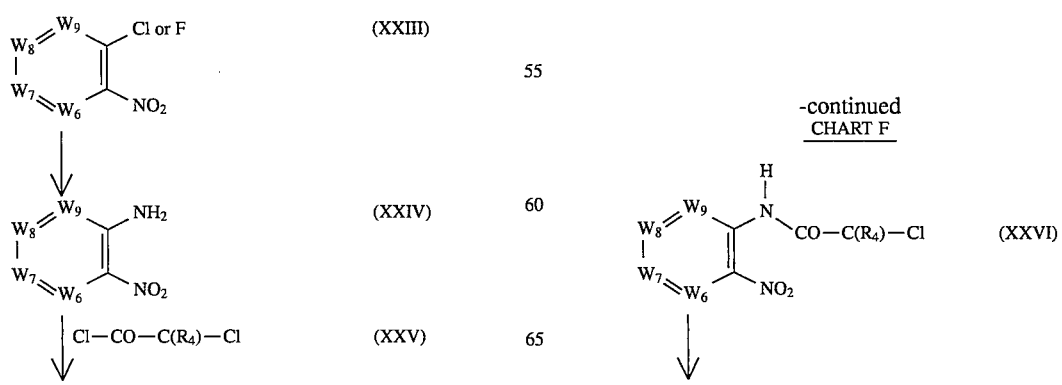

133
-continued
CHART F
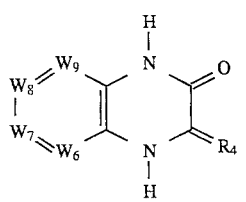
(IV)
CHART G
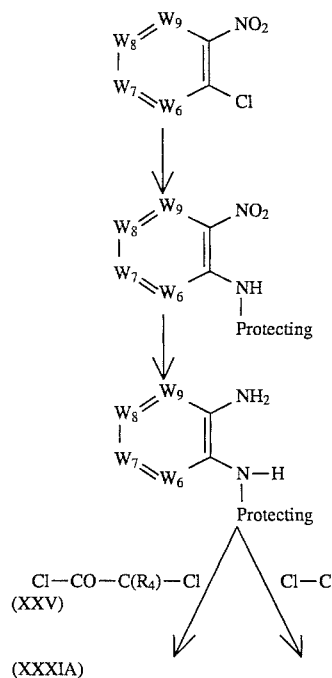
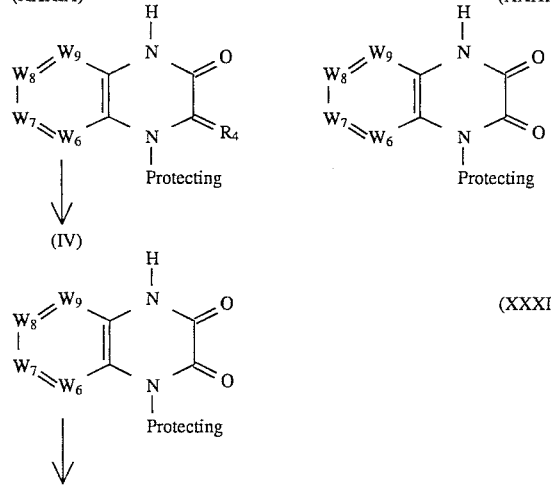
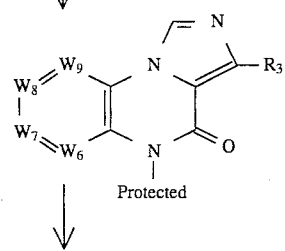
134
-continued
CHART G
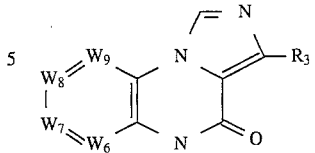
(XXXV)
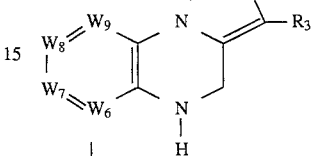
(XXXVI)
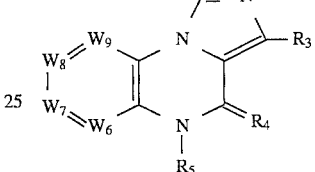
(I)
CHART H
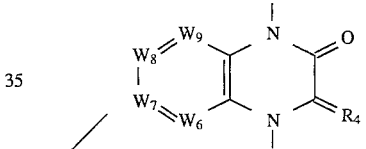
(IV)
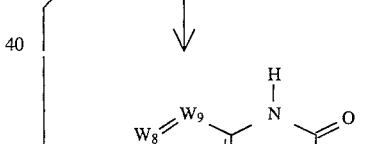
(XXXII)
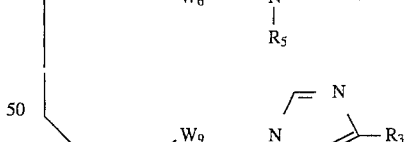
(XXXIII)

CHART H
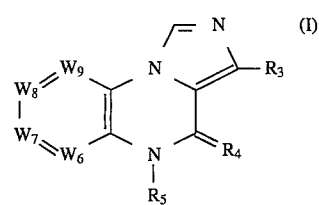
CHART I
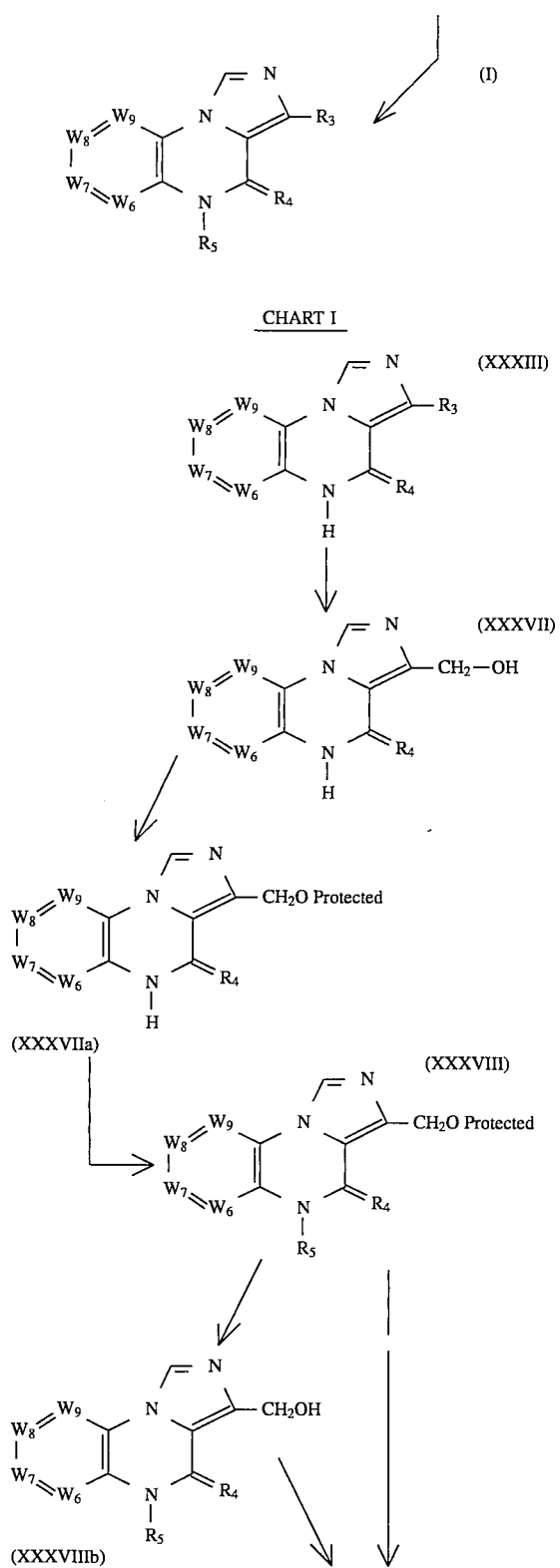
CHART J
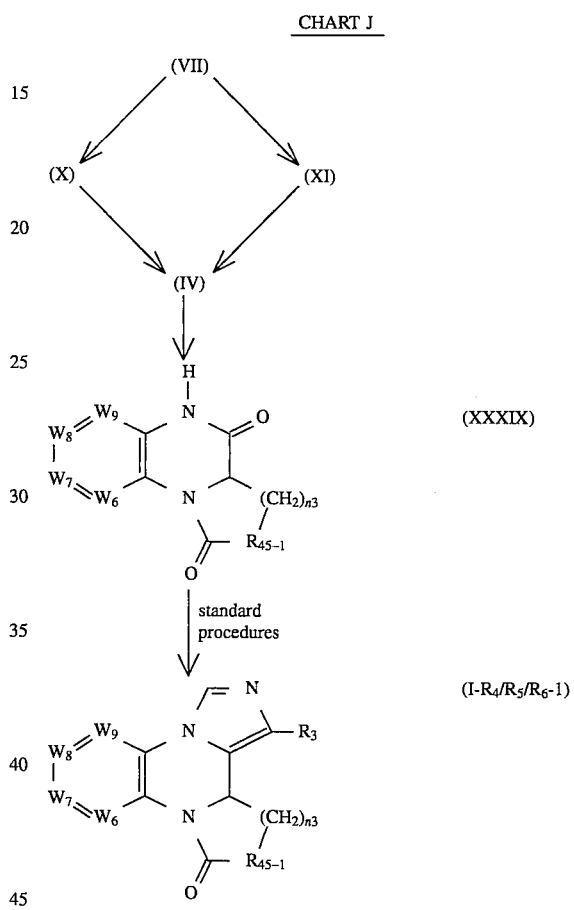
CHART K

CHART K -continued
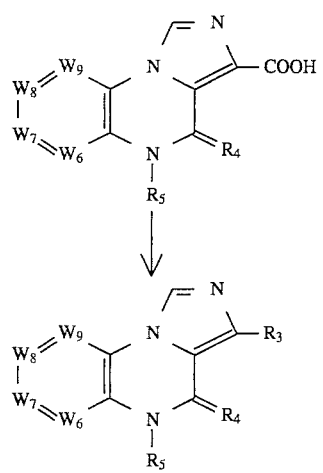
(I-acid)
(I)
CHART L
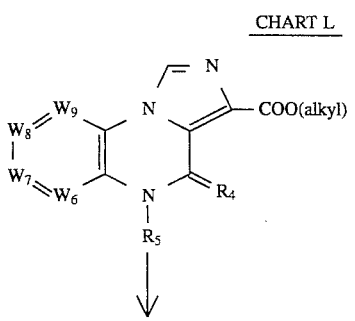
(I)
CHART L -continued
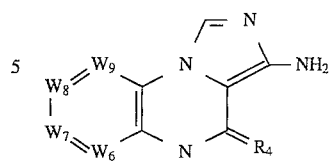
(XLI)
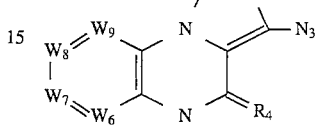
(XLII)
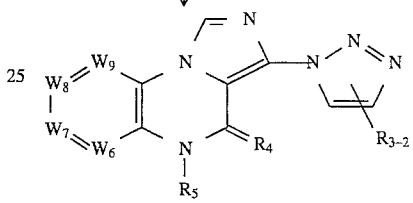
(I-F-Aryl-LXI)
CHART M
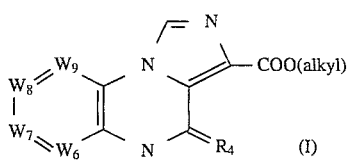
(I)
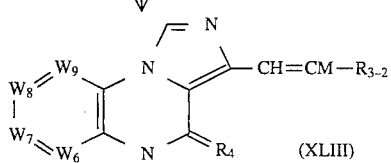
(XLIII)

-continued
CHART M
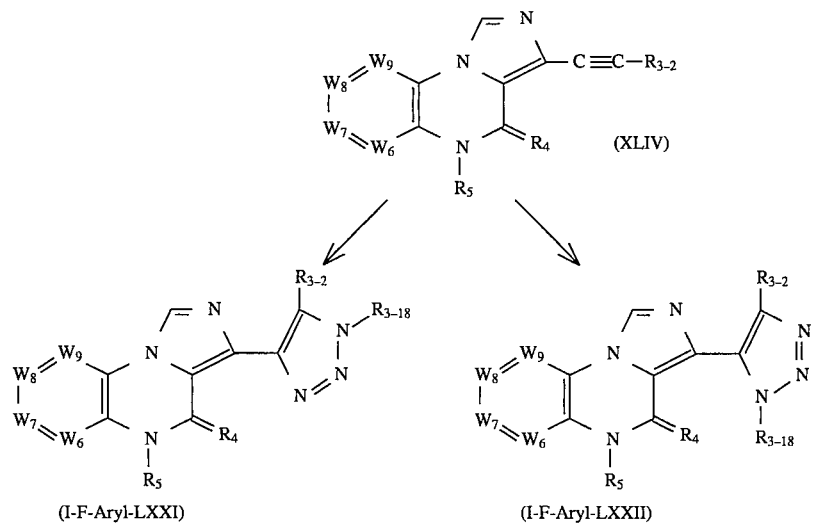
(I-F-Aryl-LXXI)     (I-F-Aryl-LXXII)
CHART N
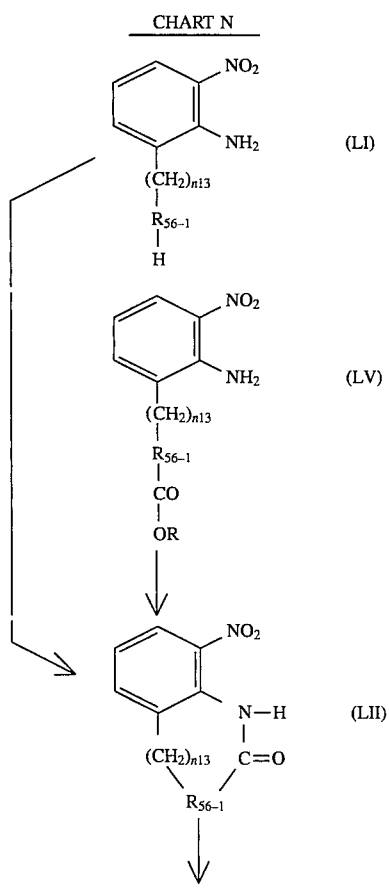
-continued
CHART N
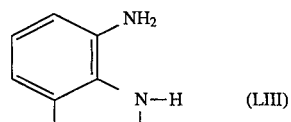
(LIII)
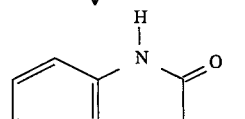
(LIV)
standard cyclization
(I)
CHART O
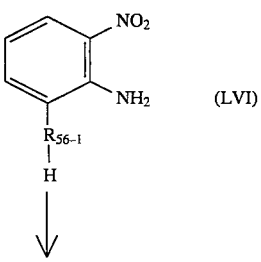
(LVI)

-continued
CHART O

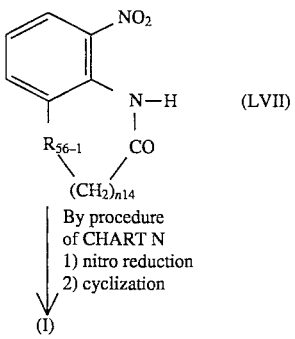

(LVII)

By procedure
of CHART N
1) nitro reduction
2) cyclization (I)

We claim:
1. Imidazo[1,5-a]quinoxalines of formula (I)

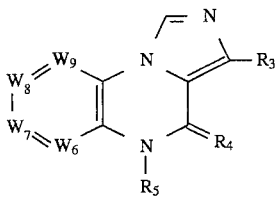

(I)

where $R_3$ is
A—$COOR_{3-1}$ where $R_{3-1}$ is
(1) —H,
(2) $C_1$-$C_9$ alkyl,
(3) $C_3$-$C_7$ cycloalkyl,
(4) —$(CH_2)_{n6}$—O—$R_{3-3}$ where $n_6$ is 2 thru 4 and $R_{3-3}$ is —H, $C_1$-$C_4$ alkyl or $C_3$-$C_7$ cycloalkyl,
(5) —$(CH_2)_{n6}$—$NR_{3-4}R_{3-5}$ where $R_{3-4}$ is —H, $C_1$-$C_4$ alkyl, $C_3$-$C_7$ cycloalkyl or —φ, $R_{3-5}$ is —H, $C_1$-$C_6$ alkyl or $C_3$-$C_7$ cycloalkyl and where $R_{3-4}$ and $R_{3-5}$ are taken together with the attached nitrogen atom to form a heterocyclic ring selected from the group consisting of —N*—$(CHR_{3-8})_{nA}$—$(CH_2)_{n1}$—$R_{3-6}$—$(CH_2)_{n2}$—$(C^*HR_{3-9})_{nB}$—

—N*—$(CH_2)_{n1}$—$(CHR_{3-8})_{nA}$—$R_{3-6}$—$(CHR_{3-9})_{nB}$—$(C^*H_2)_{n2}$— where $R_{3-8}$ is —H or $C_1$-$C_3$ alkyl, $n_A$ is 1 or 2, $n_1$ is 0 thru 2, $n_2$ is 0 thru 2, $R_{3-9}$ is —H or $C_1$-$C_3$ alkyl, $n_B$ is 1 or 2, where the atoms marked with an asterisk (*) are bonded to each other resulting in the formation of a ring, with the proviso that the ring not contain more than 5 atoms, and where $R_{3-6}$ is
—O—,
—S—,
—CO—
—$CR_{3-61}R_{3-62}$ where $R_{3-61}$ and $R_{3-62}$ are the same or different and are —H or $C_1$-$C_3$ alkyl,
—$NR_{3-7}$ where $R_{3-7}$ is
—H,
$C_1$-$C_4$ alkyl,
$C_3$-$C_7$ cycloalkyl,
—$(CH_2)_{n7}$—φ where $n_7$ is 0 thru 4 and φ is optionally substituted with 1, 2 or 3 $R_{3-2}$ where $R_{3-2}$ is selected from the group consisting of
—F,
—Cl,
—Br,
—I,
—CN,
—$NO_2$,
—O—CO—$R_{3-2a}$
where
$R_{3-2a}$ is —H, $C_1$-$C_4$ alkyl or $C_3$-$C_7$ cycloalkyl,
—$(CH_2)_{n30}$—$CF_3$
where
$n_{30}$ is 0 thru 3,
—O—$CF_3$,
$C_1$-$C_6$ alkyl,
$C_3$-$C_7$ cycloalkyl,
—$CH_2$-($C_3$-$C_7$ cycloalkyl),
—$CH_2CH(CF_3)CH_3$,
—$C(OH)(CH_2OH)(CH_2CH_3)$,
—$C(OH)(CH_2OH)CH_3$,
—$C(CH_3)(OH)(CH_2OH)$,
—$CH(OH)(CH_2OH)$,
—$CH(OH)(CH_3)$,
—$CH_2CH_2OH$,
—$C(CH_3)_2(CH_2OH)$,
—$CH(CH_2OH)_2$,
—$C(CH_2$-$OH)_3$,
—$C(CH_3)_2$—OH,
—$C(CH_3)_2$-F,
—$NR_{3-2b}$—CO—$R_{3-2c}$
where
$R_{3-2b}$ is —H or $C_1$-$C_4$ alkyl, and where $R_{3-2c}$ is
—H,
$C_1$-$C_6$ alkyl,
—φ,
—$CH_2$—φ,
—$(CH_2)_{n8}$—$OR_{3-2d}$
where
where $n_8$ is 0 thru 3 and
$R_{3-2d}$ is —H or $C_1$-$C_4$ alkyl,
—$(CH_2)_{n21}$—OH
where
$n_{21}$ is 3 thru 4,
—$(CH_2)_{n22}$—φ
where
$n_{22}$ is 0 thru 3 and
where —φ is optionally substituted with —F, —Cl, —Br, —I or $C_1$-$C_4$ alkyl,
—$(CH_2)_{n8}$—$N(R_{3-2d})_2$
where
$n_8$ and $R_{3-2d}$
are as defined above and where the two $R_{3-2d}$'s may be taken together with the attached nitrogen atom to form a ring selected from the group consisting of 1-pyrrolidinyl, 1-piperidinyl, 1-piperazinyl, 4-morpholinyl, 1-(4-methyl)piperazinyl,
—S—$R_{3-2d}$
where
$R_{3-2d}$ is as defined above,
—$SO_2$—$N(R_{3-2e})_2$
where
$R_{3-2e}$ is —H or $C_1$-$C_4$ alkyl,
—CO—$N(R_{3-2e})_2$
where
$R_{3-2e}$ is as defined
above and where the two $R_{3-2e}$'s may be taken together with the attached nitrogen atom to from a ring selected from the group consisting of 1-pyrrolidinyl, 1-piperidinyl, 1-piperazinyl, 4-morpholinyl, 1-(4-methyl)piperazinyl,
—$NR_{3-2f}R_{3-2g}$
where
$R_{3-2f}$ and $R_{3-2g}$ are
the same or different and are —H or $C_1$-$C_4$ alkyl and where $R_{3-2f}$ and $R_{3-2g}$ may be taken together with the attached nitrogen atom to form a ring, which may contain an additional heteroatom, selected from the group consisting of piperazine, morpholine, pyrrolidine or piperidine,
with the proviso that when $R_{3-6}$ is —O—, —S— or —$NR_{3-7}$—, $n_1$ and $n_2$ are 1 or 2, (6) aryl, where aryl is
—φ optionally substituted with one or two $R_{3-2}$, where $R_{3-2}$ is as defined above,
1-naphthyl optionally substituted with one or two $R_{3-2}$, where $R_{3-2}$ is as defined above,
2-naphthyl optionally substituted with one or two $R_{3-2}$, where $R_{3-2}$ is as defined above,
2-imidazolyl optionally substituted with one or two $R_{3-2}$ and $R_{3-12}$ where $R_{3-12}$ is —H, $C_1$-$C_4$ alkyl or —CHO, where $R_{3-2}$ is as defined above,
4-imidazolyl optionally substituted with one or two $R_{3-2}$, where $R_{3-2}$ and $R_{3-12}$ are as defined above,
3-isoxazolyl optionally substituted with one or two $R_{3-2}$, where $R_{3-2}$ is as defined above,
4-isoxazolyl optionally substituted with one or two $R_{3-2}$ where $R_{3-2}$ is as defined above,
5-isoxazolyl optionally substituted with one or two $R_{3-2}$, where $R_{3-2}$ is as defined above,
3-pyrazolyl optionally substituted with one or two $R_{3-2}$ and where $R_{3-12}$ and $R_{3-2}$ are as defined above,
4-pyrazolyl optionally substituted with one or two $R_{3-2}$ where $R_{3-12}$ and $R_{3-2}$ are as defined above,
5-pyrazolyl optionally substituted with one or two $R_{3-2}$, where $R_{3-12}$ and $R_{3-2}$ are as defined above,
2-oxazolyl optionally substituted with one or two $R_{3-2}$, where $R_{3-2}$ is as defined above,
4-oxazolyl optionally substituted with one or two $R_{3-2}$ where $R_{3-2}$ is as defined above,
2-thiazolyl optionally substituted with one or two $R_{3-2}$, where $R_{3-2}$ is as defined above,
4-thiazolyl optionally substituted with one or two $R_{3-2}$, where $R_{3-2}$ is as defined above,
2-furanyl optionally substituted with one one or two $R_{3-2}$, where $R_{3-2}$ is as defined above,
3-furanyl optionally substituted with one or two $R_{3-2}$, where $R_{3-2}$ is as defined above,
2-thienyl optionally substituted with one or two $R_{3-2}$ where $R_{3-2}$ is as defined above,
3-thienyl optionally substituted with one or two $R_{3-2}$, where $R_{3-2}$ is as defined above,
2-pyrrolyl optionally substituted with one or two $R_{3-2}$, where $R_{3-12}$ and $R_{3-2}$ are as defined above,
3-pyrrolyl optionally substituted with one or two $R_{3-2}$, where $R_{3-12}$ and $R_{3-2}$ are as defined above,
1,2,4-oxadiazol-3-yl optionally substituted with one $R_{3-2}$, where $R_{3-2}$ is as defined above,
1,2,4-oxadiazol-5-yl optionally substituted with one $R_{3-2}$, where $R_{3-2}$ is as defined above,
1,2,4-thiadiazol-3-yl optionally substituted with one $R_{3-2}$, where $R_{3-2}$ is as defined above,
1,2,4-thiadiazol-5-yl optionally substituted with one $R_{3-2}$ where $R_{3-2}$ is as defined above,
1,2,4-triazol-3-yl optionally substituted with one $R_{3-2}$, where $R_{3-12}$ and $R_{3-2}$ are as defined above,
1,2,4-triazol-5-yl optionally substituted with one $R_{3-2}$, where $R_{3-12}$ and $R_{3-2}$ are as defined above,
1,2,3,4-tetrazol-5-yl substituted with $R_{3-12}$ where $R_{3-12}$ is as defined above,
5-oxazolyl optionally substituted with one or two $R_{3-2}$ where $R_{3-2}$ is as defined above,
5-thiazolyl optionally substituted with with one or two $R_{3-2}$, where $R_{3-2}$ is as defined above, (B) —CO—$NR_{3-10}R_{3-11}$ where $R_{3-10}$ and $R_{3-11}$ are the same or different and are $C_1$-$C_4$ alkyl, $C_3$-$C_7$ cycloalkyl or —φ,
(C) —CN,
(D) aryl, where aryl is as defined above,
(E) —C≡C—$R_{3-1}$ where $R_{3-1}$ is as defined above,
(F) —CO—$R_{3-1}$ where $R_{3-1}$ is as defined above,
(G) —CS—$R_{3-1}$ where $R_{3-1}$ is as defined above,
(H) —CO—$R_{3-13}$ where $R_{3-13}$ is selected from the group consisting of
1-imidazolyl optionally substituted with one or two $R_{3-2}$, where $R_{3-2}$ is as defined above,
1-pyrrolyl optionally substituted with one or two $R_{3-2}$, where $R_{3-2}$ is as defined above,
1-pyrazolyl optionally substituted with one or two $R_{3-2}$, where $R_{3-2}$ is as defined above,
1,2,3-triazol-1-yl optionally substituted with one or two $R_{3-2}$, where $R_{3-2}$ is as defined above,
1,2,4-triazol-1-yl optionally substituted with one or two $R_{3-2}$, where $R_{3-2}$ is as defined above,
1-tetrazolyl optionally substituted with one or two $R_{3-2}$, where $R_{3-2}$ is as defined above,
2-furanyl optionally substituted with one or two $R_{3-2}$, where $R_{3-2}$ is as defined above,
3-furanyl optionally substituted with one or two $R_{3-2}$, where $R_{3-2}$ is as defined above,
2-thienyl optionally substituted with one or two or two $R_{3-2}$, where $R_{3-2}$ is as defined above,
3-thienyl optionally substituted with one or two R3-2, where $R_{3-2}$ is as defined above,
2-oxazolyl optionally substituted with one or two $R_{3-2}$, where $R_{3-2}$ is as defined above,
4-oxazolyl optionally substituted with one or two $R_{3-2}$, where $R_{3-2}$ is as defined above,
5-oxazolyl optionally substituted with one or two $R_{3-2}$, where $R_{3-2}$ is as defined above,
3-isoxazolyl optionally substituted with one or two $R_{3-2}$, where $R_{3-2}$ is as defined above,
4-isoxazolyl optionally substituted with one or two $R_{3-2}$, where $R_{3-2}$ is as defined above,
5-isoxazolyl optionally substituted with one or two $R_{3-2}$, where $R_{3-2}$ is as defined above,
2-thiazolyl optionally substituted with one or two $R_{3-2}$, where $R_{3-2}$ is as defined above,
4-thiazolyl optionally substituted with one or two $R_{3-2}$, where $R_{3-2}$ is as defined above,
5-thiazolyl optionally substituted with one or two $R_{3-2}$, where $R_{3-2}$ is as defined above,
3-isothiazolyl optionally substituted with one or two $R_{3-2}$, where $R_{3-2}$ is as defined above,
4-isothiazolyl optionally substituted with one or two $R_{3-2}$, where $R_{3-2}$ is as defined above,
5-isothiazolyl optionally substituted with one or two $R_{3-2}$, where $R_{3-2}$ is as defined above;

(I) —$C^*$=N—$C(R_{3-14})_2$—$[C(R_{3-15})_2]_{n23}$—$R^*_{3-16}$ where the atoms marked with an asterisk (*) are bonded to each other resulting in the formation of a ring,
where the $R_{3-14}$'s are the same or different and are —H or $C_1$-$C_3$ alkyl, where $n_{23}$ is 1 thru 3, where the $R_{3-15}$'s are the same or different and are —H or $C_1$-$C_3$ alkyl, where $R_{3-16}$ is —O—, —S—, —C($R_{3-14}$)$_2$—, —NR$_{3-12}$ where $R_{3-12}$ and $R_{3-14}$ are as defined above, (J) —CH(OH)$R_{3-1}$ where $R_{3-1}$ is as defined above, (K) —CH$_2$—O—$R_{3-1}$ where $R_{3-1}$ is as defined above, (L) —CH$_2$—NR$_{3-4}$R$_{3-5}$ where $R_{3-4}$ and $R_{3-5}$ are as defined above;

where $R_4$ is $C_3$-$C_5$ spirocycloalkyl or α—$R_{4-5}$:β—$R_{4-6}$ where $R_{4-5}$ and $R_{4-6}$ are the same or different and are —H or $C_1$ alkyl, where $R_5$ is:
- —(CH$_2$)$_{n29}$—CO—H where $n_{29}$ is 0 thru 4,
- —(CH$_2$)$_{n29}$—CO—($C_1$-$C_6$ alkyl) where $n_{29}$ is as defined above,
- —(CH$_2$)$_{n29}$—CO—($C_3$-$C_7$ cycloalkyl) where $n_{29}$ is as defined above,
- —(CH$_2$)$_{n29}$—CS—($C_1$-$C_6$ alkyl) where $n_{29}$ is as defined above,
- —(CH$_2$)$_{n29}$—CO—(CH$_2$)$_{n28}$—NR$_{5-4}$((CH$_2$)$_{n29}$—OR$_{5-1}$) where $n_{28}$ is 0 thru 3, where $R_{5-1}$ is as defined for $R_{3-1}$ with the proviso that $R_{3-1}$ and $R_{5-1}$ may be the same or different, where $R_{5-4}$ is —H, $C_1$-$C_6$ alkyl, —CH$_2$—CH$_2$—OH, —CH$_2$—CH$_2$—OCH$_3$ or —φ optionally substituted with 1 or 2 $R_{3-2}$'s where $R_{3-2}$ is as defined above, and where the $n_{29}$'s may be the same or different and are as defined above,
- —(CH$_2$)$_{n29}$—CO—(CH$_2$)$_{n28}$—NR$_{5-4}$((CH$_2$)$_{n29}$—NR$_{5-1}$R$_{5-5}$) where $R_{5-5}$ is —H, $C_1$-$C_6$ alkyl, —CH$_2$—CH$_2$—OH, —CH$_2$—CH$_2$—OCH$_3$, where $n_{28}$, $R_{5-1}$, and $R_{5-4}$ are as defined above, where the $n_{29}$'s may be the same or different and are as defined above, and where $R_{5-4}$ and $R_{5-5}$ are taken together with the attached nitrogen atom to form a ring selected from the group consisting of 1-pyrrolidinyl, 1-piperidinyl, 1-piperazinyl, 4-morpholinyl, 1-(4-methyl)piperazinyl,
- —(CH$_2$)$_{n29}$—CS—($C_3$-$C_7$ cycloalkyl) where $n_{29}$ is as defined above,
- —(CH$_2$)$_{n29}$—CO—aryl where aryl and $n_{29}$ are as defined above,
- —(CH$_2$)$_{n29}$—CS—aryl where aryl and $n_{29}$ are as defined above,
- —(CH$_2$)$_{n29}$—CO—O—$R_{5-1}$ where $R_{5-1}$ and $n_{29}$ is as defined above,
- —(CH$_2$)$_{n29}$—CO—S—$R_{5-1}$ where $R_{5-1}$ and $n_{29}$ are as defined above,
- —(CH$_2$)$_{n29}$—CO—(CH$_2$)$_{n28}$—NR$_{5-4}$ R$_{5-5}$ where $n_{28}$, $n_{29}$, $R_{5-4}$ and $R_{5-5}$ are as defined above and where $R_{5-4}$ and $R_{5-5}$ are taken together with the attached nitrogen atom to from a heterocyclic ring selected form the group consisting of —N*—(CHR$_{5-8}$)$_{nA}$—(CH$_2$)$_{n1}$—R$_{5-6}$—(CH$_2$)$_{n2}$—(C*HR$_{5-9}$)$_{nB}$—

—N*—(CH$_2$)$_{n1}$—(CHR$_{5-8}$)$_{nA}$—R$_{5-6}$—(CHR$_{5-9nB}$(C*H$_2$)$_{n2}$— where $R_{5-8}$ is —H or $C_1$-$C_3$ alkyl, $n_A$ is 1 or 2, $n_1$ is 0 thru 2, $n_2$ is 0 thru 2, $R_{5-9}$ is H or $C_1$-$C_3$ alkyl, $n_B$ is 1 or 2, where the atoms marked with an asterisk (*) are bonded to each other resulting in the formation of a ring, with the proviso that the ring not contain more than 6 atoms, and where $R_{5-6}$ is
—O—,
—S—,
—CO—,
—CR$_{5-8}$R$_{5-9}$ where $R_{5-8}$ and $R_{5-9}$ are the same or different and are —H or $C_1$-$C_4$ alkyl,
—NR$_{5-7}$ where $R_{5-7}$ is —H,
$C_1$-$C_6$ alkyl,
—(CH$_2$)$_{n18}$—φ where $n_{18}$ is 0 thru 4 and where —φ is optionally substituted with —F, —Cl, —Br, —I or $C_1$-$C_3$ alkyl,
—(CH$_2$)$_{n19}$—OH where $n_{19}$ is 2 thru 4, with the proviso that when $R_{5-6}$ is —O—, —S— or —NR$_{5-7}$—, $n_1$ and $n_2$ are 1 or 2, —(CH$_2$)$_{n29}$—CO—CO—NR$_{5-4}$R$_{5-5}$ where $R_{5-4}$, $R_{5-5}$ and $n_{29}$ are as defined above, —(CH$_2$)$_{n29}$—CO—COOR$_{5-8}$ where $n_{29}$ is as defined above and where $R_{5-8}$ is —H,
$C_1$-$C_4$ alkyl,
—(CH$_2$)$_{n20}$—φ where $n_{20}$ is 1 thru 4,
—φ optionally substituted with 1 or 2—F, —Cl, —Br, —I or $C_1$-$C_3$ alkyl,
—(CH$_2$)$_{n29}$—CO—R$_{5-13}$ where $n_{29}$ is as defined above and where $R_{5-13}$ is defined as being selected from the same group as $R_{3-13}$
—(CH$_2$)$_{n29}$—C*=N—C(R$_{5-10}$)$_2$—[C(R$_{5-11}$)$_2$]$_{n27}$—R*$_{5-12}$ where the atoms marked with an asterisk (*) are bonded to each other resulting in the formation of a ring,
where the $R_{5-10}$'s are the same or different and are —H or $C_1$-$C_3$ alkyl,
where $n_{27}$ is 1 thru 3,
where the $R_{5-11}$'s are the same or different and are —H or $C_1$-$C_3$ alkyl,
where $R_{5-12}$ is —O—, —S—, —C(R$_{5-13}$)$_2$—, —NR$_{5-14}$ where $R_{5-13}$ and $R_{5-14}$ are —H or $C_1$-$C_3$ alkyl, and where $R_6$ is —H,
—F,
—Cl,
—Br,
—I,
—CN,
—NO$_2$,
—O—CO—R$_{6-1}$ where $R_{6-1}$ is —H, $C_1$-$C_4$ alkyl or $C_3$-$C_7$ cycloalkyl,
—CF$_3$,
—O—CF$_3$,
$C_1$-$C_6$ alkyl,
$C_3$-$C_7$ cycloalkyl,
—CH$_2$CH$_2$OH,
—NR$_{6-2}$—CO—R$_{6-3}$ where $R_{6-2}$ is —H or $C_1$-$C_4$ alkyl, and where $R_{6-3}$ is
—H,
$C_1$-$C_6$ alkyl,
—φ optionally substituted with —F, —Cl, —Br, —I or $C_1$-$C_4$ alkyl,
—CH$_2$—φ,
—(CH$_2$)$_{n24}$—OR$_{6-4}$ where $n_{24}$ is 0 thru 3 and $R_{6-4}$ is $C_1$-$C_4$ alkyl,
—(CH$_2$)$_{n25}$—OH where $n_{25}$ is 2 thru 4,
—(CH$_2$)$_{n26}$—φ where $n_{26}$ is 0 thru 3,
—(CH$_2$)$_{n24}$—N(R$_{6-4}$)$_2$ where $n_{24}$ and $R_{6-4}$ are as defined above,
—S—R$_{6-4}$ where $R_{6-4}$ is as defined above,
—SO$_2$—N(R$_{6-5}$)$_2$ where $R_{6-5}$ is —H or $C_1$-$C_4$ alkyl,
—CO—N(R$_{6-5}$)$_2$ where $R_{6-5}$ is as defined above,
—CO$_2$—R$_{6-4}$ where $R_{6-4}$ is as defined above,
—NR$_{6-6}$R$_{6-7}$ where $R_{6-6}$ and $R_{6-7}$ are the same or different and are —H or $C_1$-$C_4$ alkyl and where $R_{6-6}$ and $R_{6-7}$ may be taken together with the attached nitrogen atom to form a ring, which may contain an additional heteroatom, selected from the group consisting of piperazine, morpholine, pyrrolidine or piperidine;

where $W_6$ is —$CR_6$= where $R_6$ is as defined above;
where $W_7$ is $CR_7$= where $R_7$ is as defined for $R_6$, the $R_6$, $R_7$, $R_8$ and $R_9$ may be the same or different;
where $W_8$ is —$CR_8$= where $R_8$ is as defined for $R_6$, the $R_6$, $R_7$, $R_8$ and $R_9$ may be the same or different;
where $W_9$ is —$CR_9$= where $R_9$ is as defined for $R_6$, the $R_6$, $R_7$, $R_8$ and $R_9$ may be the same or different; and pharmaceutically acceptable salts thereof where such exist.

2. An imidazo[1,5-a]quinoxaline (I) according to claim 1 where $R_3$ is selected from the group consisting of —$COOR_{3-1}$, aryl or —$CO$—$NR_{3-10}R_{3-11}$.

3. An imidazo[1,5-a]quinoxaline (I) according to claim 2 where aryl is selected from the group consisting of 1,2,4-oxadiazol-3-yl or 1,2,4-oxadiazol-5-yl.

4. An imidazo[1,5-a]quinoxaline (I) according to claim 3 where the 1,2,4-oxadiazol-3-yl or 1,2,4-oxadiazol-5-yl is substituted with $C_2$-$C_4$ alkyl and $C_3$-$C_5$ cycloalkyl.

5. An imidazo[1,5-a]quinoxaline (I) according to claim 1 where $R_4$ is α-$R_{4-5}$:β-$R_{4-6}$ where $R_{4-5}$ and $R_{4-6}$ are —H:—H.

6. An imidazo[1,5-a]quinoxaline (I) according to claim 1 where $R_4$ is α-$R_{4-5}$:β-$R_{4-6}$ where $R_{4-5}$ and $R_{4-6}$ are $C_1$ alkyl:$C_1$ alkyl.

7. An imidazo[1,5-a]quinoxaline (I) according to claim 1 where $R_5$ is selected from the group consisting of
—$(CH_2)_{n29}$—$CO$—$(C_1$-$C_6$ alkyl),
—$(CH_2)_{n29}$—$CO$—$(CH_2)_{n28}$—$NR_{5-4}R_{5-5}$,
—$(CH_2)_{n29}$—$CO$—aryl,
—$(CH_2)_{n29}$—$CO$—$O$—$(C_1$-$C_6$ alkyl),
—$(CH_2)_{n29}$—$CO$—$(C_3$-$C_7$ cycloalkyl),
—$(CH_2)_{n29}$—$CO$—$R_{3-13}$.

8. An imidazo[1,5-a]quinoxaline (I) according to claim 7 where $R_5$ is selected from the group consisting of —$(CH_2)_{n29}$—$CO$—$(CH_2)_{n28}$—$NR_{5-4}R_{5-5}$, —$(CH_2)_{n29}$—$CO$—aryl and —$(CH_2)_{n29}$—$CO$—$O$—$(C_1$-$C_6$ alkyl).

9. An imidazo[1,5-a]quinoxaline (I) according to claim 1 where $W_6$ is —$CR_6$=, $W_7$ is —$CR_7$=, $W_8$ is —$CR_8$= and $W_9$ is —$CR_9$=.

10. An imidazo[1,5-a]quinoxaline (I) according to claim 9 where $R_6$, $R_7$, $R_8$ and $R_9$ are all –H.

11. An imidazo[1,5-a]quinoxaline (I) according to claim 1 where $W_6$ is —CF=, —CCl= or —CCH_3=.

12. An imidazo[1,5-a]quinoxaline (I) according to claim 1 where $W_7$ is —CF=, —CCl= or —CCH_3=.

13. An imidazo[1,5-a]quinoxaline (I) according to claim 1 which is selected from the group consisting of tert-butyl 6-fluoro-4,5-dihydro-5-[(pyrrolidino)carbonyl] imidazo[1,5-a]quinoxaline-3 -carboxylate, 6-fluoro-4,5-dihydro-3-(5-isopropyl-1,2,4-oxadiazol-3-yl)-5-[(pyrrolidino)carbonyl]-imidazo[1,5-a]quinoxaline, 7-fluoro-4,5-dihydro-4,4-dimethyl-3-(5-isopropyl-1,2,4-oxadiazol-3-yl)-5-[(pyrrolidino) -carbonyl]imidazo[1,5-a]quinoxaline, tert-butyl 7-fluoro-4,5-dihydro-4,4-dimethyl-5-[(pyrrolidino)carbonyl]imidazo[1,5 -a9 quinoxaline-3-carboxylate, 5-(tert-butyloxycarbonyl)-3-(5-cyclopropyl-1,2,4-oxadiazol-3-yl)-4,5-dihydroimidazo[1,5 -a]quinoxaline, 5-benzoyl-3-(5-cyclopropyl-1,2,4-oxadiazol-3-yl)-4,5-dihydroimidazo[1,5-a]quinoxaline, 5-acetyl-3-(5-cyclopropyl-1,2,4-oxadiazol-3-yl)-4,5-dihydroimidazo[1,5-a]quinoxaline, 3-(5-cyclopropyl-1,2,4-oxadiazol-3-yl)-5-(2-furoyl)-4,5-dihydroimidazo[1,5 -a]quinoxaline, 5-(tert-butyloxycarbonyl)-3-(5-cyclopropyl-1,2,4-oxadiazol-3-yl)-4,5-dihydro-6 -methylimidazo[1,5-a]quinoxaline, 7-chloro-3-(5-cyclopropyl-1,2,4-oxadiazol-3-yl)4,5-dihydro-5-[(pyrrolidino)carbonyl]-imidazo[1,5-a]quinoxaline, 7-chloro-3-(5-cyclopropyl-1,2,4-oxadiazol-3-yl)-5-[(dimethylamino)carbonyl]-4,5 -dihydroitnidazo[1,5-a]quinoxaline, 5-(tert-butyloxycarbonyl)-7-chloro-3-(5-cyclopropyl-1,2,4-oxadiazol-3-yl)4,5 -dihydroimidazo[1,5-a]quinoxaline, 7-chloro-3-(5-cyclopropyl-1,2,4-oxadiazol-3-yl)-5-(2-furoyl)-4,5-dihydroimidazo[1,5-a]quinoxaline, 5-benzoyl-7-chloro-3-(5-cyclopropyl-1,2,4-oxadiazol-3-yl)-4,5-dihydroimidazo[1,5-a]quinoxaline, 5-(tert-butyloxycarbonyl)-3-(5-cyclopropyl-1,2,4-oxadiazol-3-yl)-6-fluoro4,5 -dihydroimidazo[1,5-a]quinoxaline, 5-acetyl-7-chloro-3-(5-cyclopropyl-1,2,4-oxadiazol-3-yl)4,5-dihydroimidazo[1,5-a]quinoxaline, 7-chloro-3-(5-cyclopropyl-1,2,4-oxadiazol-3-yl)-4,5-dihydro-5-propionylimidazo[1,5-a]quinoxaline, tert-butyl 7-chloro-4,5-dihydro-5-[(pyrrolidino)carbonyl] imidazo[1,5-a]quinoxaline-3 -carboxylate, tert-butyl 7-Chloro-5-[(dimethylamino)carbonyl]-4,5-dihydroimidazo[1,5-a]quinoxaline-3-carboxylate, 7-chloro-4,5-dihydro-3-(5-isopropyl-1,2,4-oxadiazol-3-yl)-5-[(pyrrolidino)carbonyl]-imidazo[1,5-a]quinoxaline, 7-chloro-5-[(dimethylamino)carbonyl]-4,5-dihydro-3-(3-isopropyl-1,2,4-oxadiazol-5 -yl)imidazo[1,5-a]quinoxaline, 7-chloro-3-(5-ethyl-1,2,4-oxadiazol-3-yl)4,5-dihydro-5-[(pyrrolidino)carbonyl]imidazo -1,5-a]quinoxaline, 7-chloro-5-[(dimethylamino)carbonyl]-3-(5-ethyl-1,2,4-oxadiazol-3-yl)-4,5 -dihydroimidazo[1,5-a]quinoxaline, tert-butyl 7-fluoro-4,5-dihydro-5-[(pyrrolidino)carbonyl] imidazo[1,5-a]quinoxaline-3-carboxylate, 7-fluoro-4,5-dihydro-3-(5-isopropyl-1,2,4-oxadiazol-3-yl)-5-[(pyrrolidino)carbonyl]imidazo[1,5-a]quinoxaline, 7-chloro-5-[(dimethylamino)carbonyl]4,5-dihydro-3-(5-isopropyl-1,2,4-oxadiazol-3 -yl)imidazo[1,5-a]quinoxaline, tert-butyl 6-chloro-4,5-dihydro-5-[(pyrrolidino)carbonyl] imidazo[1,5-a]quinoxaline-3-carboxylate, 6-chloro-4,5-dihydro-3-(5-isopropyl-1,2,4-oxadiazol-3-yl)-5-[(pyrrolidino)carbonyl]imidazo[1,5-a]quinoxaline, tert-butyl 6-chloro-5-[(dimethylamino)carbonyl]4,5-dihydmimidazo[1,5-a]quinoxaline-3-carboxylate, 6-chloro-3-(5-ethyl-1,2,4-oxadiazol-3-yl)-4,5-dihydro-5-[(pyrrolidino)carbonyl]imidazo[1,5-a]quinoxaline, 6-chloro-5-[(dimethylamino)carbonyl]-4,5-dihydro-3-(5-isopropyl-1,2,4-oxadiazol-3 -yl)imidazo[1,5-a]quinoxaline, 6-chloro-4,5-dihydro-3-(3-isopropyl-1,2,4-oxadiazol-5-yl)-5-[(pyrrolidino)carbonyl]imidazo[1,5-a]quinoxaline, 6-chloro-5-[(dimethylamino)carbonyl]-3-(5-ethyl-1,2,4-oxadiazol-3-yl)-4,5-dihydroimidazo[1,5-a]quinoxaline, 6-chloro-5-[(dimethylamino)carbonyl]-4,5-dihydro-3-(3-isopropyl-1,2,4-oxadiazol-5-yl)imidazo[1,5-a]quinoxaline, 7-chloro-3-(5-cyclopropyl-1,2,4-oxadiazol-3-yl)-4,5-dihydro-4,4-dimethyl-5-(pyrrolidino)carbonyl]imidazo[1,5-a]quinoxaline, 7-chloro-3-(5-cyclopropyl-1,2,4-oxadiazol-3-yl)-5-[(dimethylamino)carbonyl]-4,5-dihydro-4,4-dimethylimidazo[1,5-a]quinoxaline, 7-chloro-4,5-dihydro-3-(5-isopropyl-1,2,4-oxadiazol-3-yl)-4,4-dimethyl-5-(pyrrolidino)carbonyl]imidazo[1,5-a]quinoxaline, 7-chloro-5-[(dimethylamino)carbonyl]-4,5-dihydro-3-(5-isopropyl-1,2,4-oxadiazol-3-yl)-4,4-dimethylimidazo[1,5-a]quinoxaline, tert-butyl 7-chloro-4,5-dihydro-4,4-dimethyl-5-[(pyrrolidino)carbonyl]imidazo[1,5-a]quinoxaline-3-carboxylate, tert-butyl 7-chloro-5-[(dimethylamino)carbonyl]-4,5-dihydro-4,4-dimethylimidazo[1,5-a]quinoxaline-3-carboxylate, 7-chloro-5-[(dimethylamino)carbonyl]-4,5-dihydro-3-(3-isopropyl-1,2,4-oxadiazol-5-yl)-4,4-dimethylimidazo[1,5-a]quinoxaline, 7-chloro-3-(5-ethyl-1,2,4-oxadiazol-3-yl)4,5-dihydro-4,4-dimethyl-5-[(pyrrolidino)-carbonyl]imidazo[1,5-a]quinoxaline, 7-chloro-5-[(dimethylamino)carbonyl]-3-(5-ethyl-1,2,4-oxadiazol-3-yl)-4,5-dihydro4,4-dimethylimidazo[1,5-a]quinoxaline, tert-butyl 6-chloro-4,5-dihydro4,4-dimethyl-5-[(pyrrolidino)carbonyl]imidazo[1,5-a]quinoxaline-3-carboxylate, 6-chloro-4,5-dihydro-3-(5-isopropyl-1,2,4-oxadiazol-3-yl)-4,4-dimethyl-5-(pyrrolidino)carbonyl]imidazo[1,5-a]quinoxaline, 6-chloro-5-[(dimethylamino)carbonyl]-4,5-dihydro-3-(5-isopropyl-1,2,4-oxadiazol-3-yl)-4,4-dimethylimidazo[1,5-a]quinoxaline, 6-chloro-3-(5-ethyl-1,2,4-oxadiazol-3-yl)-4,5-dihydro-4,4-dimethyl-5-(pyrrolidino)carbonyl]imidazo[1,5-a]quinoxaline, 6-chloro-4,5-dihydro-3-(3-isopropyl-1,2,4-oxadiazol-5-yl)-4,4-dimethyl-5-(pyrrolidino)carbonyl]imidazo[1,5-a]quinoxaline, tert-butyl 6-chloro-5-[(dimethylamino)carbonyl]4,5-dihydro4,4-dimethylimidazo[1,5-a]quinoxaline-3-carboxylate, 6-chloro-5-[(dimethylamino)carbonyl]4,5-dihydro-3-(3-isopropyl-1,2,4-oxadiazol-5-yl)-4,4-dimethylimidazo[1,5-a]quinoxaline, 6-chloro-5-[(dimethylamino)carbonyl]-3-(5-ethyl-1,2,4-oxadiazol-3-yl)-4,5-dihydro4,4-dimethylimidazo[1,5-a]quinoxaline, 3-(5-cyclopropyl-1,2,4-oxadiazol-3-yl)-4,5-dihydro-5-propionylimidazo[1,5-a]quinoxaline, 3-(5-cyclopropyl-1,2,4-oxadiazol-3-yl)-5-(ethoxyoxazolyl)4,5-dihydroimidazo[1,5-a]quinoxaline, 5-[(2-chloro)benzoyl]-3-(5-cyclopropyl-1,2,4-oxadiazol-3-yl)-4,5-dihydroimidazo[1,5-a]quinoxaline, 3-(5-cyclopropyl-1,2,4-oxadiazol-3-yl)-4,5-dihydro-5-[(morpholino)carbonyl]imidazo[1,5-a]quinoxaline, 3-(5-cyclopropyl-1,2,4-oxadiazol-3-yl)-5-[(3,5-dimethylpyrazolo)carbonyl]-4,5-dihydroimidazo[1,5-a]quinoxaline, 5-acetyl-3-(3-cyclopropyl-1,2,4-oxadiazol-5-yl)-4,5-dihydro-4,4-dimethylimidazo[1,5-a]quinoxaline, 5-acetyl-3-(3-cyclopropyl-1,2,4-oxadiazol-5-yl)-4,5-dihydroimidazo[1,5-a]quinoxaline, 3-(5-cyclopropyl-1,2,4-oxadiazol-3-yl)-5-[(dimethylamino)carbonyl]-6-fluoro-4,5-dihydroimidazo[1,5-a]quinoxaline, 3-(5-cyclopropyl-1,2,4-oxadiazol-3-yl)-6-fluoro-4,5-dihydro-5-[(pyrrolidino)carbonyl]imidazo[1,5-a]quinoxaline, 5-acetyl-3-(5-cyclopropyl-1,2,4-oxadiazol-3-yl)-6-fluoro-4,5-dihydroimidazo[1,5-a]quinoxaline, 5-benzoyl-3-(5-cyclopropyl-1,2,4-oxadiazol-3-yl)-6-fluoro-4,5-dihydroimidazo[1,5-a]quinoxaline, 5-acetyl-3-(5-cyclopropyl-1,2,4-oxadiazol-3-yl)-7-fluoro-4,5-dihydroimidazo[1,5-a]quinoxaline, 3-(5-cyclopropyl-1,2,4-oxadiazol-3-yl)-5-[(dimethylamino)carbonyl]-7-fluoro-4,5-dihydroimidazo[1,5-a]quinoxaline, 3-(5-cyclopropyl-1,2,4-oxadiazol-3-yl)-7-fluoro-4,5-dihydro-5-[(pyrrolidino)carbonyl]imidazo[1,5-a]quinoxaline, 5-benzoyl-3-(5-cyclopropyl-1,2,4-oxadiazol-3-yl)-7-fluoro-4,5-dihydroimidazo[1,5-a]quinoxaline, 3-(5-cyclopropyl-1,2,4-oxadiazol-3-yl)-7-fluoro-4,5-dihydro-5-[(1-imidazo)carbonyl]imidazo[1,5-a]quinoxaline, 3-(5-cyclopropyl-1,2,4-oxadiazol-3-yl)-7-fluoro-4,5-dihydro-5-[(morpholino)carbonyl]imidazo[1,5-a]quinoxaline, 5-acetyl-3-(5-cyclopropyl-1,2,4-oxadiazol-3-yl)-4,5-dihydro-4,4-dimethylimidazo[1,5-a]quinoxaline, 3-(5-cyclopropyl-1,2,4-oxadiazol-3-yl)-4,5-dihydro-5-[(methoxy)carbonyl]-4,4-dimethylimidazo[1,5-a]quinoxaline, 3-(5-cyclopropyl-1,2,4-oxadiazol-3-yl)-4,5-dihydro-5-[(isopropyloxy)carbonyl]-4,4-dimethylimidazo[1,5-a]quinoxaline, 3-(5-cyclopropyl-1,2,4-oxadiazol-3-yl)-5-[(ethozolyl]-4,5-dihydro-4,4-dimethylimidazo[1,5-a]quinoxaline, 3-(5-cyclopropyl-1,2,4-oxadiazol-3-yl)-4,5-dihydro-4,4-dimethyl-5-[(phenoxy)carbonyl]imidazo[1,5-a]quinoxaline, 3-(5-cyclopropyl-1,2,4-oxadiazol-3-yl)-4,5-dihydro-4,4-dimethyl-5-[(pyrrolidino)oxazolyl]imidazo[1,5-a]quinoxaline, 6-chloro-3-(5-cyclopropyl-1,2,4-oxadiazol-3-yl)-4,5-dihydro-5-[(pyrrolidino)carbonyl]imidazo[1,5-a]quinoxaline, 6-chloro-3-(5-cyclopropyl-1,2,4-oxadiazol-3-yl)-5-[(dimethylamino)carbonyl]-4,5-dihydroimidazo[1,5-a]quinoxaline, 6-chloro-3-(5-cyclopropyl-1,2,4-oxadiazol-3-yl)-4,5-dihydro-5-[(methanethio)carbonyl]imidazo[1,5-a]quinoxaline, 3-(5-cyclopropyl-1,2,4-oxadiazol-3-yl)-4,5-dihydro-5-(trifluoroacetyl)imidazo[1,5-a]quinoxaline, 3-(5-cyclopropyl-1,2,4-oxadiazol-3-yl)-4,5-dihydro-5-[(1-imidazolyl)carbonyl]imidazo[1,5-a]quinoxaline, 3-(5-cyclopropyl-1,2,4-oxadiazol-3-yl)-4,5-dihydro-5-[(2-pyrrolyl)carbonyl]imidazo[1,5-a]quinoxaline, 5-[(anilino)carbonyl]-3-(5-cyclopropyl-1,2,4-oxadiazol-3-yl)-4,5-dihydroimidazo[1,5-a]quinoxaline, 3-(5-cyclopropyl-1,2,4-oxadiazol-3-yl)-5-[(dimethylamino)carbonyl]4,5-dihydroimidazo[1,5-a]quinoxaline, 3-(5-cyclopropyl-1,2,4-oxadiazol-3-yl)-4,5-dihydro-5-[(methylamino)carbonyl]imidazo[1,5-a]quinoxaline, 5-[(2-chlorophenylamino)carbonyl]-3-(5-cyclopropyl-1,2,4-oxadiazol-3-yl)-4,5-dihydroimidazo[1,5-a]quinoxaline, 3-(5-cyclopropyl-1,2,4-oxadiazol-3-yl)-4,5-dihydro-5-[(isopropylamino) carbonyl]imidazo[1,5-a]quinoxaline, 3-(5-cyclopropyl-1,2,4-oxadiazol-3-yl)-5-[(diethylamino)carbonyl]-4,5-dihydroimidazo[1,5-a]quinoxaline, 3-(5-cyclopropyl-1,2,4-oxadiazol-3-yl)-4,5-dihydro-5-[(pyrrolidino)carbonyl]imidazo[1,5-a]quinoxaline, 5-[(benzenethio)carbonyl]-3-(5-cyclopropyl-1,2,4-oxadiazol-3-yl)-4,5-dihydmidazo[1,5-a]quinoxaline, 3-(5-cyclopropyl-1,2,4-oxadiazol-3-yl)-5-[(ethanethio)carbonyl]-4,5-dihydroimidazo[1,5-a]quinoxaline, 3-(5-cyclopropyl-1,2,4-oxadiazol-3-yl)-5-[(ethylamino)carbonyl]-4,5-dihydroimidazo[1,5-a]quinoxaline, 5-(carbamoyl)-3-(5-cyclopropyl-1,2,4-oxadiazol-3-yl)-4,5-dihydmimidazo[1,5-a]quinoxaline, 3-(5-cyclopropyl-1,2,4-oxadiazol-3-yl)-4,5-dihydro-5-[(methanethio)carbonyl]imidazo[1,5-a]quinoxaline, 3-(5-cyclopropyl-1,2,4-oxadiazol-3-yl)-4,5-dihydro-4,4-dimethyl-5-[(pyrrolidino) carbonyl]imidazo[1,5-a]quinoxaline, 3-(5-cyclopropyl-1,2,4-oxadiazol-3-yl)-5-[(dimethylamino)carbonyl]-4,5-dihydro-4,4-dimethylimidazo[1,5-a]quinoxaline, b 5-[(benzenethio)carbonyl]-3-(5-cyclopropyl-1,2,4-oxadiazol-3-yl)-4,5-dihydro-4,4-dimethylimidazo[1,5-a]quinoxaline, 5-(carbamoyl)-3-(5-cyclopropyl-1,2,4-oxadiazol-3-yl)-4,5-dihydro-4,4-dimethylimidazo[1,5-a]quinoxaline, 3-(5-cyclopropyl-1,2,4-oxadiazol-3-yl)-5-[(diethylamino)carbonyl]-4,5-dihydro-4,4-dimethylimidazo[1,5-a]quinoxaline, 3-(5-cyclopropyl-1,2,4-oxadiazol-3-yl)-4,5-dihydro-4,4-dimethyl-5-[(methylamino) -carbonyl]imidazo[1,5-a]quinoxaline, 3-(5-cyclopropyl-1,2,4-oxadiazol-3-yl)-5-[(ethylamino)carbonyl]-4,5-dihydro-4,4-dimethylimidazo[1,5-a]quinoxaline, 3-(5-cyclopropyl-1,2,4-oxadiazol-3-yl)-4,5-dihydro-5-[(methanethio)carbonyl]-4,4-dimethylimidazo[1,5-a]quinoxaline, 3-(5-cyclopropyl-1,2,4-oxadiazol-3-yl)-5-[(ethanethio)carbonyl]-4,5-dihydro-4,4-dimethylimidazo[1,5-a]quinoxaline, 3-(5-cyclopropyl-1,2,4-oxadiazol-3-yl)-5-formyl-4,5-dihydro-4,4-dimethylimidazo[1,5-a]quinoxaline, 3-(5-cyclopentyl-1,2,4-oxadiazol-3-yl)-4,5-dihydro-5-[(pyrrolidino)carbonyl]imidazo[1,5-a]quinoxaline, 4,5-dihydro-3-(3-isopropyl-1,2,4-oxadiazol-5-yl)4,4-dimethyl-5-[(pyrrolidino)carbonyl]imidazo[1,5-a]quinoxaline, 7-chloro-4,5-dihydro-3-(3-isopropyl-1,2,4-oxadiazol-5-yl)-4,4-dimethyl-5 -(pyrrolidino)carbonyl]imidazo[1,5-a]quinoxaline, tert-butyl 4,5-dihydro-4(S)-methyl-5-[(pyrrolidino)carbonyl]imidazo[1,5-a]quinoxaline-3 -carboxylate, tert-butyl 4,5-dihydro-4(RS)-methyl-5-[(pyrrolidino)carbonyl]imidazo[1,5-a]quinoxaline -3-carboxylate, tert-butyl 4,5-dihydro-4(S)-methyl-7-methyl-5-[(pyrrolidino)carbonyl]imidazo[1,5 -a]quinoxaline-3-carboxylate, 4,5-dihydro-3-(5-isopropyl-1,2,4-oxadiazol-3-yl)-4(S)-methyl-5-[(pyrrolidino) -carbonyl]imidazo[1,5-a]quinoxaline, 4,5-dihydro-3-(3-isopropyl-1,2,4-oxadiazol-5-yl)-4(S)-methyl-5-[(pyrrolidino) -carbonyl]imidazo[1,5-a]quinoxaline, tert-butyl 4,5-dihydro-5-[2-(morpholino)acetyl]imidazo[1,5-a]quinoxaline, tert-butyl 4,5-dihydro-7-methyl-5-[2-(morpholino)acetyl]imidazo[1,5-a]quinoxaline, 4,5-dihydro-3-(3-isopropyl-1,2,4-oxadiazol-5-yl)-5-[(pyrrolidino)carbonyl]-4 -(spirocyclopentyl)imidazo[1,5-a]quinoxaline, 7-chloro-4,5-dihydro-3-(3-isopropyl-1,2,4-oxadiazol-5-yl)-5-[(pyrrolidino) -carbonyl]imidazo[1,5-a]quinoxaline, 7-fluoro-4,5-dihydro-3-(3-isopropyl-1,2,4-oxadiazol-5-yl)-5-[(pyrrolidino) -carbonyl]imidazo[1,5-a]quinoxaline, tert-butyl 4,5-dihydro-5-[(pyrrolidino)carbonyl]-4-(spirocyclopentyl)imidazo[1,5 -a]quinoxaline, tert-butyl 4,5-dihydro-5-[2-(pyrrolidino)acetyl]imidazo[1,5-a]quinoxaline, 7-fluoro-4,5-dihydro-4(S)-methyl-N-pyrrolidino-5-[(pyrrolidino)carbonyl]imidazo[1,5 -a]quinoxaline-3-carboxamide, tert-butyl 4,5-dihydro-4,4-dimethyl-5-[2-(pyrrolidino)acetyl]imidazo[1,5-a]quinoxaline -3-carboxylate, 4,5-dihydro-3-(5-isopropyl-1,2,4-oxadiazol-3-yl)-5-[(pyrrolidino)carbonyl]-4 -(spirocyclopentyl)imidazo[1,5-a]quinoxaline, 7-fluoro-4,5-dihydro-3-(3-isopropyl-1,2,4-oxadiazol-5-yl)-4(S)-methyl-5 -(pyrrolidino)carbonyl]imidazo[1,5-a]quinoxaline, 7-fluoro-4,5-dihydro-3-(5-isopropyl-1,2,4-oxadiazol-3-yl)-4(S)-methyl-5 -(pyrrolidino)carbonyl]imidazo[1,5-a]quinoxaline, tert-butyl 7-fluoro-4,5-dihydro-4(S)-methyl-5-[(pyrrolidino)carbonyl]imidazo[1,5 -a]quinoxaline-3-carboxylate, N-tert-butylamino-4,5-dihydro-5-[(pyrrolidino)carbonyl]imidazo[1,5-a]quinoxaline-3-carboxamide, N-tert-butylamino-6-fluoro-4,5-dihydro-5-[(pyrrolidino)carbonyl]imidazo[1,5 -a]quinoxaline-3-carboxamide, N-tert-butylamino-6-chloro-4,5-dihydro-5-[(pyrrolidino)carbonyl]imidazo[1,5 -a]quinoxaline-3-carboxamide, N-tert-butylamino-7-chloro-4,5-dihydro-5-[(pyrrolidino)carbonyl]imidazo[1,5 -a]quinoxaline-3-carboxamide, 7-chloro-N-cyclohexylamino-4,5-dihydro-5-[(pyrrolidino)carbonyl]imidazo[1,5 -a]quinoxaline-3-carboxamide, N-tert-butylamino-6-chloro-4,5-dihydro-5-(2-pyrrolidino-2-oxoethyl)imidazo[1,5 -a]quinoxaline-3-carboxamide, N-tert-butylamino-7-chloro-4,5-dihydro-5-(2-pyrrolidino-2-oxoethyl)imidazo[1,5-a]quinoxaline-3-carboxamide, 4,5-dihydro-3-(hydroxymethyl)-5-[(pyrrolidino)carbonyl]imidazo-[1,5-a]quinoxaline, 4,5-dihydro-5-[(pyrrolidino)carbonyl]imidazo[1,5-a]quinoxaline-3-methanol, 3-(2-benzoxazolyl)-7-fluoro-4,5-dihydro-5-[(pyrrolidino)carbonyl]imidazo[1,5-a]quinoxaline, tert-butyl 4,5-dihydro-5-[(morpholino)carbonyl]imidazo[1,5-a]quinoxalin-3-carboxylate, 4,5-dihydro-3-(5-isopropyl-1,2,4-oxadiazol-3-yl)-5-[(morpholino)carbonyl]imidazo[1,5-a]quinoxaline, tert-butyl 5-[(di-n-propylamino)carbonyl]-4,5-dihydroimidazo[1,5-a]quinoxaline-3-carboxylate, 5-[(di-n-propylamino)carbonyl]-4,5-dihydro-3-(5-isopropyl-1,2,4-oxadiazol-3-yl)imidazo[1,5-a]quinoxaline, 7-fluoro-4,5-dihydro-3-phenyl-5-[(pyrrolidino)carbonyl]imidazo[1,5-a]quinoxaline, tert-butyl 5-(tert-butyloxycarbonyl)-4,5-dihydroimidazo[1,5-a]quinoxaline-3-carboxylate, tert-butyl 5-acetyl-4,5-dihydroimidazo[1,5-a]quinoxaline-3-carboxylate, 3-(2-benzoxazolyl)-4,5-dihydro-5-[(pyrrolidino)carbonyl]imidazo[1,5-a]quinoxaline, 3-(2-benzoxazolyl)-7-fluoro-4,5-dihydro-5-[(pyrrolidino)carbonyl]imidazo[1,5-a]quinoxaline, 7-fluoro-3-(4-fluorophenyl)-4,5-dihydro-4,4-dimethyl-5-[(pyrrolidino)carbonyl]-imidazo[1,5-a]quinoxaline, 3-(5-tert-butyl-1,2,4-oxadiazol-3-yl)-7-fluoro-4,5-dihydro-5-[(pyrrolidino)carbonyl]-imidazo[1,5-a]quinoxaline, 3-(5-tert-butyl-1,2,4-oxadiazol-3-yl)-4,5-dihydro-5-[(morpholino)carbonyl]imidazo[1,5-a]quinoxaline, 3-(5-tert-butyl-1,2,4-oxadiazol-3-yl)-7-fluoro-4,5-dihydro-4,4-dimethyl-5-(pyrrolidino)carbonyl]imidazo[1,5-a]quinoxaline, 3-(5-tert-butyl-1,2,4-oxadiazol-3-yl)-6-fluoro-4,5-dihydro-5-[(pyrrolidino)carbonyl]-imidazo[1,5-a]quinoxaline, 5-[(dimethylamino)carbonyl]-3-(5-ethyl-1,2,4-oxadiazol-3-yl)-4,5-dihydroimidazo[1,5-a]quinoxaline, 5-[(dimethylamino)carbonyl]-3-(5-ethyl-1,2,4-oxadiazol-3-yl)-4,5-dihydro-4,4-dimethylimidazo[1,5-a]quinoxaline, 3-(5-ethyl-1,2,4-oxadiazol-3-yl)-4,5-dihydro-4,4-dimethyl-5-[(pyrrolidino)carbonyl]-imidazo[1,5-a]quinoxaline, 3-(5-ethyl-1,2,4-oxadiazol-3-yl)-4,5-dihydro-5-[(pyrrolidino)carbonyl]imidazo[1,5-a]quinoxaline, 4,5-dihydro-3-(5-isopropyl-1,2,4-oxadiazol-3-yl)-5-[(piperidino)carbonyl]imidazo[1,5-a]quinoxaline, tert-butyl 4,5-dihydro-5-[(piperidino)carbonyl]imidazo[1,5-a]quinoxaline-3-carboxylate, 4,5-dihydro-3-(3-isopropyl-1,2,4-oxadiazol-5-yl)-5-[(piperidino)carbonyl]imidazo[1,5-a]quinoxaline, 3-(5-ethyl-1,2,4-oxadiazol-3-yl)-4,5-dihydro-5-[(piperidino)carbonyl]imidazo[1,5-a]quinoxaline, tert-butyl 4,5-dihydro-4,4-dimethyl-5-[(piperidino)carbonyl]imidazo[1,5-a]quinoxaline-3-carboxylate, 4,5-dihydro-3-(5-isopropyl-1,2,4-oxadiazol-3-yl)4,4-dimethyl-5-[(piperidino)carbonyl]-imidazo[1,5-a]quinoxaline, tert-butyl 5-[(dimethylamino)carbonyl]-4,5-dihydro-7-methylimidazo[1,5-a]quinoxaline-3-carboxylate, 5-[(dimethylamino)carbonyl]-4,5-dihydro-3-(5-isopropyl-1,2,4-oxadiazol-3-yl)-7-methylimidazo[1,5-a]quinoxaline, tert-butyl 4,5-dihydro-7-methyl-5-[(pyrrolidino)carbonyl]imidazo[1,5-a]quinoxaline-3-carboxylate, 4,5-dihydro-3-(5-isopropyl-1,2,4-oxadiazol-3-yl)-7-methyl-5-[(pyrrolidino)carbonyl]-imidazo[1,5-a]quinoxaline, 3-(5-tert-butyl-1,2,4-oxadiazol-3-yl)-5-[(dimethylamino)carbonyl]-4,5-dihydroimidazo[1,5-a]quinoxaline, 3-(5-tert-butyl-1,2,4-oxadiazol-3-yl)-5-[(dimethylamino)carbonyl]4,5-dihydro4,4-dimethylimidazo[1,5-a]quinoxaline, tert-butyl 4,5-dihydro-4,4-dimethyl-5-[(pyrrolidino)carbonyl]imidazo[1,5-a]quinoxaline-3-carboxylate, tert-butyl 5-[(dimethylamino)carbonyl]-4,5-dihydro-4,4-dimethylimidazo[1,5-a]quinoxaline-3-carboxylate, 4,5-dihydro-3-(5-isopropyl-1,2,4-oxadiazol-3-yl)-4,4-dimethyl-5-[(pyrrolidino)carbonyl]-imidazo[1,5-a]quinoxaline, 5-[(dimethylamino)carbonyl]-4,5-dihydro-3-(5-isopropyl-1,2,4-oxadiazol-3-yl)4,4-dimethylimidazo[1,5-a]quinoxaline, tert-butyl 4,5-dihydro-5-[(pyrrolidino)carbonyl]imidazo[1,5-a]quinoxaline-3-carboxylate, tert-butyl 5-[(dimethylamino)carbonyl]-4,5-dihydroimidazo[1,5-a]quinoxaline-3-carboxylate, 5-[(dimethylamino)carbonyl]-4,5-dihydro-3-(5-isopropyl-1,2,4-oxadiazol-3-yl)imidazo 1,5-a]quinoxaline, 4,5-dihydro-4,4-dimethyl-5-[(pyrrolidino)carbonyl]-3-(p-tolyl)imidazo[1,5-a]quinoxaline, 5-[(dimethylamino)carbonyl]-4,5-dihydro-4,4-dimethyl-3-(p-tolyl)imidazo[1,5-a]quinoxaline, 3-(4-fluorophenyl)-4,5-dihydro-4,4-dimethyl-5-[(pyrrolidino)carbonyl]imidazo[1,5-a]quinoxaline, 5-[(dimethylamino)carbonyl]-3-(4-fluorophenyl)-4,5-dihydro-4,4-dimethylimidazo[1,5-a]quinoxaline, 4,5-dihydro-3-phenyl-5-[(pyrrolidino)carbonyl]imidazo[1,5-a]quinoxaline, 4,5-dihydro-3-(5-isopropyl-1,2,4-oxadiazol-3-yl)-5-[(pyrrolidino)carbonyl]imidazo[1,5-a]quinoxaline, 5-[(dimethylamino)carbonyl]-4,5-dihydro-3-(3-isopropyl-1,2,4-oxadiazol-5-yl) imidazo[1,5-a]quinoxaline, 5-[(dimethylamino)carbonyl]-4,5-dihydro-3-(3-isopropyl-1,2,4-oxadiazol-5-yl) -4,4-dimethylimidazo[1,5-a]quinoxaline, 5-[(dimethylamino)carbonyl]-4,5-dihydro-4,4-dimethyl-3-phenylimidazo[1,5-a]quinoxaline, 6-chloro-5-[(dimethylamino)carbonyl]-4,5-dihydro-4,4-dimethyl-3-phenylimidazo[1,5-a]quinoxaline, 7-chloro-4,5-dihydro-4,4-dimethyl-3-phenyl-5-[(pyrrolidino)carbonyl]imidazo[1,5-a]quinoxaline, 7-chloro-5-[(dimethylamino)carbonyl]-4,5-dihydro-4,4-dimethyl-3-phenylimidazo[1,5-a]quinoxaline, tert-butyl 4,5-dihydro-6-methyl-5-[(pyrrolidino)carbonyl]imidazo[1,5-a]quinoxaline-3-carboxylate, 4,5-dihydro-3-(5-isopropyl-1,2,4-oxadiazol-3-yl)-6-methyl-5-[(pyrrolidino)carbonyl]-imidazo[1,5-a]quinoxaline, tert-butyl 5-[(dimethylamino)carbonyl]-4,5-dihydro-6-methylimidazo[1,5-a]quinoxaline-3-carboxylate, 5-[(dimethylamino)carbonyl]-4,5-dihydro-3-(5-isopropyl-1,2,4-oxadiazol-3-yl)-6-methylimidazo[1,5-a]quinoxaline, 3-(5-tert-butyl-1,2,4-oxadiazol-3-yl)4,5-dihydro-5-[(pyrrolidino)carbonyl]imidazo[1,5-a]quinoxaline, 3-(5-tert-butyl-1,2,4-oxadiazol-3-yl)-4,5-dihydro-4,4-dimethyl-5-[(pyrrolidino)carbonyl]imidazo[1,5-a]quinoxaline, 3-(5-tert-butyl-1,2,4-oxadiazol-3-yl)-7-chloro4,5-dihydro-5-[(pyrrolidino)carbonyl]-imidazo[1,5-a]quinoxaline, 3-(5-tert-butyl-1,2,4-oxadiazol-3-yl)-7-chloro-5-[(dimethylamino)carbonyl]4,5-dihydroimidazo[1,5-a]quinoxaline, 3-(5-tert-butyl-1,2,4-oxadiazol-3-yl)-7-chloro-5-[(dimethylamino)carbonyl]-4,5-dihydro-4,4-dimethylimidazo[1,5-a]quinoxaline, 3-(5-tert-butyl-1,2,4-oxadiazol-3-yl)-6-chloro-4,5-dihydro-4,4-dimethyl-5-[(pyrrolidino)-carbonyl]imidazo[1,5-a]quinoxaline, 3-(5-tert-butyl-1,2,4-oxadiazol-3-yl)-6-chloro-5-[(dimethylamino)carbonyl]4,5-dihydro-4,4-dimethylimidazo[1,5-a]quinoxaline, 3-(5-tert-butyl-1,2,4-oxadiazol-3-yl)-6-chloro-4,5-dihydro-5-[(pyrrolidino)carbonyl]-imidazo[1,5-a]quinoxaline, 3-(5-tert-butyl-1,2,4-oxadiazol-3-yl)-6-chloro-5-[(dimethylamino)carbonyl]4,5-dihydroimidazo[1,5-a]quinoxaline, 3-(4-fluorophenyl)-4,5-dihydro-5-[(pyrrolidino)carbonyl]imidazo[1,5-a]quinoxaline, 5-[(dimethylamino)carbonyl]-3-(4-fluorophenyl)-4,5-dihydroimidazo[1,5-a]quinoxaline, 5-[(dimethylamino)carbonyl]-4,5-dihydro-3-phenylimidazo[1,5-a]quinoxaline, 4,5-dihydro-3-phenyl-5-[(piperidino)carbonyl]imidazo[1,5-a]quinoxaline, 4,5-dihydro-5-[(pyrrolidino)carbonyl]-3-(p-tolyl)imidazo[1,5-a]quinoxaline, 5-benzoyl-3-(3-cyclopropyl-1,2,4-oxadiazol-5-yl)-4,5-dihydroimidazo[1,5-a]quinoxaline, 3-(3-cyclopropyl-1,2,4-oxadiazol-5-yl)-4,5-dihydro-5-propionylimidazo[1,5-α]quinoxaline, 3-(3-cyclopropyl-1,2,4-oxadiazol-5-yl)-4,5-dihydro-5-(phenoxycarbonyl)imidazo[1,5-a]quinoxaline, 3-(3-cyclopropyl-1,2,4-oxadiazol-5-yl)-4,5-dihydro-5-(ethoxycarbonyl)imidazo[1,5-a]quinoxaline, 3-(3-cyclopropyl-1,2,4-oxadiazol-5-yl)-5-[(diethylamino)carbonyl]-4,5-dihydroimidazo[1,2-a]quinoxaline, 3-(3-cyclopropyl-1,2,4-oxadiazol-5-yl)-4,5-dihydro-5-(2-furoyl)imidazo[1,5-a]-quinoxaline, tert-butylamino 7-fluoro-4,5-dihydro-4,4-dimethyl-5-[(pyrrolidino)carbonyl]imidazo[1,5-a]quinoxaline-3-carboxamide, 4,5-dihydro-3-[5-[1-(2-methylpropyl)]-1,2,4-oxadiazol-3-yl]-5-[(pyrrolidino)carbonyl]imidazo[1,5-a]quinoxaline, tert-butylamino 7-fluoro-4,5-dihydro-5-[(pyrrolidino)carbonyl]imidazo[1,5-a]-quinoxaline-3-carboxamide, 4,5-dihydro-5-[(pyrrolidino)carbonyl]-3-[5-(3,3,3-trifluoropropyl)-1,2,4-oxadiazol-3-yl]imidazo[1,5-a]quinoxaline, 7-fluoro-4,5-dihydro-3-[5-(2-methylpropyl)-1,2,4-oxadiazol-3-yl]-5-(pyrrolidino)carbonyl]imidazo[1,5-a]quinoxaline, 7-fluoro-4,5-dihydro-3-[5-(2-methyl-3,3,3-trifluoropropyl)-1,2,4-oxadiazol-3-yl]-5-(pyrrolidino)carbonyl]imidazo[1,5-a]quinoxaline, 4,5-dihydro-3-[5-(2-methyl-3,3,3-trifluoropropyl)-1,2,4-oxadiazol-3-yl]-5-(pyrrolidino)carbonyl]imidazo[1,5-a]quinoxaline, 4,5-dihydro-3-[5-(2-methyl-3,3,3-trifluoropropyl)-1,2,4-oxadiazol-3-yl]-5-(morpholino)carbonylmethyl]imidazo[1,5-a]quinoxaline, 3-[5-(cyclopentyl)-1,2,4-oxadiazol-3-yl]-7-fluoro-4,5-dihydro-4(R)-methyl-5-[(morpholino)carbonylmethyl]imidazo[1,5-a]quinoxaline, 7-fluoro-4,5-dihydro-3-(5-isopropyl-1,2,4-oxadiazol-3-yl)-4(R)-methyl-5-[(pyrrolidino)carbonyl]imidazo[1,5-a]quinoxaline, 3-(5-cyclopentyl-1,2,4-oxadiazol-3-yl)-7-fluoro-4,5-dihydro-4(R)-methyl-5-[2-(morpholino)acetyl]imidazo[1,5-a]quinoxaline, 3-(5-cyclopentyl-1,2,4-oxadiazol-3-yl)-7-fluoro-4,5-dihydro-4(R)-methyl-5-[(piperidino)carbonylmethyl]imidazo[1,5-a]quinoxaline, tert-butyl 7-fluoro-4,5-dihydro-4CR)-methyl-5-[(pyrrolidino)carbonyl]imidazo[1,5-a]quinoxaline-3-carboxylate, 3-(5-cyclopentyl-1,2,4-oxadiazol-3-yl)-7-fluoro-4,5-dihydro-4(R)-methyl-5-[2-(pyrrolidino)acetyl]imidazo[1,5-a]quinoxaline, 3-(5-cyclopentyl-1,2,4-oxadiazol-3-yl)-7-fluoro-4,5-dihydro-4CR)-methyl-5-[(pyrrolidino)carbonylmethyl]imidazo[1,5-a]quinoxaline, 5-benzoyl-4,5-dihydro-3-[5-[(1,1-dimethyl)ethyl]-1,2,4-oxadiazol-3-yl]imidazo[1,5-a]quinoxaline, 5-benzoyl-4,5-dihydro-3-[5-[(1,1-dimethyl)ethyl]-1,2,4-oxadiazol-3-yl]-7-fluoroimidazo[1,5-a]quinoxaline, tert-butyl 5-benzoyl-4,5-dihydroimidazo[1,5-a]quinoxaline-3-carboxylate, tert-butyl 5-benzoyl-4,5-dihydro-7-fluoroimidazo[1,5-a]quinoxaline-3-carboxylate, tert-butyl 5-(2-chlorobenzoyl)-4,5-dihydro-7-fluoroimidazo[1,5-a]quinoxaline-3-carboxylate, tert-butyl 4,5-dihydro-6-fluoro-5-[(tert-butyloxy)carbonyl]imidazo[1,5-a]quinoxalin-3-carboxylate, 5-[(tert-butyloxy)carbonyl]-4,5-dihydro-3-[(1,1-dimethyl)ethyl-1,2,4-oxadiazol-3-yl]imidazo[1,5-a]quinoxaline, 5-[(tert-butyloxy)carbonyl]-4,5-dihydro-3-[(1,1-dimethyl)ethyl-1,2,4-oxadiazol-3-yl]-6-fluoroimidazo[1,5-a]quinoxaline, 4,5-dihydro-5-methoxycarbonyl-3-(benzoxazol-2-yl)imidazo[1,5-a]quinoxaline, tert-butyl 4,5-dihydro-4,4-dimethyl-7-fluoro-5-methoxycarbonylimidazo[1,5-a]-quinoxalin-3-carboxylate, tert-butyl 4,5-dihydro-4,4-dimethyl-5-[(1-methyl)ethoxycarbonylimidazo[1,5-a]quinoxalin-3-carboxylate, tert-butyl 4,5-dihydro-6-fluoro-5-methoxycarbonylimidazo[1,5-a]quinoxalin-3-carboxylate, 4,5-dihydro-3-[5-[(1,1-dimethyl)ethyl]-1,2,4-oxadiazol-3-yl]-5-[(morpholino)carbonyl]imidazo[1,5-a]quinoxaline, 4,5-dihydro-4,4-dimethyl-3-[5-[(1,1-dimethyl)ethyl]-1,2,4-oxadiazol-3-yl]-7-fluoro-5-(pyrrolidino)carbonyl]imidazo[1,5-a]quinoxaline, -5-[[4-(tert-butyloxycarbonyl)piperazinolcarbonyl]4,5-dihydro-3-[5-[(1,1-dimethyl)ethyl]-1,2,4-oxadiazol-3-yl]imidazo[1,5-a]quinoxaline, tert-butyl 5-[[4-(tert-butyloxycarbonyl)piperazino]carbonyl]4,5-dihydroimidazo[1,5-a]quinoxaline-3-carboxylate, tert-butyl 4,5-dihydro-4,4-dimethyl-5-[(morpholino)carbonyl]imidazo[1,5-a]quinoxaline-3-carboxylate, 4,5-dihydro-5-[(pyrrolidino)carbonyl]imidazo[1,5-a]quinoxaline-3-carboxylic acid, phenyl 4,5-dihydro-5-[(pyrrolidino)carbonyl]imidazo[1,5-a]quinoxaline-3-carboxylate, N-(cyanomethyl)-4,5-dihydro-5-[(pyrrolidino)carbonyl]imidazo[1,5-a]quinoxaline-3-carboxamide, 4,5-dihydro-3-(oxazolin-2-yl)-5-[(pyrrolidino)carbonyl]imidazo[1,5-a]quinoxaline, 4,5-dihydro-3-(hydroxymethyl)imidazo[1,5-a]quinoxaline, 4,5-dihydro-3-(isopropyloxymethyl)-5-(pyrrolidinyl)carbonyl]imidazo[1,5-a]quinoxaline, 3-(5-cyclopropyl-1,2,4-oxadiazol-3-yl)-7-fluoro-4,5-dihydro-4(R)-methyl-5-(pyrrolidino)carbonyl]-imidazo[1,5-a]quinoxaline, 7-fluoro-4,5-dihydro-4(R)-methyl-3-[5-(1-methylcyclopropyl-1,2,4-oxadiazol-3-yl)-5-(pyrrolidino)carbonyl]imidazo[1,5-a]quinoxaline, 3-[3-cyclopropyl-1,2,4-oxadiazol-5-yl]-7-fluoro4,5-dihydro-4-(morpholinylcarbonyl) imidazo[1,5-a]quinoxaline, 3-(4-cyclopropylthiazol-2-yl)-4,5-dihydro-5-(morpholinylcarbonyl)imidazo[1,5-a]quinoxaline, 3-(benzoxazol-2-yl)-4,5-dihydro-5-(morpholinylcarbonyl)imidazo[1,5-a]quinoxaline, 3-(5-cyclopropyl-1,2,4-oxadiazol-3-yl)-6-fluoro-4,5-dihydro-5-(morpholinylcarbonyl) imidazo[1,5-a]quinoxaline, 3-tert-butyl 5-methyl-7-fluoro-4,5-dihydroimidazo[1,5-a]quinoxaline-3,5(4H)-dicarboxylate, 3-(5-Cyclopropyl-1,2,4-oxadiazol-3-yl)-5-[(3,5-dimethyl)morpholinylcarbonyl]-7-fluoro-4,5-dihydroimidazo[1,5-a]quinoxaline, 3-(5-tert-butyl-1,2,4-oxadiazol-3-yl)-4,5-dihydro-6-methyl-5-[(pyrrolidino)carbonyl]-imidazo[1,5-a]quinoxaline, 3-(5-tert-butyl-1,2,4-oxadiazol-3-yl)-4,5-dihydro-5-(piperidinylcarbonyl)imidazo[1,5-a]quinoxaline, 3-(5-tert-butyl-1,2,4-oxadiazol-3-yl)-5-(3-fluorobenzoyl)-4,5-dihydroimidazo[1,5-a]quinoxaline, methyl 3-(5-tert-butyl-1,2,4-oxadiazol-3-yl)-4,5-dihydroimidazo[1,5-a]quinoxaline-5-carboxylate, methyl 3-(5-tert-butyl-1,2,4-oxadiazol-3-yl)-7-chloro-4,5-dihydroimidazo[1,5-a]-quinoxaline-5-carboxylate, 3-(5-tert-butyl-1,2,4-oxadiazol-3-yl)-5-benzoyl-4,5-dihydroimidazo[1,5-a]quinoxaline, methyl 3-(5-tert-butyl-1,2,4-oxadiazol-3-yl)-7-chloro-4,4-dimethylimidazo[1,5-a]quinoxaline-5-carboxylate, 3-(5-tert-butyl-1,2,4-oxadiazol-3-yl)-7-chloro-4,4-dimethyl-5-(4-morpholinylcarbonyl) imidazo[1,5-a]quinoxaline, 3-(5-tert.-butyl-1,2,4-oxadiazol-3-yl)-6-chloro-4,4-dimethyl-5-(4-morpholinylcarbonyl) imidazo[1,5-a]quinoxaline, 3-(3-tert-butyl-1,2,4-oxadiazol-5-yl)-4,5-dihydro-5-(pyrrolidinocarbonyl)imidazo[1,5-a]quinoxaline, 3-(5-tert-butyl-1,2,4-oxadiazol-3-yl)-4,5-dihydro-5-(4-nitrobenzoyl)imidazo[1,5-a]quinoxaline, 3-(5-tert-butyl-1,2,4-oxadiazol-3-yl)-5-(4-fluorobenzoyl)-4,5-dihydroimidazo[1,5-a]quinoxaline, 3-(5-tert-butyl-1,2,4-oxadiazol-3-yl)-5-(3-chlorobenzoyl)-4,5-dihydroimidazo[1,5-a]quinoxaline, 3-(5-tert-butyl-1,2,4-oxadiazol-3-yl)-5-(2-fluorobenzoyl)-4,5-dihydroimidazo[1,5-a]quinoxaline, 4,5-dihydro-5-dimethylamino-3-(4-methylphenyl)imidazo[1,5-a]quinoxaline, 3-(4-fluorophenyl)-4,5-dihydro-5-(4-morpholinocarbonyl)imidazo[1,5-a]quinoxaline, 3-(4-fluorophenyl)-5-(3-fluorobenzoyl)-4,5-dihydroimidazo[1,5-a]quinoxaline, methyl 3-(4-fluorophenyl)-4,5-dihydroimidazo[1,5-a]quinoxaline-5-carboxylate, 5-(tert-butylaminocarbonyl)-3-(4-fluorophenyl)-4,5-dihydroimidazo[1,5-a]quinoxaline, 3-(4-fluorophenyl)-4,5-dihydro-5-(4-trifluoromethylbenzoyl)imidazo[1,5-a]quinoxaline, 5-(aminocarbonyl)-3-(4-fluorophenyl)-4,5-dihydroimidazo[1,5-a]quinoxaline, 5-(ethylaminocarbonyl)-3-(4-fluorophenyl)-4,5-dihydroimidazo[1,5-a]quinoxaline, isopropyl 3-(4-fluorophenyl)-4,5-dihydroimidazo[1,5-a]quinoxaline-5-carboxylate, 3-(4-fluorophenyl)-5-(4-fluorobenzoyl)-4,5-dihydroimidazo[1,5-a]quinoxaline, tert-butyl 7-chloro-4,5-dihydro-5-[(methoxy)carbonyl]-4,4-dimethylimidazo[1,5-a]quinoxaline-3-carboxylate, tert-butyl 5-benzoyl-7-chloro-4,5-dihydroimidazo[1,5-a]quinoxaline-3-carboxylate, tert-butyl 7-chloro-4,5-dihydro-5-[(methoxy)carbonyl]imidazo[1,5-a]quinoxaline-3-carboxylate, tert-butyl 4,5-dihydro-5-[(4-trifluoromethyl)benzoyl]imidazo[1,5-a]quinoxaline-3-carboxylate, tert-butyl 5-[(4-dimethylamino)benzoyl]-4,5-dihydroimidazo[1,5-a]quinoxaline-3-carboxylate, tert-butyl 5-benzoyl-4,5-dihydro-4,4-dimethylimidazo[1,5-a]quinoxaline-3-carboxylate, tert-butyl 4,5-dihydro-5-[(isopropoxy)carbonyl]imidazo[1,5-a]quinoxaline-3-carboxylate, tert-butyl 7-chloro-4,5-dihydro-4,4-dimethyl-5-[(morpholino)carbonyl]imidazo[1,5-a]quinoxaline-3-carboxylate, tert-butyl 4,5-dihydro-5-[(methoxy)carbonyl]-4,4-dimethylimidazo[1,5-a]quinoxaline-3-carboxylate, tert-butyl 5-[(tert-butyloxy)carbonyl]-7-chloro-4,5-dihydro-4,4-dimethylimidazo[1,5-a]quinoxaline-3-carboxylate, 3-(3-tert-butyl-5-isoxazolyl)-4,5-dihydro-5-[(pyrrolidino)carbonyl]imidazo[1,5-a]quinoxaline, tert-butyl 6-chloro-4,5-dihydro-5-[(methoxy)carbonyl]imidazo[1,5-a]quinoxaline-3-carboxylate, tert-butyl 5-benzoyl-7-chloro-4,5-dihydro-4,4-dimethylimidazo[1,5-a]quinoxaline-3-carboxylate, tert-butyl 5-[(3-fluoro)benzoyl]-4,5-dihydro-4,4-dimethylimidazo[1,5-a]quinoxaline-3-carboxylate, tert-butyl 5-[(3-fluoro)benzoyl]-7-chloro-4,5-dihydro-4,4-dimethylimidazo[1,5-a]quinoxaline-3-carboxylate, tert-butyl 6-chloro-4,5-dihydro-4,4-dimethyl-5-[(morpholino)carbonyl]imidazo[1,5-a]quinoxaline-3-carboxylate, tert-butyl 6-chloro-4,5-dihydro-5-[(methoxy)carbonyl]-4,4-dimethylimidazo[1,5-a]quinoxaline-3-carboxylate, tert-butyl 7-chloro-4,5-dihydro-5-[(isopropoxy)carbonyl]-4,4-dimethylimidazo[1,5-a]quinoxaline-3-carboxylate, tert-butyl 7-chloro-5-[(4-dimethylamino)benzoyl]-4,5-dihydroimidazo[1,5-a]quinoxaline-3-carboxylate, tert-butyl 7-chloro-4,5-dihydro-4,4-dimethyl-5-[(3,5-dimethylmorpholino)carbonyl]imidazo[1,5-a]quinoxaline-3-carboxylate, 7-chloro-3-(5-cyclopropyl-1,2,4-oxadiazol-3-yl)-4,5-dihydro-5-[(morpholino)carbonyl]imidazo[1,5-a]quinoxaline, 7-chloro-3-(3-cyclopropyl-1,2,4-oxadiazol-5-yl)-4,5dihydro-5-[(morpholino)carbonyl]imidazo[1,5-a]quinoxaline, 7-chloro-3-(5-cyclopropyl-1,2,4-oxadiazol-3-yl)4,5-dihydro-5-[(1-(4 -methyl)piperazino)carbonyl]imidazo[1,5-a]quinoxaline, 7-chloro-3-(5-cyclopropyl-1,2,4-oxadiazol-3-yl)-4,5-dihydro-5-[(4-(3,5 -dimethyl)morpholino)carbonyl]imidazo[1,5-a]quinoxaline, 7-chloro-3-(3-cyclopropyl-1,2,4-oxadiazol-5-yl)-4,5-dihydro-5-[(1-(4 -methyl)piperazino)carbonyl]imidazo[1,5-a]quinoxaline, 7-chloro-3-(3-cyclopropyl-1,2,4-oxadiazol-5-yl)-4,5-dihydro-5-[(isopropoxy)carbonyl]imidazo[1,5-a]quinoxaline, tert-butyl 5-[(ethylamino)carbonyl]-4,5-dihydroimidazo[1,5-a]quinoxaline-3-carboxylate, tert-butyl 5-[(tert-butylamino)carbonyl]-4,5-dihydroimidazo[1,5-a]quinoxaline-3-carboxylate, tert-butyl 5-carbamoyl-4,5-dihydro-4,4-dimethylimidazo[1,5-a]quinoxaline-3-carboxylate, tert-butyl 5-[(tert-butylamino)carbonyl]-4,5-dihydro-4,4-dimethylimidazo[1,5-a]-quinoxaline-3-carboxylate, tert-butyl 5-[(ethylamino)carbonyl]-4,5-dihydro-4,4-dimethylimidazo[1,5-a]quinoxaline-3-carboxylate, tert-butyl 5-carbamoyl-7-chloro-4,5-dihydro-4,4-dimethylimidazo[1,5-a]quinoxaline-3-carboxylate, tert-butyl 7-chloro-5-[(ethylamino)carbonyl]-4,5-dihydro-4,4-dimethylimidazo[1,5 -a]quinoxaline-3-carboxylate, 3-(5-cyclopropyl-1,2,4-oxadiazol-3-yl)-4,5-dihydro-5-[(2-(4-morpholinyl)ethylamino) carbonyl]imidazo[1,5-a]quinoxaline, 3-(5-cyclopropyl-1,2,4-oxadiazol-3-yl)-5-[(2-(diethylamino)ethylamino)carbonyl]-4,5 -dihydroimidazo[1,5-a]quinoxaline, 3-(5-cyclopropyl-1,2,4-oxadiazol-3-yl)-4,5-dihydro-5-[(2-(methoxy)ethylamino)carbonyl]-imidazo[1,5-a]quinoxaline, 3-(5-cyclopropyl-1,2,4-oxadiazol-3-yl)4,5-dihydro-5-[(1-(3 ,5-dimethyl)piperazino) carbonyl]imidazo[1,5-a]quinoxaline, 3-(5-cyclopropyl-1,2,4-oxadiazol-3-yl)-4,5-dihydro-5-[(2-methoxyethoxy)carbonyl]imidazo[1,5-a]quinoxaline, 7-chloro-3-(5-cyclopropyl-1,2,4-oxadiazol-3-yl)-5-[(ethylamino)carbonyl]4,5-dihydro -imidazo[1,5-a]quinoxaline, 5-(carbamoyl)-7-chloro-3-(5-cyclopropyl-1,2,4-oxadiazol-3-yl)4,5-dihydroimidazo[1,5 -a]quinoxaline, 3-(3-cyclopropyl-1,2,4-oxadiazol-5-yl)-4,5-dihydro-5-[(isopropoxy)carbonyl]-7 -methylimidazo[1,5-a]quinoxaline, 3-(3-cyclopropyl-1,2,4-oxadiazol-5-yl)-4,5-dihydro-7-methyl-5-[(morpholino)carbonyl]-imidazo[1,5-a]quinoxaline, 3-(3-cyclopropyl-1,2,4-oxadiazol-5-yl)-4,5-dihydro-5-[(1-(3,5-dimethyl)piperazino) carbonyl]-7-methylimidazo[1,5-a]quinoxaline, 5-(carbamoyl)-3-(3-cyclopropyl-1,2,4-oxadiazol-5-yl)4,5-dihydro-7-methylimidazo[1,5 -a]quinoxaline, 3-(5-cyclopropyl-1,2,4-oxadiazol-3-yl)-4,5-dihydro-5-[(1-(3,4,5-trimethyl)piperazino) -carbonyl]imidazo[1,5-a]quinoxaline, 3-(5-cyclopropyl-1,2,4-oxadiazol-3-yl)-4,5-dihydro-5-[((2-dimethylamino)ethoxy) carbonyl]imidazo[1,5-a]quinoxaline, 3-(3-cyclopropyl-1,2,4-oxadiazol-5-yl)-5-[(ethylamino)carbonyl]-4,5-dihydro-7 -methylimidazo[1,5-a]quinoxaline, 3-(3-cyclopropyl-1,2,4-oxadiazol-5-yl)-4,5-dihydro-7-methyl-5-[(1-(4-methyl) piperazino)carbonyl]imidazo[1,5-a]quinoxaline, 7-chloro-3-(3-cyclopropyl-1,2,4-oxadiazol-5-yl)4,5-dihydro-5-[(1-(3,5 -dimethyl)piperazino)carbonyl]imidazo[1,5-a]quinoxaline, 3-(5-cyclopropyl-1,2,4-oxadiazol-3-yl)-4,5-dihydro-6-methyl-5 -(morpholino)carbonylimidazo[1,5-a]quinoxaline, 3-(5-cyclopropyl-1,2,4-oxadiazol-3-yl)-4,5-dihydro-6-methyl-5-[(1-(4 -methyl)piperazino)carbonyl]imidazo[1,5-a]quinoxaline, 7-chloro-3-(3-cyclopropyl-1,2,4-oxadiazol-5-yl)-4,5-dihydro-5-[(1-(3,4,5 -trimethyl)piperazino)carbonyl]imidazo[1,5-a]quinoxaline, 5-[(2-fluoro)benzoyl]-3-(4-fluorophenyl)-4,5-dihydroimidazo[1,5-a]quinoxaline, 3-(4-fluorophenyl)-4,5-dihydro-5-[(3-trifluoromethyl)benzoyl]imidazo[1,5-a]quinoxaline, 7-fluoro-3-(4-fluorophenyl)-4,5-dihydro-5-[(morpholino)carbonyl]imidazo[1,5 -a]quinoxaline, 7-chloro-3-(4-fluorophenyl)-4,5-dihydro-5-[(morpholino)carbonyl]imidazo[1,5 -a]quinoxaline, 3-(5-cyclopropyl-1,2,4-oxadiazol-3-yl)-7-fluoro-4,5-dihydro-5-[bis-(2 -methoxyethyl)aminocarbonyl]imidazo[1,5-a]quinoxaline, tert-butyl 7-fluoro-4,4-dimethyl-5-(morpholino)carbonylimidazo[1,5-a]quinoxaline-3-carboxylate, tert-butyl 7-fluoro-5-[bis(2-methoxyethyl)aminocarbonyl]-4,4-dimethylimidazo[1,5 -a]quinoxaline-3-carboxylate, tert-butyl 7-fluoro-4,5-dihydro-5-(isopropyloxycarbonyl)imidazo[1,5-a]quinoxaline-3-carboxylate, 3-(3-cyclopropyl-1,2,4-oxadiazol-5-yl) -7-fluoro-4,5-dihydro-5-(isopropyloxycarbonyl) imidazo[1,5-a]quinoxaline, 3-(5-cyclopropyl-1,2,4-oxadiazol-3-yl)-7-fluoro-4,5-dihydro-5-(piperazinylcarbonyl) imidazo[1,5-a]quinoxaline, 3-(5-cyclopropyl-1,2,4-oxadiazol-3-yl)-6-fluoro4,5-dihydro-5 -(piperazinylcarbonyl)imidazo[1,5-a]quinoxaline, t-butyl 7-fluoro-4,5-dihydro-5-(morpholinocarbonyl)imidazo[1,5-a]quinoxaline-3-carboxylate, 3-(3-cyclopropyl-1,2,4-oxadiazol-5-yl)-4,5-dihydro-5-[(1-(4-methyl)piperazino)carbonyl]imidazo[1,5-a]quinoxaline, 3-(3-cyclopropyl-1,2,4-oxadiazol-5-yl)-7-fluoro-4,5-dihydro-5-[(1-(4-methyl) piperazino)carbonyl]imidazo[1,5-a]quinoxaline, 3-(3-cyclopropyl-1,2,4-oxadiazol-5-yl)-6-fluoro-4,5-dihydro-5-[(1-(4 -methyl)piperazino)carbonyl]imidazo[1,5-a]quinoxaline, 3-(3-cyclopropyl-1,2,4-oxadiazol-5-yl)4,5-dihydro-7-methyl-5-[(1-(4 -methyl)piperazino)carbonyl]imidazo[1,5-a]quinoxaline, 3-(5-cyclopropyl-1,2,4-oxadiazol-3-yl)-4,5-dihydro-5-[(1-(4 -methyl)piperazino)carbonyl]imidazo[1,5-a]quinoxaline, 3-(5-cyclopropyl-1,2,4-oxadiazol-3-yl)-7-fluoro-4,5-dihydro-5-[(1-(4 -methyl)piperazino)carbonyl]imidazo[1,5-a]quinoxaline, 3-(5-cyclopropyl-1,2,4-oxadiazol-3-yl)-6-fluoro-4,5-dihydro-5-[(1-(4 -methyl)piperazino)carbonyl]imidazo[1,5-a]quinoxaline, 3-(5-cyclopropyl-1,2,4-oxadiazol-3-yl)-4,5-dihydro-7-methyl-5-[(1-(4 -methyl)piperazino)carbonyl]imidazo[1,5-a]quinoxaline, 3-(4-fluorophenyl)-4,5-dihydro-5-[(1-(4-methyl)piperazino)carbonyl]imidazo[1,5 -a]quinoxaline, 7-chloro-3-(4-fluorophenyl)-4,5-dihydro-5-[(1-(4-methyl)piperazino)carbonyl]-imidazo[1,5-a]quinoxaline, 7-fluoro-3-(4-fluorophenyl)-4,5-dihydro-5-[(1-(4-methyl)piperazino)carbonyl]imidazo[1,5-a]quinoxaline, 3-(4-fluorophenyl)-4,5-dihydro-7-methyl-5-[(1-(4-methyl)piperazino)carbonyl]imidazo [1,5-a]quinoxaline, 3-(4-cyclopropylthiazol-2-yl)4,5-dihydro-5-[(1-(4-methyl)piperazino)carbonyl]imidazo [1,5-a]quinoxaline, 7-chloro-3-(4-cyclopropylthiazol-2-yl)-4,5-dihydro-5-[(1-(4-methyl)piperazino) carbonyl]imidazo[1,5-a]quinoxaline, 3-(4-cyclopropylthiazol-2-yl-7-fluoro-4,5-dihydro-5-[(1-(4-methyl)piperazino)carbonyl]imidazo[1,5-a]quinoxaline, 3-(4-cyclopropylthiazol-2-yl)-6-fluoro-4,5-dihydro-5-[(1-(4-methyl)piperazino)carbonyl ]imidazo[1,5-a]quinoxaline, 3-(4-cyclopropyl thiazol-2-yl)-4,5-dihydro-7-methyl-5-[(1-(4-methyl)piperazino)carbonyl ]imidazo[1,5-a]quinoxaline, 7-chloro-3-(3-cyclopropyl-1,2,4-oxadiazol -5-yl)-4,5-dihydro-5-[(1-(3,4,5 -trimethyl)piperazino)carbonyl]imidazo[1,5-a]quinoxaline, 3-(3-cyclopropyl-1,2,4-oxadiazol-5-yl)-7-fluoro-,4,5-dihydro-5-[(1-(3,4,5 -trimethyl)piperazino)carbonyl]imidazo[1,5-a]quinoxaline, 3-(3-cyclopropyl-1,2,4-oxadiazol-5-yl)-6-fluoro-4,5-dihydro-5-[(1-(3,4,5 -trimethyl)piperazino)carbonyl]imidazo[1,5-a]quinoxaline, 3-(3-cyclopropyl-1,2,4-oxadiazol-5-yl)-4,5-dihydro-7-methyl-5-[(1-(3,4,5 -trimethyl)piperazino)carbonyl]imidazo[1,5-a]quinoxaline, 3-(5-cyclopropyl-1,2,4-oxadiazol-3-yl)-4,5-dihydro-5-[(1-(3,4,5 -trimethyl)piperazino)carbonyl]imidazo[1,5-a]quinoxaline, 3-(5-cyclopropyl-1,2,4-oxadiazol-3-yl)-7-fluoro4,5-dihydro-5-[(1-(3,4,5 -trimethyl)piperazino)carbonyl]imidazo[1,5-a]quinoxaline, 3-(5-cyclopropyl-1,2,4-oxadiazol-3-yl)-6-fluoro4,5-dihydro-5-[(1-(3,4,5 -trimethyl)piperazino)carbonyl]imidazo[1,5-a]quinoxaline, 3-(5-cyclopropyl-1,2,4-oxadiazol-3-yl)4,5-dihydro-7-methyl-5-[(1-(3,4,5 -trimethyl)piperazino)carbonyl]imidazo[1,5-a]quinoxaline, 3-(4-fluorophenyl)-4,5-dihydro-5-[(1-(3,4,5-trimethyl)piperazino)carbonyl]imidazo [1,5-a]quinoxaline, 7(chloro-3-(4-fluorophenyl)-4,5-dihydro-5-[(1-(3,4,5 -trimethyl)piperazino)carbonyl]imidazo[1,5-a]quinoxaline, 7-fluoro-3-(4-fluorophenyl)-4,5-dihydro-5-[(1-(3,4,5 -trimethyl)piperazino)carbonyl]imidazo[1,5-a]quinoxaline, 3-(4-fluorophenyl)-4,5-dihydro-7-methyl-5-[(1-(3,4,5 -trimethyl)piperazino)carbonyl]imidazo[1,5-a]quinoxaline, 3-(4-cyclopropylthiazol-2-yl)4,5-dihydro-5-[(1-(3,4,5 -trimethyl)piperazino)carbonyl]imidazo[1,5-a]quinoxaline, 7-chloro-3-(4-cyclopropylthiazol-2-yl)-4,5-dihydro-5-[(1-(3,4,5 -trimethyl) piperazino)carbonyl]imidazo[1, 5-a]quinoxaline, 3-(4-cyclopropylthiazol-2-yl)-7-fluoro-4,5-dihydro-5-[(1-(3,4,5 -trimethyl)piperazino)carbonyl]imidazo[1,5-a]quinoxaline, 3-(4-cyclopropylthiazol-2-yl )-6-fluoro-4,5-dihydro-5-[(1-(3,4,5 -trimethyl)piperazino)carbonyl]imidazo[1,5-a]quinoxaline, 3-(4-cyclopropylthiazol-2-yl)-4,5-dihydro-7-methyl-5-[(1-(3,4,5 -trimethyl)piperazino)carbonyl]imidazo[1,5-a]quinoxaline, 7-chloro-3-(3-cyclopropyl-1,2,4-oxadiazol-5-yl)4,5-dihydro-5-[(1-(3,5 -dimethyl)piperazino)carbonyl]imidazo[1,5-a]quinoxaline, 3-(3-cyclopropyl-1,2,4-oxadiazol-5-yl)-7-fluoro4,5-dihydro-5-[(1-(3,5 -dimethyl)piperazino)carbonyl]imidazo[1,5-a]quinoxaline, 3-(3-cyclopropyl-1,2,4-oxadiazol-5-yl)-6-fluoro4,5-dihydro-5-[(1-(3,5 -dimethyl)piperazino)carbonyl]imidazo[1,5-a]quinoxaline, 3-(3-cyclopropyl-1,2,4-oxadiazol-5-yl)4,5-dihydro-7-methyl-5-[(1-(3,5 -dimethyl)piperazino)carbonyl]imidazo[1,5-a]quinoxaline, 3-(5-cyclopropyl-1,2,4-oxadiazol-3-yl)-4,5-dihydro-5-[(1-(3,5 -dimethyl)piperazino)carbonyl]imidazo[1,5-a] quinoxaline, 3-(5-cyclopropyl-1,2,4-oxadiazol-3-yl)-7-fluoro-4,5-dihydro-5-[(1-(3,5 -dimethyl)piperazino)carbonyl]imidazo[1,5-a]quinoxaline, 3-(5-cyclopropyl-1,2,4-oxadiazol-3-yl)-6-fluoro4,5-dihydro-5-[(1-(3,5 -dimethyl)piperazino)carbonyl]imidazo [1,5-a]quinoxaline, 3-(4-fluorophenyl)4,5-dihydro-5-[(1-(3,5-dimethyl)piperazino)carbonyl]imidazo [1,5-a]quinoxaline, 7-chloro-3-(4-fluorophenyl)-4,5-dihydro-5-[(1-(3,5 -dimethyl)piperazino)carbonyl]imidazo[1,5-a]quinoxaline, 7-fluoro-3-(4-fluorophenyl)-4,5-dihydro-5-[(1-(3,5 -dimethyl)piperazino)carbonyl]imidazo[1,5-a]quinoxaline, 3-(4-fluorophenyl)4,5-dihydro-7-methyl-5-[(1-(3,5 -dimethyl)piperazino)carbonyl]imidazo[1,5-a]quinoxaline, 3-(4-cyclopropylthiazol-2-yl)-4,5-dihydro-5-[(1-(3,5 -dimethyl)piperazino)caxbonyl]imidazo[1,5-a]quinoxaline, 7-chloro-3-(4-cyclopropylthiazol-2-yl)-4,5-dihydro-5-[(1-(3,5 -dimethyl)piperazino)carbonyl]imidazo[1,5-a] quinoxaline, 3-(4-cyclopropylthiazol-2-yl)-7-fluoro-4,5-dihydro-5-[(1-(3,5-dimethyl)piperazino)carbonyl]imidazo[1,5-a]quinoxaline, 3-(4-cyclopropylthiazol-2-yl)-6-fluoro-4,5-dihydro-5-[(1-(3,5-dimethyl)piperazino)carbonyl]imidazo[1,5-a]quinoxaline, 3-(4-cyclopropylthiazol-2-yl)4,5-dihydro-7-methyl-5-[(1-(3,5-dimethyl)piperazino)carbonyl]imidazo[1,5-a]quinoxaline, 3-(3-cyclopropyl-1,2,4-oxadiazol-5-yl)4,5-dihydro-5-[(1-(2,4,6-trimethyl)piperazino)carbonyl]imidazo[1,5-a]quinoxaline, 7-chloro-3-(3-cyclopropyl-1,2,4-oxadiazol-5-yl)4,5-dihydro-5-[(1-(2,4,6-trimethyl)piperazino)carbonyl]imidazo[1,5-a]quinoxaline, 3-(3-cyclopropyl-1,2,4-oxadiazol-5-yl)-7-fluoro-4,5-dihydro-5-[(1-(2,4,6-trimethyl)piperazino)carbonyl]imidazo[1,5-a]quinoxaline, 3-(3-cyclopropyl-1,2,4-oxadiazol-5-yl)-6-fluoro4,5-dihydro-5-[(1-(2,4,6-trimethyl)piperazino)carbonyl]imidazo[1,5-a]quinoxaline, 3-(3-cyclopropyl-1,2,4-oxadiazol-5-yl)4,5-dihydro-7-methyl-5-[(1-(2,4,6-trimethyl)piperazino)carbonyl]imidazo[1,5-a]quinoxaline, 3-(5-cyclopropyl-1,2,4-oxadiazol-3-yl)4,5-dihydro-5-[(1-(2,4,6-trimethyl)piperazino)carbonyl]imidazo[1,5-a]quinoxaline, 7-chloro-3-(5-cyclopropyl-1,2,4-oxadiazol-3-yl)4,5-dihydro-5-[(1-(2,4,6-trimethyl)piperazino)carbonyl]imidazo[1,5-a]quinoxaline, 3-(5-cyclopropyl-1,2,4-oxadiazol-3-yl)-7-fluoro4,5-dihydro-5-[(1-(2,4,6-trimethyl)piperazino)carbonyl]imidazo[1,5-a]quinoxaline, 3-(5-cyclopropyl-1,2,4-oxadiazol-3-yl)-6-fluoro4,5-dihydro-5-[(1-(2,4,6-trimethyl)piperazino)carbonyl]imidazo[1,5-a]quinoxaline, 3-(5-cyclopropyl-1,2,4-oxadiazol-3-yl)-4,5-dihydro-7-methyl-5-[(1-(2,4,6-trimethyl)piperazino)carbonyl]imidazo[1,5-a]quinoxaline, 3-(4-fluorophenyl)-4,5-dihydro-5-[(1-(2,4,6-trimethyl)piperazino)carbonyl]imidazo 1,5-a]quinoxaline, 7-chloro-3-(4-fluorophenyl)-4,5-dihydro-5-[(1-(2,4,6-trimethyl)piperazino)carbonyl]imidazo[1,5-a]quinoxaline, 7-fluoro-3-(4-fluorophenyl)-4,5-dihydro-5-[(1-(2,4,6-trimethyl)piperazino)carbonyl]imidazo[1,5-a]quinoxaline, 3-(4-fluorophenyl)4,5-dihydro-7-methyl-5-[(1-(2,4,6-trimethyl)piperazino)carbonyl]imidazo[1,5-a]quinoxaline, 3-(4-cyclopropylthiazol-2-yl)4,5-dihydro-5-[(1-(2,4,6-trimethyl)piperazino)carbonyl]imidazo[1,5-a]quinoxaline, 7-chloro-3-(4-cyclopropylthiazol-2-yl)-4,5-dihydro-5-[(1-(2,4,6-trimethyl)piperazino)carbonyl]imidazo[1,5-a]quinoxaline, 3-(4-cyclopropylthiazol-2-yl)-7-fluoro-4,5-dihydro-5-[(1-(2,4,6-trimethyl)piperazino)carbonyl]imidazo[1,5-a]quinoxaline, 3-(4-cyclopropylthiazol-2-yl)-6-fluoro-4,5-dihydro-5-[(1-(2,4,6-trimethyl)piperazino)carbonyl]imidazo[1,5-a]quinoxaline, 3-(4-cyclopropylthiazol-2-yl)4,5-dihydro-7-methyl-5-[(1-(2,4,6-trimethyl)piperazino)carbonyl]imidazo[1,5-a]quinoxaline, 3-(3-cyclopropyl-1,2,4-oxadiazol-5-yl)4,5-dihydro-5-[(1-(2,6-dimethyl)piperazino)carbonyl]imidazo[1,5-a]quinoxaline, 7-chloro-3-(3-cyclopropyl-1,2,4-oxadiazol-5-yl)4,5-dihydro-5-[(1-(2,6-dimethyl)piperazino)carbonyl]imidazo[1,5-a]quinoxaline, 3-(3-cyclopropyl-1,2,4-oxadiazol-5-yl)-7-fluoro-4,5-dihydro-5-[(1-(2,6-dimethyl)piperazino)carbonyl]imidazo[1,5-a]quinoxaline, 3-(3-cyclopropyl-1,2,4-oxadiazol-5-yl)-6-fluoro4,5-dihydro-5-[(1-(2,6-dimethyl)piperazino)carbonyl]imidazo[1,5-a]quinoxaline, 3-(3-cyclopropyl-1,2,4-oxadiazol-5-yl)4,5-dihydro-7-methyl-5-[(1-(2,6-dimethyl)piperazino)carbonyl]imidazo[1,5-a]quinoxaline, 3-(5-cyclopropyl-1,2,4-oxadiazol-3-yl)4,5-dihydro-5-[(1-(2,6-dimethyl)piperazino)carbonyl]imidazo[1,5-a]quinoxaline, 7-chloro-3-(5-cyclopropyl-1,2,4-oxadiazol-3-yl)4,5-dihydro-5-[(1-(2,6-dimethyl)piperazino)carbonyl]imidazo[1,5-a]quinoxaline, 3-(5-cyclopropyl-1,2,4-oxadiazol-3-yl)-7-fluoro4,5-dihydro-5-[(1-(2,6-dimethyl)piperazino)carbonyl]imidazo[1,5-a]quinoxaline, 3-(5-cyclopropyl-1,2,4-oxadiazol-3-yl)-6-fluoro4,5-dihydro-5-[(1-(2,6-dimethyl)piperazino)carbonyl]imidazo[1,5-a]quinoxaline, 3-(5-cyclopropyl-1,2,4-oxadiazol-3-yl)-4,5-dihydro-7-methyl-5-[(1-(2,6-dimethyl)piperazino)carbonyl]imidazo[1,5-a]quinoxaline, 3-(4-fluorophenyl)-4,5-dihydro-5-[(1-(2,6-dimethyl)piperazino)carbonyl]imidazo [1,5-a]quinoxaline, 7-chloro-3-(4-fluorophenyl)-4,5-dihydro-5-[(1-(2,6-dimethyl)piperazino)carbonyl]imidazo[1,5-a]quinoxaline, 7-fluoro-3-(4-fluorophenyl)-4,5-dihydro-5-[(1-(2,6-dimethyl)piperazino)carbonyl]imidazo[1,5-a]quinoxaline, 3-(4-fluorophenyl)-4,5-dihydro-7-methyl-5-[(1-(2,6-dimethyl)piperazino)carbonyl]imidazo[1,5-a]quinoxaline, 3-(4-cyclopropylthiazol-2-yl)4,5-dihydro-5-[(1-(2,6-dimethyl)piperazino)carbonyl]imidazo[1,5-a]quinoxaline, 7-chloro-3-(4-cyclopropylthiazol-2-yl)-4,5-dihydro-5-[(1-(2,6-dimethyl)piperazino)carbonyl]imidazo[1,5-a]quinoxaline, 3-(4-cyclopropylthiazol-2-yl)-7-fluoro-4,5-dihydro-5-[(1-(2,6-dimethyl)piperazino)carbonyl]imidazo[1,5-a]quinoxaline, 3-(4-cyclopropylthiazol-2-yl)-6-fluoro-4,5-dihydro-5-[(1-(2,6-dimethyl)piperazino)carbonyl]imidazo[1,5-a]quinoxaline, 3-(4-cyclopropyl thiazol-2-yl)4,5-dihydro-7-methyl-5-[(1-(2,6-dimethyl)piperazino)carbonyl]imidazo[1,5-a]quinoxaline, tert-butyl 4,5-dihydro-4,4-dimethyl-5-[(1-(3,4,5-trimethyl)piperazino)carbonyl]imidazo[1,5-a]quinoxaline-3-carboxylate, tert-butyl 7-chloro-4,5-dihydro-4,4-dimethyl-5-[(1-(3,4,5-trimethyl)piperazino)carbonyl]imidazo[1,5-a]quinoxaline-3-carboxylate, tert-butyl 7-fluoro-4,5-dihydro4,4-dimethyl-5-[(1-(3,4,5-trimethyl)piperazino)carbonyl]imidazo[1,5-a]quinoxaline-3-carboxylate, tert-butyl 6-fluoro-4,5-dihydro-4,4-dimethyl-5-[(1-(3,4,5-trimethyl)piperazino)carbonyl]imidazo[1,5-a]quinoxaline-3-carboxylate, tert-butyl 4,5-dihydro-7-methyl-4,4-dimethyl-5-[(1-(3,4,5-trimethyl)piperazino)carbonyl]imidazo[1,5-a]quinoxaline-3-carboxylate, tert-butyl 5-[(1-(3,5-dimethyl)piperazino)carbonyl]-4,5-dihydro-4,4-dimethylimidazo[1,5-a]quinoxaline-3-carboxylate, tert-butyl 7-chloro-5-[(1-(3,5-dimethyl)piperazino)carbonyl]4,5-dihydro-4,4-dimethylimidazo[1,5-a]quinoxaline-3-carboxylate, tert-butyl 5-[(1-(3,5-dimethyl)piperazino)carbonyl]-7-fluoro4,5-dihydro-4,4-dimethylimidazo[1,5-a]quinoxaline-3-carboxylate, tert-butyl 5-[(1-(3,5-dimethyl)piperazino)carbonyl]-6-fluoro4,5-dihydro-4,4-dimethylimidazo[1,5-a]quinoxaline-3-carboxylate, tert-butyl 5-[(1-(3,5-dimethyl)piperazino)carbonyl]-4,5-dihydro-7-methyl-4,4-dimethylimidazo[1,5-a]quinoxaline-3-carboxylate, tert-butyl 4,5-dihydro-4,4-dimethyl-5-[(1-(2,4,6-trimethyl)piperazino)carbonyl]imidazo[1,5-a]quinoxaline-3-carboxylate, tert-butyl 7-chloro-4,5-dihydro4,4-dimethyl-5-[(1-(2,4,6-trimethyl)piperazino)carbonyl]imidazo[1,5-a]quinoxaline-3-carboxylate, tert-butyl 7-fluoro-4,5-dihydro-4,4-dimethyl-5-[(1-(2,4,6-trimethyl)piperazino)carbonyl]imidazo[1,5-a]quinoxaline-3-carboxylate, tert-butyl 6-fluoro-4,5-dihydro4,4-dimethyl-5-[(1-(2,4,6-trimethyl)piperazino)carbonyl]imidazo[1,5-a]quinoxaline-3-carboxylate, tert-butyl 4,5-dihydro-7-methyl14,4-dimethyl-5-[(1-(2,4,6-trimethyl)piperazino)carbonyl]imidazo[1,5-a]quinoxaline-3-carboxylate, tert-butyl 5-[(1-(2,6-dimethyl)piperazino)carbonyl]-4,5-dihydro-4,4-dimethylimidazo[1,5-a]quinoxaline-3-carboxylate, tert-butyl 7-chloro-5-[(1-(2,6-dimethyl)piperazino)carbonyl]-4,5-dihydro-4,4-dimethylimidazo[1,5-a]quinoxaline-3-carboxylate, tert-butyl 5-[(1-(2,6-dimethyl)piperazino)carbonyl]-7-fluoro-4,5-dihydro-4,4-dimethylimidazo[1,5-a]quinoxaline-3-carboxylate, tert-butyl 5-[(1-(2,6-dimethyl)piperazino)carbonyl]-6-fluoro-4,5-dihydro-4,4-dimethylimidazo[1,5-a]quinoxaline-3-carboxylate, tert-butyl 5-[(1-(2,6-dimethyl)piperazino)carbonyl]-4,5-dihydro-7-methyl-4,4-dimethylimidazo[1,5-a]quinoxaline-3-carboxylate, tert-butyl 4,5-dihydro-5-[(1-(3,4,5-trimethyl)piperazino)carbonyl]imidazo 1,5-a]quinoxaline-3-carboxylate, tert-butyl 7-chloro-4,5-dihydro-5-[(1-(3,4,5-trimethyl)piperazino)carbonyl]imidazo-[1,5-a]quinoxaline-3-carboxylate, tert-butyl 7-fluoro-4,5-dihydro-5-[(1-(3,4,5-trimethyl)piperazino)carbonyl]imidazo-[1,5-a]quinoxaline-3-carboxylate, tert-butyl 6-fluoro-4,5-dihydro-5-[(1-(3,4,5-trimethyl)piperazino)carbonyl]imidazo-[1,5-a]quinoxaline-3-carboxylate, tert-butyl 4,5-dihydro-7-methyl-5-[(1-(3,4,5-trimethyl)piperazino)carbonyl]imidazo-[1,5-a]quinoxaline-3-carboxylate, tert-butyl 5-[(1-(3,5-dimethyl)piperazino)carbonyl]-4,5-dihydroimidazo-[1,5-a]-quinoxaline-3-carboxylate, tert-butyl 7-chloro-5-[(1-(3,5-dimethyl)piperazino)carbonyl]-4,5-dihydroimidazo-[1,5-a]-quinoxaline-3-carboxylate, tert-butyl 5-[(1-(3,5-dimethyl)piperazino)carbonyl]-7-fluoro-4,5-dihydroimidazo-[1,5-a]-quinoxaline-3-carboxylate, tert-butyl 5-[(1-(3,5-dimethyl)piperazino)carbonyl]-6-fluoro-4,5-dihydroimidazo-[1,5-a]-quinoxaline-3-carboxylate, tert-butyl 5-[(1-(3,5-dimethyl)piperazino)carbonyl]-4,5-dihydro-7-methylimidazo-[1,5-a]-quinoxaline-3-carboxylate, tert-butyl 4,5-dihydro-5-[(1-(2,4,6-trimethyl)piperazino)carbonyl]imidazo-[1,5-a]quinoxaline-3-carboxylate, tert-butyl 7-chloro-4,5-dihydro-5-[(1-(2,4,6-trimethyl)piperazino)carbonyl]imidazo-[1,5-a]quinoxaline-3-carboxylate, tert-butyl 7-fluoro-4,5-dihydro-5-[(1-(2,4,6-trimethyl)piperazino)carbonyl]imidazo-[1,5-a]quinoxaline-3-carboxylate, tert-butyl 6-fluoro-4,5-dihydro-5-[(1-(2,4,6-trimethyl)piperazino)carbonyl]imidazo-[1,5-a]quinoxaline-3-carboxylate, tert-butyl 4,5-dihydro-7-methyl-5-[(1-(2,4,6-trimethyl)piperazino)carbonyl]imidazo-[1,5-a]quinoxaline-3-carboxylate, tert-butyl 5-[(1-(2,6-dimethyl)piperazino)carbonyl]-4,5-dihydroimidazo-[1,5-a]quinoxaline-3-carboxylate, tert-butyl 7-chloro-5-[(1-(2,6-dimethyl)piperazino)carbonyl]-4,5-dihydroimidazo-[1,5-a]quinoxaline-3-carboxylate, tert-butyl 5-[(1-(2,6-dimethyl)piperazino)carbonyl]-7-fluoro4,5-dihydroimidazo-[1,5-a]quinoxaline-3-carboxylate, tert-butyl 5-[(1-(2,6-dimethyl)piperazino)carbonyl]-6-fluoro-4,5-dihydroimidazo-[1,5-a]quinoxaline-3-carboxylate, and tert-butyl 5-[(1-(2,6-dimethyl)piperazino)carbonyl]-4,5-dihydro-7-methylimidazo-[1,5-a]quinoxaline-3-carboxylate.

14. An imidazo[1,5-a]quinoxaline (I) according to claim 13 which is selected from the group consisting of 5-(tert-butyloxycarbonyl)-3-(5-cyclopropyl-1,2,4-oxadiazol-3-yl)-6-fluoro4,5-dihydroimidazo[1,5-a]quinoxaline, 3-(5-cyclopropyl-1,2,4-oxadiazol-3-yl)-7-fluoro-4,5-dihydro-5-[(morpholino)carbonyl]-imidazo[1,5-a]quinoxaline, 3-(5-cyclopropyl-1,2,4-oxadiazol-3-yl)-5-[(dimethylamino)carbonyl]-4,5-dihydroimidazo[1,5-a]quinoxaline, 3-(5-cyclopropyl-1,2,4-oxadiazol-3-yl)-5-[(ethylamino)carbonyl]-4,5-dihydroimidazo[1,5-a]quinoxaline, 8-fluoro-4,5-dihydro-4(R)-methyl-3-[5-(1-methylcyclopropyl-1,2,4-oxadiazol-3-yl) 5-(pyrrolidino)carbonyl]imidazo[1,5-a]quinoxaline, 3-[3-cyclopropyl-1,2,4-oxadiazol-5- yl]-7-fluoro-4,5-dihydro-4-(morpholinylcarbonyl) imidazo[1,5-a]quinoxaline, 3-(4-cyclopropylthiazol-2-yl)-4,5-dihydro-5-(morpholinylcarbonyl)imidazo[1,5-a]quinoxaline, 3-(5-cyclopropyl-1,2,4-oxadiazol-3-yl)-5-[(3,5-dimethyl-)morpholinylcarbonyl]-7-fluoro -4,5-dihydroimidazo [1,5-a]quinoxaline, isopropyl 3-(4-fluorophenyl)-4,5-dihydroimidazo[1,5-a] quinoxaline-5-carboxylate, 3-(5-cyclopropyl-1,2,4-oxadiazol-3-yl)-5-[(2-(diethylamino)ethylamino)carbonyl]-4,5 -dihydroimidazo[1,5-a]quinoxaline, 5-(carbamoyl)-7-chloro-3-(5-cyclopropyl-1,2,4-oxadiazol-3-yl)-4,5-dihydroimidazo[1,5 -a]quinoxaline, 3-(3-cyclopropyl-1,2,4-oxadiazol-5-yl)-4,5-dihydro-7-methyl-5-[(morpholino)carbonyl]-imidazo[1,5-a]quinoxaline, 5-(carbamoyl)-3-(3-cyclopropyl-1,2,4-oxadiazol-5-yl)-4,5-dihydro-7-methylimidazo[1,5 -a]quinoxaline, 3-(5-cyclopropyl-1,2,4-oxadiazol-3-yl)-4,5-dihydro-5-[(1-(3,4,5-trimethyl)piperazino) -carbonyl]imidazo[1,5-a]quinoxaline, 3-(5-cyclopropyl-1,2,4-oxadiazol-3-yl)-4,5-dihydro-5-[((2-dimethylamino)ethoxy) -carbonyl]imidazo[1,5-a]quinoxaline, 3-(5-cyclopropyl-1,2,4-oxadiazol-3-yl)-7-fluoro-4,5-dihydro-5-[bis-(2 -methoxyethyl)aminocarbonyl]imidazo[1,5-a]quinoxaline, tert-butyl 7-fluoro-5-[bis(2-methoxyethyl)aminocarbonyl]-4,4-dimethylimidazo[1,5 -a]quinoxaline-3-carboxylate, tert-butyl 7-chloro-4,5-dihydro-5-[(1-(3,4,5-trimethyl)piperazino)- carbonyl]imidazo[1,5 -a]quinoxaline-3-carboxylate, and tert-butyl 7-chloro-5-[(1-(3,5-dimethyl)piperazino)carbonyl]4,5-dihydroimidazo[1,5 -a]quinoxaline-3-carboxylate.

15. Imidazo[1,5-a]quinoxalines (LX) selected from the group consisting of tert-butyl 7-fluoro-4,5-dihydro-4(R)-methyl-5-(2-pyridylmethyl)imidazo[1,5 -a]quinoxaline-3-carboxylate, 7-fluoro-4,5-dihydro-4(R)-methyl-3-[5-(1-methylcyclopropyl)-1,2,4-oxadiazol-3-yl]-5-(2-pyridylmethyl)imidazo[1,5-a]quinoxaline, cyclopropylmethylamino 7-fluoro-4,5-dihydro-4(R)-methyl-5-(2-pyridylmethyl)imidazo [1,5-a]quinoxaline-3-carboxamide, and 7-fluoro-4,5-dihydro-4(R)-methyl-3-[5-(2-methylcyclopropyl)-1,2,4-oxadiazol-3-yl]-5-(2-pyridylmethyl)imidazo[1,5-a]quinoxaline.

16. tert-butyl 7-trifluoromethyl-5-[(1-(3,5-dimethyl)piperazino)carbonyl]4,5-dihydroimidazo [1,5-a]quinoxaline-3-carboxylate and pharmaceutically acceptable salts thereof.

17. An imidazo[1,5-a]quinoxaline according to claim 8 where $R_5$ is —$(CH_2)_{n29}$—CO—$(CH_2)_{n28}$—$NR_{5-4}R_{5-5}$.

18. An imidazo[1,5-a]quinoxaline according to claim 17 where $n_{28}$ and $n_{29}$ are both 0, $R_{5-4}$ and $R_{5-5}$ are taken together with the attached nitrogen atom to form a heterocyclic ring which is —$N^*$—$(CH_2)_{n1}$—$(CHR_{5-8})_{nA}$—$R_{5-6}$—$(CH_{5-9})_{nB}$—$(C^*H_2)_{n2}$— where the atoms marked with an asterisk (*) are bonded to each other resulting in the formation of a ring, where when $n_A$, $n_B$, $n_1$ and $n_2$ are 1, and $R_{5-8}$ and $R_{5-9}$ are $C_1$-$C_3$ alkyl, and $R_{5-6}$ is —$NR_{5-7}$ where $R_{5-7}$ is —H or $C_1$-$C_6$ alkyl the $R_{5-8}$ and $R_{5-9}$ alkyl groups are cis.

19. An imidazo[1,5-a]quinoxaline according to claim 17 where $n_{28}$ and $n_{29}$ are both 0, $R_{5-4}$ and $R_{5-5}$ are taken together with the attached nitrogen atom to form a heterocyclic ring which is —$N^*$—$(CH_2)_{n1}$—$(CHR_{5-8})_{nA}$—$R_{5-6}$—$(CHR_{5-9})_{nB}$—$(C^*H_2)_{n2}$— where the atoms marked with an asterisk (*) are bonded to each other resulting in the formation of a ring, where when $n_A$, $n_B$, $n_1$ and $n_2$ are 1, and $R_{5-8}$ and $R_{5-9}$ are $C_1$-$C_3$ alkyl, and $R_{5-6}$ is —$NR_{5-7}$ where $R_{5-7}$ is —H or $C_1$-$C_6$ alkyl the $R_{5-8}$ and $R_{5-9}$ alkyl groups are trans.

20. An imidazo[1,5-a]quinoxaline which is selected from the group consisting of 7-chloro-4 5-dihydro-N-morpholino-5-[(pyrrolidino)carbonyl]imidazo[1,5 -a]quinoxaline-3-carboxamide, 7-chloro-N-cyclohexylamino-4,5-dihydro-5-[(pyrrolidino)carbonyl]imidazo[1,5 -a]quinoxaline-3-carboxamide, 4,5-dihydro-3-(benzoylmethyl)-5-(benzoyl)imidazo[1,5-a]quinoxaline, and 4,5-dihydro-3-(benzoylmethyl)-5-(pyrrolidinyl)carbonyl]imidazo[1,5-a]quinoxaline.

* * * * *

UNITED STATES PATENT AND TRADEMARK OFFICE
CERTIFICATE OF CORRECTION

PATENT NO. : 5,541,324

DATED : July 30, 1996

INVENTOR(S) : Ruth E. TenBrink, et al.

It is certified that error appears in the above-identified patent and that said Letters Patent is hereby corrected as shown below:

```
Title page under Related U.S. Application Data reads "Continuation-in-
part of Ser. No. 843,650 Feb. 28, 1992, abandoned, which is a
continuation-in-part of Ser. No. 715,930, Jun. 14, 1991, abandoned."
``` should read

--continuation-in-part of PCT/US92/04434, filed June 1, 1992, which is a continuation-in-part of Ser. No. 07/843,650, Feb. 28, 1992, abandoned, which is a continuation-in-part Ser. No. 07/715,930, June. 14, 1991, abandoned.--

Signed and Sealed this

Eleventh Day of March, 1997

Attest:

BRUCE LEHMAN

*Attesting Officer*  Commissioner of Patents and Trademarks